(12) United States Patent
Smith

(10) Patent No.: US 11,576,944 B2
(45) Date of Patent: Feb. 14, 2023

(54) GRAPE EXTRACTS AND METHODS RELATING THERETO

(71) Applicant: Piedmont Research & Development Corporation, Advance, NC (US)

(72) Inventor: Jerry Wayne Smith, Advance, NC (US)

(73) Assignee: Piedmont Research & Development Corporation, Advance, NC (US)

( * ) Notice: Subject to any disclaimer, the term of this patent is extended or adjusted under 35 U.S.C. 154(b) by 0 days.

(21) Appl. No.: 17/410,164

(22) Filed: Aug. 24, 2021

(65) Prior Publication Data

US 2021/0393729 A1 Dec. 23, 2021

Related U.S. Application Data

(63) Continuation of application No. 16/088,483, filed as application No. PCT/US2017/025776 on Apr. 3, 2017, now Pat. No. 11,135,261.

(60) Provisional application No. 62/316,918, filed on Apr. 1, 2016.

(51) Int. Cl.
  *A61K 36/87* (2006.01)
  *A61P 35/00* (2006.01)
  *A61K 9/00* (2006.01)

(52) U.S. Cl.
  CPC ............ *A61K 36/87* (2013.01); *A61K 9/0095* (2013.01); *A61P 35/00* (2018.01); *A61K 2236/00* (2013.01); *A61K 2236/331* (2013.01)

(58) Field of Classification Search
  None
  See application file for complete search history.

(56) References Cited

U.S. PATENT DOCUMENTS

| 6,544,581 B1 | 4/2003 | Shrikhande et al. |
| 2015/0259315 A1 | 9/2015 | Shrikhande |

FOREIGN PATENT DOCUMENTS

| CN | 103435661 A | 12/2013 |
| WO | 2015184291 A1 | 12/2015 |

OTHER PUBLICATIONS

Lee, Joon-Hee et al. "Ellagic Acid and Ellagitannins Affect on Sedimentation in Muscadine Juice and Wine" J. Agric. Food Chem., 50:3971-3976 2002.
Yi W. et al. "Study of Anticancer Activities of Muscadine Grape Phenolics in Vitro" J. Agric. Food Chem., 53:8804-8812 2005.
"Gallagher PE and Tallant EA. Abstract 2825: Prevention of breast tumor growth by an extract from the muscadine grape. Cancer Research, American Association for Cancer Research, US. Aug. 2015; 75(Suppl. 15): 1 page".
"International Search Report and Written Opinion, PCT/US2017/025776, dated Jul. 11, 2017, 12 pages".
Porter BE , et al., "Abstract 4563: Muscadine grape extract reduces lung carcinogenesis in female mice exposed to 3-methycholanthrene in utero. Cancer Research, American Associate for Cancer Research, US. Aug. 2015; 75(Suppl. 15): 2 pages".
Tallant EA, et al., "Abstract 4220: Inhibition of cancer cell growth by muscadine grape seed and grape skin extracts. Cancer Research, American Association for Cancer Research, US. Apr. 2011; 71(Suppl. 8): 2 pages".
Xu C , et al., "Enzyme release of phenolics from muscadine grape (*Vitis rotundifolia* Michx.) skins and seeds. Food Chemistry. Feb. 2014; 157: 20-29".

*Primary Examiner* — Russell G Fiebig
(74) *Attorney, Agent, or Firm* — Myers Bigel, P.A.

(57) ABSTRACT

Provided are liquid and powder grape extracts having elevated phenolic content. The extracts can be made from grape seeds, grape skins, or a combination thereof. In some instances, extracts may be blends of grape seed extracts and grape skin extracts. Methods of manufacturing such extracts area also provided. Such methods involve controlled temperature conditions to increase yield of phenolic compounds in the extracts. Methods of using the extraction for treating subjects are also provided, including treatment of cancer and end-organ damage relating to hypertension.

19 Claims, 54 Drawing Sheets

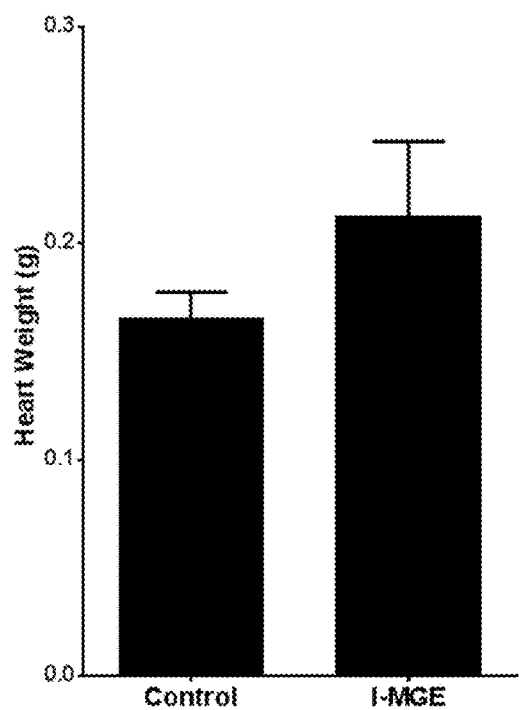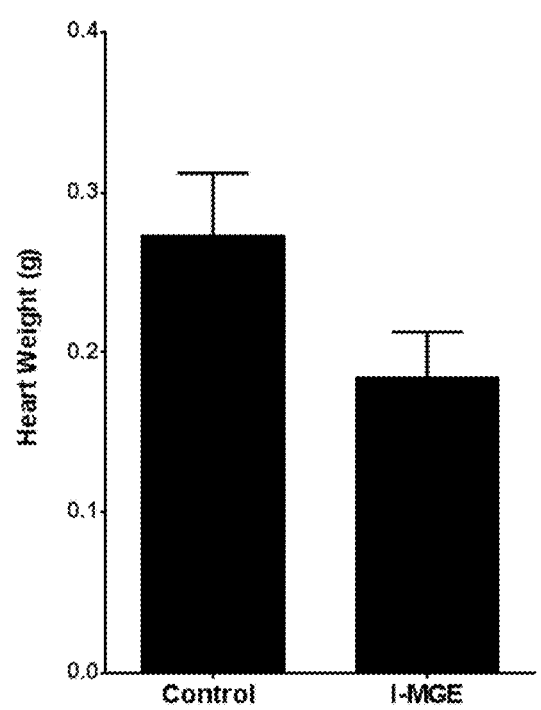
25 week old mice  31 week old mice
FIG. 5A  FIG. 5B

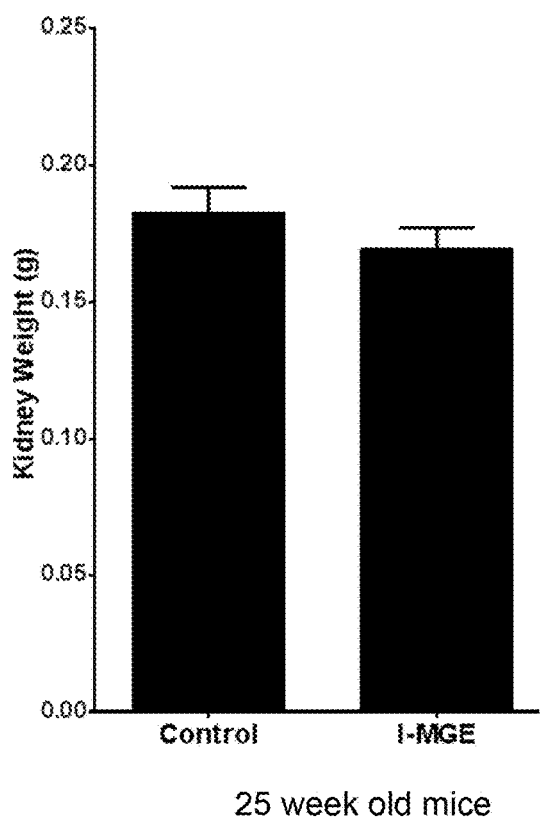
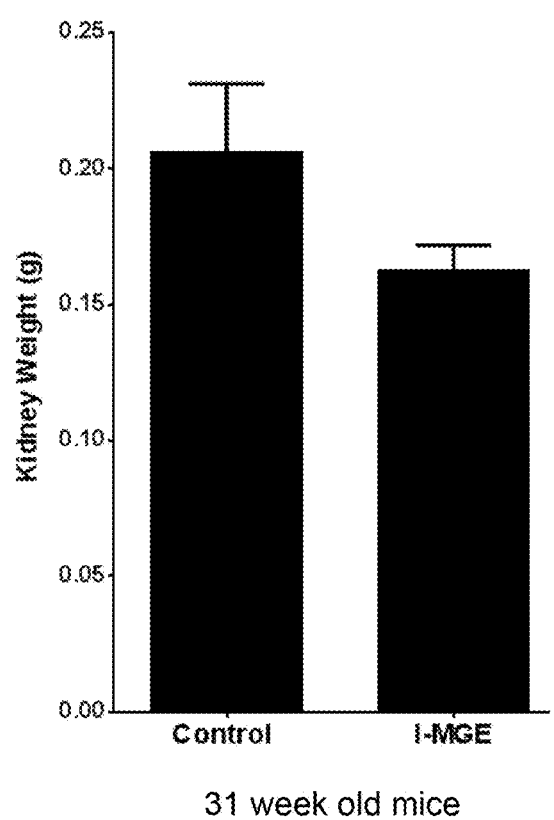
FIG. 6A  FIG. 6B

25 week old mice 31 week old mice

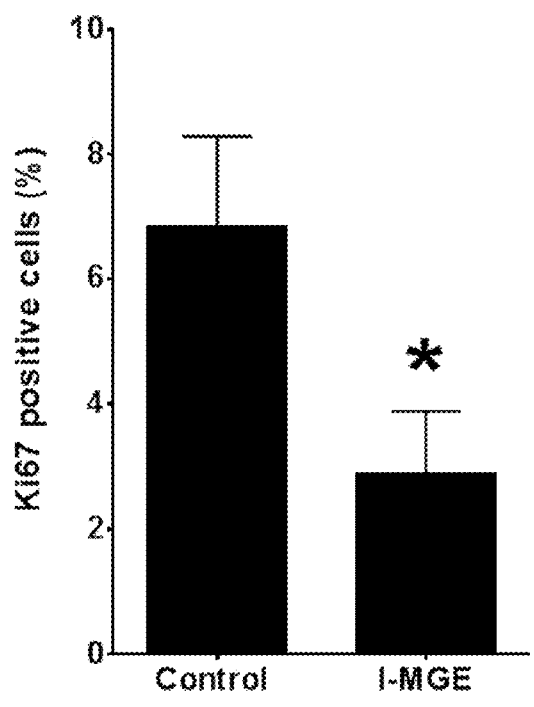
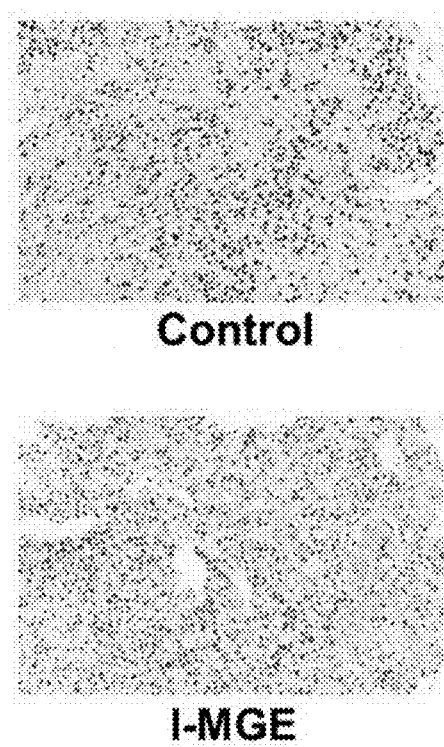
FIG. 9
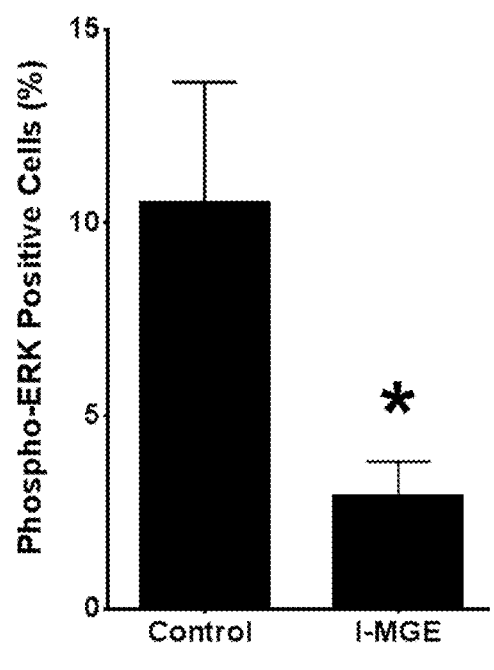
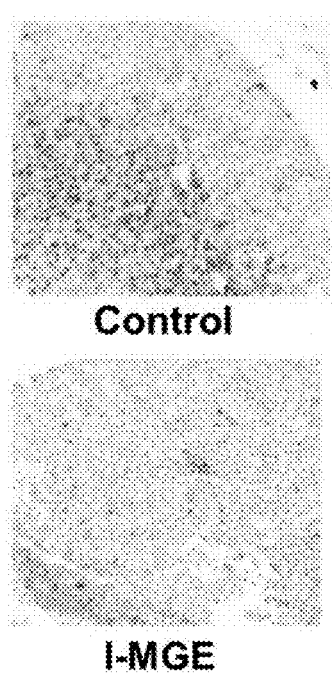
FIG. 10

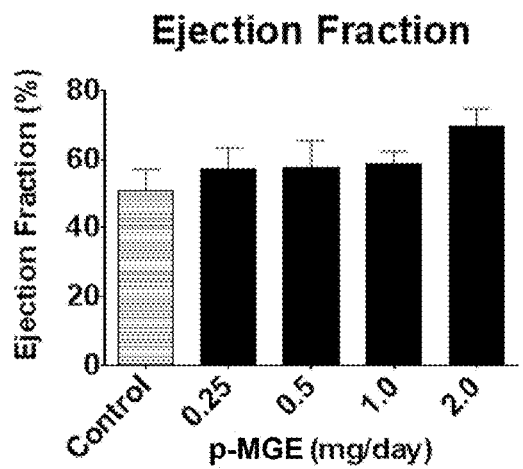
FIG. 22A
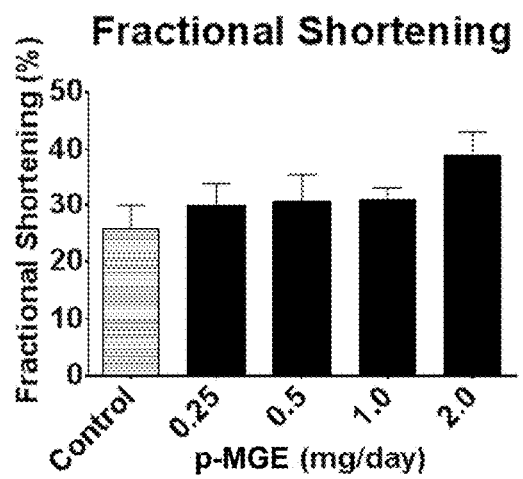
FIG. 22B
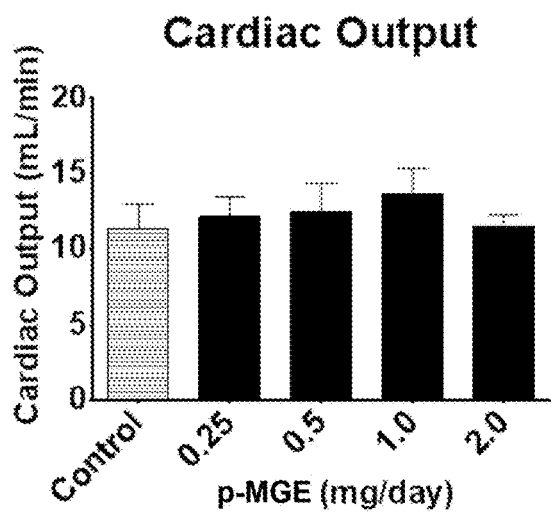
FIG. 22C
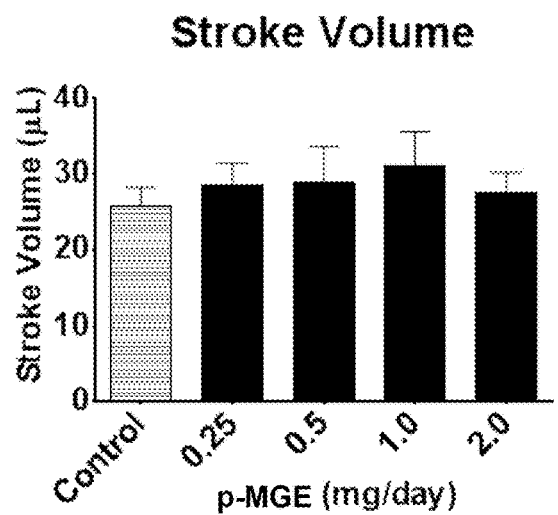
FIG. 22D
FIG. 22E
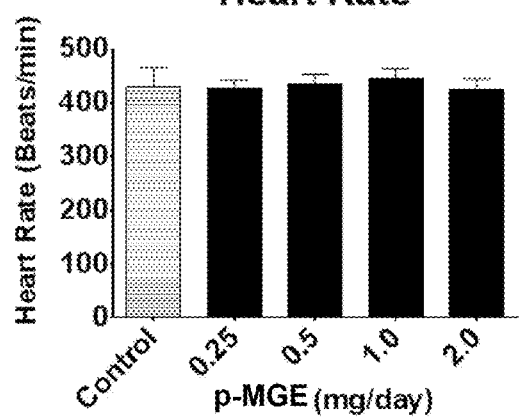

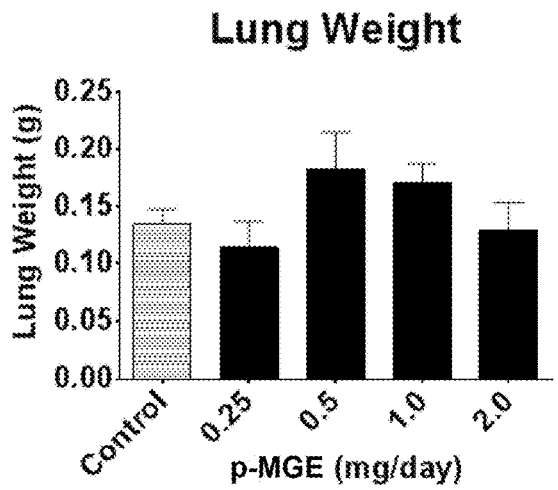
FIG. 23A
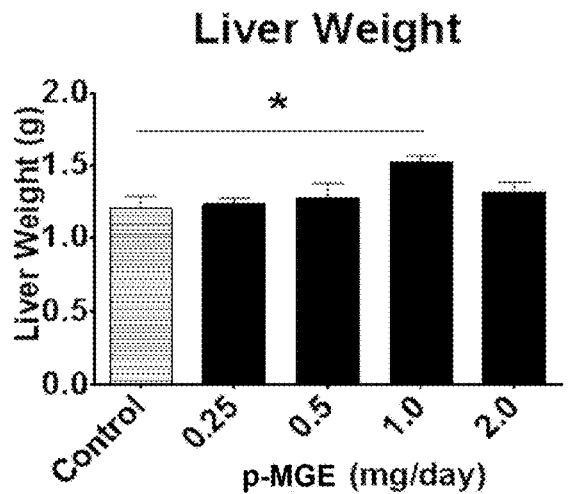
FIG. 23B
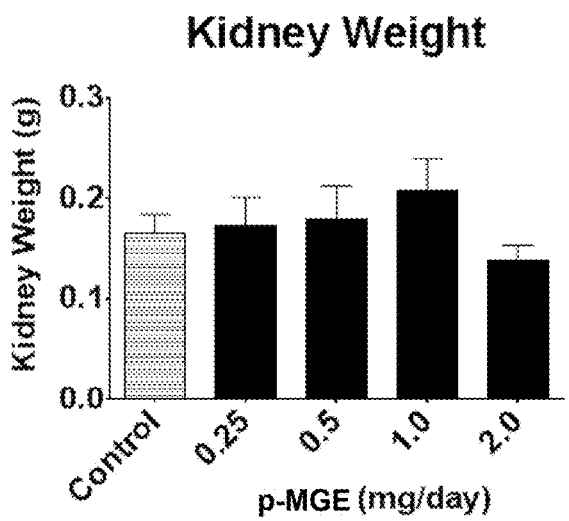
FIG. 23C
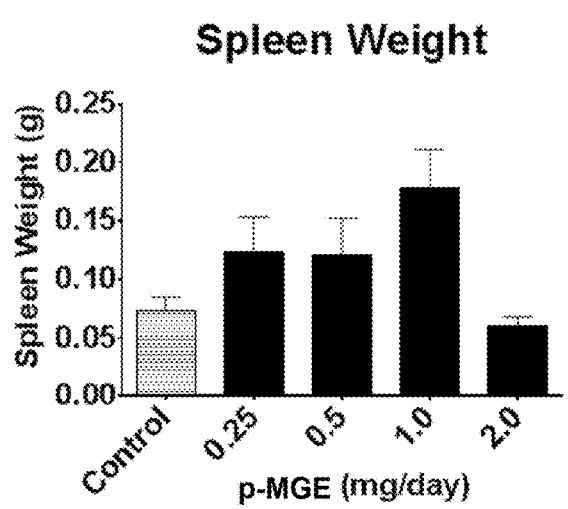
FIG. 23D
FIG. 23E
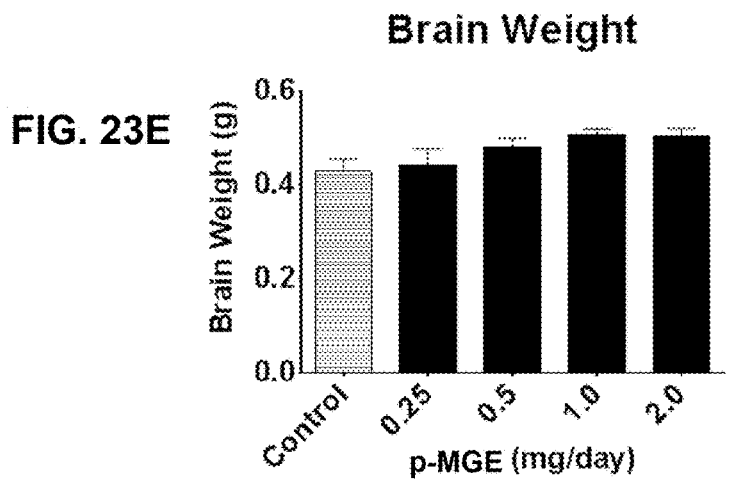

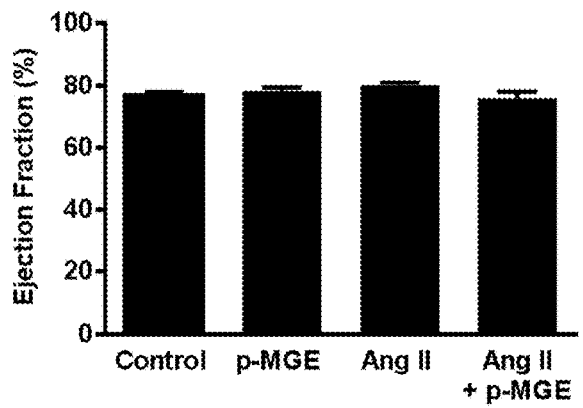
FIG. 27A
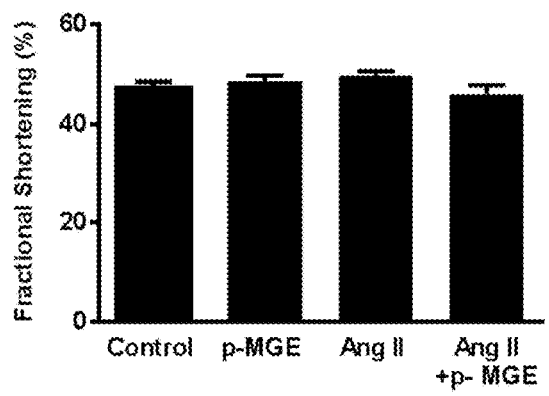
FIG. 27B
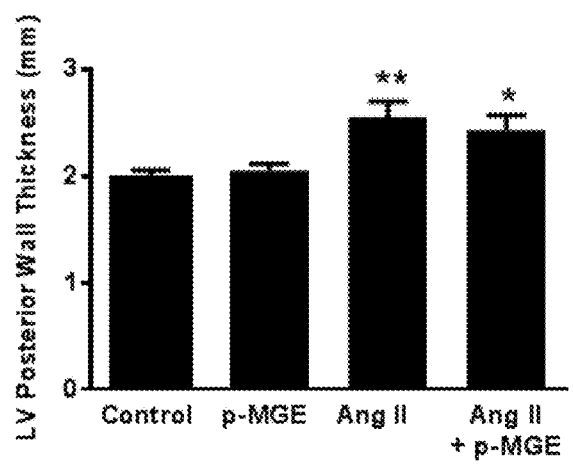
FIG. 28A
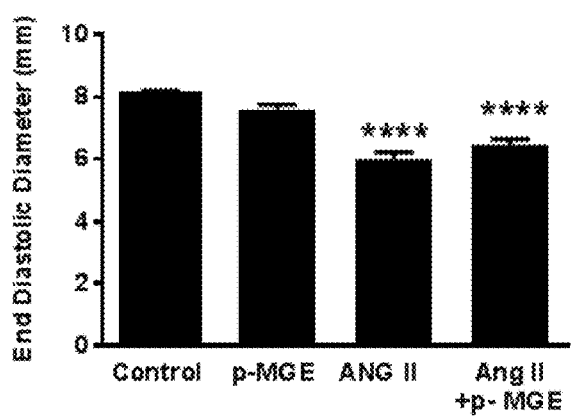
FIG. 28B
FIG. 28C
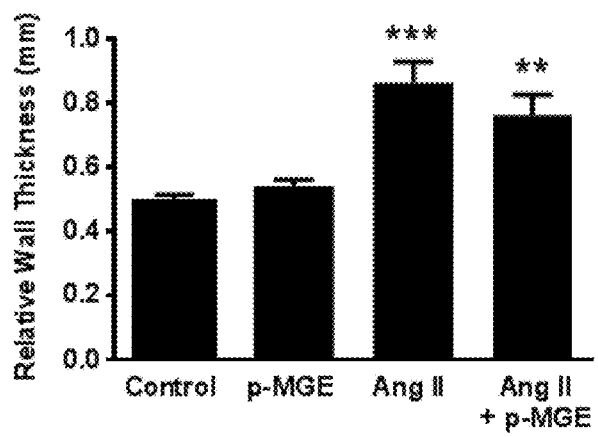

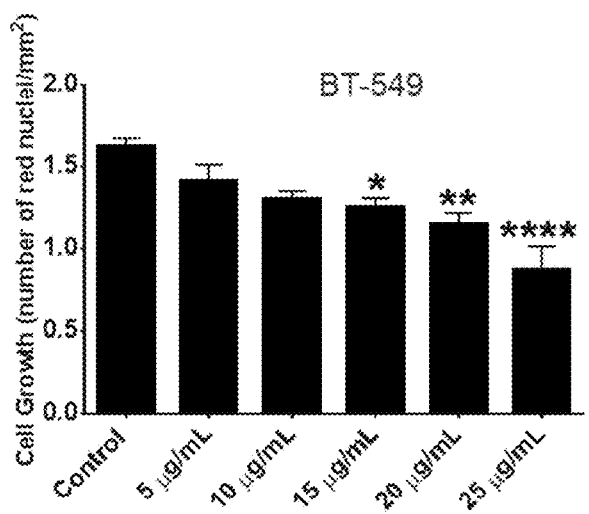
FIG. 37A
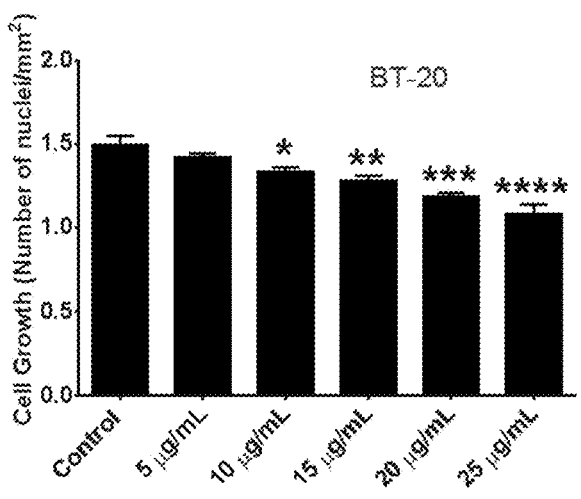
FIG. 37B
FIG. 37C
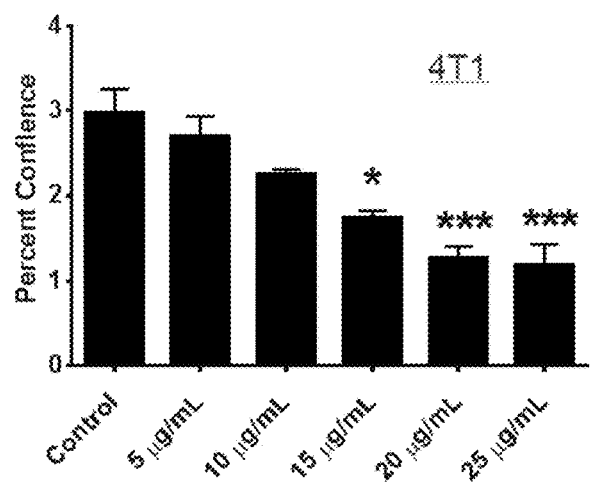

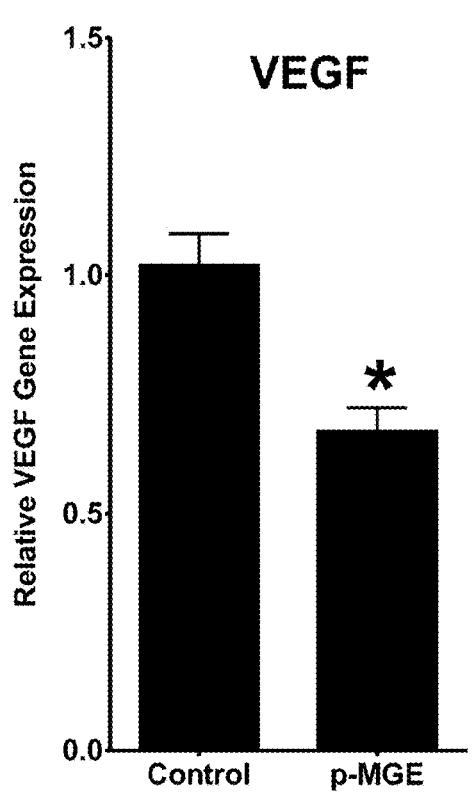
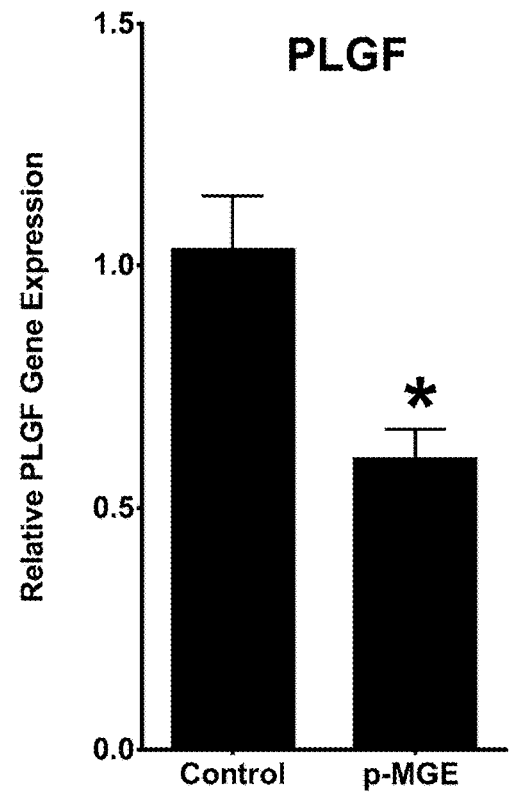
FIG. 52A        FIG. 52B
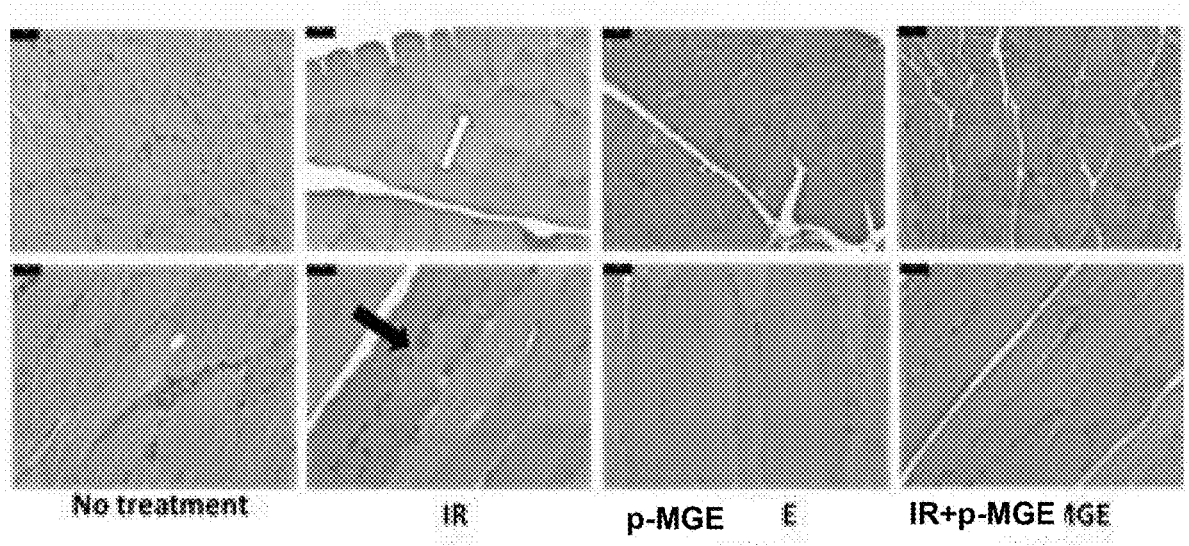
FIG. 53

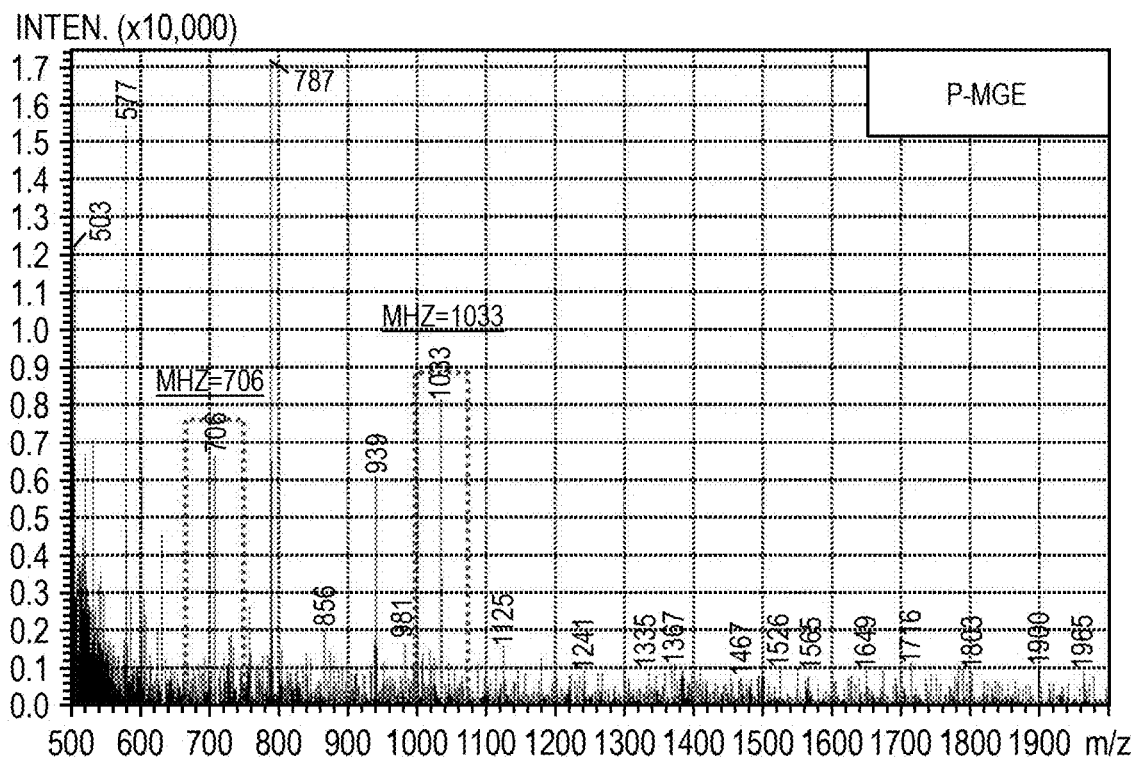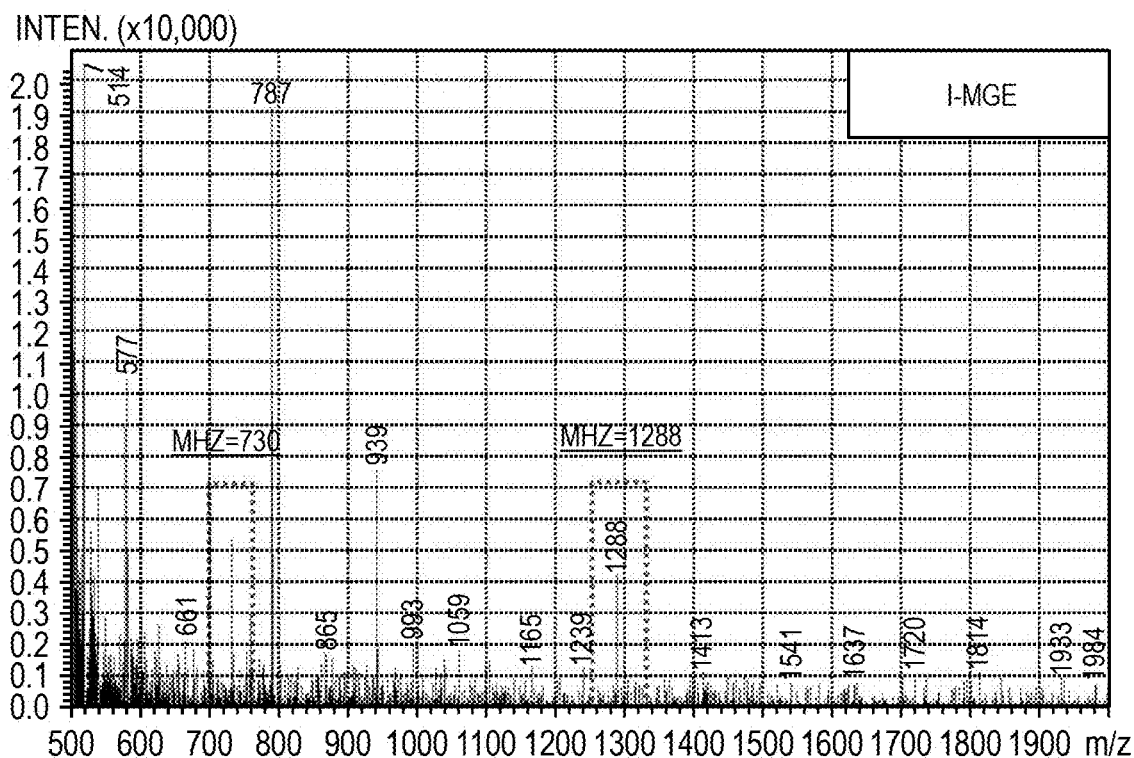
FIG. 59

GRAPE EXTRACTS AND METHODS RELATING THERETO

CROSS-REFERENCE TO RELATED APPLICATIONS

This application is a continuation application of U.S. patent application Ser. No. 16/088,483, filed on Sep. 28, 2018, which is a 35 U.S.C. § 371 national phase application of International Application Serial No. PCT/US17/25776, filed Apr. 3, 2017, which claims the benefit, under 35 U.S.C. § 119(e), of U.S. Provisional Application No. 62/316,918, filed Apr. 1, 2016, the entire contents of each of which is incorporated by reference herein.

BACKGROUND

Various processes have been developed to extract juice and nutritional components from fruits including grape. However, such known methods may not efficiently extract or preserve the valuable compounds from the fruit.

Antioxidant compounds including phenolics, flavonoids and resveratrol, can be beneficial for human health. The beneficial effects can be seen, for example, in diseases in which oxidative processes occur such as atherosclerosis, coronary heart disease, diabetes and some cancers. Flavonoids represent a widespread and common group of natural polyphenols produced by the phenylpropanoid pathway. They are an important group of soluble phenolics in grapes and are believed to be major contributors to the benefits of grape-derived products.

There is a need for improved methods of extraction of polyphenols and other plant derived phytochemicals from plants, and grapes in particular, and uses for such products to treat disease.

BRIEF SUMMARY

Described herein are extracts made from grapes and formulations thereof. The extracts of the disclosure include liquid extracts and powder extracts made therefrom. Various methods for producing different extracts and method of treatment relating to cancer are also provided.

In one aspect, provided is a method of manufacturing a liquid extract from grape seeds, grape skins, or a combination thereof, the method including the steps of: (a) providing grape seeds, grape skins, or a combination thereof; (b) contacting the grape seeds, grape skins, or a combination thereof, with distilled water to form an extraction mixture; (c) heating the extraction mixture at a temperature in the range of 120° F. to 200° F., during which heating additional distilled water is added; (d) cooling the extraction mixture; (e) filtering the extraction mixture to remove solids thereby forming a filtrate; (f) adding a food preservative to the filtrate; (g) cooling the filtrate to form a cooled filtrate; and (h) filtering the cooled filtrate thereby producing the liquid extract.

In another aspect, provided is a method of producing a grape seed extract, the method including the steps of: (a) contacting grape seeds with distilled water; (b) heating the water and grape seeds from step (a) at a temperature in the range of 120° F. to 200° F. during which additional distilled water is added; (c) cooling the grape seeds and water from step (b); (d) filtering the grape seeds and water from step (c) to produce a grape seed filtrate; (e) adding a food preservative to the filtrate from step (d); (f) cooling the filtrate from step (e) to produce a cooled filtrate; and (g) filtering the cooled filtrate from step (f), thereby producing a grape seed extract.

In another aspect, a method of producing a grape skin extract is provided, the method including the steps of: (a) contacting grape skin with distilled water; (b) heating the water and grape skin from step (a) at a temperature in the range of 120° F. to 200° F. during which additional distilled water is added; (c) cooling the grape skin and water from step (b); (d) filtering the grape skin and water from step (c) to produce a grape skin filtrate; (e) adding a food preservative to the filtrate from step (d); (f) cooling the filtrate from step (e) to produce a cooled filtrate; and (g) filtering the cooled filtrate from step (f), thereby producing the grape skin extract.

In another aspect, provided is a method of producing a grape seed and grape skin extract, the method including the steps of: (a) contacting grape seed and grape skin with distilled water; (b) heating the water and grape seed and grape skin from step (a) at a temperature in the range of 120° F. to 200° F. during which additional distilled water is added; (c) cooling the grape seed and grape skin and water from step (b); (d) filtering the grape seed and grape skin and water from step (c) to produce a grape seed and grape skin filtrate; (e) adding a food preservative to the filtrate from step (d); (f) cooling the filtrate from step (e) to produce a cooled filtrate; and (g) filtering the cooled filtrate from step (f), thereby producing the grape seed and grape skin extract.

In another aspect, provided is a method of manufacturing a grape-derived liquid extract, the method including the steps of: (a) providing a grape seed liquid extract made by a method described above; (b) providing a grape skin liquid extract made by a method described above; (c) combining the grape seed liquid extract and the grape skin liquid extract in a ratio of about 50:50 to about 85:15 (volume/volume (v/v)), thereby forming the grape-derived liquid extract.

In another aspect, provided is a method of manufacturing a grape-derived powder extract, the method including the steps of: obtaining or manufacturing a grape-derived liquid extract from grape seed, grape skin, or a combination thereof as described above and then spray-drying the liquid extract to form a powder extract.

In another aspect, provided are methods of producing powder extracts that include spray-drying a liquid extract produced by the methods described above and elsewhere in the disclosure.

In another aspect, provided is a method of producing a grape seed and grape skin extract, the method including combining a grape skin extract and a grape seed extract.

Additional aspects include extracts produced using the methods described in the disclosure and formulations produced therefrom. In one aspect, provided is a powder extract or formulation containing about 25% to 50% (weight/weight (w/w)) total phenolic compounds. In another aspect, provided is a powder extract or formulation containing at least about 30% (weight/weight (w/w)) total phenolic compounds. In another aspect, provided is an extract containing about 250-500 mg total phenolic compounds per gram of powder extract. In another aspect, provided is a powder extract containing at least one of gallic acid or ellagic acid at a concentration of at least about 6 mg per gram of powder extract. Also provided are exacts and formulations that are blends of any of the above-described extracts.

In some embodiments, the total phenolic content of the formulations provided in this disclosure remains stable over a period of at least 6 months, as characterized by total phenolic content reduction of no more than 10% at 6 months.

Further described herein are methods of treating or preventing various diseases and conditions in a subject. The methods of treating or preventing such diseases and conditions include administering to a subject an effective amount of an extract as described in this disclosure.

In another aspect, provided is a method of treating a subject with disease, an increased risk of disease, or at risk of relapse, the method including the steps of administering to a subject a pharmaceutically effective amount of a grape-derived extract as described in the preceding sections of this disclosure. In some instances, the method comprises administering a liquid extract or formulation. In some instances, the method comprises administering a powder extract or formulation. The disease may include any of cancer, hypertension-induced fibrosis, radiation-induced fibrosis, or radiation-induced bone loss.

The details of one or more aspects and embodiments are set forth in the description and drawings below. Other features, objects, and advantages will be apparent from the description and drawings, and from the claims.

BRIEF DESCRIPTION OF THE DRAWINGS

FIG. 1A shows total phenolic compound analysis using a colorimetric assay, and FIG. 1B shows analysis of select individual phenolic compounds by UPLC-mass spectrometry (catechin, gallic acid, epicatechin, ellagic acid, procyanadin, and catechin-gallate (cat-gall). ** denotes $p<0.01$.

FIGS. 5A-5B show graphs illustrating heart weight analysis in a breast cancer mouse model (c-neu mice) treated with muscadine grape seed and muscadine grape skin liquid extract (l-MGE) as described in Example 1. Mice were given l-MGE in their drinking water beginning at 3 weeks of age. Control mice drank regular water. The mice were euthanized after 25 weeks (FIG. 5A) or 31 weeks (FIG. 5B) and their hearts were removed and weighed. n=7-12 for tumors from 25 week-old mice and 7-10 for 31 week-old mice. There was no difference in the heart weight of c-neu mice which drank regular water or the l-MGE for 25 or 31 weeks, indicating that the extract had no effect on heart weight.

FIGS. 6A-6B show graphs illustrating kidney weight analysis in a breast cancer mouse model (c-neu mice) treated with muscadine grape seed and muscadine grape skin liquid extract (l-MGE) as described in Example 1. Mice were given l-MGE in their drinking water beginning at 3 weeks of age. Control mice drank regular water. The mice were euthanized after 25 weeks (FIG. 6A) or 31 weeks (FIG. 6B) and their kidneys were removed and weighed. n=7-12 for tumors from 25 week-old mice and 7-10 for 31 week-old mice. There was no difference in the weight of the kidneys of c-neu mice which drank regular water or the l-MGE for 25 or 31 weeks, indicating that the extract had no effect on kidney weight.

FIG. 9 shows an analysis of proliferation in tumors from a breast cancer mouse model (c-neu mice) treated with muscadine grape seed and muscadine grape skin liquid extract (l-MGE) as described in Example 1. Sections of tumors from 25 week-old mice fed drinking water (Control) or the l-MGE were incubated with an antibody to the proliferative marker Ki67. A graph showing the percentage of cells positive for Ki67 staining is presented next to representative microscopic images. n=8-10, * denotes p<0.05. Treatment of 25 week-old c-neu mice with the l-MGE significantly reduced the amount of Ki67 as compared to c-neu mice drinking regular water, indicating that the muscadine grape extract reduced tumor growth by decreasing tumor cell proliferation.

FIG. 10 shows an analysis of active ERK1/2 MAP kinase activities in tumors from a breast cancer mouse model (c-neu mice) treated with muscadine grape seed and muscadine grape skin liquid extract (l-MGE) as described in Example 1. Sections of tumors from 25 week-old c-neu mice fed drinking water (Control) or l-MGE were incubated with an antibody to phospho-ERK1/2. A graph showing the percentage of phospho-ERK positive cells is presented next to representative microscopic images. n=8-10, * denotes p<0.05. Treatment of 25 week-old c-neu mice with the l-MGE significantly reduced the amount of phosphorylated ERK1/2 MAP kinase as compared to c-neu mice drinking regular water, suggesting that the l-MGE reduced tumor growth by decreasing proliferative protein kinase activities.

FIGS. 22A-22E show graphs summarizing cardiac echocardiography of mice in a toxicity study assessing the impact of different doses of a muscadine grape seed and muscadine grape skin powder extract (p-MGE) as described in Example 1 according to aspects of this disclosure. Mice were anesthetized with isofluorane, during week four, using the VEVO in the M and B modes, and various cardiac parameters were calculated including ejection fraction (FIG. 22A), fractional shortening (FIG. 22B), cardiac output (FIG. 22C), stroke volume (FIG. 22D) and heart rate (FIG. 22E). n=5. There was no difference in the fraction of blood ejected from the heart during systole in mice treated with increasing concentrations of p-MGE. There was no difference in cardiac contractility, measured as fractional shortening, in the hearts of mice treated with p-MGE compared to untreated mice. There was no difference in cardiac output, as a measure of how much blood is being pumped by the heart, in untreated mice (Controls) and mice treated with p-MGE. There was no difference in stroke volume or heart rate between untreated mice (Control) and mice treated with p-MGE.

FIGS. 23A-22E show graphs summarizing organ weight assessment of mice in a toxicity study assessing the impact of different doses of a muscadine grape seed and muscadine grape skin powder extract (p-MGE) as described in Example 1 according to aspects of this disclosure. Select organs of mice in each treatment group were removed and weighed at the end of the treatment period, to determine the effect of p-MGE on organ weight (n=5). There was no difference in lung, kidney, spleen, or brain weight of mice treated with p-MGE (FIGS. 23A, 23C-23E). As shown in FIG. 23B, there was a small but significant increase in the weight of the liver using the second to the highest dose of p-MGE compared to the Control ($p<0.05$). The weight of the livers of mice at the end of the 4-week treatment period was similar with the two lowest concentrations compared to the Control group. Mice treated with the second to the highest concentration of p-MGE had a small but significant increase in liver weight compared to the Control group. However, liver weight of mice treated with the highest concentration of p-MGE was no different than Control.

As shown in FIG. 24A, there was no difference in the amount of urinary albumin in the urine of mice treated with increasing concentrations for 4 weeks compared to untreated mice, as a measure of renal function and in agreement with the lack of any pathology in the glomeruli or tubules of the same animals. Urinary angiotensinogen (Aogen) was measured by radioimmunoassay as an indicator of renal damage/function in the urine of mice treated for 4 weeks with increasing concentrations of p-MGE as compared to untreated mice (Control). Urinary creatinine was also measured in the urine and the amount of Aogen is expressed as ng Aogen/mg creatinine. n=5. As shown in FIG. 24B, there was no difference in the amount of urinary Aogen between untreated and treated mice, suggesting that the p-MGE did not damage the kidney, in agreement with the lack of pathology in the kidney glomeruli and tubules as assessed by pathology.

FIG. 27A-27B show an assessment of cardiac systolic function in Sprague-Dawley rats treated with Ang II and/or a muscadine grape seed and muscadine grape skin powder extract (p-MGE) as described in Example 1 according to aspects of this disclosure. FIG. 27A shows ejection fraction and FIG. 27B shows fractional shortening in rats treated with Ang II, p-MGE, or both, for 4 weeks as measured using the VisualSonics Vevo 2100 High-Resolution Imaging System (M mode parasternal short axis view at mid-papillary level). n=8. Neither Ang II nor p-MGE alone or in combination modified ejection fraction and fractional shortening as compared to Control, suggesting that Ang II and p-MGE administration had no effect on cardiac systolic function.

FIG. 27A-27B show analysis of cardiac features in the rats described with respect to FIG. 27A-27B according to aspects of this disclosure. FIG. 28A shows measurements of left posterior wall thickness, FIG. 28B shows measurements of end diastolic diameter, and FIG. 28C shows measurements of relative wall thickness in rats treated with Ang II, p-MGE, or both, for 4 weeks, assessed in M mode parasternal short axis view at mid-papillary level with the VisualSonics Vevo 2100 High-Resolution Imaging System. n=8; *$p<0.05$, $p<0.01$, *$p<0.001$ and ****$p<0.0001$ compared with control. Ang II increased left ventricular (LV) posterior wall thickness, decreased end diastolic internal diameter of the LV and increased relative wall thickness, suggesting that treatment with Ang II induces left ventricular concentric remodeling. p-MGE did not exacerbate or reduce the Ang II-mediated changes.

FIG. 2A shows assessment of e' as a measure of LV relaxation and FIG. 29B shows assessment of E/e' as an indication of left ventricular filling pressure. n=8; *$p<0.05$, $p<0.01$, and **$p<0.0001$ compared with control; # $p<0.05$ compared to Ang II alone. Ang II-induced diastolic dysfunction, reflected in impaired ventricular relaxation and increased left ventricular filling pressure. Co-administration of p-MGE reduced the Ang-II mediated increase in E/e' and tended to increase e', suggesting that p-MGE improves Ang II-induced diastolic dysfunction.

FIG. 32A shows a graph illustrating that a 4-week treatment with increasing concentrations of p-MGE reduced the volume of human triple negative breast tumors in athymic mice. * denotes p<0.05,  denotes p<0.01, * denotes p<0.001 and **** denotes p<0.0001. The tumors from these mice (n=8) were removed and weighed. FIG. 32B shows a graph illustrating that treatment with increasing concentrations of p-MGE reduced the weight of the tumors in mice compared to untreated mice, suggesting that administration of p-MGE will reduce breast tumor growth.; * denotes p<0.05, * denotes p<0.001 and  denotes p<0.0001. FIG. 32C-32E show an analysis of mRNA levels of dual specificity phosphatase 1, also known as MAP kinase phosphatase 1 (DUSP1/MKP1), platelet-derived growth factor (PDGF), and cyclin-dependent kinase inhibitor 1 (p21), respectively, in the MDA-MB-231 tumors of mice treated with 0.1 mg phenolics/mL of p-MGE in their drinking water or control mice as described with respect to FIG. 32A and FIG. 32B. The RNA was isolated from the tumors using TRIzol, and the mRNA was quantified using target-specific primer/probe sets (Applied Biosystems) and using 18S rRNA as an internal control. The results were quantified as Ct values, where Ct was defined as the threshold cycle of PCR at which the amplified product is first detected and defined as relative gene expression (the ratio of target/control). n=8, ** denotes p<0.0001. FIG. 32C shows a graph illustrating that treatment with p-MGE reduced the relative expression of DUSP1/MAKP1. DUSP1/MAKP1 is known to dephosphorylate and, thus, inactivate ERK1 and ERK2 protein kinases, which are known to participate in the proliferation of cancer cells. The increase in DUSP1/MAKP1 may account for the reduction in phospho-ERK1 and phosho-ERK2 observed in both MDA-MB-231 cells treated with p-MGE and brain-specific breast cancer cells treated with the extract. FIG. 32D shows a graph illustrating that treatment with p-MGE reduced the relative expression of PDGF, one of the primary growth factors involved in the regulation of cell growth. The reduction in PDGF by treatment with p-MGE may participate in the p-MGE-induced reduction in tumor growth. FIG. 32E shows a graph illustrating that treatment with p-MGE increased the relative expression of p21, a cyclin-dependent kinase inhibitor (CKI) that inhibits cyclin/cyclin-dependent kinase (CDK) complexes. The reduction in p21 by treatment with p-MGE suggests that p-MGE may inhibit the cell cycle to reduce tumor growth, in agreement with the reduction in cyclin D which was observed in brain-specific breast cancer cells treated with p-MGE. FIG. 32F shows the cell cycle pathway involved in the regulation of cell proliferation with a circle indicating the role of p21 in this process. The p-MGE-induced increase in p21 could participate in the regulation cell growth by reducing progression through the cell cycle.

Figure 35:
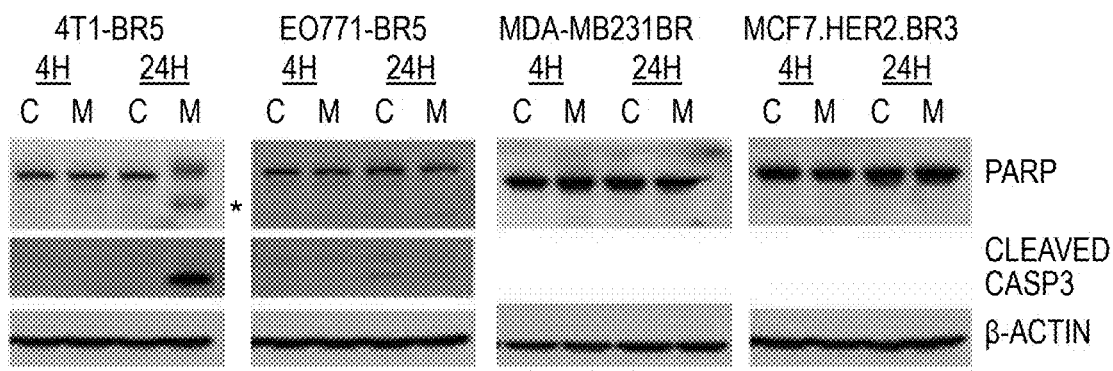

FIG. 35 shows the effect of a muscadine grape seed and muscadine grape skin powder extract (p-MGE) as described in Example 1 on growth of brain-specific breast cancer cell lines according to aspects of this disclosure. Brain-specific breast cancer cells (4T1-Br5, Eo771-Br5, MDA-MB231Br, and MCF7.HER2.Br3) were incubated with 10 µg/mL p-MGE (M) or without p-MGE (C for control) for 4 or 24 h, as indicated, and analyzed by Western blot for PARP or cleaved caspase 3; β-actin was used as loading control. *PARP cleavage product. Data shown are representative of 3 independent experiments for each cell line. p-MGE stimulated apoptosis in the brain-specific 4T1 cell line, detected by an increase in cleaved PARP and cleaved caspase 3, as markers of apoptosis. In contrast, apoptosis was not increased by p-MGE in the other 3 brain-specific cell lines, suggesting that different mechanisms are responsible for a reduction in cell growth in different types of metastatic breast cancer.

Figure 36A:
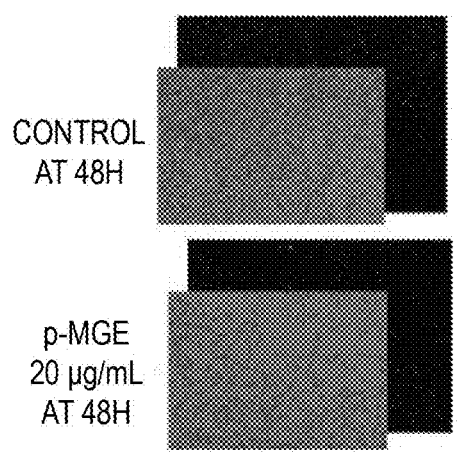
Figure 36B:
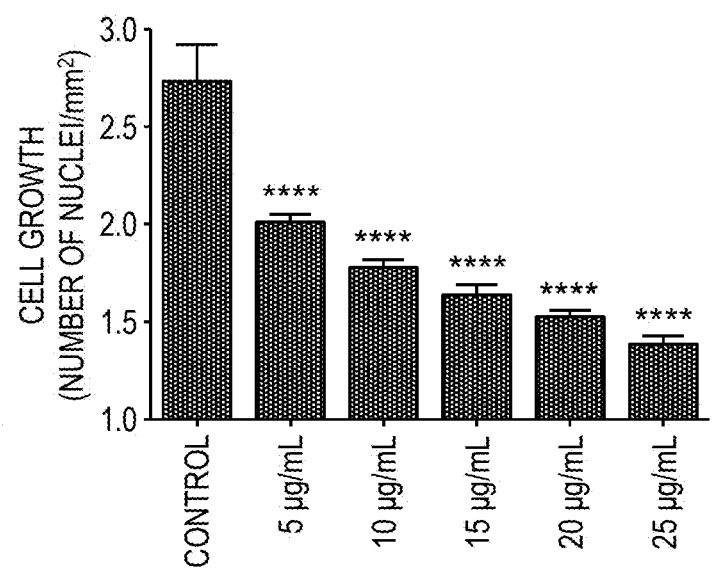

FIG. 36A-36B show the effect of a muscadine grape seed and muscadine grape skin powder extract (p-MGE) as described in Example 1 on triple-negative breast cancer cell proliferation according to aspects of this disclosure. MDA-MB-231 human TNBC cells were transfected with IncuCyte™ NucLight™ Red Lentivirus Reagent (EF1α, Puro) from Essen Bioscience, to label cell nuclei, according to the manufacturer's directions. Transfections were performed according to the manufacturer directions and transfected cells were selected and maintained using puromycin. Labeled cells were seeded into 96-well plates and treated with increasing concentrations of p-MGE, calculated as µg phenolics/mL of culture media. Cell proliferation was measured at 48 h, as shown in Panel A, and quantified in Panel B. n=3 in quadruplicate, **** denotes p<0.0001. p-MGE significantly reduced the proliferation of human MDA-MB-231 cells, in agreement with the reduction in tumor growth.

FIG. 37A-37C show the effect of a muscadine grape seed and muscadine grape skin powder extract (p-MGE) as described in Example 1 on triple-negative breast cancer (TNBC) cell proliferation according to aspects of this disclosure. Cell proliferation was measured in BT-549 (FIG. 37A), BT-20 (FIG. 37B), and 4T1 (FIG. 37C) TNBC cell lines, in response to increasing concentrations of p-MGE. n=3 in quadruplicate; * denotes p<0.05,  denotes p<0.005, * denotes p<0.001 and **** denotes p<0.0001. The growth of BT-549 and BT-20 human triple negative breast cancer cells and 4T1 mouse TNBC cells was reduced by increasing concentrations of p-MGE, suggesting that TNBC is a target for treatment with p-MGE.

Figure 38A:
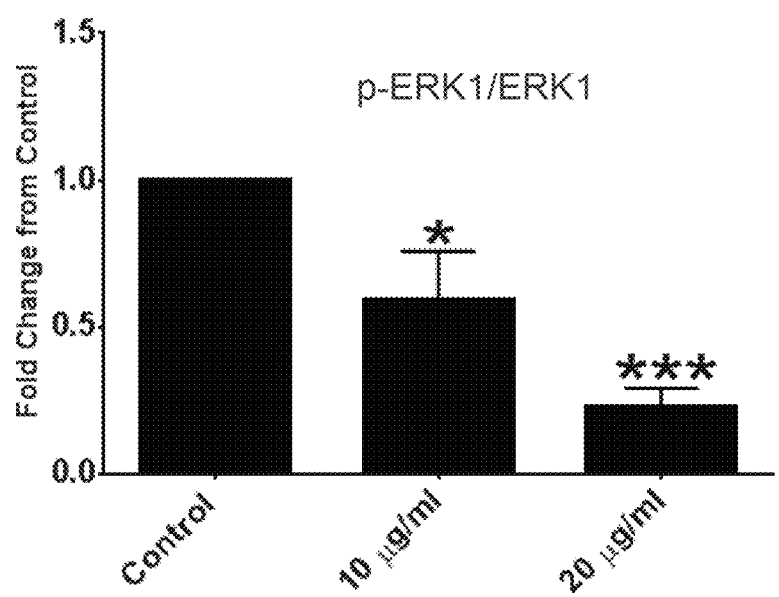
Figure 38B:
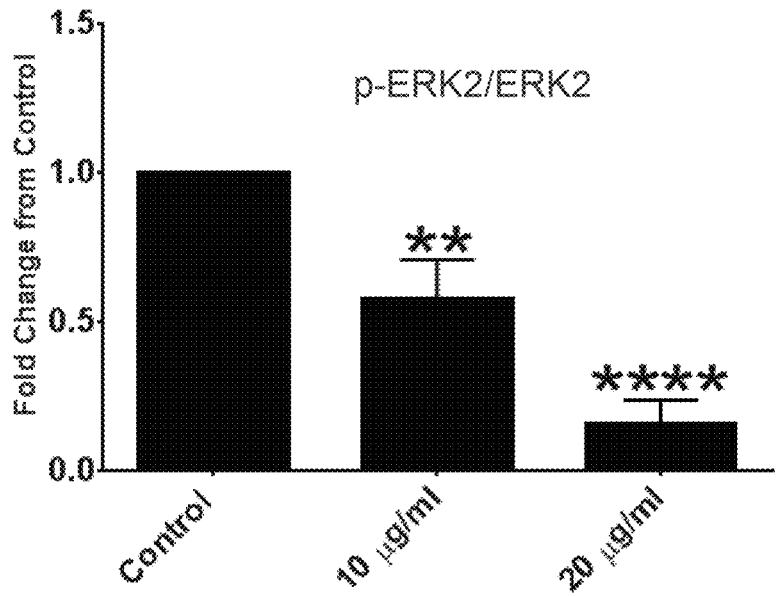
Figure 38C:
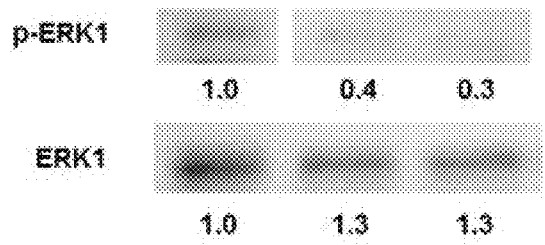
Figure 38D:
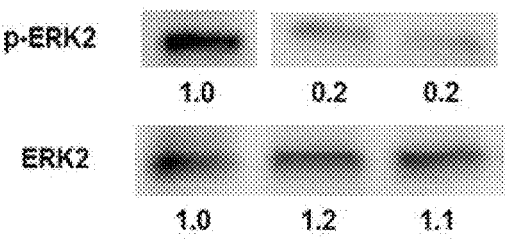

FIG. 38A-38D show an analysis of MAP kinase signaling in triple-negative breast cancer (TNBC) cells treated with a muscadine grape seed and muscadine grape skin powder extract (p-MGE) as described in Example 1 according to aspects of this disclosure. 4T1 cells were treated for 12 h with p-MGE, either 10 µg/mL or 20 µg/mL, and cell lysates were prepared for analysis by Western blot using an antibody for the phosphorylated and activated MAP kinases p-ERK1 and p-ERK2 and the MAP kinases ERK1 and ERK2. The amounts of phospho-ERK1 and ERK2 were normalized to the amount of unphosphorylated ERK1 and unphosphorylated ERK2 as shown in FIG. 38A and FIG. 38B, respectively, with representative blot images shown in FIG. 38C and FIG. 38D. n=6, * denotes p<0.05,  denotes p<0.01, * denotes p<0.001, and **** denotes p<0.0001. p-MGE significantly reduced both phosphorylated activated ERK1 and ERK2, MAP kinases that participate in the regulation of cells growth, suggesting that a reduction in ERK1/2 activities participates in the decrease in cell proliferation and breast tumor growth.

Figure 39:
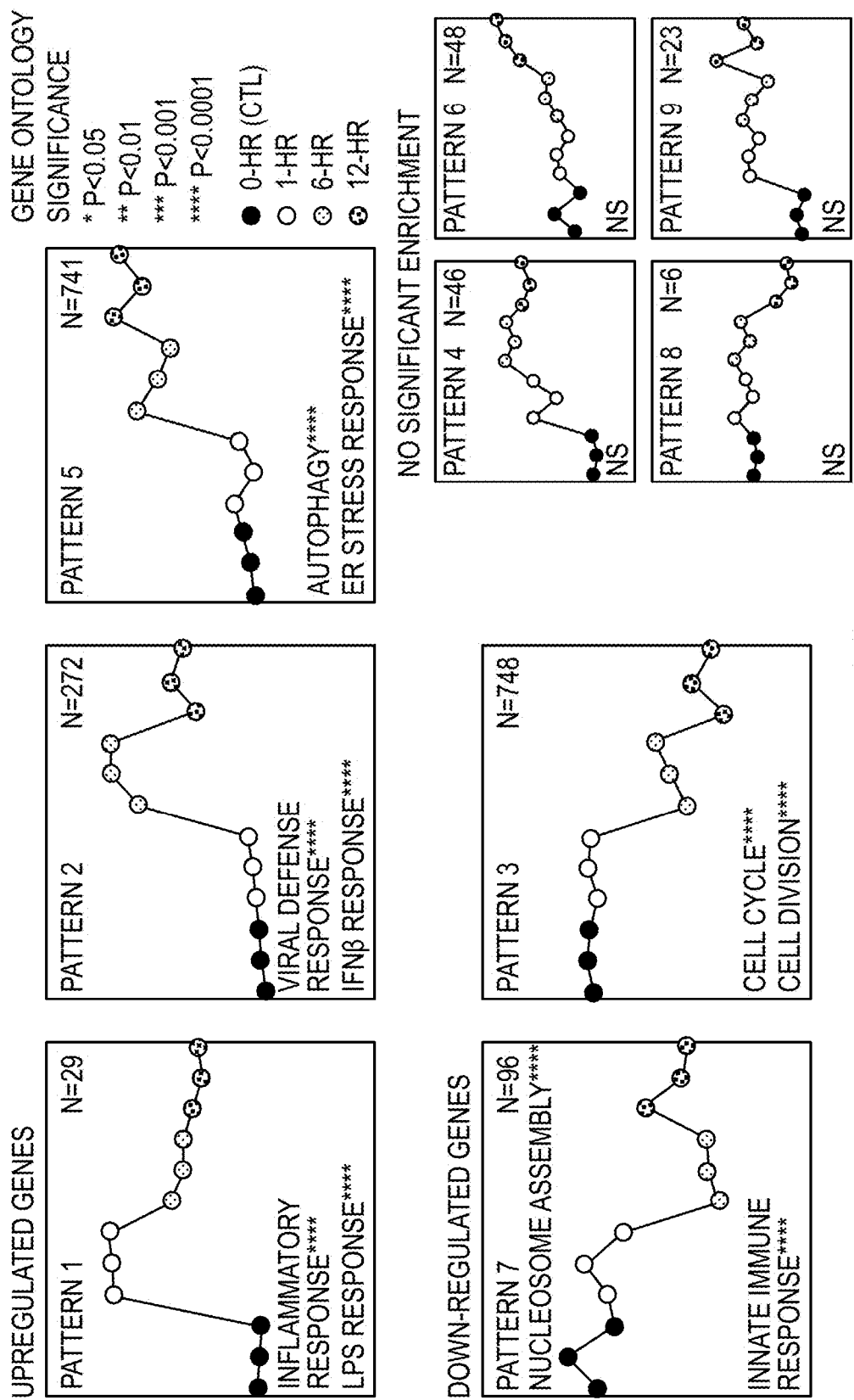

FIG. 39 shows the results of differential gene analysis in triple negative breast cancer cells treated with a muscadine grape seed and muscadine grape skin powder extract (p-MGE) as described in Example 1 according to aspects of this disclosure. 4T1 mouse triple negative breast cancer cells were incubated with 20 µg phenolics/mL of p-MGE for 0, 1, 6 or 12 h and total RNA was isolated using TRIzol. Differential gene expression was analyzed using RNAseq in the Wake Forest University Comprehensive Cancer Center Cancer Genomics Shared Resource. The data were analyzed using EPIG (which is a method for Extracting microarray gene expression Patterns and Identifying co-expressed Genes) Global Gene Pattern analysis, showing up-regulation, down-regulation or no significant change of 2009 genes across 9 distinct patterns. Families of genes that were up-regulated by p-MGE included 29 genes involved in the inflammatory or lipopolysaccharide (LPS) response, 272 genes involved in the viral defense or IFNβ response, and 741 genes involved in autophagy or the endoplasmic reticulum (ER) stress response. In contrast, 96 genes were down-regulated that are involved in nucleosome assembly or the innate immune response and 748 genes which were involved in the cell cycle or cell division. Four additional patterns of genes showed no significant enrichment.

Figure 40A:
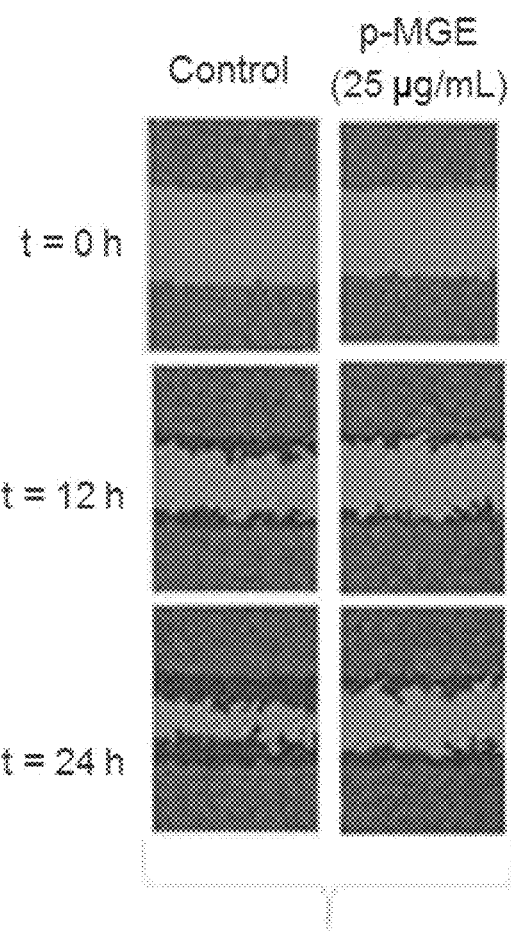
Figure 40B:
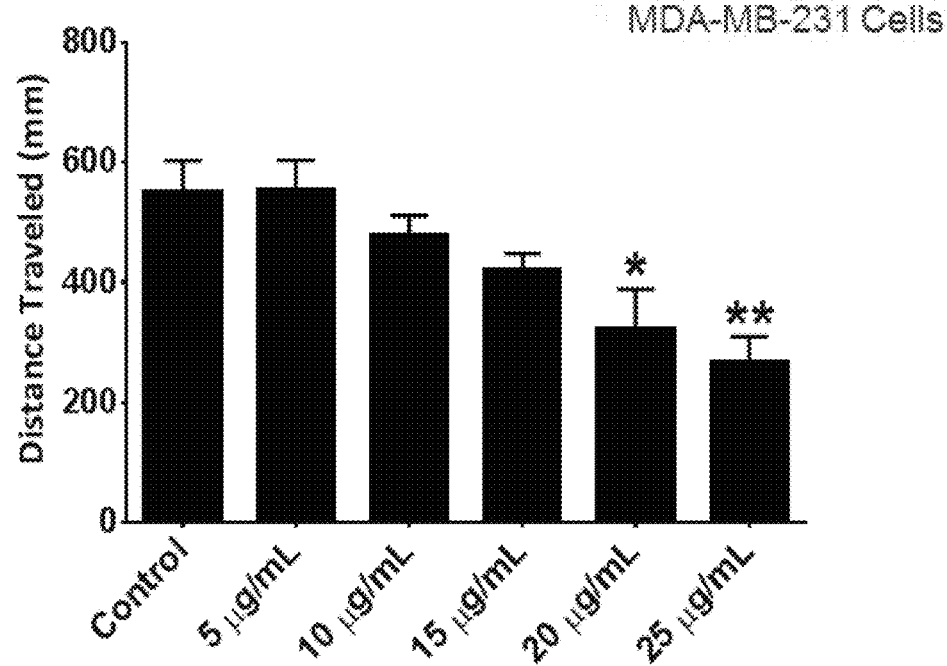

FIG. 40A-40B show the effect of a muscadine grape seed and muscadine grape skin powder extract (p-MGE) as described in Example 1 on migration of triple negative breast cancer cells according to aspects of this disclosure. MDA-MB-231 TNBC cells were grown to confluence in 96 well plates and an 800 micro area was denuded using the IncuCyte™ WoundMaker™. The cells were then treated with increasing concentrations of p-MGE (as indicated in figures). FIG. 40A shows representative images depicting the distance traveled to migrate into the denuded area during a 24 h treatment period during which the cells were treated with p-MGE at a concentration of 25 µg phenolics/mL. FIG. 40B shows the quantified distance that the cells migrated in 24 h at each concentration of p-MGE. n=3 in quadruplicate;  denotes p<0.05 and ** denotes p<0.01. p-MGE inhibited the migration of MDA-MB-231 TNBC cells, suggesting that p-MGE would reduce invasion as part of the process of migration leading to metastatic TNBC.

Figure 40C:
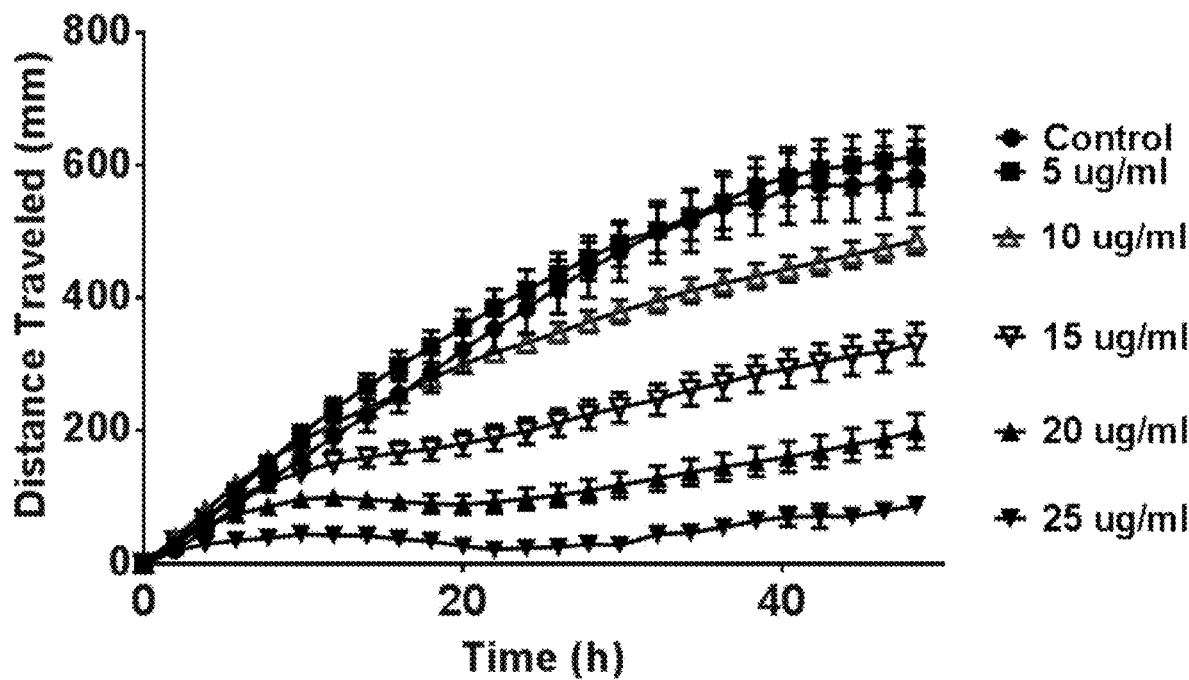
Figure 40D:
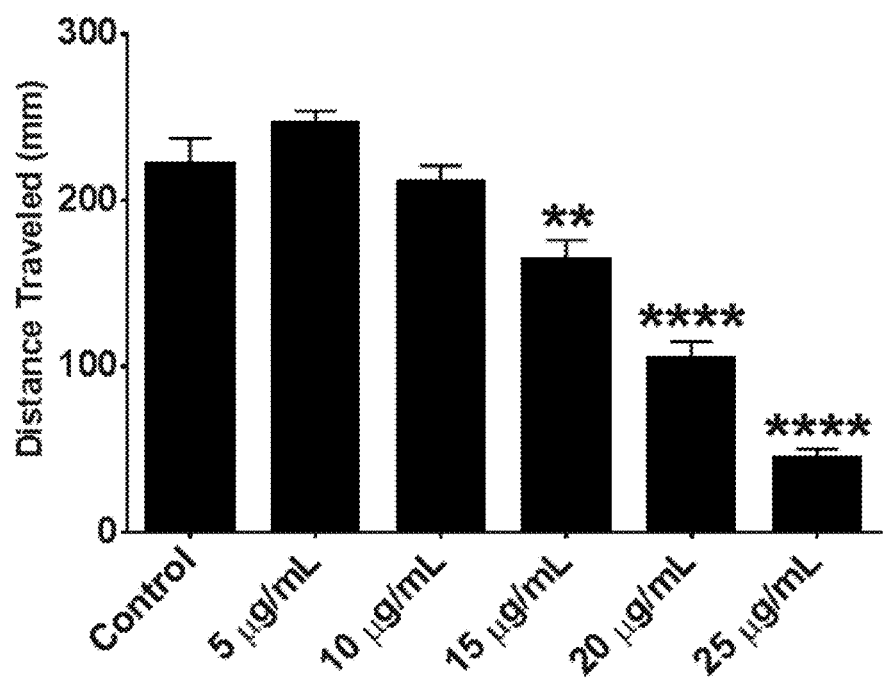

FIG. 40C-40D show the effect of a muscadine grape seed and muscadine grape skin powder extract (p-MGE) as described in Example 1 on migration of triple negative breast cancer cells according to aspects of this disclosure. 4T1 TNBC cells were grown to confluence in 96 well plates and an 800 µm area was denuded using the IncuCyte™ WoundMaker™. The cells were treated with increasing concentrations of p-MGE and the distance traveled to close the wound was calculated during a 48 h treatment period as shown in the graph of FIG. 40C. The distance that the cells migrated at 24 h was quantified as shown in the graph of FIG. 40D. n=3 in quadruplicate;  denotes p<0.005 and ** denotes p<0.0001. p-MGE inhibited the migration of 4T1 TNBC cells, suggesting that p-MGE would reduce migration of TNBC as part of the process of invasion and metastatic growth.

Figure 41A:
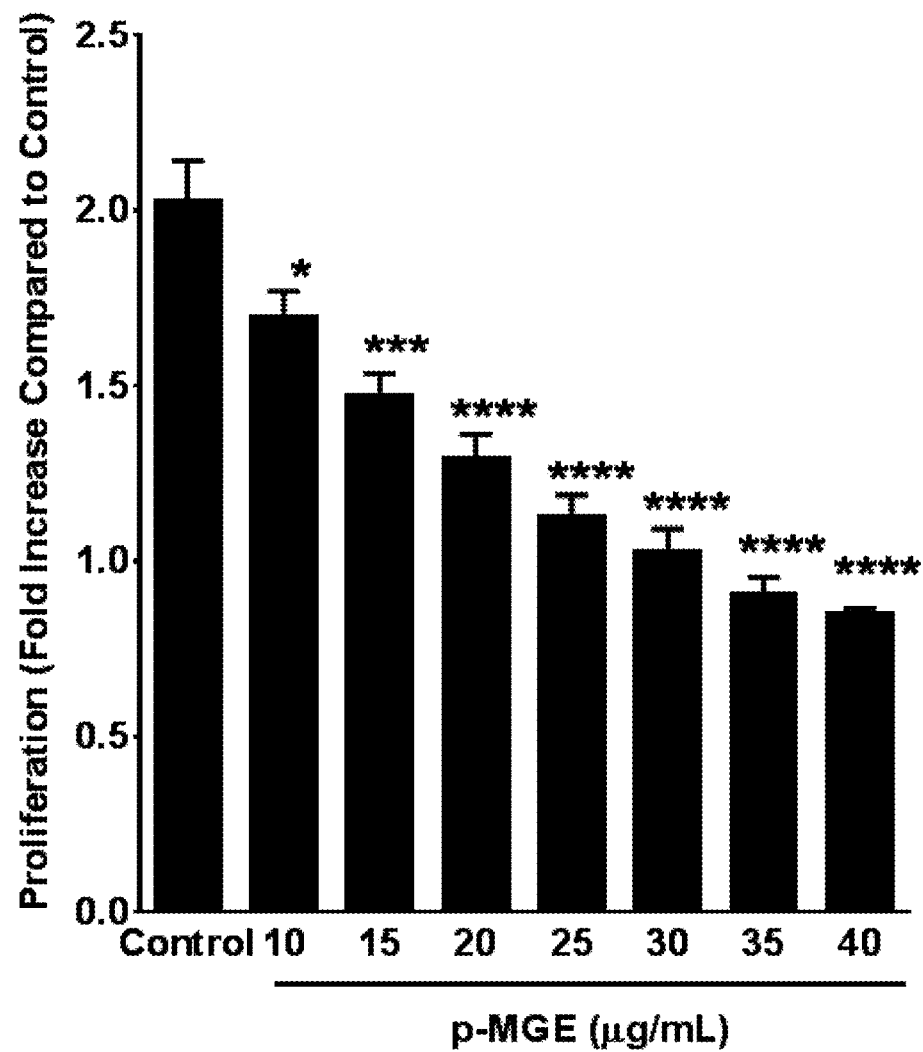

FIG. 41A shows the effect of a muscadine grape seed and muscadine grape skin powder extract (p-MGE) as described in Example 1 on proliferation of HER2 positive breast cancer cells according to aspects of this disclosure. SKBr3 human HER2 breast cancer cells were treated with increasing concentrations of p-MGE, calculated as µg phenolics/mL of culture media. Cell proliferation was measured at 48 h and quantified as the percent of the Control. n=3 in quadruplicate, * denotes p<0.05,  denotes p<0 01, * denotes p<0.001 and **** denotes p<0.0001. p-MGE significantly reduced the proliferation of human SKBr3 human HER2 over-expressing cells, suggesting that the extract may reduce the growth of HER2 over-expressing breast tumors.

Figure 41D:
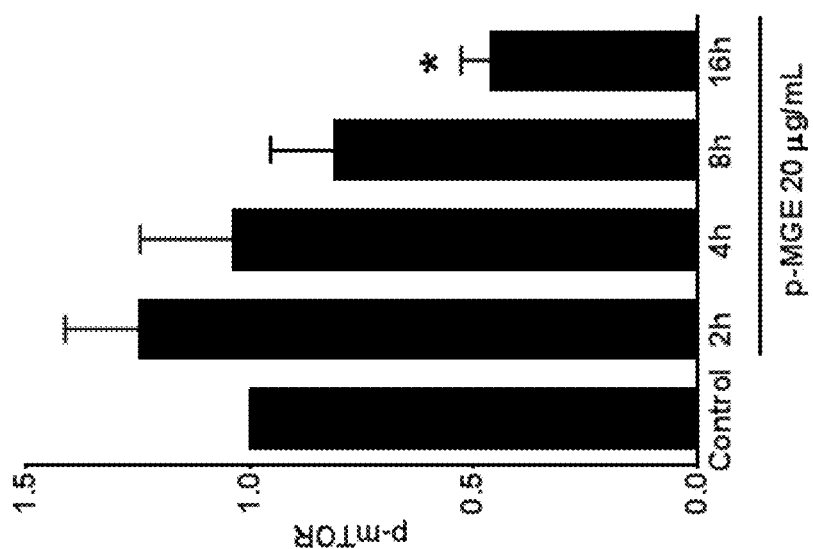
Figure 41C:
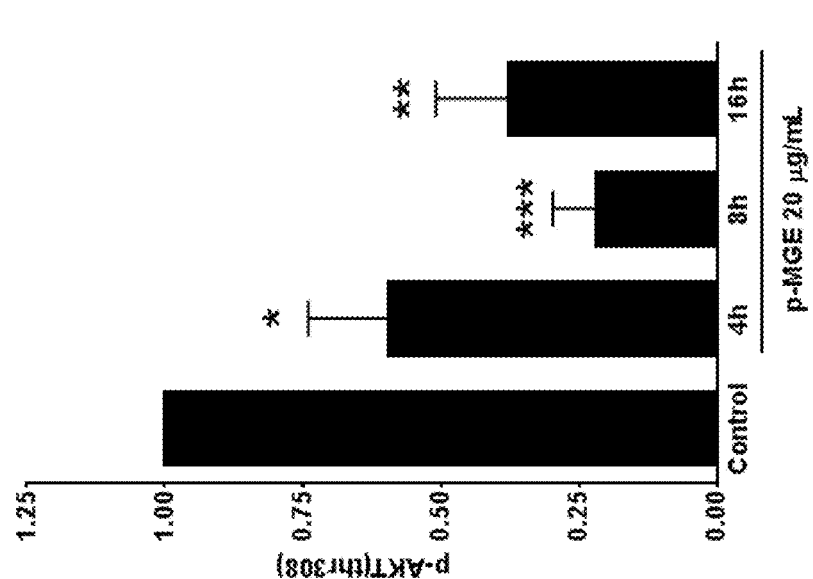
Figure 41B:
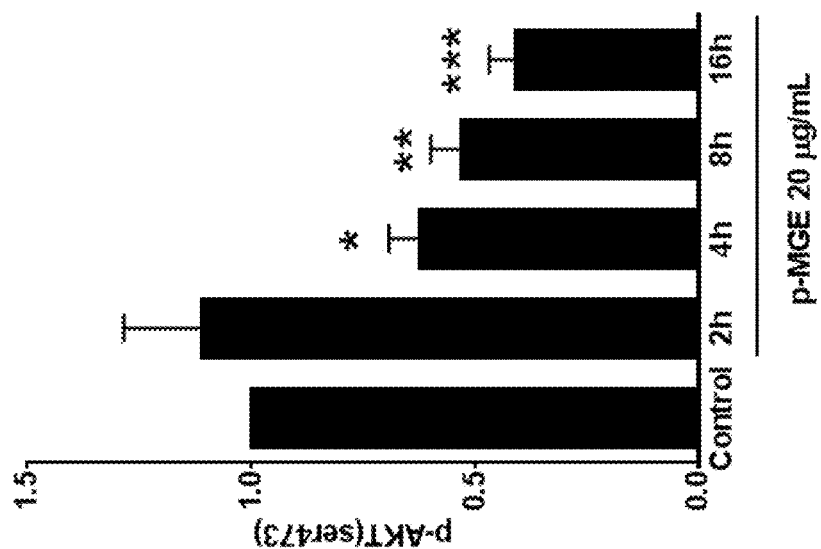

FIG. 41B-41D show the effect of a muscadine grape seed and muscadine grape skin powder extract (p-MGE) as described in Example 1 on the phosphorylation state of proteins in the AKT/mTOR signaling pathway according to aspects of this disclosure. SKBr3 human HER2 cells were treated for increasing periods of time with 20 µg/mL pMGE and cell lysates were prepared, for analysis by Western blot. Gels were analyzed using a GelDoc and immunoreactive bands were normalized for loading by analysis of the total amount of protein loaded/lane. A representative image is shown below the graph. n=5, * denotes p<0.05,  denotes p<0.01 and * denotes p<0.001. FIG. 41B shows AKT phosphorylation at serine 473, FIG. 41C shows AKT phosphorylation at threonine 308, and FIG. 41D shows phosphorylation at m-TOR (p-mTOR). p-MGE significantly reduced phosphorylation and activation of AKT and m-TOR, suggesting that the AKT pathway and activation of mTOR participates in the regulation of proliferation and survival in HER2 over-expressing breast cancer cells and tumors.

Figure 42A:
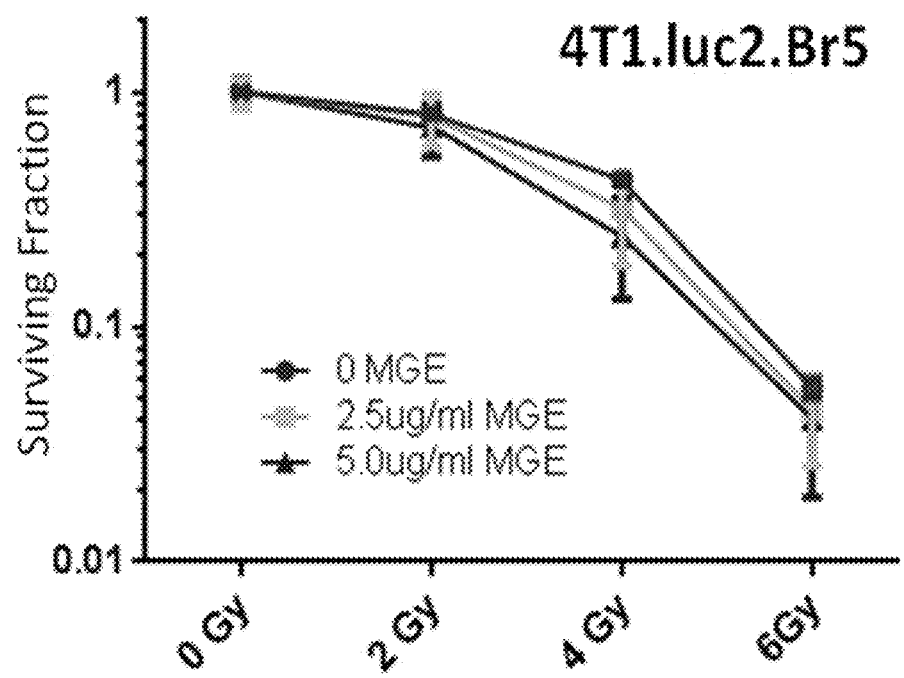
Figure 42B:
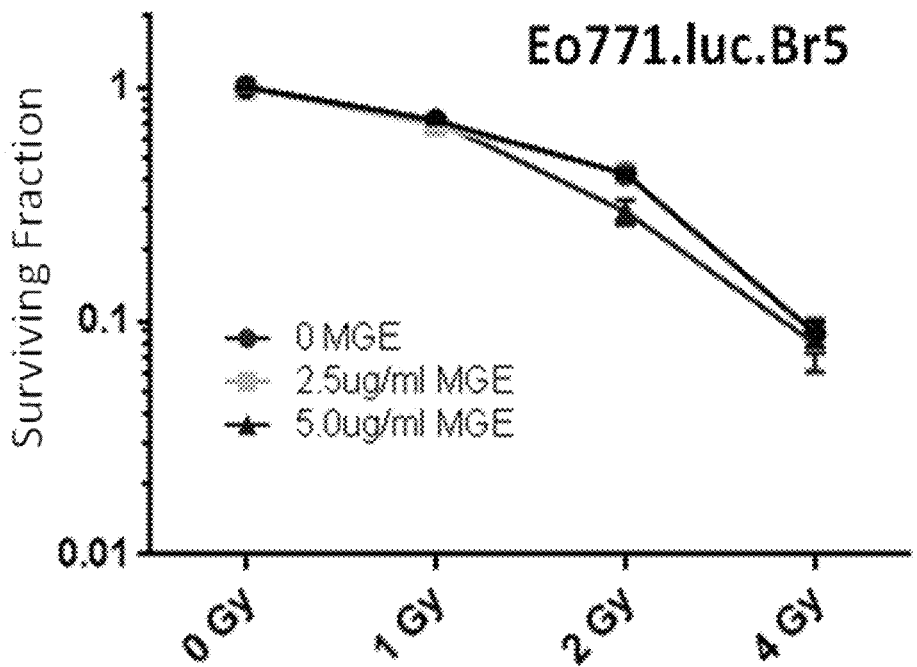
Figure 42C:
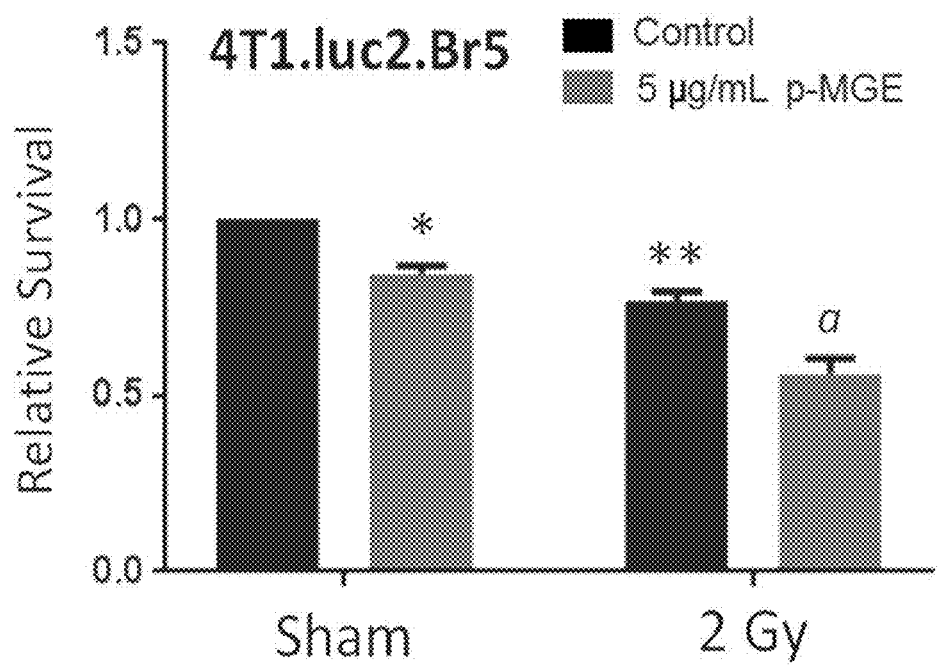
Figure 42D:
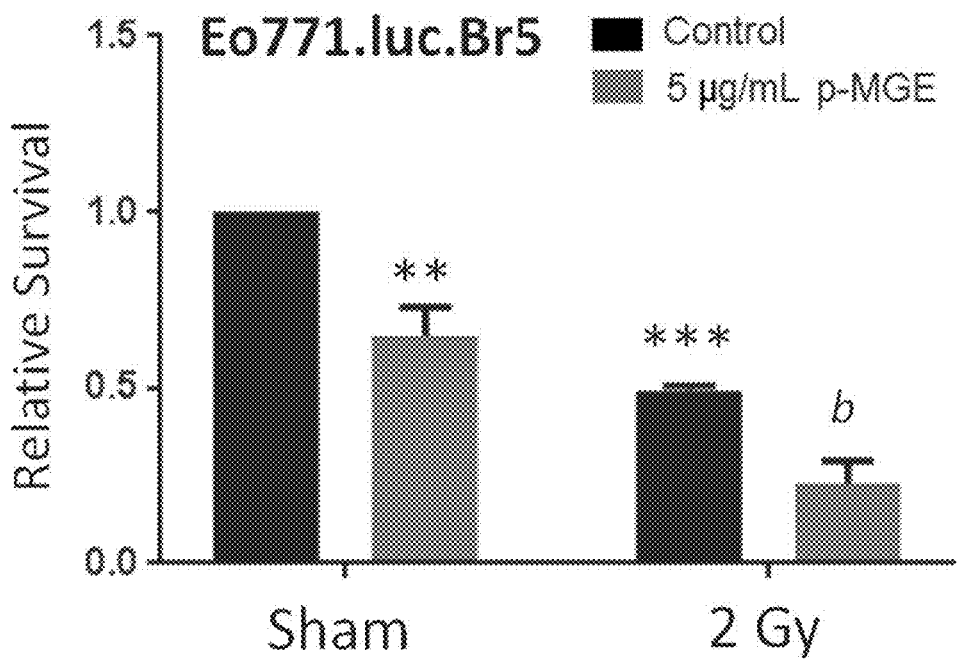

FIG. 42A-42D show the effect of radiation and/or a muscadine grape seed and muscadine grape skin powder extract (p-MGE) as described in Example 1 on colony growth for brain-specific metastatic breast cancer cells according to aspects of this disclosure. 4T1.luc2.Br5 or Eo771.luc.Br5 cells were plated at clonogenic density overnight, exposed to p-MGE (indicated as MGE in the figures) for 24 h, and irradiated (IR) as indicated. The colonies were stained and quantified as shown in FIG. 42A (4T1.luc2.Br5) and FIG. 42B (Eo771.luc.Br5). Surviving fraction=# colonies/number of cell plated * plating efficiency of sham-irradiated cells. Data represent the mean±SEM for 3-4 independent experiments, each performed in triplicate. FIG. 42C is data from FIG. 42A showing relative colony count for 4T1.luc2.Br5 cells; the combination of p-MGE and IR results in greater loss that either condition alone.  denotes p<0.01 vs. Control Sham; ** denotes p<0.001 vs. Control Sham; b, p<0.05 compared to 2 Gy Control, p<0.001 vs. p-MGE Sham. n=3 experiments performed in triplicate. FIG. 42D is data from FIG. 42B showing relative colony count with Eo771.luc.Br5 cells; the combination of p-MGE and IR results in greater loss that either condition alone. * denotes p<0.05 vs. Control Sham; ** denotes p<0.01 vs. Control Sham; a, p<0.01 compared to 2 Gy Control, p<0.001 vs. p-MGE Sham. n=4 experiments performed in triplicate. The combination of p-MGE with radiation that is typically used to treat patients with metastatic brain cancer resulted in a reduction in growth that was greater than with either p-MGE or radiation alone, suggesting that co-administration of p-MGE with radiation may be more effective in reducing tumor growth.

Figure 43:
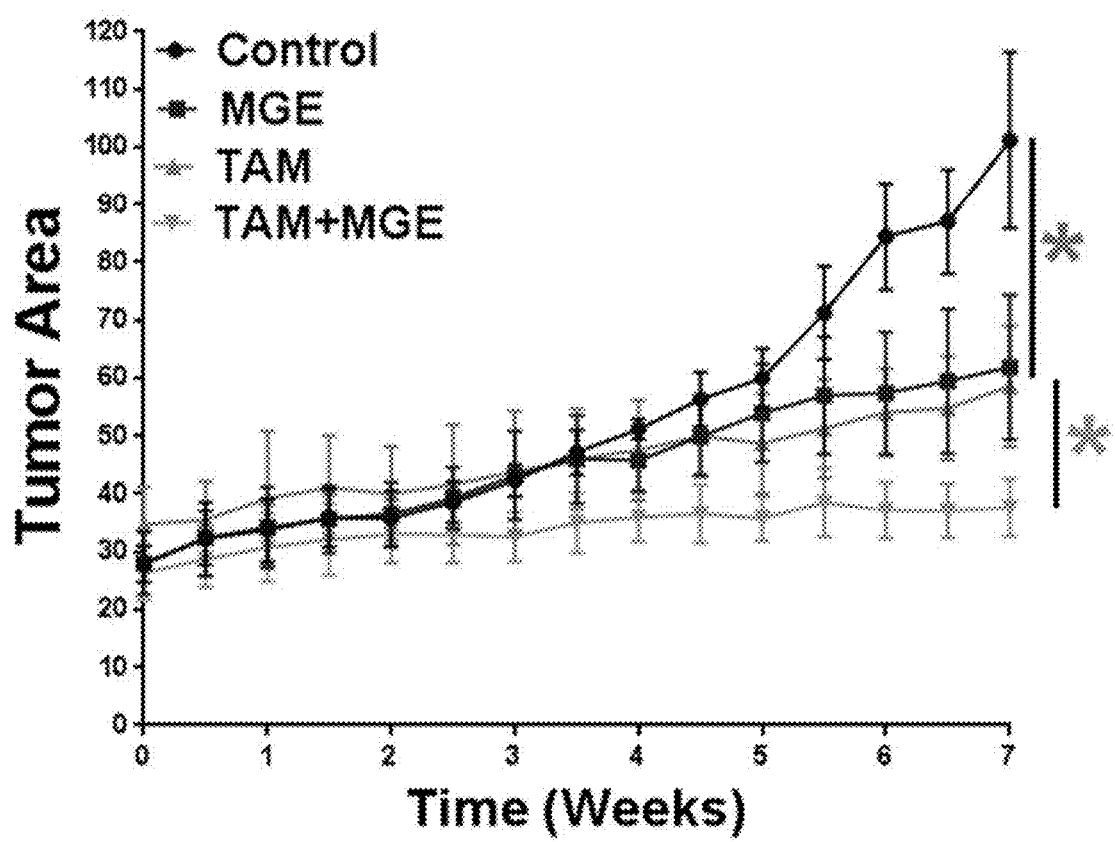

FIG. 43 shows the effect of tamoxifen and/or a muscadine grape seed and muscadine grape skin powder extract (p-MGE) as described in Example 1 on ER+ breast cancer tumor growth according to aspects of this disclosure. The mammary fat pads of athymic mice were injected with ZR-75-1 ER+ cells ($1\times10^6$ cells), and tumor growth was measured every third day using a caliper. When the tumors reached a size of 30 mm$^3$, the mice were treated for 7 weeks with water/regular chow (Control), 0.1 mg phenolics/mL p-MGE (labeled in the figure as MGE)/regular chow, an approximate dose of 32 mg/kg/d tamoxifen (TAM, administered in chow containing 400 ppm TAM citrate from Harlan-Teklad)/regular water or p-MGE and tamoxifen (TAM+MGE in the figure). Tumor size was calculated using the formula for a semi-ellipsoid. * denotes p<0.05; n=7-8. Treatment with p-MGE significantly reduced tumor volume over the 7 weeks of treatment, compared to mice drinking regular water. Treatment with tamoxifen alone also reduced tumor size. However, the combination of p-MGE and tamoxifen caused an additive effect in reducing tumor volume, which was significant compared to p-MGE or tamoxifen alone. These results suggest that p-MGE can be used in combination with tamoxifen to reduce ER+ tumor growth.

Figure 44:
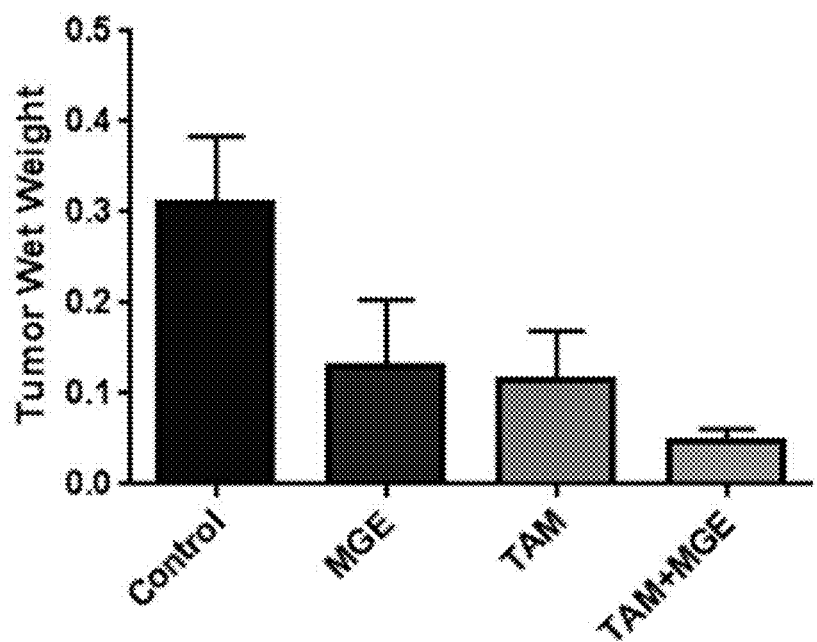

FIG. 44 shows the effect of tamoxifen and/or a muscadine grape seed and muscadine grape skin powder extract (p-MGE) as described in Example 1 on ER+ breast cancer tumor weight according to aspects of this disclosure. ZR-75-1 tumors treated with or without p-MGE and/or tamoxifen as described in FIG. 43 were removed after 7 weeks of treatment and weighed. n=7-8. Treatment with p-MGE significantly reduced tumor weight over the 7 weeks of treatment, compared to mice drinking regular water. Treatment with tamoxifen alone (TAM) also reduced tumor weight. However, the combination of p-MGE and tamoxifen (TAM+MGE) caused an additive effect in reducing tumor weight, which was significant compared to p-MGE or tamoxifen alone. These results suggest that p-MGE can be used in combination with tamoxifen to reduce ER+ tumor growth.

Figure 45A:
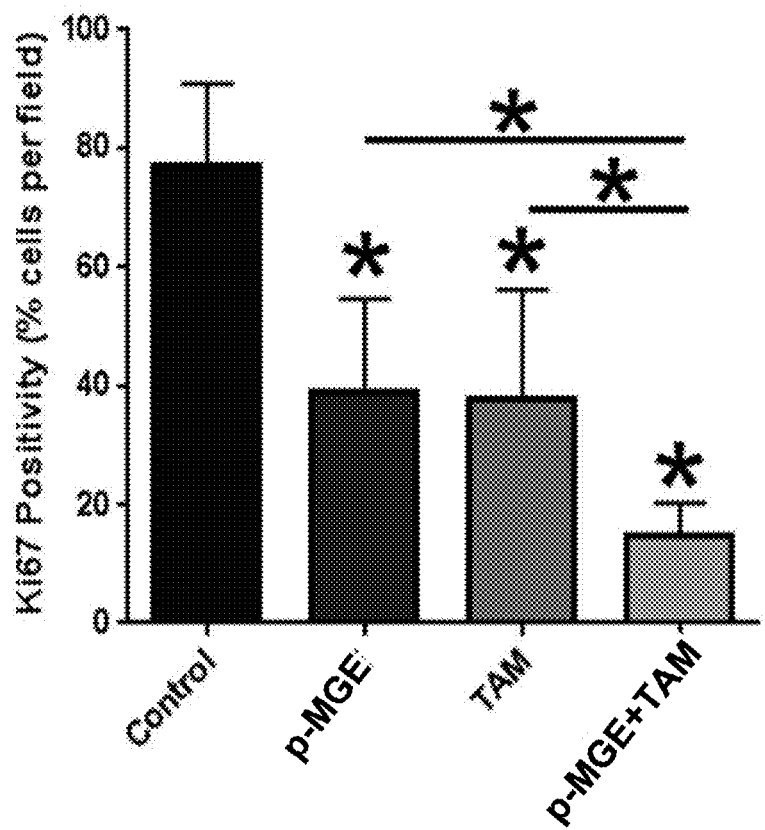
Figure 45B:
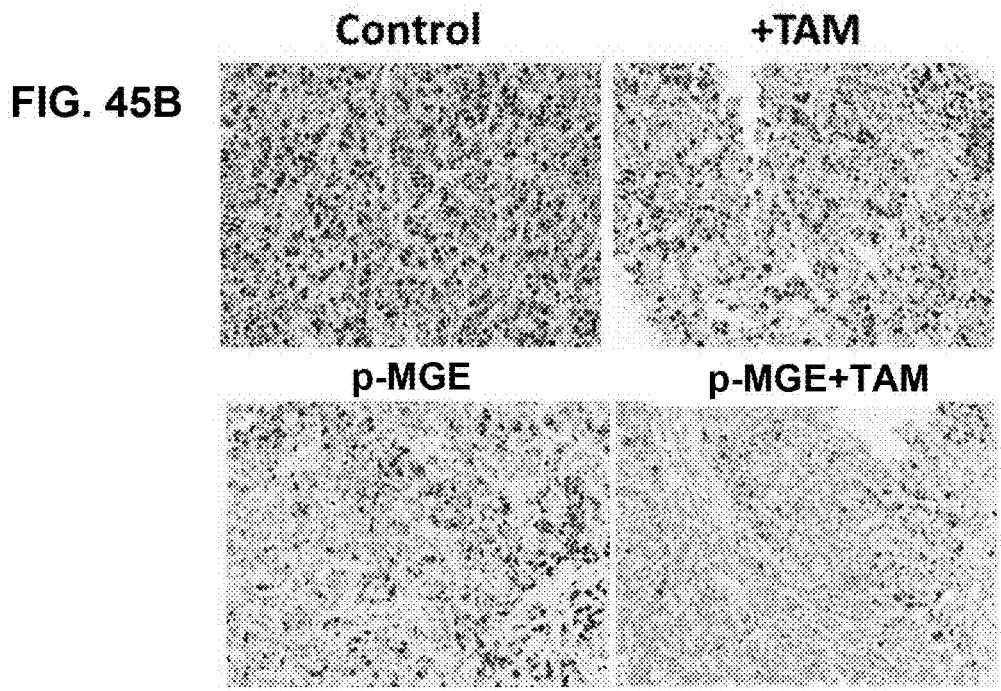

FIG. 45A-45B shows the effect of tamoxifen and/or a muscadine grape seed and muscadine grape skin powder extract (p-MGE) as described in Example 1 on ER+ breast cancer tumor cell proliferation according to aspects of this disclosure. ZR-75-1 tumors treated with or without tamoxifen and/or p-MGE (labeled as TAM and MGE in the figure) as described in FIG. 43 were removed after 7 weeks of treatment, fixed in formalin, embedded in paraffin and sectioned. Sections were incubated with an antibody to Ki67, a marker of proliferation. The number of Ki67 cells were counted per field and averaged, as shown in FIG. 45A. Representative pictures from each treatment group are shown in FIG. 45B. * denotes p<0.05; n=7-8. Treatment with p-MGE alone significantly reduced Ki67 immunoreactivity, suggesting that the extract inhibits the proliferation of ER+ breast tumors. The estrogen receptor antagonist Tamoxifen (TAM) also significantly reduced proliferation. Treatment with p-MGE and tamoxifen (MGE+TAM) reduced proliferation more significantly than treatment with p-MGE or tamoxifen alone. These results suggest that p-MGE can be used in combination with tamoxifen to reduce ER+ tumor growth.

Figure 46:
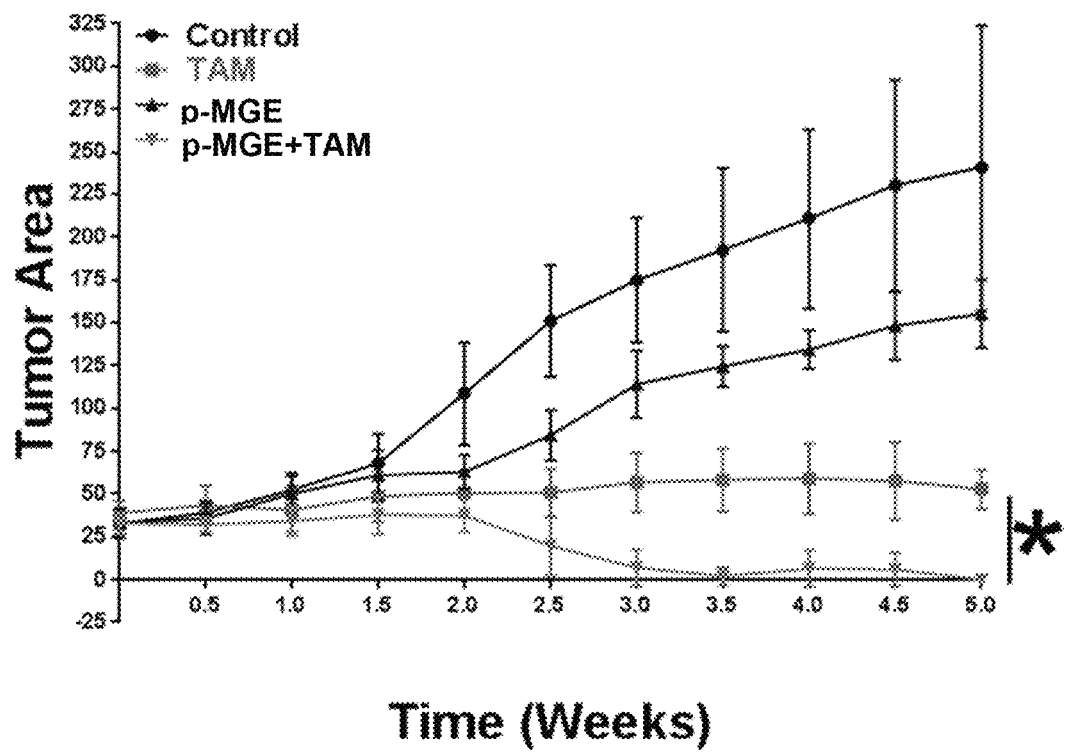

FIG. 46 shows the effect of tamoxifen and/or a muscadine grape seed and muscadine grape skin powder extract (p-MGE) as described in Example 1 on ER+ breast cancer tumor volume according to aspects of this disclosure. The mammary fat pads of athymic mice were injected with MCF7 human ER+ cells ($1\times10^6$ cells) and tumor growth was measured every third day using a caliper. When the tumors reached a size of 30 mm$^3$, the mice were treated for 5 weeks with water/regular chow (Control), 0.1 mg phenolics/mL p-MGE (labeled as MGE in the figure)/regular chow, approximate dose of 32 mg/kg/d tamoxifen (TAM, administered in chow containing 400 ppm TAM citrate from Harlan-Teklad) (TAM, administered in their chow)/regular water or p-MGE and tamoxifen (MGE+TAM). Tumor size was calculated using the formula for a semi-ellipsoid. * denotes $p<0.05$, n=7-8. Treatment with p-MGE reduced MCF7 tumor volume over the 5 weeks of treatment compared to mice drinking regular water. Treatment with tamoxifen alone also reduced tumor size. However, the combination of p-MGE and tamoxifen caused an additive effect in reducing tumor volume, which was significant compared to p-MGE or tamoxifen alone. These results suggest that p-MGE can be used in combination with tamoxifen to reduce ER+ tumor growth.

Figure 47:
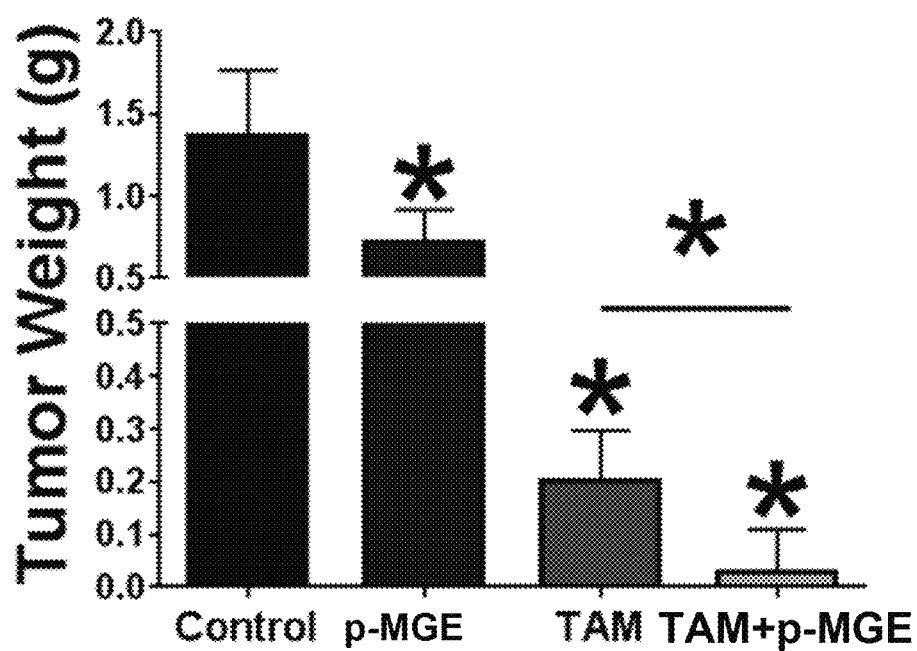

FIG. 47 shows the effect of tamoxifen and/or a muscadine grape seed and muscadine grape skin powder extract (p-MGE) as described in Example 1 on ER+ breast cancer tumor weight according to aspects of this disclosure. MCF7 human ER+ breast tumors treated as described in FIG. 46 were removed after 5 weeks of treatment and weighed. * denotes $p<0.05$, n=7-8. Treatment with p-MGE significantly reduced tumor weight over the 5 weeks of treatment, compared to mice drinking regular water. Treatment with tamoxifen alone also reduced tumor weight. However, the combination of p-MGE and tamoxifen caused an additive effect in reducing tumor weight, which was significant compared to p-MGE or tamoxifen alone. These results suggest that p-MGE can be used in combination with tamoxifen to reduce ER+ tumor growth.

Figures 48, 49:
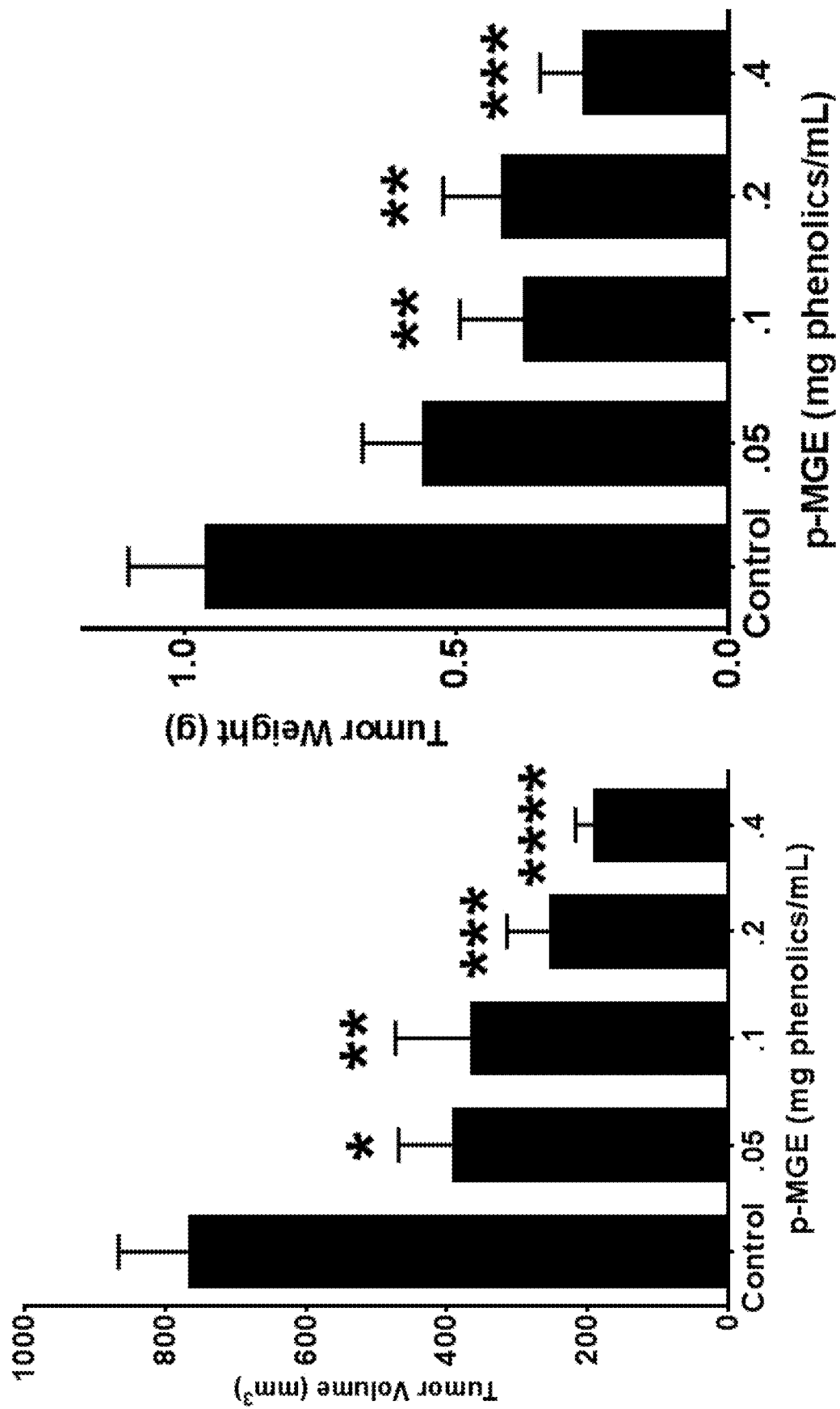

FIG. 48 shows the effect a muscadine grape seed and muscadine grape skin powder extract (p-MGE) as described in Example 1 on prostate tumor size according to aspects of this disclosure. Athymic mice were injected with LNCaP human prostate cancer cells and treated with increasing concentrations of p-MGE, administered in their drinking water, for 5 weeks. Tumor volume at the end of the 5-week treatment period was measured in conscious mice and tumor size was calculated using the formula for a semi-ellipsoid. n=5-6; * denotes $p<0.05$,  denotes $p<0.01$, * denotes $p<0.001$ and **** denotes $p<0.0001$. Treatment with increasing concentrations of p-MGE caused a dose-dependent reduction in the size of human prostate tumors in athymic mice.

FIG. 49 shows the effect a muscadine grape seed and muscadine grape skin powder extract (p-MGE) as described in Example 1 on prostate tumor growth according to aspects of this disclosure. LNCaP prostate tumors from athymic mice either untreated (Control) or treated with increasing concentrations of p-MGE were removed after 5 weeks of treatment and weighed. n=5-6,  denotes $p<0.01$ and * denotes $p<0.001$. Treatment with increasing concentrations of p-MGE caused a dose-dependent reduction in the weight of human prostate tumors in athymic mice compared to untreated mice, suggesting that administration of p-MGE will reduce prostate tumor growth.

Figure 50:
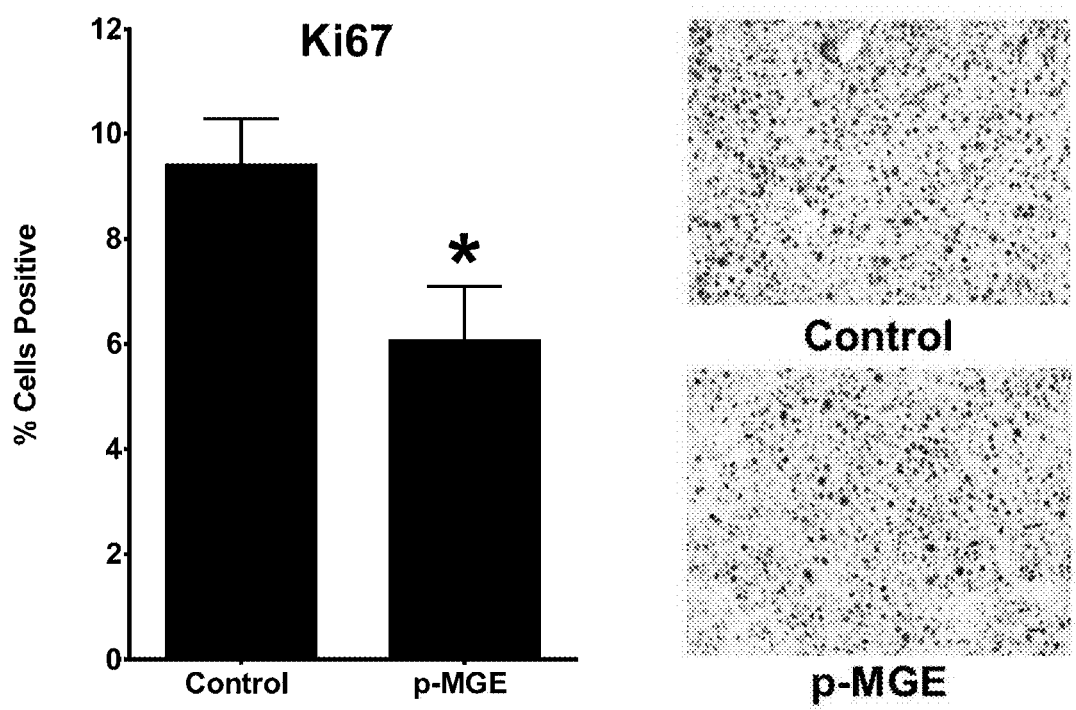

FIG. 50 shows the effect a muscadine grape seed and muscadine grape skin powder extract (p-MGE) as described in Example 1 on prostate tumor cell proliferation according to aspects of this disclosure. LNCaP prostate tumors from athymic mice either untreated (Control) or treated with 0.1 mg phenolics/mL of p-MGE (p-MGE) were fixed in paraformaldehyde, embedded in paraffin, cut into sections and stained with an antibody to Ki67. The number of Ki67 positive cells/field were counted, as shown in the graph to the left. Representative sections are shown on the right. n=6, * denotes $p<0.05$. Treatment with p-MGE reduced the percent of cells stained with Ki67, a marker of proliferation, suggesting that the extract reduced the proliferation of prostate tumor cells.

Figure 51:
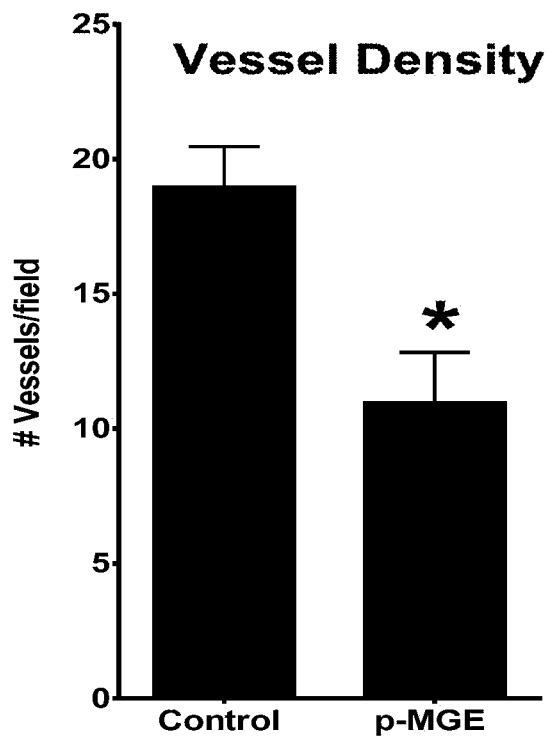

FIG. 51 shows the effect a muscadine grape seed and muscadine grape skin powder extract (p-MGE) as described in Example 1 on angiogenesis as reflected by blood vessel number in prostate tumors according to aspects of this disclosure. LNCaP prostate tumors from athymic mice either untreated (Control) or treated with 0.1 mg phenolics/mL of p-MGE (p-MGE) were fixed in paraformaldehyde, embedded in paraffin, cut into 0.5 mm sections and stained with an antibody to CD34, which stains endothelial cells. The number of blood vessels/field were identified by both positive immunoreactivity and morphology. n=6, * denotes $p<0.05$. Treatment with p-MGE reduced the number of blood vessels per field, suggesting that the extract inhibited angiogenesis in prostate tumors.

FIG. 52 shows the effect a muscadine grape seed and muscadine grape skin powder extract (p-MGE) as described in Example 1 on expression of VEGF and PLGF, growth factors that regulate angiogenesis, in prostate tumors according to aspects of this disclosure. RNA was isolated from LNCaP prostate tumors from athymic mice either untreated (Control) or treated with 0.1 mg phenolics/mL of p-MGE (p-MGE) using TRIzol reagent, according to the manufacturer's direction. Vascular endothelial growth factor (VEGF) and placental growth factor (PLGF) were quantified using VEGF- or PLGF-specific primer/probe set (Applied Biosystems) and 18S rRNA served as an internal control. The results were quantified as $C_t$ values, where $C_t$ was defined as the threshold cycle of PCR at which the amplified product is first detected and defined as relative gene expression (the ratio of target/control). n=6, * denotes $p<0.05$. Treatment with p-MGE reduced the relative expression of both VEGF and PLGF, which is in agreement with a reduction in the number of blood vessels as shown in FIG. 51, providing further evidence that the extract prohibited angiogenesis in prostate tumors.

FIG. 53 shows the effect a muscadine grape seed and muscadine grape skin powder extract (p-MGE) as described in Example 1 on myofibril formation and immune cell infiltration in response to radiation treatment according to aspects of this disclosure. Healthy mice received either no treatment or were treated with radiation (IR), p-MGE, or radiation and p-MGE together (IR+p-MGE) for 6 weeks. The tibialis anterior muscles were isolated and stained with H&E to visualize the morphology of the muscle tissue. Muscles that received radiation treatment showed a significant amount of regenerating myofibers (white arrow) and infiltration of immune cells (black arrow). Treatment of the hindlimb of mice with radiation resulted in regenerating myofibrils and movement of immune cells into the muscle, which was reduced by co-administration of the p-MGE.

Figure 54:
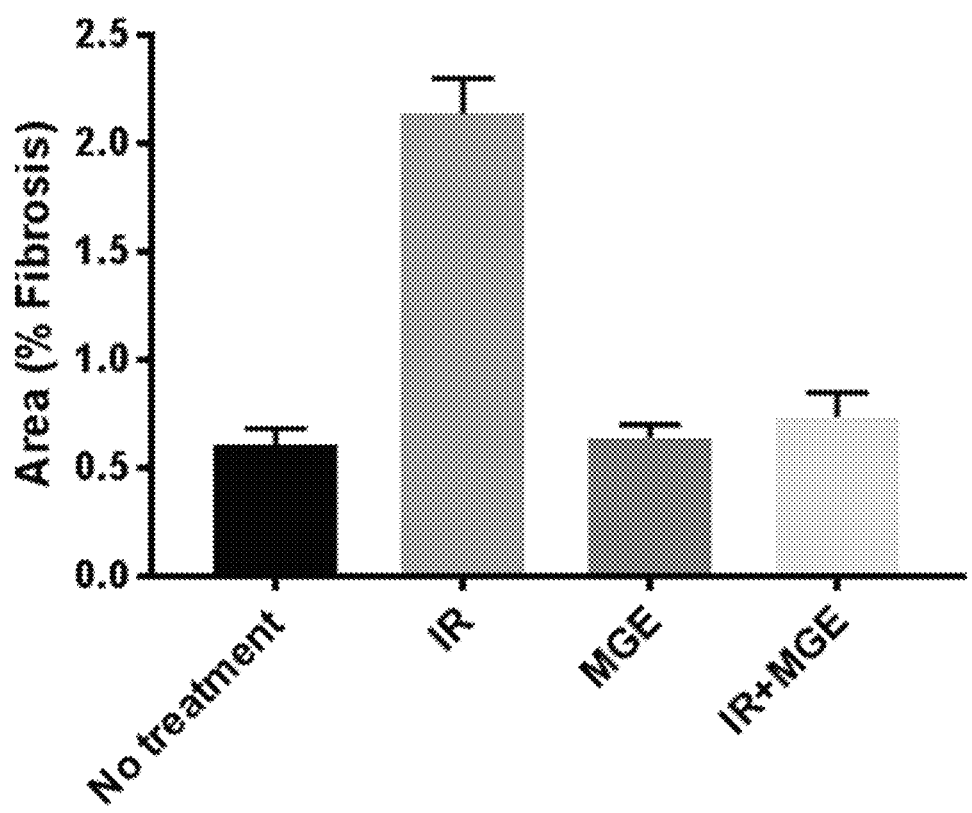

FIG. 54 shows the effect a muscadine grape seed and muscadine grape skin powder extract (p-MGE) as described in Example 1 on radiation-induced fibrosis according to aspects of this disclosure. Healthy mice received either no treatment or were treated with radiation (IR), p-MGE, or radiation and p-MGE (IR+p-MGE) for 6 weeks. The tibialis anterior muscles were isolated and stained with Masson's Trichrome stain to identify areas of tissue fibrosis. The percent of fibrosis in the tissue was quantified using ImageJ software. Treatment with radiation significantly increased the area of fibrosis which was reduced by administration of p-MGE while treatment with the extract alone had no effect, demonstrating that p-MGE treatment significantly reduced radiation-induced fibrosis.

Figure 55A:
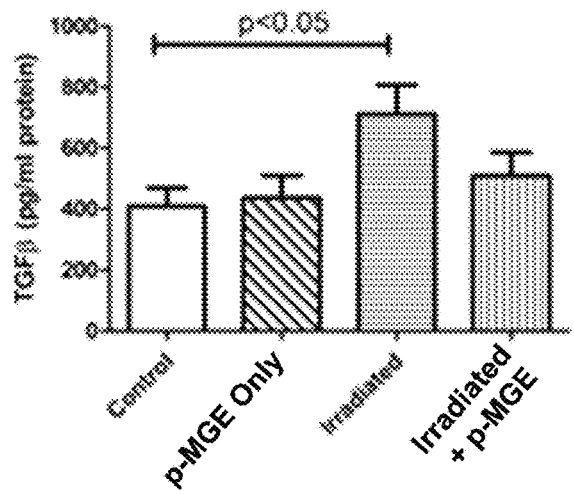
Figure 55B:
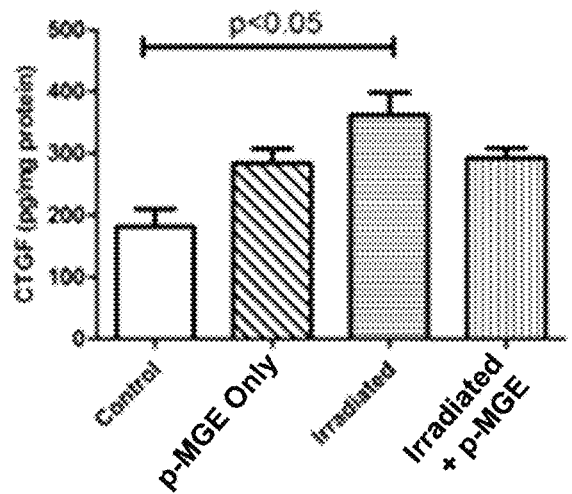
Figure 55C:
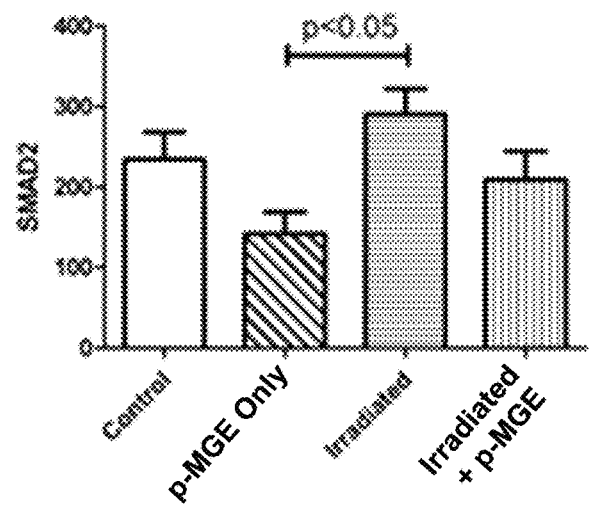

FIG. 55A-55C shows assessment of the TGBβ, CTGF, and SMAD2 protein levels in muscle tissue in response to irradiation in mice treated with a muscadine grape seed and muscadine grape skin powder extract (p-MGE) as described in Example 1 according to aspects of this disclosure. Healthy mice were irradiated with four total fractions of 7.3 Gy/fraction provided twice weekly for two weeks (to model radiation cancer treatment in humans) and administered water (Control, no radiation treatment), p-MGE in their drinking water (p-MGE only), radiation alone (Irradiated), or radiation and p-MGE (Irradiated+p-MGE). The concentration of TGFβ, CTGF or SMAD2 in muscle tissue was measured by ELISA and compared to Control or p-MGE alone. Irradiation increased the muscle concentration of TGFβ, CTGF and SMAD2. Administration of p-MGE alone had no significant effect on any of the three factors. However, administration of p-MGE before, during and after irradiation returned the tissue levels of TFGβ and CTGF to levels that were not different than Control and SMAD2 to a level that was not different than p-MGE alone. These results suggest that radiation treatment activates the TGBβ/CTGF/SMAD pathway to increased tissue fibrosis and that p-MGE reduces fibrosis by attenuating this pathway.

Figures 56, 57:
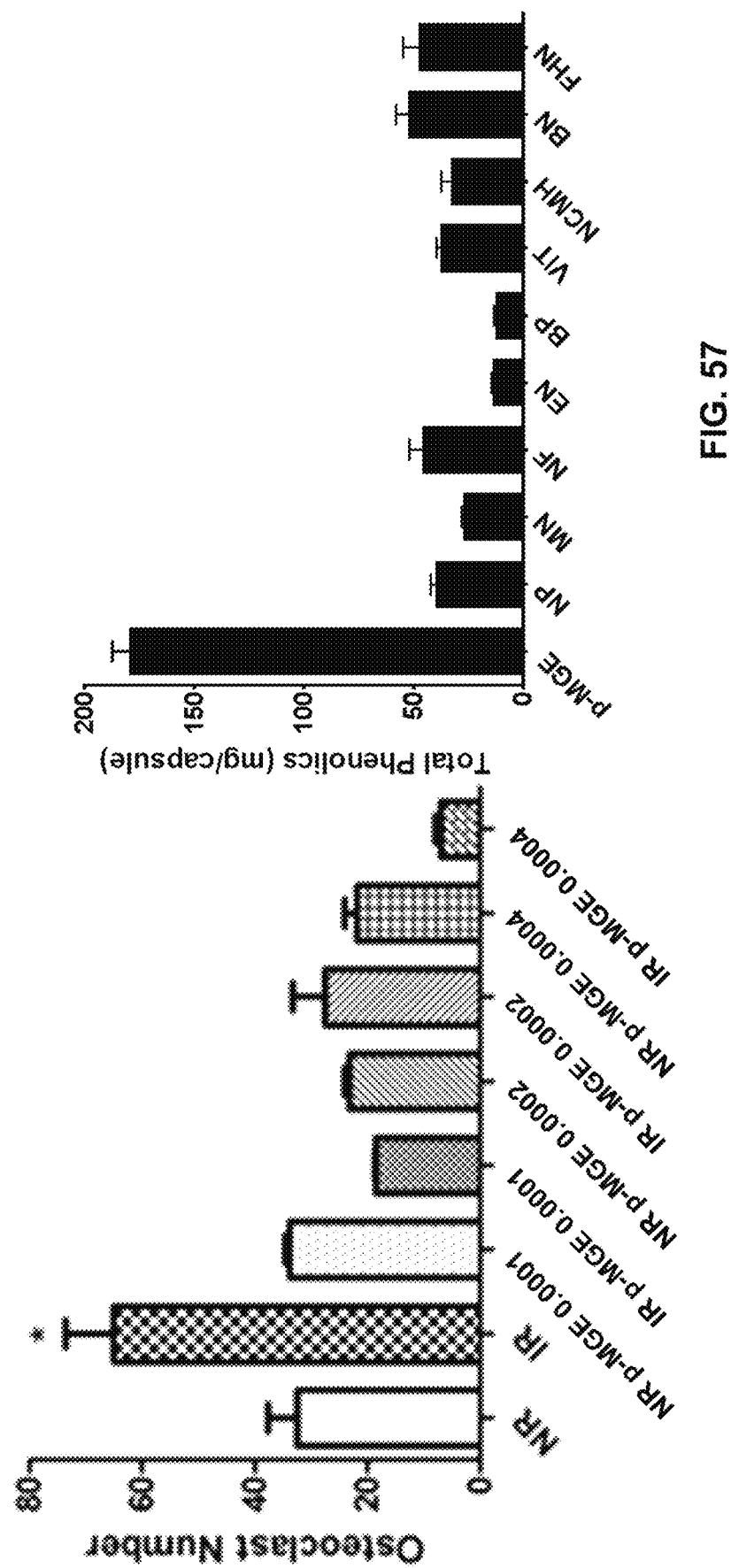

FIG. 56 shows the effect of treatment with a muscadine grape seed and muscadine grape skin powder extract (p-MGE) as described in Example 1 on osteoclast induction in response to irradiation according to aspects of this disclosure. RAW264.7 preosteoclasts were treated with 0.0001, 0.0002, and 0.0004 µg/mL of p-MGE for 24 hours prior to 2 Gy irradiation and the numbers of osteoclasts were counted on Day 7. NR, no radiation; IR, radiation with 2 Gy; NR MGE 0.0001, 0002 or 0.0004, no radiation and treatment with increasing concentrations of p-MGE; and IR MGE 0.0001, 0.0002 or 0.0004, radiation with 2 Gy and treatment with increasing concentrations of p-MGE. n=2, in replicate; * denotes p<0.05 compared to Control alone. Treatment with 2 Gy alone increased the conversion of preosteoclasts to osteoclasts. The radiation-induced increase in osteoclast number was prevented by 24 hour pretreatment with 0.0001, 0.0002, and 0.0004 µg/mL p-MGE, suggesting that the extract protects the bone from the increase in active osteoclasts.

FIG. 57 shows an analysis of phenolic content in various commercial muscadine grape products in comparison to the muscadine grape seed and muscadine grape skin powder extract (p-MGE) as described in Example 1 according to aspects of this disclosure. The phenolic content of capsules from 9 different commercially available products made from muscadine grapes was assessed resuspended in water and homogenized using a TissueLyzer™ (Qiagen) prior to the measurement of total phenolics using a modification of the colorimetric Folin-Ciocalteau method and gallic acid as a standard. The amount of phenolics was quantified per capsule. Information on each product and the abbreviations used for this figure is provided in Table 3. The phenolic content of the capsules containing the p-MGE was highest compared to the 9 commercially available muscadine grape products tested.

Figure 58:
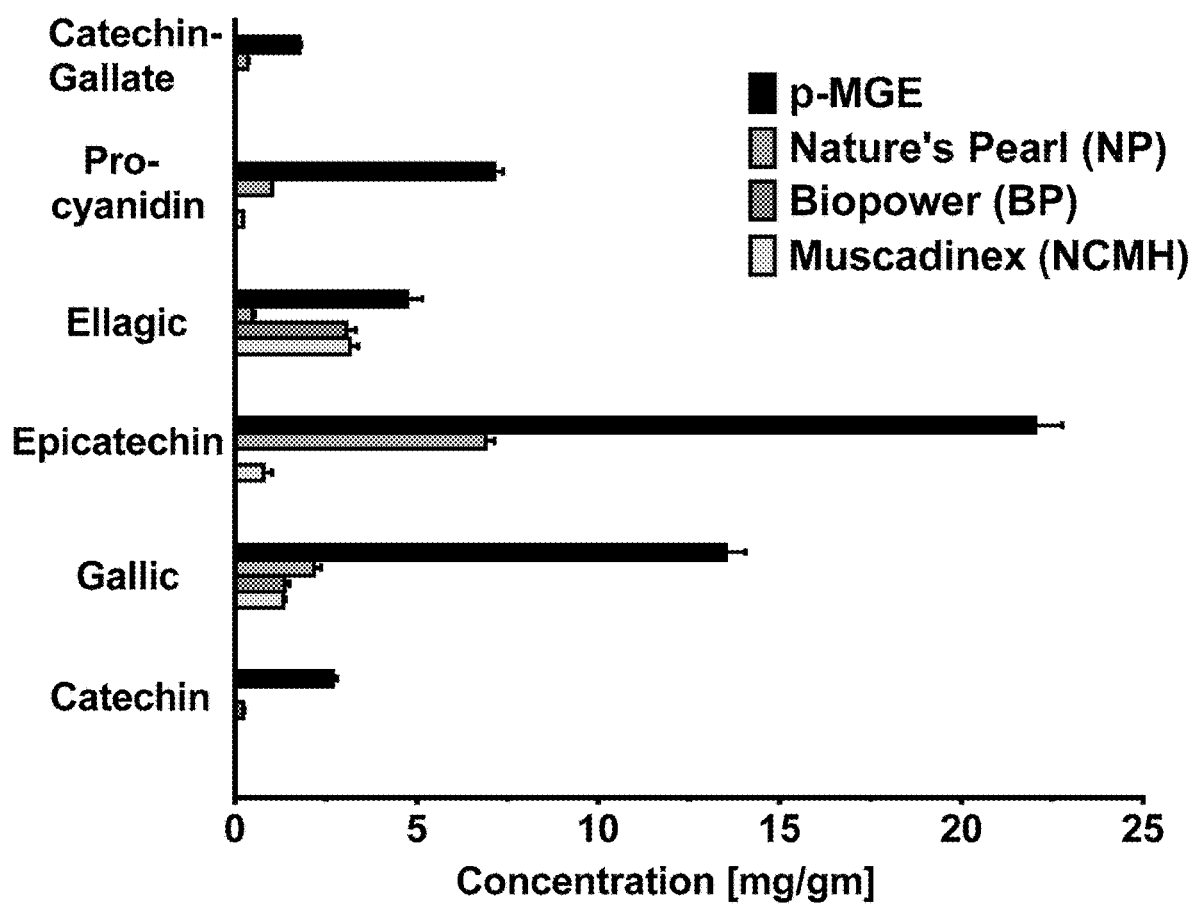

FIG. 58 shows an analysis of phenolic compounds in various muscadine grape products in comparison to the muscadine grape seed and muscadine grape skin powder extract (p-MGE) as described in Example 1 according to aspects of this disclosure. p-MGE and three of the muscadine grape products assessed in FIG. 57 were further analyzed for individual polyphenolics. Samples were extracted in 70% methanol/1% formic acid and homogenized in a Qiagen TissueLyser™; insoluble material was removed by centrifugation at 100,000×g for 60 min. The extracts were spiked with isotopically-labeled catechin as an internal standard and applied directly for UHPLC-MS analysis using gradient conditions that resolve 17 phenolic standards with a limit of detection of 200 pg/µL. The identification of the primary components—epitcatechin, gallic acid, procyanidin, catechin and catechin-gallate—was determined and quantified by comparison to standards. p-MGE contained the highest content of catechin-gallate, pro-cyanidin, ellagic acid, epicatechin, gallic acid and catechin compared to the product from Nature's Pearl, Biopower, or Muscadinex.

FIG. 59 shows the results of a chromatographic, mass spectrometry analysis of the muscadine grape seed and muscadine grape skin liquid extract (l-MGE) and the muscadine grape seed and muscadine grape skin powder extract (p-MGE) described in Example 1 according to aspects of this disclosure. The extracts were assessed by UHPLC-MS analysis using gradient conditions that resolve 17 phenolic standards with a limit of detection of 200 pg/µL. The resolution of the analysis of products between approximately 500 and 2000 molecular weight was enhanced. Certain distinguishing peaks illustrating the different phenolic composition of the extracts are indicated by clotted-line boxes.

DETAILED DESCRIPTION

Described herein are extracts made from grapes and formulations thereof. The extracts of the disclosure include liquid extracts and powder extracts made therefrom. Various methods for producing different extracts and method of treatment relating to cancer are also provided. Compared to existing grape extracts, the extracts of the disclosure have increased phenolic content. In particular, the methods of manufacturing described herein include steps to preserve the phenolic compound content of the extracts (both powder and liquid) and minimize insoluble content.

The aspects and features of the disclosure will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in this disclosure is for the purpose of describing particular embodiments and features only and is not intended to be limiting.

Unless the context indicates otherwise, it is specifically intended that the various features and aspects described herein can be used in any combination. Moreover, this disclosure also contemplates that in some embodiments, any feature or combination of features set forth herein can be excluded or omitted. To illustrate, where a composition is stated to comprise components A, B and C, it is specifically intended that any of A, B or C, or a combination thereof, can be omitted and disclaimed singularly or in any combination.

As used in the disclosure and the appended claims, the singular forms "a," "an," and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, refers to a variation of 0.1%, 0.25%, 0.5%, 0.75%, 1%, 2%, 3%, 4%, 5%, 6,%, 7%, 8%, 9%, 10%, 15% or even 20% of the specified amount. For example, if an amount is described as comprising "about 50% X," it is to be understood that, in some embodiments, the composition comprises 50% X, while in other embodiments it may comprise anywhere from, for example, 40% to 60% X (i.e., 50±10%).

As used herein, the term "and/or" refers to and encompasses any and all possible combinations of one or more of the associated listed items, as well as the lack of combinations when interpreted in the alternative ("or").

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

The term "pharmaceutically effective amount" is used interchangeably with "therapeutically effective amount" in this disclosure and refers to an amount of a pharmacological agent effective to treat, eliminate, or mitigate at least one symptom of the disease or condition being treated in a subject. In some cases, "therapeutically effective amount" or "effective amount" can refer to an amount of a functional agent or of a pharmaceutical composition useful for exhibiting a detectable therapeutic or inhibitory effect in a subject. The effect can be detected by any assay method known in the art. In some instances, where the disease being treated is cancer, the effective amount can be an amount effective to invoke an anti-cancer response that include a reduction in any of cell proliferation, cell migration, angiogenesis, fibrosis, and inflammation.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, or more as compared to a control.

As used herein, the terms "reduce" and "decrease" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99%, or more as compared to a control.

The term, "pomace" as used herein, refers to the pulpy material remaining after the juice has been pressed from fruit. Pomace includes the pulp, seeds and skin of the fruit.

I. Methods of Making Extracts and Formulations

The extracts described herein can be prepared in a variety of ways. The extracts described herein can be prepared from readily available starting materials.

Provided are methods of producing extracts from grape seeds, grape skins or a combination thereof. Prior to extracting the grape seeds and grape skins, the grapes are pressed to produce juice and pomace, and the pomace is separated from the juice. Generally, the pressing of the grapes and separating of the pomace from the juice occurs at room temperature (for example, about 70° F.). The pomace is cooled to a temperature in the range of at least about −20° F. to a maximum of −50° F., which reduces oxygen levels in the pomace to zero or near zero, thereby increasing the stability (reduces microbial contamination and the like) of the pomace and maintaining high phenolic levels. Prior to extraction, the pomace is thawed and then dried. The skins and seeds in the dried pomace are separated from each other. Optionally, the skins and seeds may be washed to remove unwanted debris. In some instances, the seeds and skins can be recombined and then extracted. In other instances, the seeds and skins can be extracted separately as described further. Optionally, extracts made from the seeds and skins may be combined.

In one aspect, a method of producing a grape seed and grape skin extract is provided, comprising contacting grape seeds and grape skins with distilled water, optionally fractional vapor compression distilled water; (b) heating the water, grape seeds and grape skins from step (a) at a temperature in the range of about 120° F. to a maximum of 200° F. (e.g., about 120° F., 125° F., 130° F., 135° F., 140° F., 145° F., 150° F., 155° F., 160° F., 165° F., 170° F., 175° F., 180° F., 185° F., 190° F., 195° F., 200° F., or any range or value therein, but not to exceed 200° F.), during which time additional distilled water, optionally fractional vapor compression distilled water, is added; (c) cooling the grape seeds, grape skins and water from step (b); (d) filtering the grape seeds, grape skins and water from step (c) to produce a grape seed and skin filtrate; (e) adding a food preservative to the filtrate from step (d); (f) cooling the filtrate from step (e) to produce a cooled filtrate; and (g) filtering the cooled filtrate from step (f), thereby producing a grape seed and grape skin extract. In some embodiments, the step of heating (b) may further comprise agitating the grape seeds and grape skins in the distilled water. In still further embodiments, the heating may be carried out under atmospheric pressure. In some embodiments, the ratio of grape seeds to grape skins can be about 85% seeds to about 15% skins, about 80% seeds to about 20% skins, about 75% seeds to about 25% skins, about 70% seeds to about 30% skins or about 65% seeds to about 35% skins. In some embodiments, the ratio of grape seeds to grape skins can be about 70% seeds to about 30% skins. In further embodiments, the ratio of grape seeds to grape skins can be about 85% seeds to about 15% skins.

In another aspect, a method of producing a grape seed extract is provided, comprising: (a) contacting grape seeds with distilled water, optionally fractional vapor compression distilled water; (b) heating the water and grape seeds from step (a) at a temperature in the range of about 120° F. to a maximum of 200° F. (e.g., about 120° F., 125° F., 130° F., 135° F., 140° F., 145° F., 150° F., 155° F., 160° F., 165° F., 170° F., 175° F., 180° F., 185° F., 190° F., 195° F., 200° F., or any range or value therein, but not to exceed 200° F.), during which time additional distilled water, optionally fractional vapor compression distilled water, is added; (c) cooling the grape seeds and water from step (b); (d) filtering the grape seeds and water from step (c) to produce a grape seed filtrate; (e) adding a food preservative to the filtrate from step (d); (f) cooling the filtrate from step (e) to produce a cooled filtrate; and (g) filtering the cooled filtrate from step (f), thereby producing a grape seed extract. In some embodiments, the step of heating (b) may further comprise agitating the grape seeds in the distilled water. In still further embodiments, the heating may be carried out under atmospheric pressure.

In a further aspect, a method of producing a grape skin extract is provided, comprising: (a) contacting grape skin (no seeds or pulp) with distilled water, optionally fractional vapor compression distilled water; (b) heating the water and grape skin from step (a) at a temperature in the range of about 120° F. to a maximum of 200° F. during which additional distilled water, optionally fractional vapor compression distilled water, is added; (c) cooling the grape skin and water from step (b); (d) filtering the grape skin and water from step (c) to produce a grape skin filtrate; (e) adding a food preservative to the filtrate from step (d); (f) cooling the filtrate from step (e) to produce a cooled filtrate; and (g) filtering the cooled filtrate from step (f), thereby producing a grape seed extract. In some embodiments, the step of heating (b) may further comprise agitating the grape skins in the distilled water. In still further embodiments, the heating may be carried out under atmospheric pressure. The phenolics concentration in the extract produced by this method may be at least about 3 g/L to about 8 g/L.

Surprisingly, extracting grape seeds and grape skins separately from each other using the methods described herein provides extracts having reduced insoluble material and a higher polyphenolic content. The grape seed and grape skin can be obtained from one or more suitable grape species. Thus, in some aspects, the grape seed and grape skin can be obtained from one or more grape species including, but not limited to, *Vitis rotundifolia* (hereinafter "muscadine grapes"), *Vitis vinifera* (hereinafter "*vinifera* grapes"), *Vitis labrusca, Vitis riparia, Vitis aestivalis, Vitis rupestris, Vitis coignetiae, Vitis vulpina,* and/or *Vitis amurensis.* In some embodiments, the grape seed and/or grape skin can be obtained from one or more muscadine grape varieties. For example, in some embodiments, the grape seed and/or grape skin can be obtained from African Queen, Alachua, Albermarle, Black Beauty, Black Fry, Carlos, Cowart, Darlene, Dixieland, Dixie Red, Doreen, Flowers, Fry, Fry Seedless, GA-1, Golden Isles, Granny Val, Higgins, Hunt, Ison, James, Jumbo, Magnolia, Memory, Mish, Nesbitt, NC-1, Noble, Polyanna, Rosa, Redgate, Regale, Scarlett, Scuppernong, Sterling, Sugargate, Summit, Supreme, Sweet Jenny, Tara, Tarheel, Thomas, Triumph and/or Welder muscadine grapes, or any combination of two or more muscadine varieties thereof.

The extracts may be prepared using distilled water. The distilled water used can be prepared using conventional techniques, including distillation, reverse osmosis, activated carbon filtration, ion exchange, or a combination thereof. In some instances, "fractional vapor compression distilled water" may be used. As used herein, the term "fractional vapor compression distilled water" means a high purity steam distilled water. The fractional distillation system has degassers, which vent-off organic compounds, thereby removing fractions of chemicals that can contaminate undistilled water. Pure water is composed of 11% hydrogen and 89% oxygen. Undistilled water (such as tap water or spring water) can contain impurities (like, for example, dissolved solids and organic compounds), while fractional vapor compression distilled water has substantially reduced levels of these impurities. In some instances, fractional vapor compression distilled water may have about 1 ppm, 2 ppm, 3 ppm, 4 ppm, 5 ppm, or up to about 10-20 ppm. In some instances, fractional vapor compression distilled water may be about 99.9%, 99.8%, 99.7%, 99.6%, 99.5% 99.4%, 99.3%, 99.2%, 99.1%, or 99% pure water. As an example, fractional vapor compression distilled water has no or substantially reduced levels of chlorine as compared to undistilled water. Chlorine is a strong oxidizer that can destroy polyphenolic compounds and therefore can interfere with the extraction of phenolics. Fractional vapor compression distilled water also contains reduced levels of dissolved solids typically found in undistilled water (such as tap water or spring water) such as, for example, sodium, calcium, magnesium, iron and many other inorganic elements. The presence of inorganic elements such as these can affect the efficiency of the extraction process and, as such, the extraction processes described in this disclosure use water with minimal contaminants.

In some aspects, contacting the grape seeds with distilled water comprises contacting the grape seeds with the distilled water at a ratio in a range from about 4.5 lbs grape seeds to about 0.5 gal water up to about 4.5 lbs grape seeds to about 2.5 gals water (e.g., from about 1 lb grape seeds to about 0.11 gal water up to about 1 lb grape seeds to about 0.56 gal water) and any range or amount therein. In representative embodiments, the ratio can be about 1 lb grape seeds to about 0.22 gal water. In other aspects, contacting the grape skins with distilled water comprises contacting the grape skins with the water at a ratio of about 2 lbs of grape skins to about 0.5 gal water up to about 2 lbs of grape skins to about 2.5 gal water (e.g., from about 1 lb grape skins to about 0.25 gal up to about 1 lb grape skins to about 1.25 gal water). In representative embodiments, the ratio can be about 2 lbs of grape skins to about 1 gal water (e.g., about 1 lb of grape skins to about 0.5 gal water). In some embodiments, 450 lbs of grape seeds or about 200 lbs of grape skins may be contacted with a total of about 140 gallons of distilled water. Notably, polyphenolics are extracted more efficiently from the grape skins and grape seeds when the grape seeds and grape skins are extracted separately from each other. However, in some embodiments, the seeds and skins may be extracted together. Thus, in a representative embodiment, the method comprises extracting about 314 lbs of grape seed and about 59 lbs of grape skin in a total of about 140 gallons of fractional vapor compression distilled water. In one example, the ratio of contacting the combination of grape skins and grape seeds with distilled water comprises a ratio of about 3.7 lbs of the combination of grape seeds and grape skins to about 0.5 gal water up to about 3.7 lbs of the combination of grape seeds and grape skins to about 2.5 gal water. In another example, contacting the combination of grape skins and grape seeds with distilled water comprises a ratio of about 3.7 lbs of the combination of grape skins and grape seeds to about 1.0 gal water.

There are various suitable vessels that may be used for the heating step. The vessel needs to hold the desired amount of water and grape seeds and/or grape skins. Thus, for example, an appropriate vessel can include but is not limited to a steam kettle. In some aspects, the method may be carried out under atmospheric pressure. The inventor has found that in addition to boiling, high pressure conditions can destroy polyphenolic compounds, thereby reducing the efficiency of the extraction of the grape skins/seeds. Therefore, in some embodiments, a pressure vessel is not a suitable vessel for extracting the grape skins and/or seeds. In some instances, the vessel is not a closed vessel. In some instances, the vessel may include, or be fitted with, an agitation means to agitate the contents of the vessel during the heating step.

The antioxidant compounds present in the seeds and skins of the grape, including phenolics, flavonoids, and resveratrol, can be destroyed by high temperatures. The maximum heating temperature of 200° F. disclosed herein minimizes the destruction of the antioxidant compounds during extraction. In some embodiments, the heating can be for about 1 hour to about 6 hours (e.g., about 1 hour to about 5 hours, about 1 hour to about 4 hours, about 1 hour to about 3 hours, or about 1 hour to about 2 hours, about 1 hr, 1.5 hr, 2 hr, 2.5 hr, 3 hr, 3.5 hr, 4 hr, 4.5 hr, 5 hr, 5.5 hr, 6 hrs, or any range or value therein) at a temperature of about 120° F. to a maximum of 200° F. (e.g., 120, 125, 130, 135, 140, 145, 150, 155, 160, 165, 170, 175, 180, 185, 190, 195, 200° F., and any range or value therein). In some instances, the heating can be for 1 to 2 hours at a temperature in the range of 120° F. up to 200° F. In particular instances, the heating can be for 1 to 2 hours at a temperature in the range of about 175° F. to no more than 200° F.

Additional distilled water, optionally fractional vapor compression distilled water, is added at step (b) (for any of the grape skin extraction, the grape seed extraction or grape seed and grape skin extraction method). This additional water may be added at one time or incrementally/periodically throughout the heating period. When added incrementally, the periodicity of adding the additional water can be about every 5 minutes to about every 60 minutes (e.g., about every 5, 10, 15, 20, 25, 30, 15, 40, 45, 50, 55, 60 min, or any range or value therein), or some combination thereof, while heating, to achieve a total amount of water to seeds and/or skins in the range of about 1 lb grape seeds or grape skins to about 0.92 gal water up to about 1 lb grape seeds or grape skins to about 4.6 gal water. Therefore, in some embodiments, the additional fractional vapor compression distilled water can be added about every 5 minutes to about every 60 minutes, or some combination thereof, over the period during which the water and grape skin or grape seed from step (a) is heated. In representative embodiments, the additional fractional vapor compression distilled water can be added about every 15 minutes to about every 30 minutes, or some combination thereof, over the period during which the water and grape skin or grape seed from step (a) is heated.

Following the heating of the grape seeds or grape skins with the distilled water and prior to filtering, the grape seeds or grape skins in the distilled water can be cooled. In some embodiments, the cooling can be to a temperature in the range of about 40° F. to about 180° F. (e.g., about 40, 45, 50, 55, 60, 65, 70, 75, 80, 85, 90, 95, 100, 105, 110, 115, 120, 125, 130, 135, 140, 145, 150, 155, 160, 165, 170, 175, 180° F., or any range or value therein). In representative embodiments, the cooling may be to a temperature in the range of about 170° F. to about 180° F. (e.g., 170° F., 171° F., 172° F., 173° F., 174° F., 175° F., 176 F, 177° F., 178° F., 179° F., 180° F., or any range or value therein).

In some embodiments, the filtering of the grape seeds and water, the grape skins and water, or the grape skins, grape seeds and water comprises filtering through a sieve size from about 20 microns to about 50 microns (e.g., about 20, 25, 30, 35, 40, 45, 50 microns; e.g., about 600 mesh to about 300 mesh (e.g., about 600, 500, 400, 300 mesh)), and any range or value therein.

In some embodiments, the filter that is used is comprised of stainless steel rather than plastic, thereby avoiding leaching chemicals that may be present in plastics into the extract. Thus, the filter is not plastic. Similarly, other containers and instruments used in this process are not plastic. For example, a vessel for collecting a filtrate or extract may include, but is not limited to, a stainless steel barrel.

In some embodiments, a food preservative can be added to the grape skin filtrate or grape seed filtrate in an amount from about 0.1% to about 20% (weight/volume (w/v)) (e.g., about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20% w/v). In some embodiments, the food preservative can be added to the grape skin filtrate or grape seed filtrate at an amount of about 0.1% to about 15%, about 0.1% to about 10%, about 0.1% to about 5%, about 0.1% to about 1%, and any value or range therein. In representative embodiments, the food preservative can be added to the grape seed filtrate or the grape skin filtrate at an amount of about 0.1% to about 1.0% w/v. In some embodiments, the food preservative can include, but is not limited to, at least one of potassium sorbate, citric acid, acetic acid, or vitamin E (e.g., tocopherols, tocotrienols). In some instances, the food preservative can be potassium sorbate. In particular instances, the food preservative may be potassium sorbate added to the grape seed filtrate, the grape skin filtrate, or the grape seed and grape skin filtrate at an amount of about 0.1% to about 1.0% w/v.

Following the addition of a food preservative to the grape seed filtrate, the grape skin filtrate, or the grape seed and grape skin filtrate, the filtrate can then be refrigerated or cooled. In some instances, the filtrate may be cooled to a temperature in the range of about 35° F. to about 45° F. (e.g., about 35° F., 36° F., 37° F., 38° F., 39° F., 40° F., 41° F., 42° F., 43° F., 44° F., 45° F., and any range or value therein). In some instances, the filtrate may be refrigerated (cooled) for about 24 hours to about 120 hours (i.e., about 1 day to about 5 days) (e.g., about 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 hours, or any range or value therein). In some embodiments, the cooling can be for about 24 hours to about 72 hours. In representative embodiments, the cooling of the grape seed filtrate, the grape skin filtrate, or the grape seed and grape skin filtrate can be for about 24 hours.

Following refrigeration, the cooled grape seed filtrate, the cooled grape skin filtrate, or the cooled grape seed and grape skin filtrate can be filtered again. In some embodiments, the filtering of the cooled filtrate comprises filtering through a filter having a sieve size from about 1 micron to about 10 microns (e.g., 1, 2, 3, 4, 5, 6, 7, 8, 9, 10 microns) or any range or value therein (e.g., 12,000 mesh to about 1250 mesh).

After filtration of the cooled grape seed filtrate, the cooled grape skin filtrate, or the cooled grape seed and grape skin filtrate (step (g)), food grade ethanol may be added to the filtrate as a preservative. In some instances, the ethanol can be added at an amount of about 2% to about 5% of the extract (v/v) (e.g., about 2%, 3%, 4%, 5% or any range or value therein). In particular instances, the ethanol can be added to an amount of 2% of the extract (v/v). The added food grade ethanol may be about 190 proof (i.e., 95% ethanol). In some embodiments, the food grade ethanol can be made from any plant source including, but not limited to, corn, wheat, sugar cane, and/or grape. In representative embodiments, the food grade ethanol can be organic ethanol. As used herein the term "organic alcohol" refers to alcohol that is made from, for example, organic corn, wheat, sugar cane, grape and/or other organic sources of ethanol. The requirements for labeling a food as organic are set out by the U.S. Department of Agriculture (www.ams.usda.gov/rules-regulations/organic/labeling).

Thus, in some aspects, a method of producing a grape seed and grape skin extract is provided, comprising contacting grape seeds and grape skins with distilled water, optionally fractional vapor compression distilled water; (b) heating the water, grape seeds and grape skins from step (a) at a temperature in the range of about 120° F. to a maximum of 200° F., during which time additional distilled water, optionally fractional vapor compression distilled water, is added; (c) cooling the grape seeds and grape skins and water from step (b); (d) filtering the grape seeds, grape skins and water from step (c) to produce a grape seed and grape skin filtrate; (e) adding a food preservative to the filtrate from step (d); (f) cooling the filtrate from step (e) to produce a cooled filtrate; (g) filtering the cooled filtrate from step (f); and (h) adding food grade ethanol to the filtrate from step (g), thereby producing a liquid extract. In some embodiments, the step of heating (b) may further comprise agitating the grape seeds and grape skins in the fractional vapor compression distilled water. In still further embodiments, the heating may be carried out under atmospheric pressure. In some embodiments, the ratio of grape seeds to grape skins can be about 85% seeds to about 15% skins, about 80% seeds to about 20% skins, about 75% seeds to about 25% skins, about 70% seeds to about 30% skins or about 65% seeds to about 35% skins. In some embodiments, the ratio of grape seeds to grape skins can be about 70% seeds to about 30% skins. In further embodiments, the ratio of grape seeds to grape skins can be about 85% seeds to about 15% skins.

In another aspect, a method of producing a grape seed extract is provided, comprising: (a) contacting grape seeds with distilled water, optionally fractional vapor compression distilled water; (b) heating the water and grape seeds from step (a) at a temperature in the range of about 120° F. to a maximum of 200° F. (e.g., about 120° F., 125° F., 130° F., 135° F., 140° F., 145° F., 150° F., 155° F., 160° F., 165° F., 170° F., 175° F., 180° F., 185° F., 190° F., 195° F., 200° F., or any range or value therein, but not to exceed 200° F.), during which time additional distilled water, optionally fractional vapor compression distilled water, is added; (c) cooling the grape seeds and water from step (b); (d) filtering the grape seeds and water from step (c) to produce a grape seed filtrate; (e) adding a food preservative to the filtrate from step (d); (f) cooling the filtrate from step (e) to produce a cooled filtrate; (g) filtering the cooled filtrate from step (f); and (h) adding food grade ethanol to the filtrate from step (g), thereby producing a liquid extract. In some embodiments, the step of heating (b) may further comprise agitating the grape seeds in the distilled water. In still further embodiments, the heating may be carried out under atmospheric pressure.

In a further aspect, a method of producing a grape skin extract is provided, comprising: (a) contacting grape skin (no seeds or pulp) with distilled water, optionally fractional vapor compression distilled water; (b) heating the water and grape skin from step (a) at a temperature in the range of about 120° F. to a maximum of 200° F. during which additional distilled water, optionally fractional vapor compression distilled water, is added; (c) cooling the grape skin and water from step (b); (d) filtering the grape skin and water from step (c) to produce a grape skin filtrate; (e) adding a food preservative to the filtrate from step (d); (f) cooling the filtrate from step (e) to produce a cooled filtrate; (g) filtering the cooled filtrate from step (f); and (h) adding food grade ethanol to the filtrate from step (g), thereby producing a liquid extract. In some embodiments, the step of heating (b) may further comprise agitating the grape skins in the distilled water. In still further embodiments, the heating may be carried out under atmospheric pressure.

In a further aspect, a method of producing a grape skin and grape seed extract is provided, comprising providing a grape seed liquid extract made by the methods described herein; providing a grape skin liquid extract made by the methods described herein; and combining the grape seed liquid extract and the grape skin liquid extract in a ratio of about 50:50 to about 85:15 (volume/volume (v/v)), thereby forming the grape-derived liquid extract. The ratio of grape seed extract to grape skin extract can be about 85% seed extract to about 15% skins, about 80% seed extract to about 20% skin extract, about 75% seed extract to about 25% skin extract, about 70% seed extract to about 30% skin extract or about 65% seed extract to about 35% skin extract. In some embodiments, the ratio of grape seeds to grape skins can be about 70% seed extract to about 30% skin extract. In further embodiments, the ratio of grape seeds to grape skin extract can be about 85% seed extract to about 15% skin extract.

In one instance, a method of producing a powdered grape seed and grape skin extract is provided, comprising contacting grape seeds and grape skins with distilled water, optionally fractional vapor compression distilled water; (b) heating the water, grape seeds and grape skins from step (a) at a temperature of about 120° F. to a maximum of 200° F., during which time additional distilled water, optionally fractional vapor compression distilled water, is added; (c) cooling the grape seeds and grape skins and water from step (b); (d) filtering the grape seeds, grape skins and water from step (c) to produce a grape seed and grape skin filtrate; (e) adding a food preservative to the filtrate from step (d); (f) cooling the filtrate from step (e) to produce a cooled filtrate; (g) filtering the cooled filtrate from step (f); (h) adding food grade ethanol to the filtrate from step (g), thereby producing a liquid extract and (h) spray-drying the liquid extract to produce a powdered grape seed and grape skin extract. In some embodiments, the step of heating (b) may further comprise agitating the grape seeds and grape skins in the distilled water. In still further embodiments, the heating may be carried out under atmospheric pressure. In some embodiments, the ratio of grape seeds to grape skins can be about 85% seeds to about 15% skins, about 80% seeds to about 20% skins, about 75% seeds to about 25% skins, about 70% seeds to about 30% skins or about 65% seeds to about 35% skins. In some embodiments, the ratio of grape seeds to grape skins can be about 70% seeds to about 30% skins. In further embodiments, the ratio of grape seeds to grape skins can be about 85% seeds to about 15% skins.

In another instance, a method of producing a powdered grape seed extract is provided, comprising: (a) contacting grape seeds with distilled water, optionally fractional vapor compression distilled water; (b) heating the water and grape seeds from step (a) at a temperature of about 120° F. to a maximum of 200° F. (e.g., about 120° F., 125° F., 130° F., 135° F., 140° F., 145° F., 150° F., 155° F., 160° F., 165° F., 170° F., 175° F., 180° F., 185° F., 190° F., 195° F., 200° F., or any range or value therein, but not to exceed 200° F.), during which time additional distilled water, optionally fractional vapor compression distilled water, is added; (c) cooling the grape seeds and water from step (b); (d) filtering the grape seeds and water from step (c) to produce a grape seed filtrate; (e) adding a food preservative to the filtrate from step (d); (f) cooling the filtrate from step (e) to produce a cooled filtrate; (g) filtering the cooled filtrate from step (f); (h) adding food grade ethanol to the filtrate from step (g), thereby producing a liquid extract and (h) spray-drying the liquid extract to produce a powdered grape seed extract. In some embodiments, the step of heating (b) may further comprise agitating the grape seeds in the distilled water. In still further embodiments, the heating may be carried out under atmospheric pressure.

In a further instance, a method of producing a powdered grape skin extract is provided, comprising: (a) contacting grape skin (no seeds or pulp) with distilled water, optionally fractional vapor compression distilled water; (b) heating the water and grape skin from step (a) at a temperature in the range of about 120° F. to a maximum of 200° F. during which additional distilled water, optionally fractional vapor compression distilled water, is added; (c) cooling the grape skin and water from step (b); (d) filtering the grape skin and water from step (c) to produce a grape skin filtrate; (e) adding a food preservative to the filtrate from step (d); (f) cooling the filtrate from step (e) to produce a cooled filtrate; (g) filtering the cooled filtrate from step (f); (h) adding food grade ethanol to the filtrate from step (g), thereby producing a liquid extract and (h) spray-drying the liquid extract to produce a powdered grape skin extract. In some embodiments, the step of heating (b) may further comprise agitating the grape skins in the distilled water. In still further embodiments, the heating may be carried out under atmospheric pressure.

In addition to methods of manufacturing liquid extracts, methods of producing powder extracts are also provided. Powdered extracts of the disclosure may be prepared by drying the liquid extracts made as described herein. In some instances, the liquid extract may be spray dried. The term "spray drying" broadly refers to processes involving breaking up liquid mixtures into small droplets (atomization) and rapidly removing solvent from the mixture. In a typical spray drying apparatus, a strong driving force evaporates the solvent from the droplets, which may be provided by providing a drying gas. By way of non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream from the drying chamber. Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying.

Spray drying may be performed in a conventional manner in the processes described herein. The drying gas may be any suitable gas, although inert gases such as nitrogen, nitrogen-enriched air; and argon are preferred. In some embodiments, nitrogen gas is used. The amorphous co-precipitate produced by spray drying may be recovered by techniques commonly used in the art, such as using a cyclone or a filter.

Removal of solvent may also be accomplished, for example, by substantially complete evaporation of the solvent, concentrating the solution, or distillation of solvent, under inert atmosphere to obtain powder extract.

In one embodiment, the drying is carried out at atmospheric pressure or reduced pressures such as, for example, below about 200 mm Hg, or below about 50 mm Hg, at temperatures such as about 25° C. to about 90° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing conditions should be considered as only a general guidance. Drying can be suitably carried out in a tray dryer, vacuum oven, air oven, or using a fluidized bed drier, spin flash dryer, flash dryer, and the like. Drying equipment selection is well within the ordinary skill in the art. In some instances, the resultant powder extract may have a residual moisture content of about 3.0-3.4%.

In one example, the liquid extract may be atomized, with a spray thereof introduced into a 44 inch×32 inch dryer, mixing with heated natural gas at a temperature in the range of about 200-400° F. (e.g., inlet temperature about 400° F. and outlet temperature about 200° F.) at a flow rate of 18,000-22,000 cfm.

In one example, such as Example 1 of this disclosure, provided is a method of producing a grape seed and grape skin powder extract comprising atomizing the liquid extract containing grape seed and grape skin to produce a spray and drying the spray. In some embodiments, drying is performed in a dryer using a natural gas at a flow rate of 18,000-22,000 cfm. In some embodiments drying is performed at a temperature in the range of about 200-400° F. In some cases, the produced powder extract has a residual moisture content of about 3.0-3.4%. The powder extract formed by this process can be encapsulated or can be reconstituted to form a liquid. In some instances, the powder extract can be formulated in a hypromellose capsule. The extracts, particularly powder extracts, may be stable for a period of at least 3, 4, 5, 6, 8, 10, 18, or 24 months, as characterized by a phenolic level at the end of the period of at least 90%, e.g., at least 92%, at least 95%, at least 98%, or at least 99% of the phenolic level at the beginning of the period.

In some instances, compared to known commercial extracts containing ground grape seed or skin (or both), the extracts produced according to the methods described above generally have more phenolics, total or individually, than the commercially available capsules containing ground grape seeds. The enhanced (enriched) phenolics in the described extracts include, for example, catechin, gallic acid, epicatechin, ellagic acid, procyanadin, and catechin-gallate (catgall).

In one example, such as Example 2 of this disclosure, provided is a method of producing muscadine grape seed extract comprising placing grape seeds into an open steam kettle and adding a desired amount of fractional vapor compression distilled water, for example, 450 pounds of grape seed with 100 gallons of fractional vapor compression distilled water. The grape seeds in the fractional vapor compression distilled water may be heated for about 1-2 hours at about 175 -200° F. Optionally during heating, additional fractional vapor compression distilled water may be added, e.g., in 5 gallons increments every 15-30 minutes, until reaching a desired total amount of water, e.g., 140 gallons. After heating, the temperature may be reduced and cooled to about 170-180° F. The grape seed in water may then be filtered through a mesh stainless steel sieve and filtrate may be collected. Optionally, potassium sorbate may be added to the grape seed filtrate. The extracts, particularly powder extracts, may be stable for a period of at least 3, 4, 5, 6, 8, 10, 18, or 24 months, as characterized by a phenolic level at the end of the period of at least 90%, e.g., at least 92%, at least 95%, at least 98%, or at least 99% of the phenolic level at the beginning of the period.

In one example, such as Example 3 of this disclosure, provided is a method of producing muscadine grape skin extract comprising placing grape skins into an open steam kettle and adding a desired amount of fractional vapor compression distilled water, for example, 450 pounds of grape skins with 100 gallons of fractional vapor compression distilled water. The grape skins in the fractional vapor compression distilled water may be heated for about 1-2 hours at about 175-200° F. Optionally during heating, additional fractional vapor compression distilled water may be added, e.g., in 5 gallons increments every 15-30 minutes, until reaching a desired total amount of water, e.g., 140 gallons. After heating, the temperature may be reduced and cooled to about 170-180° F. The grape skins in water may then be filtered through a mesh stainless steel sieve and filtrate may be collected. Optionally, potassium sorbate may be added to the grape skins filtrate. The extracts, particularly powder extracts, may be stable for a period of at least 3, 4, 5, 6, 8, 10, 18, or 24 months, as characterized by a phenolic level at the end of the period of at least 90%, e.g., at least 92%, at least 95%, at least 98%, or at least 99% of the phenolic level at the beginning of the period.

Extract composition can be monitored at any stage of the methods described herein according to any suitable method known in the art. For example, composition can be monitored by spectroscopic means, such as nuclear magnetic resonance spectroscopy (such as $^1H$ or $^{13}C$), infrared spectroscopy, spectrophotometry (such as UV-visible), mass spectrometry, or by chromatography such as high performance liquid chromatography (HPLC) or thin layer chromatography, or by a combination thereof.

In one aspect, provided is a method of manufacturing a liquid extract from grape seeds, grape skins, or a combination thereof, the method comprising: (a) providing grape seeds, grape skins, or a combination thereof; (b) contacting the grape seeds, grape skins, or a combination thereof, with distilled water to form an extraction mixture; (c) heating the extraction mixture at a temperature in the range of 120° F. to 200° F., during which heating additional distilled water is added; (d) cooling the extraction mixture; (e) filtering the extraction mixture to remove solids thereby forming a filtrate; (f) adding a food preservative to the filtrate; (g) cooling the filtrate to form a cooled filtrate; and (h) filtering the cooled filtrate thereby producing the liquid extract.

In some embodiments, the grape seeds, the grape skins, or combination thereof is derived from a grape selected from the group consisting of *Vitis rotundifolia, Vitis vinifera, Vitis labrusca, Vitis riparia, Vitis aestivalis, Vitis rupestris, Vitis coignetiae, Vitis vulpina,* and *Vitis amurensis.* In certain embodiments, the grape seeds, the grape skins, or combination thereof is derived from a *Vitis rotundifolia* grape.

In some embodiments, grape seeds are provided for the method. In one embodiment, the distilled water is fractional vapor compression distilled water. In one embodiment, contacting the grape seeds with distilled water comprises a ratio of about 4.5 lbs grape seeds to about 0.5 gal water up to about 4.5 lbs grape seeds to about 2.5 gals water. In one embodiment, contacting the grape seeds with distilled water comprises a ratio of about 4.5 lbs grape seeds to about 1 gal water. In one embodiment, the additional distilled water is added to achieve a ratio of about 1 lb grape seeds to about 0.92 gal water up to about 1 lb grape seeds to about 4.6 gal water.

In other embodiments, grape skins are provided for the method. In one embodiment, contacting the grape skins with distilled water comprises a ratio of about 2 lbs of grape skins to about 0.5 gal water up to about 2 lbs of grape skins to about 1.25 gal water. In one embodiment, contacting the grape skins with distilled water comprises a ratio of about 2 lbs grape skins to about 1 gal water. In one embodiment, the additional distilled water is added to achieve a ratio of about 1 lb grape skins to about 0.92 gal water up to about 1 lb grape skins to about 4.6 gal water.

In other embodiments, a combination of grape seeds and grape skins are provided for the method.

In one embodiment, the combination of grape seeds and grape skins has a ratio of about 50% grape seeds to 50% grape skins (weight/weight (w/w)) to about 85% grape seeds to 15% grape skins. In one embodiment, the ratio of contacting the combination of grape skins and grape seeds with distilled water comprises a ratio of about 3.7 lbs of the combination of grape seeds and grape skins to about 0.5 gal water up to about 3.7 lbs of the combination of grape seeds and grape skins to about 2.5 gal water. In one embodiment, contacting the combination of grape seeds and grape skins with distilled water comprises a ratio of about 3.7 lbs of the combination of grape seeds and grape skins to about 1.0 gal water.

In some instances, the provided methods of manufacturing extracts of grape seed, grape skin, or combinations thereof, comprise heating the extraction mixture for about 1 to about 6 hours. In some instances, the heating is performed for about 1 to about 2 hours. In one embodiment, the additional distilled water is added to the extraction mixture in a plurality of portions during the heating. In one embodiment, a portion of the additional distilled water is added to the extraction mixture about every 5 min to about every 60 min during the heating. In one embodiment, a portion of the additional distilled water is added to the extraction mixture about every 15 to about every 30 min during the heating.

In some embodiments, the extraction mixture is cooled to a temperature of about 40° F. to about 170° F. In some embodiments, the extraction mixture is filtered through a filter having a sieve size from about 20 microns to about 50 microns.

In some embodiments, the food preservative is added to the filtrate at an amount of about 0.1 percent to about 20 percent (weight/volume (w/v)). In one embodiment, the food preservative is added to the filtrate at an amount of about 0.1% to about 1% (w/v). In one embodiment, the preservative comprises at least one of potassium sorbate, citric acid, acetic acid, or vitamin E.

In some embodiments, the filtrate is cooled at a temperature from about 35° F. to about 45° F. In one embodiment, the filtrate is cooled for about 24 hours to about 120 hours.

In one embodiment, the filtrate is cooled for about 24 hours. In one embodiment, filtering the cooled filtrate comprises filtering the cooled filtrate through a filter having a sieve size from about 1 micron to about 10 microns.

In some embodiments, food grade ethanol is added to the filtered cooled filtrate of step (g), thereby producing the liquid extract. In one embodiment, the food grade ethanol is about 190 proof (95% ethanol). In one embodiment, the food grade ethanol is made from corn, wheat, sugar cane, or grape. In one embodiment, the food grade ethanol is organic food grade ethanol. In one embodiment, the volume of food grade ethanol added to the filtered cooled filtrate of step (g) is about 2% to about 5% of the liquid extract volume.

In another aspect, provided is a method of manufacturing a grape-derived liquid extract, comprising: (a) providing a grape seed liquid extract made by a method described above; (b) providing a grape skin liquid extract made by a method described above; (c) combining the grape seed liquid extract and the grape skin liquid extract in a ratio of about 50:50 to about 85:15 (volume/volume (v/v)), thereby forming the grape-derived liquid extract.

In another aspect, provided is a method of manufacturing a grape-derived powder extract, comprising: obtaining or manufacturing a grape-derived liquid extract from grape seed, grape skin, or a combination thereof as described above and then spray-drying the liquid extract to form a powder extract.

II. Extracts

Also provided in this disclosure are extracts made from grape seeds, grape skins, or combinations thereof. Both liquid extracts and powder extracts are provided.

The extracts of this disclosure are extracts made by the methods described in Section I. In some embodiments, the extract is made from grape seeds. In some embodiments, the extract is a grape seed liquid or powder extract. In some embodiments, the extract is made from grape skins. In some embodiments, the extract is a grape skin liquid or powder extract. In some embodiments, the extract is made from grape seeds and grape skins. Where the extract is a grape seed and skin powder extract, it may comprise a spray-dried powder extract made from a grape seed and skin liquid extract. Alternatively, the grape seed and skin powder extract may comprise a spray-dried powder extract made from a blend of a grape seed liquid extract and a grape skin liquid extract. Alternatively, the grape seed and skin powder extract may comprise a blend of a spray-dried powder extract made from a grape seed liquid extract and a spray-dried powder extract made from a grape skin liquid extract. Where the extract is a grape seed and skin liquid extract, it may comprise a blend of a grape seed liquid extract and a grape skin liquid extract, a blend of a grape seed powder extract with a grape seed liquid extract, a blend of a grape skin powder extract with a grape skin extract, a blend of a grape seed powder extract with a grape skin liquid extract, a blend of a grape skin powder extract with a grape seed liquid extract, or a solution comprising at least one of a grape seed powder extract or a grape skin powder extract dissolved therein. In some instances, the grape seed and skin liquid extracts of this disclosure do not include a liquid extract made by a method comprising the steps of (a) providing a combination of grape seeds and grape skins; (b) contacting the combination of grape seeds and grape skins with distilled water to form an extraction mixture; (c) heating the extraction mixture at a temperature in the range of 120° F. to 200° F., during which heating additional distilled water is added; (d) cooling the extraction mixture; (e) filtering the extraction mixture to remove solids thereby forming a filtrate; (f) adding a food preservative to the filtrate; (g) cooling the filtrate to form a cooled filtrate; and (h) filtering the cooled filtrate thereby producing the liquid extract.

The present invention further provides an extract made by the method of the invention. The final concentration of the polyphenolics in the extract produced may be adjusted by adjusting the ratio of water to grape seeds or skins that is used in the process. Thus, in some aspects, when using about 140 gallons of water with about 450 lbs of grape seeds, an extract produced by the methods of the invention may comprise a total polyphenolic content of 15-25 g/L (e.g., 15, 16, 17, 18, 19, 20, 21, 22, 23, 24, 25 g/L and any range or value therein). In some instances, the final concentration of polyphenolics in an extract produced from the grape skins may be 3 g/L to 8 g/L.

Extracts as described herein may comprise 100% grape seed extract, 100% grape skin extract, 100% grape seed and grape skin extract, or any combination thereof. Thus, in some aspects, extracts produced from grape skins and extracts produced from grape seeds can be combined to produce a combined grape seed and grape skin extract. The ratio of grape seed extract to grape skin extract may be 95:5, 90:10, 85:15, 80:20, 75:25, 70:30, 65:35, 60:40, 55:45, 50:50, and the like. In particular aspects, the ratio of grape seed extract to grape skin extract may be 70:30. In other aspects, the ratio of grape seed extract to grape skin extract may be 85:15.

In one instance, provided are liquid extracts made by the extraction methods described in this disclosure. In some instances, the total phenolic compound content of the liquid extract may be about 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL mg/mL, 200 mg/mL, 225 mg/mL, 250 mg/mL, 275 mg/mL, 300 mg/mL, and any value or range therein. In some instances, the liquid extract may have a total phenolic compound content of about 20 mg/mL to 200 mg/mL.

In some instances, the liquid extract is a blend of grape seed liquid extract and grape skin liquid extract. For example, the grape seed liquid extract and the grape skin liquid extract may be in a ratio of about 50:50 to about 85:15 (volume/volume (v/v)). The ratio of grape seed extract to grape skin extract may be about 85% seed extract to about 15% skins, about 80% seed extract to about 20% skin extract, about 75% seed extract to about 25% skin extract, about 70% seed extract to about 30% skin extract or about 65% seed extract to about 35% skin extract. In some embodiments, the ratio of grape seeds to grape skins can be about 70% seed extract to about 30% skin extract. In further embodiments, the ratio of grape seeds to grape skin extract can be about 85% seed extract to about 15% skin extract.

In another instance, provided are powder extracts made by the extraction method described in this disclosure. In some instances, the powder extract includes about 25% to 50% (weight/weight (w/w)) total phenolic compounds. In another instance, provided are powder extracts comprising at least about 30% (weight/weight (w/w)) total phenolic compounds. In another instance, provided are powder extracts having about 250-500 mg total phenolic compounds per gram of powder extract. In some instances, a powder extract may include at least one of gallic acid or ellagic acid at a concentration of at least about 6 mg per gram of powder extract. In some instances, the powder extract has a total phenolic concentration of about 150 mg/g to about 600 mg/g (e.g., about 150, 175, 200, 225, 250, 275, 300, 325, 350, 375, 400, 425, 475, 500, 525, 550, 575, 600 mg/g, and any value or range therein). In representative embodiments, the powder extracts may have a phenolics concentration of about 250 mg/g to about 400 mg/g, or about 270 mg/g to about 350 mg/g.

In some instances, the extracts include a food preservative such as potassium sorbate, citric acid, acetic acid, or vitamin E (e.g., tocopherols, tocotrienols). For example, liquid extracts may include 0.1% w/v potassium sorbate. In some instances, the extracts may include food grade ethanol. For example, liquid extracts may include ethanol at about 2% to about 5% v/v of the liquid extract volume. In some instances, the ethanol is 95% ethanol (190 proof).

In some embodiments, the grape-derived powder extract comprises about 25% to 50% (weight/weight (w/w)) total phenolic compounds.

In some embodiments, the grape-derived powder extract comprises at least about 30% (weight/weight (w/w)) total phenolic compounds.

In some embodiments, the grape-derived powder extract comprises about 250-500 mg total phenolic compounds per gram of powder extract.

In some embodiments, the grape-derived powder extract comprises at least one of gallic acid or ellagic acid at a concentration of at least about 6 mg per gram of the powder extract.

In some embodiments, the grape-derived powder extract comprises unique components with molecular masses of 706 and 1033 when subjected to high performance liquid chromatography, mass spectroscopy analysis.

In some embodiments, the grape-derived powder extract does not comprise components with molecular masses of 730 or 1288 when subjected to high performance liquid chromatography, mass spectroscopy analysis in amount that would make the components with molecular masses of 730 or 1288 amongst the largest 30% of peaks on a chromatograph generated from the analysis.

In some embodiments, the total phenolic content of the extracts provided in this disclosure remains stable over a period of at least 6 months, as characterized by total phenolic content reduction of no more than 10% at 6 months.

III. Characterization of the Extracts

Muscadine grape extracts provided by this disclosure, such as those produced using the methods described in Examples 1-3, can be analyzed for the phenolic content using methods well known in the art. In some instances, gallic acid may be used as a standard for the assay for phenolic content analysis. In one embodiment, the phenolic content may be assessed by a Folin-Ciocalteau method, for example, such as described in Example 1. When assessing a powder extract, the powder extract may be resuspended in water or other suitable solvent and homogenized prior to measurement of phenolics contained therein. Extracts manufactured according to the methods described in this disclosure may have at least 5 times, at least 10 times, at least 12 times, at least 15 times, at least 16 times, at least 20 times higher phenolic content as compared to the phenolic content of supplements or extracts from muscadine grapes that are not manufactured according to the methods described in this disclosure. In one example, the extract is a powder extract of muscadine grape seed and skin made according to the method described in Example 1 (p-MGE) having 162.3 mg phenolics/capsule. Non-limiting examples of such supplements and extracts include commercially available Premium Muscadine Grape Seed Dietary Supplement ("NP"), Muscadine Plus Dietary Supplement ("MN"), Premium Muscadine ("NF"), Muscadine Berries ("EN"), Muscadine Grape Seed from Biopower Nutrition ("BP"), Muscadine Grape Seed Herbal Supplement ("VIT"), Muscadinex Dietary Supplement ("NCMH"), Pure Muscadine Grape Seed ("BN"), and Muscadine Grape Seed ("FHN"). In one embodiment, as shown in FIG. 57, the phenolic content of the p-MGE is 16 times of the phenolic content of the BP product. In another embodiment, the p-MGE formulation has 12.4 times greater total phenolic content per capsule and 14.9 times greater total phenolic content based on the mg phenolics/gram powder than the EN product.

Muscadine grape extracts produced according to the methods described in Examples 1-3 may be enriched for one or more individual phenolic compounds. For example, such phenolics may include, but are not limited to, epitcatechin, gallic acid, procyanidin B, ellagic acid catechin and catechin gallate. In some instances, the provided extracts may have significantly higher levels of such individual phenolics as compared to commercial supplements manufactured from muscadine grapes, including those described in the previous paragraph. In some embodiments, for example as shown in FIG. 58, a muscadine grape seed and skin powder extract (p-MGE) may comprises at least 5 times, at least 10 times, at least 12 times, at least 15 times, at least 16 times, at least 20 times higher levels of at least one type of phenolic compound than as found in a commercial supplement, such as those described in the prior paragraphs of Section III. The enriched phenolic compound may be one or more of epitcatechin, gallic acid, procyanidin B, ellagic acid catechin or catechin gallate. The commercial supplement that is used for this comparison may be any one of the Premium Muscadine Grape Seed Dietary Supplement ("NP"), Muscadine Plus Dietary Supplement ("MN"), Premium Muscadine ("NF"), Muscadine Berries ("EN"), Muscadine Grape Seed from Biopower Nutrition ("BP"), Muscadine Grape Seed Herbal Supplement ("VIT"), Muscadinex Dietary Supplement ("NCMH"), Pure Muscadine Grape Seed ("BN"), Muscadine Grape Seed ("FHN"). In some cases, the commercial supplement is NP, BP, or NCMH. In one particular embodiment, a p-MGE as provided herein may contain 22.0±0.7 mg/g of epitcatechin, 13.5±0.6 mg/g of gallic acid, 7.1±0.3 mg/g of procyanidin B, 4.7±0.4 mg/g of ellagic acid, 2.7±0.1 mg/g of catechin, and 1.8±0.1 mg/g of catechin gallate.

Mass spectroscopy ("MS") may also be used to analyze the extracts. In one embodiment, the mass spectroscopy is Shimadzu ultra-high performance liquid chromatography (UHPLC) coupled to mass spectroscopy detection (UHPLC-MS). In some cases, l-MGE manufactured according to Example 5 may be processed by spray film method to produce a powdered form of extract (p-MGE), as described in Example 1, which is then encapsulated. In some instances, a p-MGE as provided herein is enriched for compounds that have molecular masses of 706 and 1033 according to mass spectroscopy analysis, which are absent (or substantially reduced) from the l-MGE, as shown in FIG. 59. In some instances, a p-MGE as provided herein does not contain (or contains substantially reduced amounts) of compounds that have molecular masses of 730 and 1288, which are present in l-MGE, as shown in FIG. 59.

The phenolics in the extracts may decrease over time. The grape extracts produced according to Examples 1-3 may demonstrate excellent stability for commercial purposes (shelf-life). For example, the extracts can remain stable for at least six months, at least 12 months, at least 18 months, at least 2 years, or longer at ambient temperature ranging from 65° F. to 77° F. Many standards can be used to assess whether a grape extract provided by this disclosure is stable. In some cases, a grape extract is deemed stable when there is no decrease, less than 2% decrease, less than 5% decrease, less than 10% decrease, less than 15% decrease, less than 20% decrease, or less than 25% decrease in total phenolics content in the extract after being stored for a period of time. In some cases, for example, as shown in Table 4, the total phenolics content of p-MGE remain substantially the same, e.g., no decrease or shows less than 5%, or less than 3% decrease after one year.

The extracts produced according to this disclosure are generally biologically stable as well, having low or no microbial growth over a period of at least 12 months, at least 16 months, or at least 18 months. For example, as shown in Table 5, a p-MGE extract made according to the method described in Example 1 can remain free of microbes including E. coli, Staphylococcus aureus, and salmonella over a period of 16 months. In another, the extracts of the disclosure, in particular the provided powder extracts, and more particularly a p-MGE made according to the method described in Example 1, may have yeast and mold count of less than 10 pcu/g and/or aerobic count of less than 10 pcu/g after 16 months.

IV. Formulations

The extracts described herein can be provided in a pharmaceutical composition (formulation). Depending on the intended mode of administration, the pharmaceutical composition can be in the form of solid, semi-solid, liquid dosage forms, or combinations thereof, such as, for example, tablets, suppositories, pills, capsules, powders, liquids, or suspensions, preferably in unit dosage form suitable for single administration of a precise dosage. The compositions include a pharmaceutically effective amount of the extracts described herein, in particular the phenolic compounds therein, in combination with a pharmaceutically acceptable carrier and, in addition, may include other medicinal agents, pharmaceutical agents, carriers, or diluents. The term pharmaceutically acceptable refers to a material that is not biologically or otherwise undesirable, which can be administered to an individual along with the selected compound without causing unacceptable biological effects or interacting in a deleterious manner with the other components of the pharmaceutical composition in which it is contained.

In some instances, the concentration of the phenolic compounds in a liquid pharmaceutical formulation may be in the range of 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL mg/mL, 200 mg/mL, 225 mg/mL, 250 mg/mL, 275 mg/mL, 300 mg/mL, or any value or range therein. In some instances, the formulation may have a total phenolic compound content of about 20 mg/mL to 200 mg/mL. In some instances, the amount of the phenolic compounds in a solid pharmaceutical formulation may be in the range of about 150 mg/g to about 600 mg/g (e.g., about 150, 175, 200, 225, 250, 275, 300, 325, 350, 375, 400, 425, 475, 500, 525, 550, 575, 600 mg/g, or any value or range therein). For example, the formulation may have about 250-500 mg total phenolic compounds per gram of powder extract. In one example, the formulation may have a phenolic concentration of about 250 mg/g to about 400 mg/g. In some instances, the amount of the phenolic compounds in a semi-solid pharmaceutical formulation may be in the range of about 150 mg/g to about 600 mg/g (e.g., about 150, 175, 200, 225, 250, 275, 300, 325, 350, 375, 400, 425, 475, 500, 525, 550, 575, 600 mg/g, or any value or range therein). For example, the formulation may have about 250-500 mg total phenolic compounds per gram of powder extract. In one example, the formulation may have a phenolic concentration of about 250 mg/g to about 400 mg/g.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, for example, *Remington: The Science and Practice of Pharmacy,* 22d Edition, Lloyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

The described compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like, may also be included.

Solid dosage forms for oral administration of the compounds described herein or derivatives thereof include capsules, tablets, pills, powders, and granules. In such solid dosage forms, the powder extracts described herein may admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active ingredient in a certain part of the intestinal tract in a delayed manner.

Examples of embedding compositions that can be used are polymeric substances and waxes. The active compounds can also be in micro-encapsulated form, if appropriate, with one or more of the above-mentioned excipients. In some instances, the coating or shell may be plant-derived such as, for example, a capsule or shell made from hydroxypropyl methylcellulose (HPMC or hypromellose).

Liquid dosage forms for oral administration of the extracts described herein include pharmaceutically acceptable emulsions, solutions, suspensions, syrups, and elixirs. In addition to the extract, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances and the like.

Besides such inert diluents, the composition can also include additional agents, such as wetting, emulsifying, suspending, sweetening, flavoring, or perfuming agents.

Suspensions, in addition to the extracts, may contain additional agents such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances and the like.

Dosage forms for topical administration of the extracts described herein include ointments, powders, sprays, and inhalants. The extracts described herein may be admixed under sterile conditions with a physiologically acceptable carrier and any preservatives, buffers, or propellants as may be required. Ophthalmic formulations, ointments, powders, and solutions are also contemplated as being within the scope of the compositions.

In some embodiments, the powder formulations comprise about 25% to 50% (weight/weight (w/w)) total phenolic compounds.

In some embodiments, the powder formulations comprise at least about 30% (weight/weight (w/w)) total phenolic compounds.

In some embodiments, the powder formulations comprise about 250-500 mg total phenolic compounds per gram of powder extract.

In some embodiments, the powder formulations comprise at least one of gallic acid or ellagic acid at a concentration of at least about 6 mg per gram of the powder extract.

In some embodiments, the powder formulations comprise unique components with molecular masses of 706 and 1033 when subjected to high performance liquid chromatography, mass spectroscopy analysis.

In some embodiments, the powder formulations do not comprise components with molecular masses of 730 or 1288 when subjected to high performance liquid chromatography, mass spectroscopy analysis in amount that would make the components with molecular masses of 730 or 1288 amongst the largest 30% of peaks on a chromatograph generated from the analysis.

In some embodiments, the total phenolic content of the formulations provided in this disclosure remains stable over a period of at least 6 months, as characterized by total phenolic content reduction of no more than 10% at 6 months.

V. Methods of Treatment

The provided extracts may be used in foods, beverages, cosmetics, dietary supplements, nutraceuticals, and the like, thereby providing products with increased antioxidant content.

Several phytochemicals produced by muscadine grapes, such as ellagic acid and resveratrol, have extensive biomedical documentation for their health benefits. Flavonoids are generally good antioxidants, and the plants that make them use them for antioxidant protection. These compounds can directly quench oxidative free radicals. Flavonoids can chelate metal ions that are often the catalysts for free radical production. These compounds may help to regulate gene expression in beneficial ways. Chronic disease states often involve adverse patterns of gene expression. Flavonoids are powerful regulators of healthy gene expression patterns.

In some aspects, the disclosure provides a food product including an extract as described herein, wherein the food product can be a liquid (e.g., a beverage or a liquid for enteral feeding or intravenous administration), a solid (e.g., bar), a tablet, and/or a powder. In some embodiments, the food product can be a powder that is encapsulated. In some embodiments, the food product can be a medical food that can be provided, for example, in a liquid, solid, powder or pill form.

A "medical food," as used herein, is as defined in section 5(b)(3) of the Orphan Drug Act (21 U.S.C. 360ee(b)(3)) and refers to "a food which is formulated to be consumed or administered enterally under the supervision of a physician and which is intended for the specific dietary management of a disease or condition for which distinctive nutritional requirements, based on recognized scientific principles, are established by medical evaluation."

In some instances, the extracts provided may be used to prepare an antioxidant composition, wherein the antioxidant composition is administered to a subject to treat diseases and disorders associated with oxidative stress and/or inflammation. Thus, in some embodiments, a method of treating a disease and disorder associated with oxidative stress and/or inflammation is provided, comprising administering to a subject in need thereof a therapeutically effective amount of a composition comprising the extracts of the invention.

The extracts and formulations described herein are useful in the area of oncology. Provided herein are methods of using the described extracts and formulations to treat a subject with cancer. Also provided are methods of treating a subject with an increased risk of cancer. Also provided are methods of treating a subject at risk of cancer relapse. Generally, the methods involve administering to a subject with a disease or condition an effective amount of an extract or formulation described herein. An effective amount, when used to describe an amount of the extract or formulation administered in provided methods, refers to the amount of the extract or phenolic compound content of the extract or formulation that achieves the desired pharmacological effect or other biological effect.

In some instances, the total daily dose of total phenolic compound in the extract administered to the subject is 300 mg to 6000 mg. For example, the subject may be administered via the extract a total daily dose of total phenolic compound of 300 mg, 325 mg, 350 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, or 1800 mg (or amounts within 5% of any of these doses). In some examples, the subject may be administered via the extract a total daily dose of total phenolic compound of 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 3900 mg, 4000 mg, 4100 mg, 4200 mg, 4300 mg, 4400 mg, 4500 mg, 4600 mg, 4700 mg, 4800 mg, 4900 mg, 5000 mg, 5100 mg, 5200 mg, 5300 mg, 5400 mg, 5500 mg, 5600 mg, 5700 mg, 5800 mg, 5900 mg, or 6000 mg (or amounts within 5% of any of these doses). In certain examples, the subject may be administered via the extract a total daily dose of total phenolic compound in the extract of 324 mg, 648 mg, 700 mg, 972 mg, 1400, 1620 mg, 2800, or 5600 mg. The mouse studies described in this disclosure may be useful in determining dosing for humans. For example, an average mouse weighs 0.025 kg. Administering 0.25, 0.5, 1 and 2 mg of total phenolics via the extract, such as the powdered muscadine grape seed and skin extract made according to the method described in Example 1 per mouse per day corresponds to a dose range of 10, 20, 40, and 80 mg of phenolics/kg/day. If an average human adult is assumed to have a weight of 70 kg, the corresponding human dosage would be 700, 1400, 2800, and 5600 mg of total phenolics per day.

In some instances, the subject is administered a dose of the extract or formulation at least twice daily. For example, in some instances, the subject is administered a dose of the extract or formulation 2 times, 3 times, 4 times, 5 times, or 6 times daily.

In some instances, a powder extract, or formulation containing a powder extract, is administered to the subject. In some instances, the total phenolic compound content of the powder extract or formulation per dose may be about 30-50% (mg/mg). In some instances, a dose of the powder extract or formulation includes about 150-500 mg total phenolic compounds.

In some instances, the subject may be administered a total daily dose of the liquid extract or the powder extract comprising at least about 10 mg of total phenolic compounds per kg body weight. For example, the subject may be administered a total daily dose of the liquid extract or the powder extract comprising about 10 mg, 20 mg, 40 mg, or 80 mg of total phenolic compounds per kg body weight.

In some instances, the total phenolic compound content of the liquid extract or formulation per dose is at least about 20 mg/mL. In some instances, the total phenolic compound content of the liquid extract or formulation per dose may be 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL 200 mg/mL, 225 mg/mL, 250 mg/mL, 275 mg/mL, 300 mg/mL, or any value or range therein. In some instances, total phenolic compound content may be in the range of about 20 mg/mL to 200 mg/mL. In one example, a dose of the liquid extract may include about 2.5 g to about 3.5 g total phenolic compounds.

As used herein, subject means both mammals and non-mammals. Mammals include, for example, humans, non-human primates (such as apes and monkeys), cattle, horses, sheep, rats, dogs, cats, mice, pigs, and goats. Non-mammals include, for example, fish, amphibians, reptiles, and birds. The extracts and formulations described herein are useful for treating diseases and conditions in humans, including, without limitation, pediatric and geriatric populations, and in animals, such as for veterinary applications.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (for example, size of the tumor or rate of tumor growth) of the disease in a subject as compared to a control. As used herein, control refers to the untreated condition (for example, the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

The extracts and formulations described herein are useful for both prophylactic and therapeutic methods of treatment. For prophylactic use, a pharmaceutically effective amount of an extract or formulation as described herein are administered to a subject prior to onset (that is before obvious signs of the diseases), during early onset (such as upon initial signs and symptoms of the disease), or after the development of the disease. Prophylactic administration can occur for several days to years prior to the manifestation of symptoms of disease. Therapeutic treatment involves administering to a subject a pharmaceutically effective amount of the compounds and compositions or pharmaceutically acceptable salts thereof as described herein after disease or condition is diagnosed.

Exemplary routes of administration include, but are not limited to, oral, enteral, dermal, injection (such as subcutaneous, intramuscular, intradermal, intraperitoneal, intravenous, and intratumoral), sublingual, transdermal, intranasal, topical and inhalation routes. Discussion of such routes is provided above in relation to formulations as described in Section III.

Administration of the compositions described herein can be carried out using pharmaceutically effective amounts for periods of time effective to treat a disease or condition. The effective amount of the extracts and compositions described herein may be determined by one of ordinary skill in the art and includes exemplary dosage amounts for a mammal of from about 600 mg to 6000 mg per kg of body weight of total phenolic compounds per day, which may be administered in a single dose or in the form of individual divided doses, such as at least twice day. Depending on the disease or condition of the subject, a pharmaceutically effective amount of the extracts or compositions may result in a different therapeutic effect.

Those of skill in the art will understand that the specific dose level and frequency of dosage for any particular subject may be varied and will depend upon a variety of factors, including the activity of the specific extract or formulation employed; the metabolic stability and length of action of that compound; the species, age, body weight, general health, sex and diet of the subject; the mode and time of administration; rate of excretion; drug combination; the nature of the disease or condition experienced by the subject, and severity of the particular disease or condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

In one aspect, provided herein are methods to treat or ameliorate cancer in a subject comprising administering the extracts provided in this disclosure. Also provided are methods to prevent or reduce the likelihood of cancer occurring in a subject comprising administering the extracts provided in this disclosure. Also provided are methods to prevent or reduce the likelihood of metastasis occurring in a subject having cancer comprising administering the extracts provided in this disclosure. Also provided are methods of inhibiting cancer cell growth or proliferation in a subject, methods of inhibiting angiogenesis in a tissue, and methods of inhibiting fibrosis in a tissue comprising administering the extracts provided in this disclosure. In some instances, the method of treating cancer in a subject includes administering to the subject an effective amount of an extract or formulation provided in this disclosure. In some instances, administering the extract or formulation inhibits cancer cell growth or proliferation in the subject. In some instances, administering the extract or formulation prevents or reduces the likelihood of tumor growth, metastasis, or both tumor growth and metastasis. In some instances, administering the extract or formulation inhibits at least one of cancer cell growth or proliferation, angiogenesis, inflammation, or fibrosis. In some instances, administering the extract or formulation inhibits cell growth or proliferation of endothelial cells (in vivo, in vitro).

In one aspect, provided is a method of treating a subject with cancer, an increased risk of cancer, or at risk of relapse, the method comprising administering to a subject a pharmaceutically effective amount of a liquid extract, a powder extract, or a formulation comprising either, as described in this disclosure. In some instances, administering the extract inhibits at least one of cancer-related cell growth or proliferation, angiogenesis, inflammation, or fibrosis.

The extracts provided by this disclosure have broad utility for treatment of cancer. Such cancers include, without limitation, carcinomas, sarcomas, myelomas, leukemias, lymphomas, and mixed type cancers. In one embodiment, the cancer is a bone cancer, for example, Ewing's sarcoma, osteosarcoma and rhabdomyosarcoma and other soft-tissue sarcomas. In another embodiment, the cancer is brain cancer, for example, oligodendroglioma, ependymoma, menengioma, lymphoma, schwannoma, or medulloblastoma. In some instances, the cancer is a glioma. In another embodiment, the cancer is breast cancer. In some instances, the breast cancer is HER2 over-expressing breast cancer, estrogen receptor (ER) positive breast cancer, or triple negative breast cancer. In some instances, the cancer is brain-specific metastatic breast cancer. In another embodiment, the cancer is an endocrine system cancer, for example, adrenal, pancreatic, parathyroid, pituitary, and thyroid cancers. In another embodiment, the cancer is a gastrointestinal cancer, for example, anal, colon, colorectal, esophageal, gall bladder, gastric, liver, and small intestine cancers. For example, the cancer may be biliary tract carcinoma or cholangiocarcinoma. In one example, the cancer is liver cancer. In another example, the cancer is hepatocellular carcinoma. In another embodiment, the cancer is a gynecological cancer, for example, cervical, endometrial, uterine, fallopian tube, gestational trophoblastic disease, choriocarcinoma, ovarian, vaginal, or vulvar cancer. In another embodiment, the cancer is a head and neck cancer, for example, laryngeal, pharyngeal, esophageal, oropharyngeal, parathyroid, or thyroid cancer. In another embodiment, the cancer is melanoma, squamous cell carcinoma, or basal cell carcinoma. In another embodiment, the cancer is a leukemic cancer, for example, acute lymphocytic leukemia, acute myelogenous leukemia, chronic lymphocytic leukemia, chronic myelogenous leukemia, hairy cell leukemia, or a myeloproliferative disorder. In another embodiment, the cancer is a lung cancer, for example, a mesothelioma or non-small cell lung cancer. In another embodiment, the cancer is a lymphoma, such as cutaneous T cell lymphoma, Hodgkin's disease, or non-Hodgkin's disease. In another embodiment, the cancer is a myeloma, for example, a multiple myeloma. In another embodiment, the cancer is penile cancer. In another embodiment, the cancer is prostate cancer. In another embodiment, the cancer is testicular cancer. In another embodiment, the cancer is thyroid cancer, for example, papillary, follicular, medullary, anaplastic, or undifferentiated thyroid carcinoma. In another embodiment, the cancer is a urinary tract cancer, bladder cancer, or a renal cancer such as kidney cancer and hepatocellular carcinoma. In some instances, the cancer is a genitourinary cancer. In some instances, the cancer is a peritoneal cancer. In another example, the cancer is sarcoma. For example, the cancer may be synovial carcinoma. In specific embodiments, the cancer may be breast cancer, prostate cancer, colon cancer, glioblastoma, lung cancer, skin cancer, leukemia, or lymphoma. In another embodiment, the cancer is HER2 over-expressing such as, for example, breast cancer, ovarian cancer, non-small cell lung cancer, colon cancer, prostate cancer, or pancreatic cancer. In other instances, the cancer is metastatic cancer. In some cases, the cancer is a primary cancer.

The methods of treating or preventing cancer in a subject can further comprise administering to the subject a therapeutic agent, radiation therapy, or a combination thereof. Thus, the provided compositions and methods can include one or more additional agents. The one or more additional agents and the extracts or formulations described herein can be administered in any order, including concomitant, simultaneous, or sequential administration. Sequential administration can be administration in a temporally spaced order of up to several days apart. The methods can also include more than a single administration of the one or more additional agents and/or the extracts or formulations described herein. The administration of the one or more additional agents and the extracts or formulations can be by the same or different routes and concurrently or sequentially.

Additional therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (including anthracyclines such as doxorubicin, liposomal doxorubicin, and diethylstilbestrol doxorubicin, bleomycin, daunorubicin, and dactinomycin); antiandrogens (such as enzalutamide, flutamide, nilutamide, bicalutamide, and ARN-509); antiestrogens (such as tamoxifen); antimetabolites (such as fluorouracil (FU), 5-FU, methotrexate, floxuridine, interferon alpha-2B, glutamic acid, plicamycin, mercaptopurine, and 6-thioguanine); cytotoxic agents (such as carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (such as medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (such as mephalen, chlorambucil, mechlorethamine (nitrogen mustard) and thiotepa); steroids (such as bethamethasone sodium phosphate); Akt inhibitors; glucocorticoid receptor inhibitors (such as beclometasone, betamethasone, budesonide, ciclesonide, flunisolide, fluticasone, mifepristone, mometasone, and triamcinolone); and survival factor inhibitors (such as inhibitors of neurotrophins, cytokines, epidermal growth factor (EGF), platelet-derived growth factor (PDGF), fibroblast growth factor (FGF), insulin-like growth factor (IGF), heparin-binding epidermal growth factor (HB-EGF), vascular endothelial growth factor (VEGF), pigment epithelium-derived factor (PEDF), schwannoma-derived growth factor (SDGF), hepatocyte growth factor (HGF), transforming growth factor-α (TGF-α), transforming growth factor-β (TGF-β), bone morphogenetic proteins (such as BMP1-BMP15), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO).

Optionally, the one or more additional agents can include antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Exemplary antibodies include trastuzumab, alemtuzumab, ibritumomab, blinatumomab, bevacizumab, and cetuximab.

Optionally, the one or more additional agent can include cancer vaccines, such as, for example, sipuleucel-T (PROVENGE®, manufactured by Dendreon), which was approved in 2010 by the U.S. Federal and Drug Administration for use in some men with metastatic prostate cancer.

Any of the aforementioned additional agents can be used in any combination with the extracts or formulations described herein. Combinations are administered either concomitantly (such as an admixture), separately but simultaneously (such as via separate intravenous lines into the same subject), or sequentially (such as one of the compounds or agents is given first followed by the second). Thus, the term combination is used to refer to concomitant, simultaneous, or sequential administration of two or more agents.

Figure 32A:
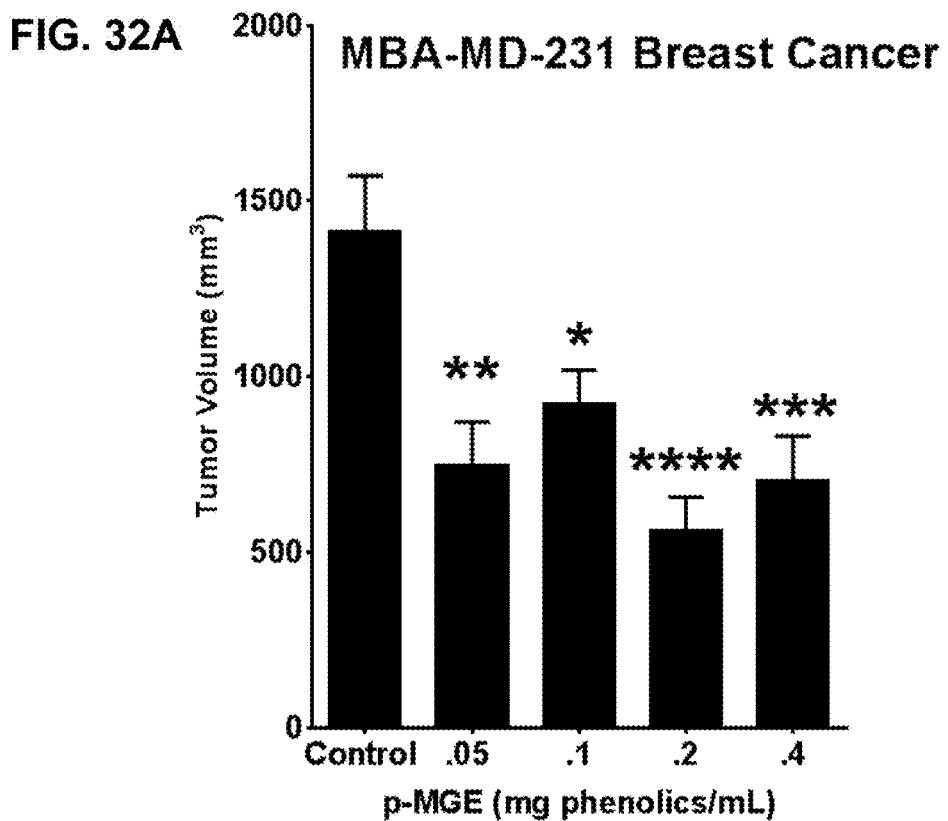
FIGS. 32A-32F show graphs summarizing the effect of a muscadine grape seed and muscadine grape skin powder extract (p-MGE) as described in Example 1 on the growth of human MDA-MB-231 triple negative breast tumors according to aspects of this disclosure. Athymic mice (n=8) were injected with MDA-MB-231 cells and treated with p-MGE, administered in their drinking water, for 4 weeks. Tumor size was measured twice per week in conscious mice and tumor size was calculated using the formula for a semi-ellipsoid.
Figure 32B:
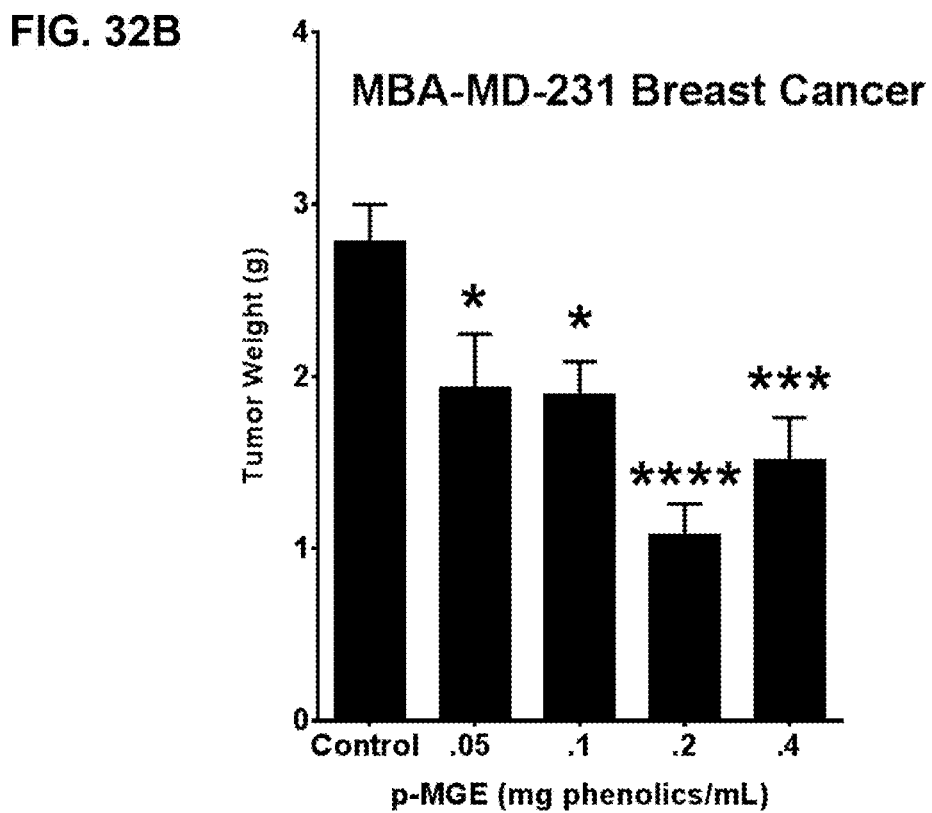
Figures 32C, 32D, 32E:
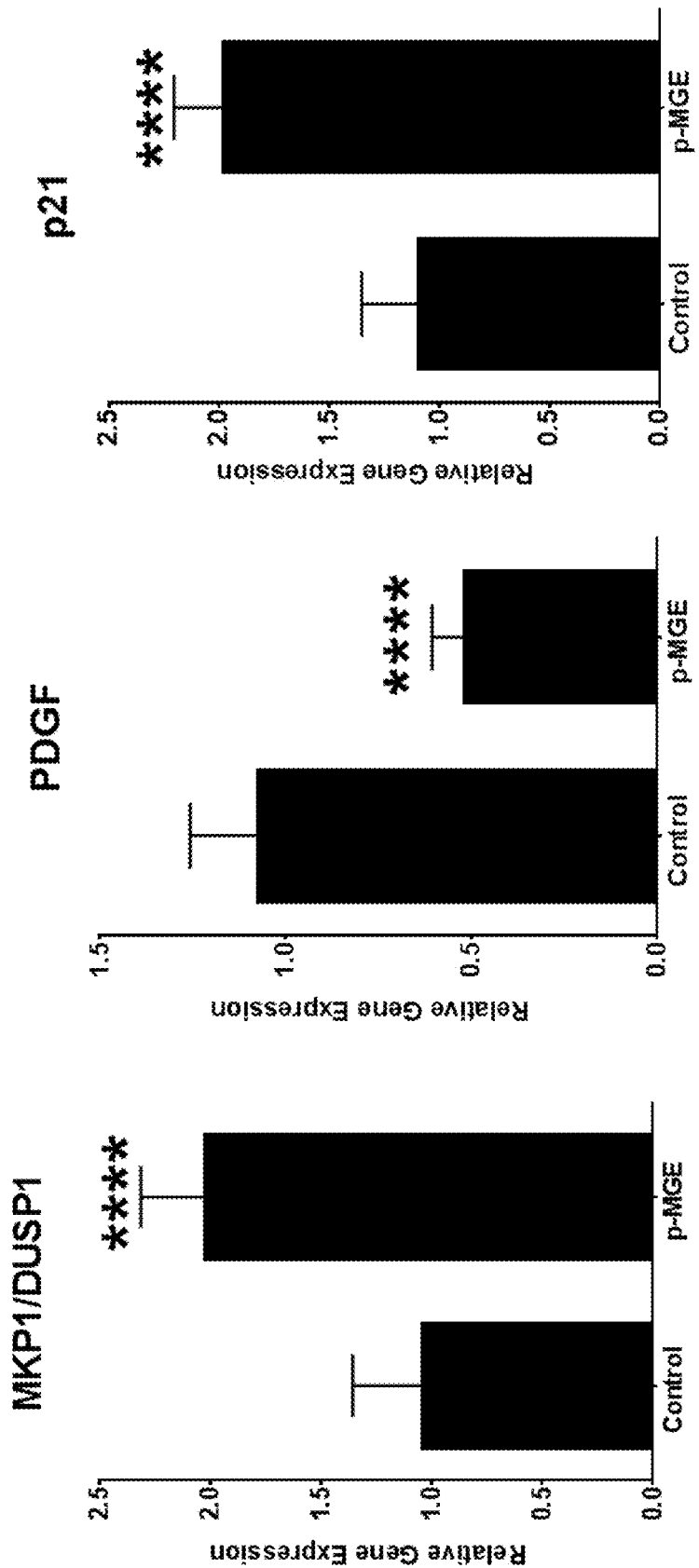

In some instances, administration of a muscadine grape extract as produced in Examples 1-3, for example, a muscadine grape seed and grape skin powder extract (p-MGE) manufactured according to the method described in Example 1, in a pharmaceutically effective amount can reduce the growth of triple negative breast tumors. In some cases, the reduction in tumor size can be at least 30%, at least 40%, at least 50%, or at least 66%, e.g., about 66%. The therapeutic effective amount may depend on the weight of the subject. For example, for a 25 mg mouse, the dosage may be 0.5 mg to 5 mg of phenolics per day, e.g., 0.5 to 2 mg per day. In some instances, the therapeutic effective amount of the extract can be in the range of 20-80 mg of total phenolics/kg/day, i.e., 20-80 mg of total phenolics per day per each kg of the patient's mass. In one instance, as shown in FIG. 32A, administration of p-MGE to mice (average 25 mg body weight) that bear human triple negative breast tumors at doses of 0.05, 0.1, 0.2, or 0.4 mg phenolics/mL, equivalent to 0.25, 0.5, 1, or 2 mg phenolics per day, can reduce tumor volume by 50% to 65%. In one instance, as shown in FIG. 32B, administration of p-MGE at 0.05, 0.1, 0.2, or 0.4, equivalent to 0.25, 0.5, 1, or 2 mg of phenolics per day, can reduce tumor weight by 405 to 70% as compared to untreated mice at the end of the 30-day treatment period. In one instance, as shown in FIG. 32C, administration of p-MGE at 0.5 mg phenolics per day for a 25 gram mouse can increase the expression of DUSP1 (MKP1) by about 50%, resulting in a reduction in the amount of phosphorylated, activated MAP kinases. In one instance, as shown in FIG. 32D, administration of p-MGE at 0.1 mg/mL, equivalent to 0.5 mg of phenolics per day for a 25 gram mouse, reduces PDGF expression by about 50%. In another instance, as shown in FIG. 32E, administration of p-MGE at 0.1 mg/mL, i.e., 0.5 mg of phenolics per day for a 25 gram mouse, increases the expression of p21 to about 2 fold of that of the untreated subjects. Thus, in some instances, administration of the extracts provided by this disclosure may reduce breast cancer tumor volume or weight by 40-70%, particularly when administered at a dose of 10-80, e.g., 20-80 mg of total phenolics per day per kg of the subject's mass (weight). For example, in some instances, administration of the extracts provided by this disclosure may reduce breast cancer tumor volume or weight (or both) by at least 30%, 35%, 40%, 45%, 50%, 60%, 65%, or 70% (or to a degree within 5% of these values).

In some instances, administration of a muscadine grape extract as produced in Examples 1-3, for example, a muscadine grape seed and grape skin powder extract (p-MGE) manufactured according to the method described in Example 1, in a pharmaceutically effective amount can reduce the growth of prostate tumors. For example, the p-MGE may be administered in the range of 10-80 mg, e.g., 20 mg, of total phenolics per day per each kg of the patient's mass. In some instances, the volume reduction of the prostate tumor may be at least 25%, at least 30%, at least 40%, or at least 50%, e.g., about 46%, or about 52% as compared to untreated controls. One example of this is described herein with respect to FIG. 48. In some cases, p-MGE treatment reduces the proliferation of prostate tumor cells by at least 20%, 25%, 30%, 35%, or 40% (or to a degree within 5% of these values). For example, as described herein with respect to FIG. 50, administering 0.1 mg phenolics/mL of p-MGE to mice harboring prostate tumors caused a 36% reduction in the number of Ki67 positive cells per field, suggesting that p-MGE reduces the proliferation of prostate tumor cells. In another instance, as described herein with respect to FIG. 48, treating mice harboring prostate tumors with p-MGE at 0.5 mg phenolics per day or 2 mg phenolics per day can reduce tumor volume by about by about 52% or 75%, respectively, as compared to untreated mice. In some cases, the weight reduction of the prostate tumor may be at least 30%, at least 40%, or at least 50%, e.g., about 59%. One example of this is described herein with respect to FIG. 49. Thus, in some instances, administration of the extracts provided by this disclosure may reduce prostate cancer tumor volume or weight by 40% to 75%, particularly when administered at a dose of 20-80 mg of total phenolics per day per kg of the subject's mass (weight). For example, in some instances, administration of the extracts provided by this disclosure may reduce prostate cancer tumor volume or weight (or both) by at least 30%, 35%, 40%, 45%, 50%, 60%, 65%, 70%, or 75% (or to a degree within 5% of these values).

In some instances, a muscadine grape extract as produced in Examples 1-3, for example, a muscadine grape seed and grape skin powder extract (p-MGE) manufactured according to the method described in Example 1, administered to a subject may inhibit angiogenesis in prostate tumors. In some cases, p-MGE can reduce the number of blood vessels in the prostate tumors by at least 15%, at least 20%, at least 25%, or at least 30% as compared to untreated controls. In one instance, as described herein with respect to FIG. 51, treating mice harboring prostate tumors with the p-MGE 0.1 mg phenolics/mL, which is equivalent to 0.5 mg phenolics per day, can reduce the number of the blood vessel by about 42% as compared to untreated mice. Thus, in some instances, administration of the extracts provided by this disclosure may reduce blood vessel formation by at least 20%, 25%, 30%, 35%, 40%, 45%, or 50% (or to a degree within 5% of these values). In some instances, p-MGE may reduce the relative expression of both VEGF and PLGF (growth factors that regulate angiogenesis) in tumor cells by at least 15%, at least 20%, at least 25%, or at least 30% as compared to untreated controls. In some instances, as described herein with respect to FIG. 52A-52B, treating mice harboring prostate tumors with the p-MGE at 0.1 mg phenolics/mL, which is equivalent to 0.5 mg phenolics per day, can reduce expression of VEGF and PLGF by about 30% to 40%. Thus, in some instances, administration of the extracts provided by this disclosure may reduce VEGF expression, PLGF expression, or both, by at least 20%, 25%, 30%, 35%, 40%, or 45% (or to a degree within 5% of these values).

Figure 33A:
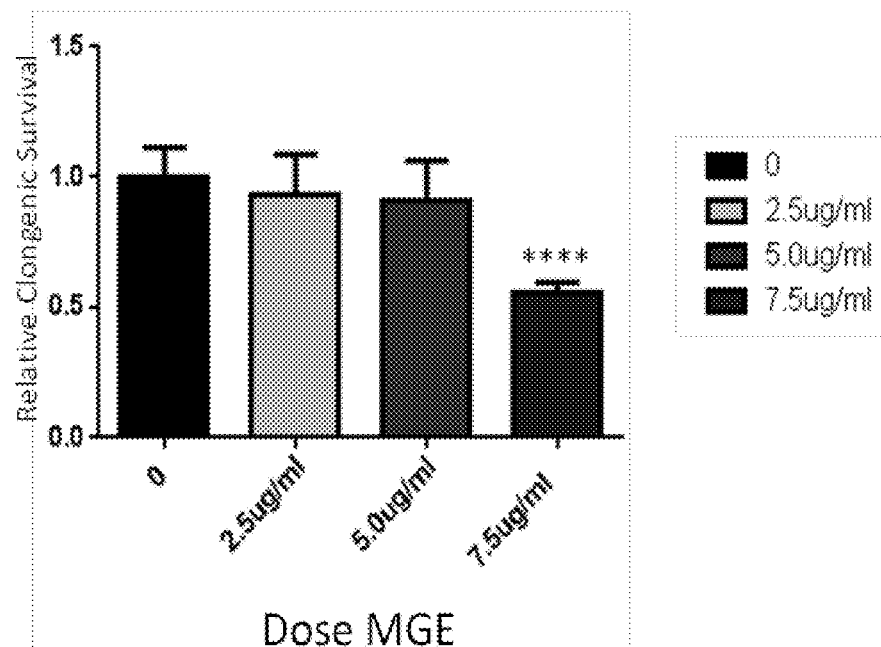
FIG. 33A-33B shows the effect of a muscadine grape seed and muscadine grape skin powder extract (p-MGE) as described in Example 1 on growth of brain-specific metastatic breast cancer cell lines according to aspects of this disclosure. Cell lines 4T1.luc.2Br5 or Eo771.luc.Br5 were plated at clonogenic density and exposed to the indicated concentration of p-MGE (labeled as MGE in these figures). Resulting colonies were stained and quantified, and normalized to no (0) p-MGE control. Data represent mean +/− SEM of 3 experiments, each performed in at least triplicate. * denotes p<0.001 and ** denotes p<0.0001. p-MGE reduced the growth of two different brain-specific breast cancer cells lines, which were derived from a triple negative breast cancer parent cell line (4T1) and an ER+ parent cell line (Eo771), suggesting that the extract will inhibit the growth of metastatic breast cancer.
Figure 33B:
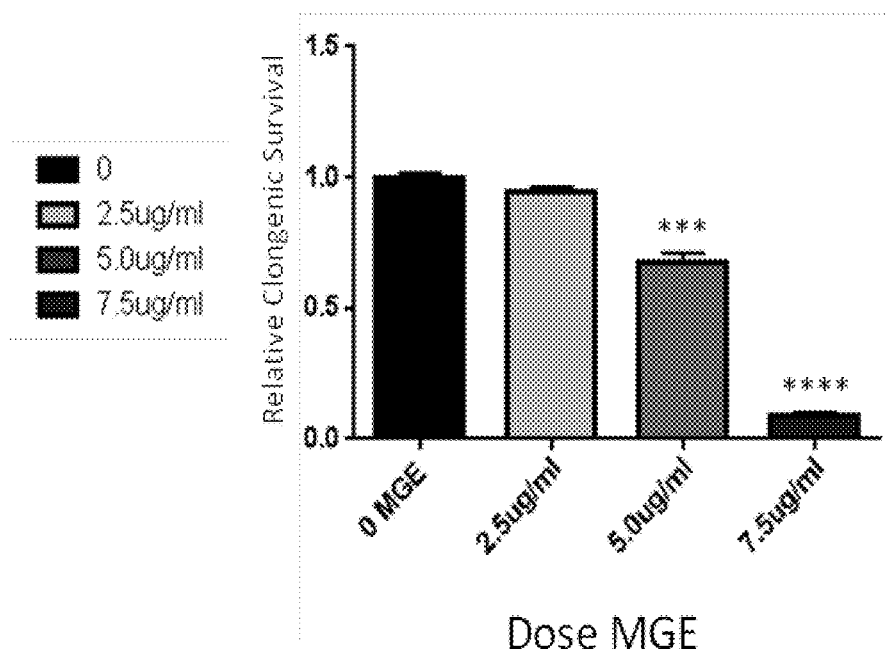

In some instances, a muscadine grape extract as produced in Examples 1-3, for example, a muscadine grape seed and grape skin powder extract (p-MGE) manufactured according to the method described in Example 1, can be administered in a pharmaceutically effective amount to inhibit the growth of brain-specific metastatic breast cancer cells. These cells may be triple negative breast cancer cells ("TNBC") that specifically metastasized to the brain. In some instances, as described herein with respect to FIG. 33A-33B, administration p-MGE may reduce the growth of brain-specific metastatic breast cancer cells that are derived from triple negative breast cancer cells, ER+ breast cancer cells, or both. For example, p-MGE may inhibit the growth of brain-specific breast cancer cells derived from cancers that behave similarly to triple negative breast cancer cell lines 4T1 or cell lines derived from ER+ cell line Eo7714T1. In another example, p-MGE may inhibit the growth of brain-specific breast cancer cells that behave similarly to brain-specific breast cancer cell line luc.2Br5, Eo771.luc.Br5, or both. In some cases, the power extract can inhibit cell cycle progression and/or induce apoptosis of the brain-specific metastatic breast cancer cells. In some instances, as described herein with respect to FIG. 34A, administering p-MGE to brain specific breast cancer cells can significantly decreases in ERK1/2 phosphorylation. For example, as described herein with respect to FIG. 34B, administration of p-MGE may inhibit tumor cell growth through inhibiting cell cycle progression, such as, e.g., by reducing cyclin level in the cells. In addition, in some instance, as described herein with respect to FIG. 35, p-MGE treatment at 10 μg/mL for 24 hours can induce apoptosis as indicated by the presence of cleaved PARP and active cleaved form of caspase 3.

In some instances, a muscadine grape extract as produced in Examples 1-3, for example, a muscadine grape seed and grape skin powder extract (p-MGE) manufactured according to the method described in Example 1, can be administered in a pharmaceutically effective amount to reduce proliferation of triple negative breast cancer cells (TNBCs). In some instances, administration of a therapeutic amount of an extract provided by this disclosure can reduce primary growth of TNBC. For example, as described herein with respect to FIG. 36A-36B and FIG. 37A-37C, p-MGE can decrease the proliferation of TNBC at concentrations from 5 μg/ml and 25 μg/ml (phenolics per dose). In some instances, as described herein with respect to FIG. 38A-38D, administration of p-MGE can significantly reduce both phosphorylated and activated ERK1 and ERK2, which are MAP kinases that participate in the regulation of cell growth. Thus, in some instances, administration of the extracts provided by this disclosure may reduce cancer cell proliferation by up to 80%, particularly with respect to breast cancer cells, and more particularly with respect to triple negative breast cancer cells, when administered at a dose of 20-80 mg of total phenolics per day per kg of the subject's mass (weight). For example, administration of the extracts provided by this disclosure reduce cancer cell proliferation, particularly breast cancer cells, and more particularly triple negative breast cancer cells, by at least 40%, 45%, 50%, 55%, 60%, 65%, 70%, 75%, 80%, 85%, 90%, or 95% (or to a degree within 5% of these values).

In some instances, a muscadine grape extract as produced in Examples 1-3, for example, a muscadine grape seed and grape skin powder extract (p-MGE) manufactured according to the method described in Example 1, can be administered in a pharmaceutically effective amount to a subject with triple negative breast cancer to upregulate or downregulate gene pathways or families as described herein with respect to FIG. 39. For example, treatment of triple negative breast cancer cells with 20 μg/mL p-MGE (phenolics per dose) may upregulate genes involved in the inflammatory or lipopolysaccharide (LPS) response, genes involved in the viral defense or interferon beta (IFNβ) response, and genes involved in autophagy or the endoplasmic reticulum (ER) stress response. In another example, treatment of triple negative breast cancer cells with 20 μg/mL p-MGE (phenolics per dose) may, down-regulate genes involved in nucleosome assembly, genes involved in the innate immune response, and genes involved in the cell cycle or cell division, which may be reflective of the changes in MAP kinase signaling and proteins involved in regulation of the cell cycle observed upon treatment with p-MGE.

In some instances, a muscadine grape extract as produced in Examples 1-3, for example, a muscadine grape seed and grape skin powder extract (p-MGE) manufactured according to the method described in Example 1, can be administered in a pharmaceutically effective amount to reduce proliferation of HER2 over-expressing (positive) breast cancer cells. In some instances, administration of a therapeutic amount of an extract provided by this disclosure can reduce primary growth of such cells. For example, as described herein with respect to FIG. 41A, p-MGE can decrease the proliferation of HER2 over-expressing (positive) breast cancer cells at concentrations from 10 μg/ml and 40 μg/ml (phenolics per dose). In some instances, as described herein with respect to FIG. 41B-41D, administration of p-MGE can significantly reduce phosphorylated activated AKT and m-TOR, which are key components of intracellular signaling pathways important to cell growth and survival in physiological as well as pathological conditions such as cancer. Thus, in some instances, administration of the extracts provided by this disclosure may reduce cancer cell proliferation by about 60% particularly with respect to breast cancer cells, and more particularly with respect to HER2 over-expressing (positive) breast cancer cells, when administered at a dose of 20-80 mg of total phenolics per day per kg of the subject's mass (weight). For example, administration of the extracts provided by this disclosure reduce cancer cell proliferation, particularly breast cancer cells, and more particularly HER2 over-expressing (positive) breast cancer cells, by at least 40%, 45%, 50%, 55%, 60%, 65%, 70%, 75%, 80%, 85%, 90%, or 95% (or to a degree within 5% of these values).

In some instances, a muscadine grape extract as produced in Examples 1-3, for example, a muscadine grape seed and grape skin powder extract (p-MGE) manufactured according to the method described in Example 1, can be administered in a pharmaceutically effective amount to reduce the migration of triple negative breast cancer cells (TNBCs). In some instances, administration of a therapeutic amount of an extract provided by this disclosure can reduce invasive growth of TNBC. For example, this may reduce the invasiveness of such tumor cells. In some instances, as described herein with respect to FIG. 40A-40D, p-MGE reduces the migration of TNBC away from the primary tumor when administered at a dose ranging from 10 μg/ml and 25 μg/ml (phenolics per dose) for total dosages of 10 μg/mL and 25 μg/mL. Thus, in some instances, administration of the extracts provided by this disclosure may reduce cancer cell migration by 25% to 50%, particularly with respect to breast cancer cells, and more particularly with respect to triple negative breast cancer cells, when administered at a dose of 20-80 mg of total phenolics per day per kg of the subject's mass (weight). For example, administration of the extracts provided by this disclosure reduce cancer cell migration, particularly breast cancer cells, and more particularly triple negative breast cancer cells, by at least 20%, 25%, 30%, 35%, 40%, 55%, or 60% (or to a degree within 5% of these values).

In some instances, administration of a muscadine grape extract as produced in Examples 1-3, for example, a muscadine grape seed and grape skin powder extract (p-MGE) manufactured according to the method described in Example 1, in a pharmaceutically effective amount, can reduce the growth of estrogen receptor positive (ER+) human breast tumors. For example, the treatment period may be at least 6 weeks, at least 7 weeks, or at least 8 weeks. In some cases, administration of p-MGE may inhibit tumor growth at least 30%, at least 40%, at least 50% relative to tumor growth in untreated control subjects. In some instances, p-MGE can be administered to a subject in combination with an estrogen receptor antagonist to treat ER+ human breast tumors. In some instances, the estrogen receptor antagonist may be tamoxifen. In some instances, combination treatment with p-MGE and an estrogen receptor antagonist may reduce tumor growth more than either treatment alone. In one instance, as described herein with respect to FIGS. 43, 44, 46, and 47, p-MGE is administered to ER+ mice bearing ER+ tumors formed by ZR-75-1 cells or MCF7 cells, at a dose of 0.5 mg phenolics per mouse per day for a 25 gram mouse, significantly reduces growth of the tumors, and a reduction in tumor growth is associated with the reduction of number of cells that are positive for proliferation marker Ki67, as described herein with respect to FIG. 45. Thus, in some instances, administration of the extracts provided by this disclosure, alone or in combination with a chemotherapeutic, may reduce tumor growth, tumor size, or both, by 50% to 95%, when administered at a dose of 20-80 mg of total phenolics per day per kg of the subject's mass (weight). In some instances, administration of the extracts provided by this disclosure, alone or in combination with a chemotherapeutic, may reduce tumor growth, tumor size, or both, by at least 40%, 45%, 50%, 55%, 60%, 65%, 70%, 75%, 80%, 85%, 90%, or 95% (or to a degree within 5% of these values).

In some cases, a muscadine grape extract as produced in Examples 1-3, for example, a muscadine grape seed and grape skin powder extract (p-MGE) manufactured according to the method described in Example 1, in a pharmaceutically effective amount, may be administered in combination with radiation to treat a patient during the course of their disease, for example, cancer. In some cases, the extract may be administered in combination with 2 Gy radiation. In some cases, the combination treatment inhibits diseased cell growth and/or kills diseased cells to a greater extent than either radiation treatment or p-MGE treatment alone. In one example, as described herein with respect to FIG. 42A-42B, radiation does not significantly increase radiation sensitivity. In another example, as described herein with respect to FIG. 42C-42D, administration of p-MGE can cause greater reduction in mouse brain-specific metastatic breast cancer cells, e.g., 4T1.luc2.BR5 cells or Eo771.luc.Br 5 cells, than either treatment alone. Thus, in some instances, administration of the extracts provided by this disclosure may reduce brain metastatic cancer cells, particularly brain metastatic breast cancer cells, by 15% to 50%, when administered at a dose of 20-80 mg of total phenolics per day per kg of the subject's mass (weight). For example, administration of the extracts provided by this disclosure, alone or in combination with a chemotherapeutic, may reduce tumor growth, tumor size, or both, by at least 10%, 15%, 20%, 25%, 30%, 35%, 40%, 45%, or 50% (or to a degree within 5% of these values). In some instances, administration of the extracts provided by this disclosure together with radiation therapy may reduce brain metastatic cancer cells, particularly brain metastatic breast cancer cells, by 50% to 80%, when administered at a dose of 20-80 mg of total phenolics per day per kg of the subject's mass (weight). For example, administration of the extracts provided by this disclosure in combination with radiation therapy may brain metastatic cancer cells, particularly brain metastatic breast cancer cells, by at least 40%, 45%, 50%, 55%, 60%, 65%, 70%, 75%, or 80% (or to a degree within 5% of these values).

In some instances, administration of a muscadine grape extract as produced in Examples 1-3, for example, a muscadine grape seed and grape skin powder extract (p-MGE) manufactured according to the method described in Example 1, in a pharmaceutically effective amount, in combination with a chemotherapeutic agent, can cause greater growth reduction of ER+ tumors, as compared to administering either grape extract or the chemotherapeutic agent alone. In one embodiment, the chemotherapeutic agent is tamoxifen. One example of this is described herein with respect to FIG. 43. In some instances, as described herein with respect to FIG. 44, treating subjects having ER+ tumor with p-MGE in combination with tamoxifen has an additive effect in inhibiting tumor growth, i.e., the combination significantly reduces tumor weight to an extent is greater than either p-MGE or tamoxifen treatment alone. The combination therapy may also decrease the percent of Ki67 positive tumor cells as compared to either treatment alone, as described herein with respect to FIG. 45A-45B, which indicates the combination of the grape extract and tamoxifen can reduce tumor cell proliferation to a greater extent than either treatment alone. Thus, in some instances, administration of the extracts provided by this disclosure and a chemotherapeutic agent may reduce tumor size (area), particularly breast cancer tumors, and more particularly ER+ breast cancer tumors, by 30% to 40% more than extract alone, by 30% to 50% more than chemotherapeutic alone, or both, when administered at a dose of 20-80 mg of total phenolics per day per kg of the subject's mass (weight). For example, the extracts provided by this disclosure together with a chemotherapeutic agent may reduce tumor size (area), particularly breast cancer tumors, and more particularly ER+ breast cancer tumors, by at least 20%, 25%, 30%, 35%, 40%, 45%, or 50% (or to a degree within 5% of these values) more than extract alone, chemotherapeutic alone, or both. In some instances, administration of the extracts provided by this disclosure and a chemotherapeutic agent may reduce tumor weight, particularly breast cancer tumors, and more particularly ER+ breast cancer tumors, by 25% to 50% more than extract alone or by 10% to 20% more than chemotherapeutic alone, or both, when administered at a dose of 20-80 mg of total phenolics per day per kg of the subject's mass (weight). For example, the extracts provided by this disclosure together with a chemotherapeutic agent may reduce tumor weight, particularly breast cancer tumors, and more particularly ER+ breast cancer tumors, by at least 10%, 15%, 20%, 25%, 30%, 35%, 40%, 45%, or 50% (or to a degree within 5% of these values) more than extract alone, chemotherapeutic alone, or both. In some instances, administration of the extracts provided by this disclosure and a chemotherapeutic agent may reduce tumor cell proliferation, such as determined Ki67 positive expression, by 20% to 30% more than either the extract alone or the chemotherapeutic alone, or both, when administered at a dose of 20-80 mg of total phenolics per day per kg of the subject's mass (weight).

In another aspect, provided herein are methods to reduce or ameliorate radiation-induced fibrosis and bone loss in a subject comprising administering the extracts provided in this disclosure. Administration of a muscadine grape extract as produced in Examples 1-3, for example, a muscadine grape seed and grape skin powder extract (p-MGE) manufactured according to the method described in Example 1, in a pharmaceutically effective amount can reduce the radiation-induced fibrosis. The extracts may prevent skeletal muscle fibrosis after irradiation, reduce radiation-induced bone damage, or both. The reduction in fibrosis may be demonstrated/reflected by reduced inflammation in the irradiated tissue. In one embodiment, the reduced fibrosis is detected by tissue staining, i.e., Masson's Trichrome staining. In one embodiment, as described herein with respect to FIG. 53 and FIG. 54, treatment with p-MGE can reduce radiation treatment-induced fibrosis to the levels of non-irradiated. The extracts may reduce fibrosis by inhibiting radiation-induced production of TGFβ, CTGF, or SMAD2, as described herein with respect to FIG. 55A-55C. Thus, in some instances, administration of the extracts provided by this disclosure may reduce fibrosis in skeletal muscle of a subject exposed to radiation, by 80% to 90%, when administered at a dose of 20-80 mg of total phenolics per day per kg of the subject's mass (weight). For example, the extracts provided by this disclosure may reduce fibrosis in skeletal muscle of a subject exposed to radiation by at least 50%, 55%, 60%, 65%, 70%, 75%, 80%, 85%, or 90% (or to a degree within 5% of these values) compared to subject who do not receive the extract. In one example, as described herein with respect to FIG. 56 and FIG. 57, treating pre-osteoclasts with p-MGE simultaneously with radiation or prior to radiation can reduce the numbers of osteoclast formed by pre-osteoclasts as compared to radiation alone. Treatment with the grape extracts may reduce radiation-induced increase in active osteoclasts, the reduction in active osteoclasts thereby reducing bone resorption and preventing bone loss, as compared to subjects exposed to radiation but to which an extract of the disclosure is not administered. Thus, in some instances, administration of the extracts provided by this disclosure may reduce bone loss (bone density loss, mineral content), including by reducing the number of pre-osteoclasts or reducing maturation of pre-osteoclasts to osteocloasts, by 95% to 100%, when administered at a dose of 20-80 mg of total phenolics per day per kg of the subject's mass (weight). For example, the extracts provided by this disclosure may reduce bone loss (bone density loss, mineral content), including by reducing the number of pre-osteoclasts or reducing maturation of pre-osteoclasts to osteocloasts, by at least 50%, 55%, 60%, 65%, 70%, 75%, 80%, 85%, 90%, 95%, or 100% (or to a degree within 5% of these values) compared to subject who do not receive the extract.

In another aspect, the grape extracts disclosed herein can be used to treat patients having hypertension. In some instances, the patients are treated to reduce the effects of hypertension on organs, such as end-organ damage. Hypertension is a condition in which the long-term force of blood against artery walls is abnormally high such that it may eventually cause health problems. Heart diseases are commonly associated with hypertension. Hypertension is typically diagnosed by measuring blood pressures given in millimeters of mercury (mm Hg), including systolic pressure and diastolic pressure. Normal blood pressure is below 120/80 mm Hg, prehypertension is a condition of having a systolic pressure ranging from 120 to 139 mm Hg or a diastolic pressure ranging from 80 to 89 mm Hg. Stage 1 hypertension is a condition of having a systolic pressure ranging from 140 to 159 mm Hg or a diastolic pressure ranging from 90 to 99 mm Hg. More severe hypertension, stage 2 hypertension is a condition of having a systolic pressure of 160 mm Hg or higher or a diastolic pressure of 100 mm Hg or higher. Patients who can benefit from treatment of grape extracts disclosed herein include, but not limited to, stage 1 and stage 2 hypertension patients. In particular, the extracts provided by this disclosure are useful for reducing end-organ damage associated with hypertension such as fibrosis, which often develops in heart muscle, leading to stiffening of the muscle and reduced heart function.

In some embodiments, a muscadine grape extract as produced in Examples 1-3, for example, a muscadine grape seed and grape skin powder extract (p-MGE) manufactured according to the method described in Example 1, can be administered in a pharmaceutically effective amount to a patient having hypertension at a pharmaceutically effective dose without exacerbating Ang II-induced hypertension. For example, p-MGE may be administered at a dose in the range of 10-80 mg of total phenolics per kg of patient mass per day (10-80 mg/kg/day). In some cases, as described herein with respect to FIG. 25, administration of p-MGE does not exacerbate hypertension as indicated by no substantial change in systolic blood pressure in treated subjects having Ang-II induced hypertension and in subjects not treated with the p-MGE treatment. In another example, as described herein with respect to FIG. 26, p-MGE treatment does not exacerbate Ang II-induced reduction in body weight. This is indicated by the fact that the weight of treated subjects having Ang-II induced hypertension is substantially the same as subjects not treated with the p-MGE treatment. In another example, p-MGE treatment may have no effect on cardiac contractility or left ventricular remodeling of the hypertension patient, as described herein with respect to FIG. 27A-27B. In some instances, as described herein with respect to FIG. 28A-28C, administration of p-MGE to a subject having Ang II-induced increase in blood pressure has no effect on wall thickness or the inner diameter of the left ventricle as compared to subjects that are not treated with p-MGE. Thus, the extracts of this disclosure generally do not exacerbate hypertension. However, in some embodiments, as described herein with respect to FIG. 29A-29B, administration of p-MGE can prevent an Ang II-induced increase in E/e'value as compared to subjects not treated with p-MGE. Thus, in some embodiments, p-MGE can improve the Ang II-induced diastolic dysfunction. In some instances, as described herein with respect to FIG. 31A-31B, administration of p-MGE in a subject with hypertension may decrease cardiac hypertrophy, for example, by decreasing the mean cross-sectional area (size) of the myocytes in the left ventricle. In some instances, as described herein with respect to FIG. 30A-30B, administration of p-MGE can attenuate Ang II-mediated increase in collagen, thereby decreasing the stiffness of the left ventricle. In some instances, p-MGE treatment can significantly attenuate cardiomyocyte hypertrophy, diastolic dysfunction, reduce cardiac interstitial fibrosis, and/or reduce cardiomyocyte size. Thus, in some instances, administration of the extracts provided by this disclosure may reduce hypertension associated fibrosis, particularly reducing cardiac hypertrophy by 90% to 100%, when administered at a dose of 20-80 mg of total phenolics per day per kg of the subject's mass (weight). For example, the extracts provided by this disclosure reduce hypertension associated fibrosis, particularly reducing cardiac hypertrophy by at least 50%, 55%, 60%, 65%, 70%, 75%, 80%, 85%, 90%, 95%, or 100% (or to a degree within 5% of these values) compared to subject who do not receive the extract. In some instances, administration of the extracts provided by this disclosure may reduce hypertension associated fibrosis, particularly reducing collagen production, by 60% to 70%, when administered at a dose of 20-80 mg of total phenolics per day per kg of the subject's mass (weight). For example, the extracts provided by this disclosure reduce hypertension associated fibrosis, particularly reducing collagen production, by at least 50%, 55%, 60%, 65%, 70%, or 75% (or to a degree within 5% of these values) compared to subject who do not receive the extract.

In some embodiments, the grape extracts produced according to Examples 1-3 can be used in combination with one or more additional agents that is effective in treating hypertension. The one or more additional agents and the extracts or formulations described herein can be administered in any order, including concomitant, simultaneous, or sequential administration. Sequential administration can be administration in a temporally spaced order of up to several days apart. The methods can also include more than a single administration of the one or more additional agents and/or the extracts or formulations described herein. The administration of the one or more additional agents and the extracts or formulations can be by the same or different routes and concurrently or sequentially. Non-limiting examples of such agent include diuretics, ACE inhibitors, angiotensin II receptor blockers, calcium channel blockers, alpha blockers, alpha-2 receptor agonists, combined alpha and beta-blockers, central agonists, peripheral adrenergic inhibitors, blood vessel dilators (vasodilators), and beta-blockers. Methods and dose regimens of how to administer these agents are well known to those skilled in the art.

Generally, administration of p-MGE to women of child-bearing age or pregnant women does not adversely impact the general health of the mothers or their off-spring, with regard to cardiovascular function (including cardiovascular measures of cardiac contractility and systolic function), blood pressure, body weight, or organ weight of the mothers or the number or length of newborns as discussed in Example 7.

In one aspect, provided is a method of treating a subject with disease, an increased risk of disease, or at risk of relapse, the method comprising administering to a subject a pharmaceutically effective amount of a grape-derived extract as described in the preceding sections of this disclosure. In some instances, the method comprises administering a liquid extract or formulation. In some instances, the method comprises administering a powder extract or formulation. In some embodiments, the subject is administered a dose of the powder extract or formulation at least twice daily.

In some embodiments, the total phenolic compound content of the powder extract or formulation per dose is about 30-50% (mg/mg). In some embodiments, a dose of the powder extract or formulation comprises about 150-500 mg total phenolic compounds.

In some embodiments, the subject is administered a total daily dose of the liquid extract or the powder extract comprising at least about 10 mg of total phenolic compounds per kg body weight. In some embodiments, the subject is administered a total daily dose of the liquid extract or the powder extract comprising about 10 mg, 20 mg, 40 mg, or 80 mg of total phenolic compounds per kg body weight. In some embodiments, the total phenolic compound content of the liquid extract or formulation per dose is at about 20 mg/mL. In some embodiments, a dose of the liquid extract comprises about 2.5 g to about 3.5 g total phenolic compounds.

In some embodiments, the disease is cancer. In some embodiments, administering the extract inhibits at least one of cancer-related cell growth or proliferation, angiogenesis, inflammation, or fibrosis. In some embodiments, the cancer comprises at least one of breast cancer, prostate cancer, colon cancer, glioblastoma, lung cancer, skin cancer, leukemia, or lymphoma. In some embodiments, the breast cancer is at least one of triple negative breast cancer, estrogen receptor positive breast cancer, or HER2 over-expressing breast cancer. In some embodiments, the cancer comprises brain metastatic breast cancer. In some embodiments, the extract is administered in combination with at least one of a chemotherapeutic agent or radiation therapy.

In some embodiments, the disease is hypertension-induced fibrosis.

In some embodiments, the disease is radiation-induced fibrosis.

In some embodiments, the disease is radiation-induced bone loss. This can be reflected in loss of bone strength and/or increased bone fragility, decreased calcium content, and reduced bone mass.

While aspects of the invention will now be described in connection with certain preferred embodiments in the following examples and with reference to the attached figures so that aspects thereof may be more fully understood and appreciated, it is not intended to limit the invention to these particular embodiments. On the contrary, this application is intended to cover all alternatives, modifications and equivalents as may be included within the scope of the invention as defined by the appended claims. Thus, the following examples, which include preferred embodiments, will serve to illustrate the practice of the described compositions, methods, and kits, it being understood that the particulars shown are by way of example and for purposes of illustrative discussion of preferred embodiments only, and are presented in the cause of providing what is believed to be useful and readily understood description of formulation procedures, as well as of the principles and conceptual aspects of the invention. It will be evident to those skilled in the art that the invention described herein may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

EXAMPLES

Example 1

Production of Muscadine Grape Seed and Grape Skin Liquid and Powders Extracts (1) 314 pounds of grape seed and 59 pounds of skins were placed into an open steam kettle.

(2) 100 gallons of fractional vapor compression distilled water was added to the grape seeds and grape skins in the vessel.

(3) The grape seeds and grape skins in the fractional vapor compression distilled water were heated for about 1 hour to about 2 hours at about 175° F. to 200° F. maximum. Extraction was performed at atmospheric pressure. The maximum temperature of 200° F. is set to avoid boiling the grape seeds, grape skins and water because boiling can destroy the phenolic compounds, reducing overall total phenolic compound content in the final extract. During heating, additional fractional vapor compression distilled water was added in 5 gallon increments every 15 to 30 minutes to reach a total of 140 gallons of water. During heating, the mixture of grape seeds, grape skins, and fractional vapor compression distilled water were agitated by stirring with a paddle. While an open steam kettle was used, any vessel that can hold the desired amount of water and grape seeds and skins at atmospheric pressure may be suitable.

(4) After heating, the temperature was reduced and contents of the kettle were cooled to about 170° F. to about 180° F. and then filtered through a 600 mesh stainless steel sieve. The filtrate was collected in a stainless steel barrel.

(5) Potassium sorbate was added to 0.1% w/v to the grape seed and grape skin filtrate of (3).

(6) The filtrate of (5) was refrigerated for at least 24 hours at a temperature of about 35° F. to about 40° F. and then filtered through a 1 micron filter. Organic food grade alcohol (95%) was added to 2% (v/v) of the extract to produce the grape seed and grape skin liquid extract. The liquid extract formed by this process was used in the studies described in Example 5.

The following steps were performed to produce a grape seed and grape skin powder extract.

(7) The liquid extract was processed into a powder extract by spray-drying. The liquid extract was atomized, with the spray being introduced into a 44 inch×32 inch dryer. Drying was performed with natural gas with a flow rate of 18,000-22,000 cfm and at a temperature in the range of about 200-400° F. (e.g., inlet temperature about 400° F. and outlet temperature about 200° F.). The resultant powder extract had a residual moisture content of about 3.0-3.4%.

The powder extract formed by this process may be, for example, encapsulated or reconstituted to form a liquid. For the studies described in Examples 6 and 7, the powder extract made as described in this example was formulated in a hypromellose capsule.

The stability of the powdered extract formulated in a hypromellose capsule at room temperature was assessed over 3-6 months. Initial total phenolic levels were 301.4±18.0 mg/g (n=3) and 296.6±22.5 mg/g (n=3) after 3-6 months. There was no evidence of microbial contamination after 6 months storage.

An exemplary analysis of the liquid extract produced as described above is provided in Tables 1. The analysis was performed with high performance liquid chromatograph (HPLC); methodology noted below by footnote. ND means "not detected."

TABLE 1

Liquid extract component analysis.

| Component | mg/L |
| --- | --- |
| Trans-Resveratrol[1] | 1.1 |
| Total Ellagic acid[1] | 967.73 |
| Myricetin[2] | 32.58 |
| Quercetin[2] | 44.11 |
| Free Ellagic acid[3] | 106.81 |
| Total Ellagic acid[3] | 967.73 |
| Ascorbic acid[4] | 41.11 |
| Pantothenic acid[4] | 3450.81 |
| Folic acid[4] | 184.3 |
| Cyanocobalamin[4] | 32.45 |
| Riboflavin[4] | 8.74 |
| Thiamin[4] | ND |
| Nicotinamide[4] | ND |
| Pyridoxamine[4] | ND |
| Gallic acid[5] | 80.19 |
| Caffeic acid[5] | 468.83 |
| Gallocatechin[6] | 185.53 |
| Epigallocatechin[6] | ND |
| Catechin[6] | 33.42 |
| Epicatechin[6] | 738.26 |
| Epigallocatechin gallate[6] | ND |
| Gallocatechin gallate[6] | ND |
| Epicatechin gallate[6] | 72.53 |
| Catechin gallate[6] | 41.39 |
| Total Anthocyanin[7] | 340 |
| Kaempferol[8] | ND |
| Piccatannol[9] | ND |
| Proanthocyanidin (PAC)[10] | 2686.7 |

TABLE 1-continued

Liquid extract component analysis.

| Component | mg/L |
|---|---|
| Monomer[10] | 1113.2 |
| Dimer[10] | 345.3 |
| 3mer[10] | 158.6 |
| 4mer[10] | 88.6 |
| 5mer[10] | 54.3 |
| 6mer[10] | 645.4 |
| >10mer[10] | 281.3 |

Ftnt 1: Analysis performed according to Wang, S. Y., et al., Resveratrol Content in Strawberry Fruit is Affected by Preharvest Conditions, *J. Agri. Food Chem.* 2007, 55:8269-8274. Limit of detection: 0.05 µg/mL.

Ftnt 2: Analysis performed according to Lui, X., et al., Simultaneous determination of seven active flavonols in the flowers of abelmoschus manihot by HPLC, *J. Chromatogr. Sci.* 2009, 47:206-210.

Ftnt 3: Analysis performed according to Urska, V., et al., Concentration and mean degree of polymerization of rubus ellagitannins evaluated by optimized acid methanolysis, *J. Agric. Food Chem.* 2006, 54:4469-4475.

Ftnt 4: Analysis performed according to Heudi, O., et al., Separation of water-soluble vitamins by reversed-phase high performance liquid chromatography with ultra-violet detection: Application to polyvitaminated premixes. *J. Chromatography* 2005, 1070: 49-56. Limit of detection: thiamin—0.2 µg/mL, nicotinamide—0.2 µg/mL, pyridoxamine—0.1 µg/mL.

Ftnt 5: Analysis performed according to Chen, G., et al., Melatonin in Chinese medicinal herbs, *Life Sciences* 2003, 73:19-26.

Ftnt 6: Analysis performed according to Santasania, C. T., et al., Application Report 194—LC-MS Analysis of Catechins on Ascentis™ RP-Amide, 2004, available at sigma-aldrich.com/supelco.

Ftnt 7: Analysis performed according to Cheng, G. W. et al., Activity of phenylalanine ammonia-lyase (pal) and concentrations of anthocyanins and phenolics in developing strawberry fruit. J. Am. Soc. Hortic. Sci. 1991, 116(5):865-869. The anthocyanin result is expressed as milligram cyanidine-3-glucoside equivalency per liter.

Ftnt 8: Analysis performed according to Chen, J., et al., Determination of Seven Flavonoids in Ixeridium gracile (DC.) Shih by High-Performance Liquid Chromatorgraphy, J. AOAC Int. 2009, 92:773-778. Limits of detection: 0.14 µg/mL.

Ftnt 9: Analysis performed according to Lin, L. L., et al., An effective sample preparation approach for screening the anticancer compound piceatannol using HPLC coupled with UV and fluorescence detection, *J. Chromatogr. B Analyt. Technol. Biomed Life Sci.* 2007, 853:175-182. Limit of detection: 0.14 µg/mL.

Ftnt 10: Analysis performed according to Robbins, R. J., et al., Method performance and multi-laboratory assessment of a normal phase high pressure liquid chromatography-fluorescence detection method for the quantification of flavanols and procyanidins in cocoa and chocolate containing samples, *J. Chromatorg. A* 2009, 1216:4831-4840. Limit of detection: 0.9 µg/mL.

Figure 1A:
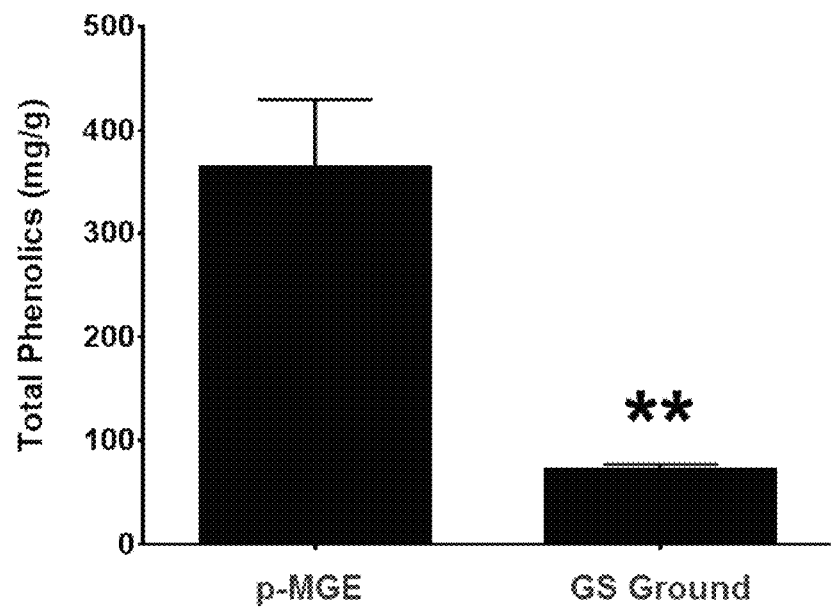
FIGS. 1A-1B show assessment of phenolic compound content of a muscadine grape seed and grape skin powder extract (p-MGE) made according to the method of Example 1 in comparison to a commercial supplement containing ground muscadine grape seed (GS Ground).
Figure 1B:
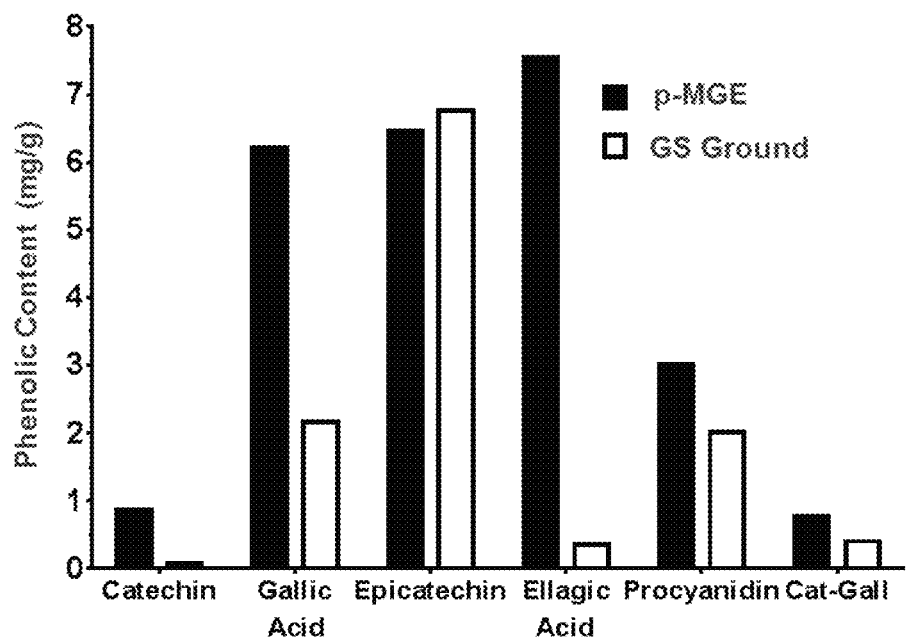

An exemplary analysis of the powder extract produced as described above is shown in FIGS. 1A-1B. The powder extract (p-MGE) was removed from the capsule from which it had been formulated (446 mg total powder extract). A comparison analysis was also performed on a commercially available ground grape seed product (Premium Muscadine Grape Seed Supplement, Nature's Pearl, Advance NC). Total phenolics were measured using a modification of the colorimetric Folin-Ciocalteau method, using gallic acid as a standard. The powder and the contents from the commercial product were resuspended in water and homogenized using a TissueLyzer™ (Qiagen). The data are expressed as mg phenolics per gram powder or solids in FIG. 1A. n=3, ** denotes p<0.01. The powder extract of the disclosure contains significantly more phenolics than the commercially available capsules containing ground grape seeds. Individual polyphenolics—catechin, gallic acid, epicatechin, ellagic acid, procyanadin, and catechin-gallate (cat-gall)—in the powder extract and the commercial ground grape seed capsule were also measured by Shimadzu ultra-high performance liquid chromatography (UPLC) coupled to mass spectroscopy detection (UPLC-MS) and identified by comparison to standards. The data are expressed as mg per gram powder in FIG. 1B. The individual phenolic compounds assessed were either comparable between the two products or substantially elevated in the powder extract of the disclosure.

Example 2

Production of Muscadine Grape Seed Extract (1) 450 pounds of grape seed were placed into an open steam kettle, and 100 gallons of fractional vapor compression distilled water was added. As in Example 1, an open steam kettle was used but any vessel that can hold the desired amount of water and grape seeds and skins at atmospheric pressure may be suitable.

(2) The grape seeds in the fractional vapor compression distilled water were heated for about 1 hour to about 2 hours at about 175° F. to 200° F. maximum. The maximum temperature of 200° F. is set to avoid boiling the grape seeds and water because boiling destroys the phenolic compounds. During heating, additional fractional vapor compression distilled water was added in 5 gallon increments every 15 to 30 minutes to reach a total of 140 gallons of water.

(3) After heating, the temperature was reduced and the grape seeds in the water were cooled to about 170° F. to about 180° F. and then filtered through a 600 mesh stainless steel sieve. The filtrate was collected in a stainless steel barrel.

(4) Potassium sorbate was added to 0.1% w/v to the grape seed filtrate of (3).

(5) The filtrate of (4) was refrigerated for at least 24 hours at a temperature of about 35° F. to about 40° F. and then filtered through a 1 micron filter. Organic food grade alcohol was added to 2% (v/v) of the extract to produce the grape seed liquid extract.

The grape seed liquid extract prepared using the above method may be combined (blended) with grape skin liquid extract made using the method described in Example 3. The grape skin liquid extract, or a combination of the grape skin liquid extract and grape seed liquid extract made using the method described in Example 2, may be spray-dried as described in Example 1, to produce a powdered extract, which may be, for example, encapsulated or reconstituted to form a liquid.

Example 3

Production of Muscadine Grape Skin Extract (1) 200 pounds of grape skin were placed into an open steam kettle, and 100 gallons of fractional vapor compression distilled water was added. As in Example 1 and 2, an open steam kettle was used but any vessel that can hold the desired amount of water and grape seeds and skins at atmospheric pressure may be suitable.

(2) The grape skins were heated in the fractional vapor compression distilled water for about 1 hour to about 2 hours at about 175° F. to a maximum of 200° F. The maximum temperature of 200° F. avoids boiling the grape skins and water and destroying the phenolic compounds. During heating, additional fractional vapor compression distilled water is added in 5 gallon increments every 15 to 30 minutes for a total of 140 gallons of water added.

(3) After heating, the temperature was reduced and the grape skins in water were cooled to about 170° F. to about 180° F. and then filtered through 600 mesh stainless steel sieve. The filtrate was collected in a stainless steel barrel.

(4) Potassium sorbate was then added to 0.1% w/v to the grape skin filtrate.

(5) The filtrate was then refrigerated for at least 24 hours at a temperature of about 35° F. to about 40° F. and then filtered through a 1 micron filter. Organic food grade alcohol was added to 2% to produce the grape skin liquid extract.

In some aspects, the total phenolics in an extract of the grape skins can be at least about 3 g/L to about 8 g/L.

The grape skin liquid extract, alone or in combination with a portion of the grape seed liquid extract made using the method described in Example 2. The grape skin liquid extract, or a combination of the grape skin liquid extract and the grape seed liquid extract made using the method described in Example 2, may be spray-dried as described in Example 1, to produce a powdered extract, which may be, for example, encapsulated or reconstituted to form a liquid.

Example 4

In vitro Studies in Human Cancer Cells Using Known Muscadine Grape Seed and Grape Skin Extracts The studies described in this example were performed with a muscadine grape seed liquid extract or muscadine grape skin liquid extract manufactured by different methods than described in this disclosure. In particular, the extraction process was performed in a pressurized vessel, the extraction temperature reaching at least 212° F. (boiling).

Figure 2A:
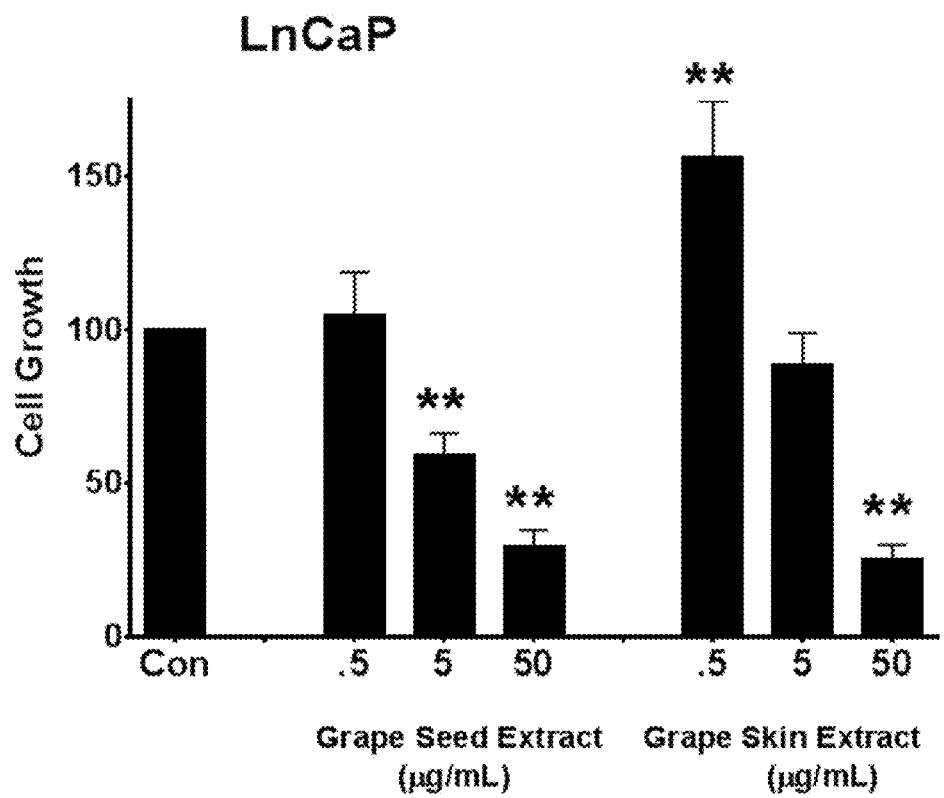
FIG. 2A and FIG. 2B show graphs illustrating cell growth analysis for cell lines treated with grape skin extract or grape seed extract made using different methods from those described herein. LnCaP (FIG. 2A) or PC3 (FIG. 2B) human prostate cancer cells were incubated with increasing concentrations of either muscadine grape seed or grape skin extracts and cell proliferation was quantified by counting the number of cells per well. The data is presented as the percent of the Control (Con), which was not treated with either extract. $n=12$, ** denotes $p<0.01$. The growth of human prostate cancer cells was inhibited by increasing concentrations of either an extract isolated form muscadine grape seeds or grape skins. There was no difference in the proliferation of prostate cancer cells using extracts from muscadine grape skin compared to muscadine grape seeds.
Figure 2B:
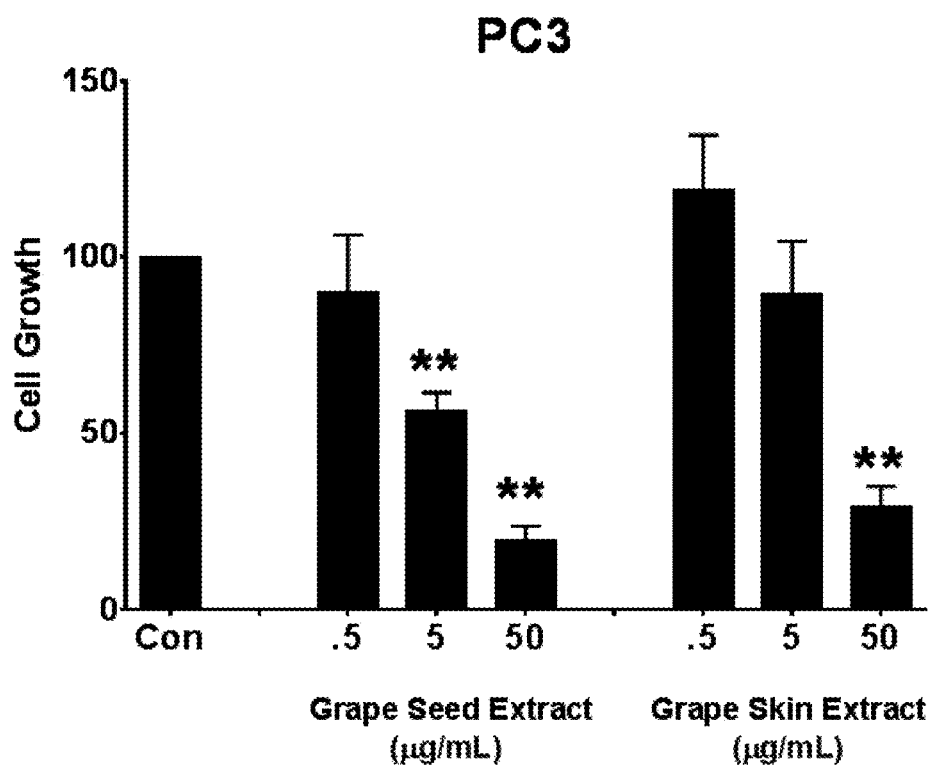
Figure 2C:
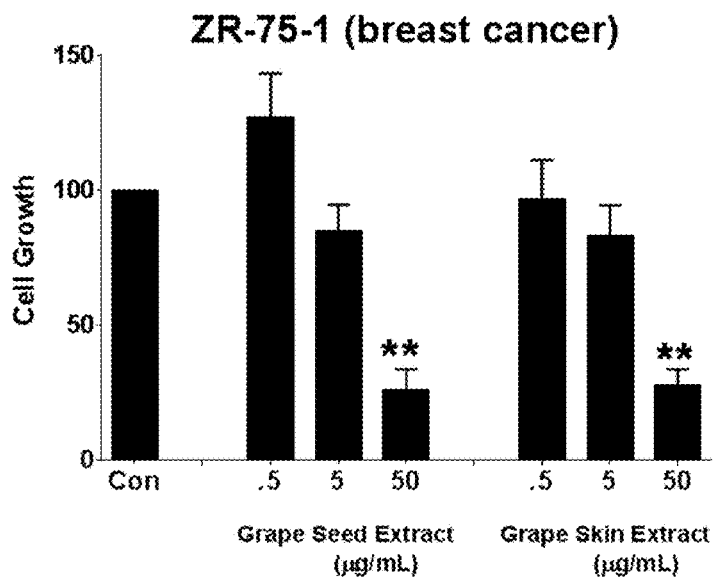
FIGS. 2C-2E show graphs illustrating cell growth analysis for cell lines treated with grape seed extract or grape seed extract made using different methods from those described herein. ZR-75-1 cells are human estrogen-receptor positive breast cancer cells, MDA-MD-231 are human triple-negative breast cancer cells, and SKBR3 cells are human epidermal growth factor 2 (HER2) over-expressing breast cancer cells. ZR-75-1, MDA-MD-231, and SKBR3 cells were incubated with increasing concentrations of either muscadine grape seed or grape skin extracts and cell proliferation was quantified by counting the number of cells per well. The data is presented as the percent of the Control (Con), which was not treated with either extract. $n=9$ for ZR-75-1 cells, $n=6$ for MDA-MB-231 cells, and $n=18$ for SKBR3 cells; * denotes $p<0.05$ and ** denotes $p<0.01$ compared to control. The growth of human breast cancer cells was inhibited by increasing concentrations of either extract.
Figure 2D:
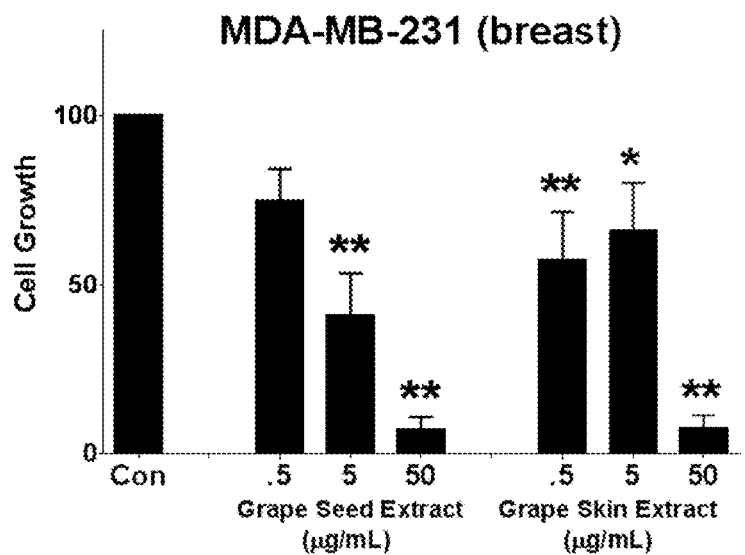
Figure 2E:
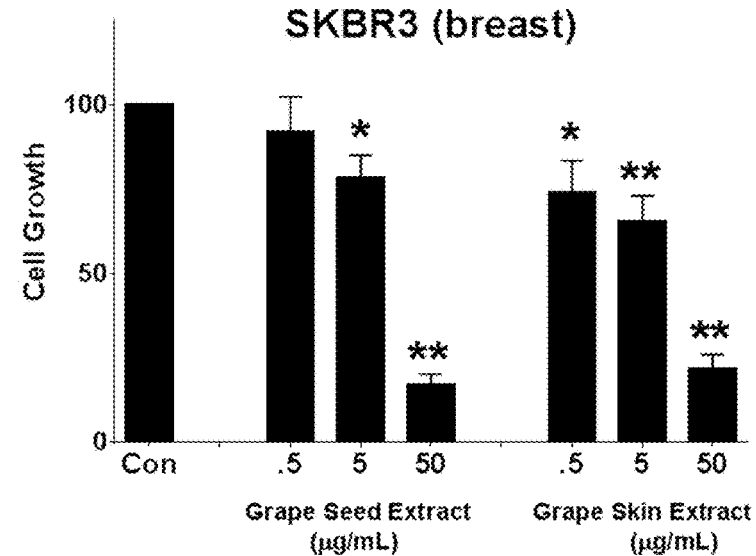
Figure 2F:
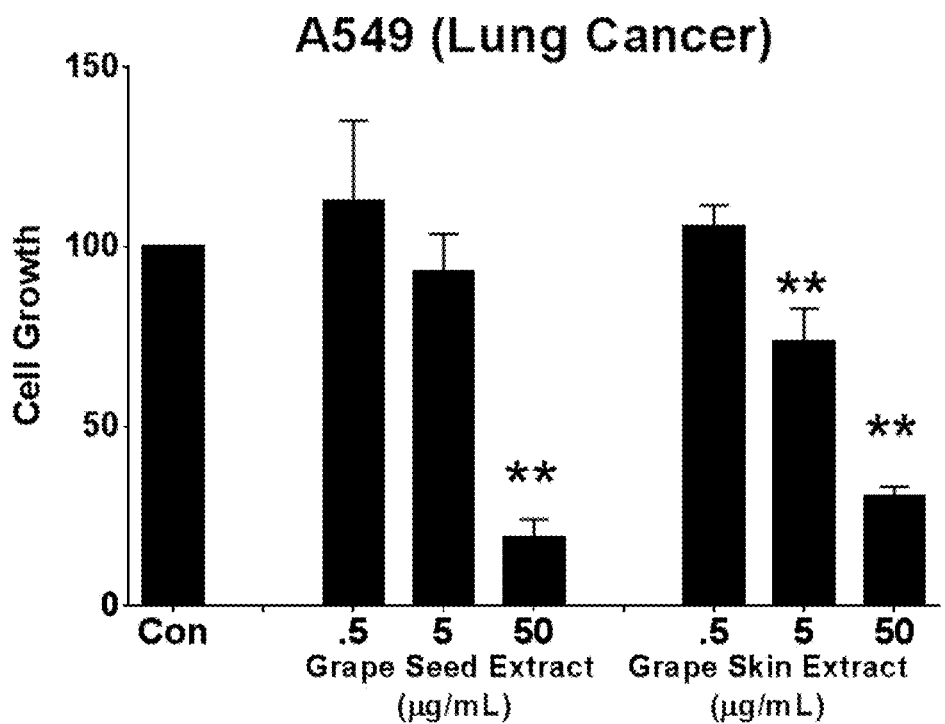
FIGS. 2F-2G show graphs illustrating cell growth analysis for cell lines treated with grape seed extract or grape seed extract made using different methods from those described herein. A549 and SK-LU-1 human lung cancer cells were incubated with increasing concentrations of either muscadine grape seed or grape skin extracts and cell proliferation was quantified by counting the number of cells per well. The data is presented as the percent of the Control (Con), which was not treated with either extract. $n=12$ for A549 cells and $n=9$ for SK-LU-1 cells; ** denotes $p<0.01$. The growth of human lung cancer cells was inhibited by increasing concentrations of either an extract isolated form muscadine grape seeds or grape skins. There was no difference in the proliferation of lung cancer cells treated with either muscadine grape seed or grape skin extracts.
Figure 2G:
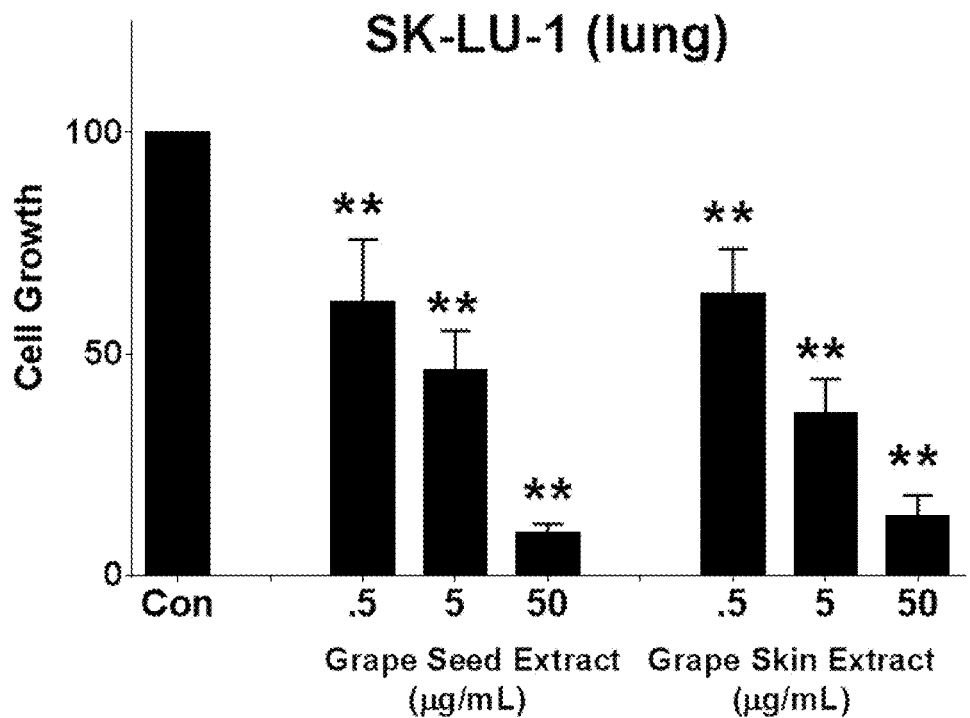
Figure 2H:
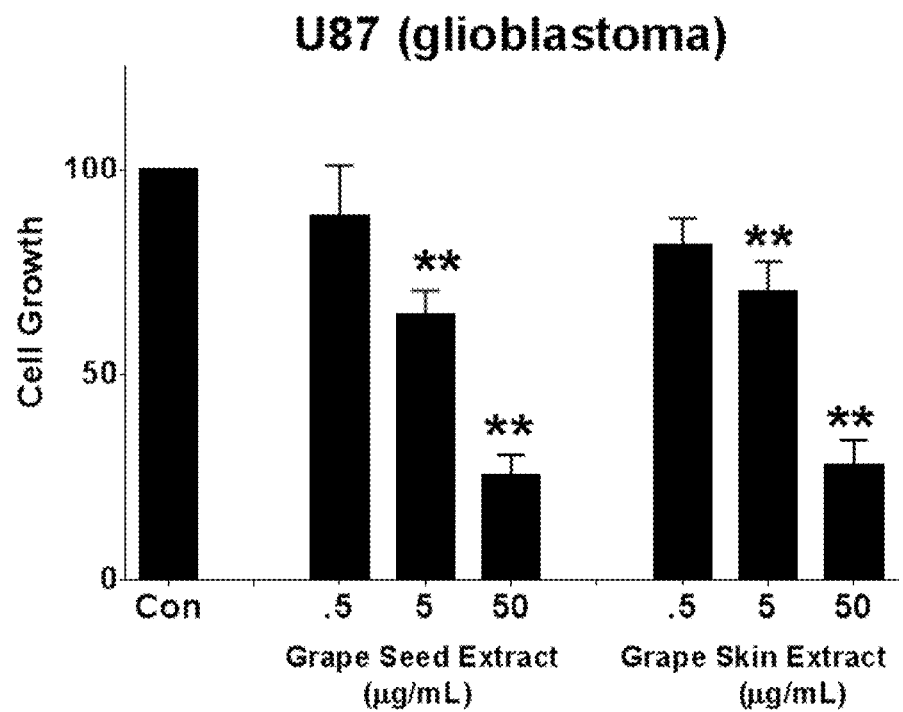
FIGS. 2H-2I show graphs illustrating cell growth analysis for cell lines treated with grape seed extract or grape seed extract made using different methods from those described herein. U87 and U373 human glioblastoma were incubated with increasing concentrations of either muscadine grape seed or grape skin extracts and cell proliferation was quantified by counting the number of cells per well. The data is presented as the percent of the Control (Con), which was not treated with either extract. $n=12$ for U87 cells and $n=9$ for U373 cells; ** denotes $p<0.01$. The growth of human glioblastoma was inhibited by increasing concentrations of either an extract isolated form muscadine grape seeds or grape skins. There was no difference in the proliferation of glioblastoma treated with either muscadine grape seed or grape skin extracts.
Figure 2I:
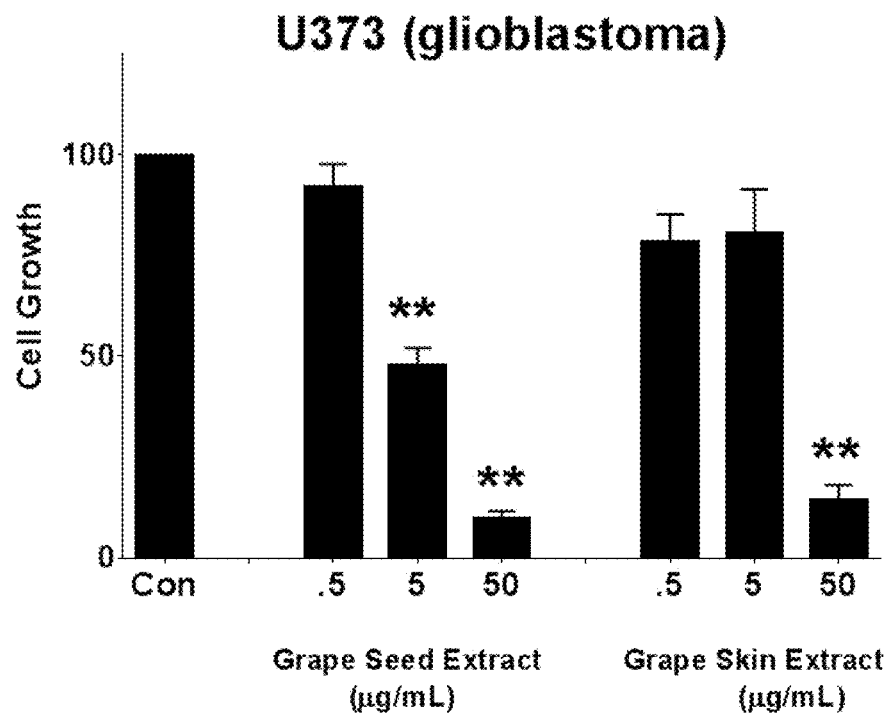
Figure 2J:
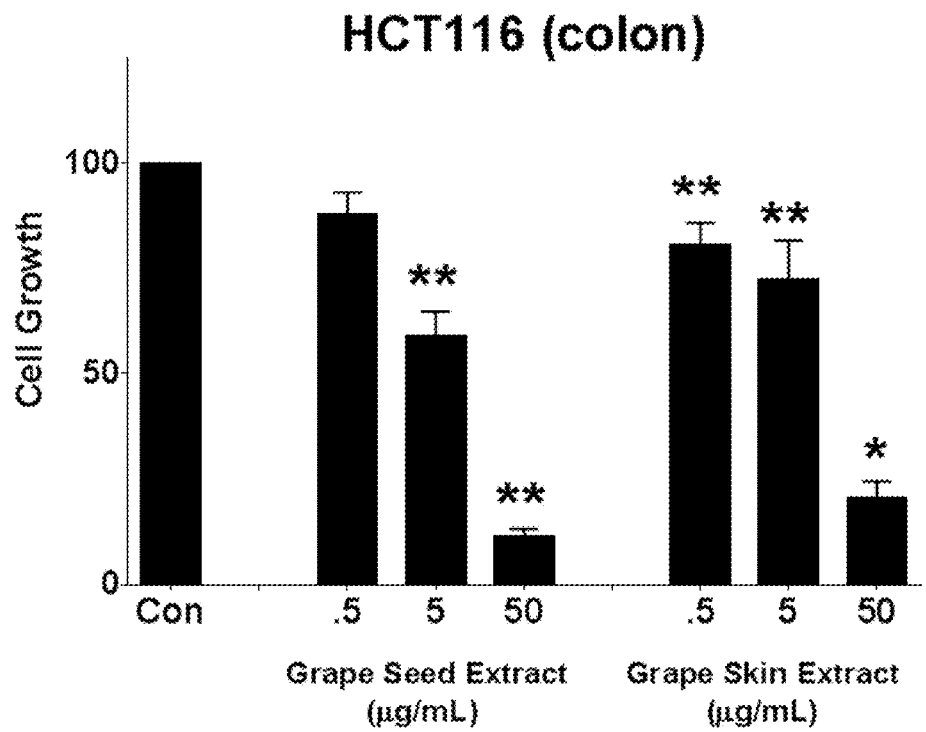
FIGS. 2J-2K show graphs illustrating cell growth analysis for cell lines treated with grape seed extract or grape seed extract made using different methods from those described herein. HCT116 and HT29 human colon cancer cells were incubated with increasing concentrations of either muscadine grape seed or grape skin extracts and cell proliferation was quantified by counting the number of cells per well. The data is presented as the percent of the Control (Con), which was not treated with either extract. $n=15-18$ for HCT116 cells and $n=12$ for HT29 cells; * denotes $p<0.05$ and ** denotes $p<0.01$. The growth of human colon cancer cells was inhibited by increasing concentrations of either an extract isolated form muscadine grape seeds or grape skins. There was no difference in the proliferation of colon cancer cells treated with either muscadine grape seed or grape skin extracts.
Figure 2K:
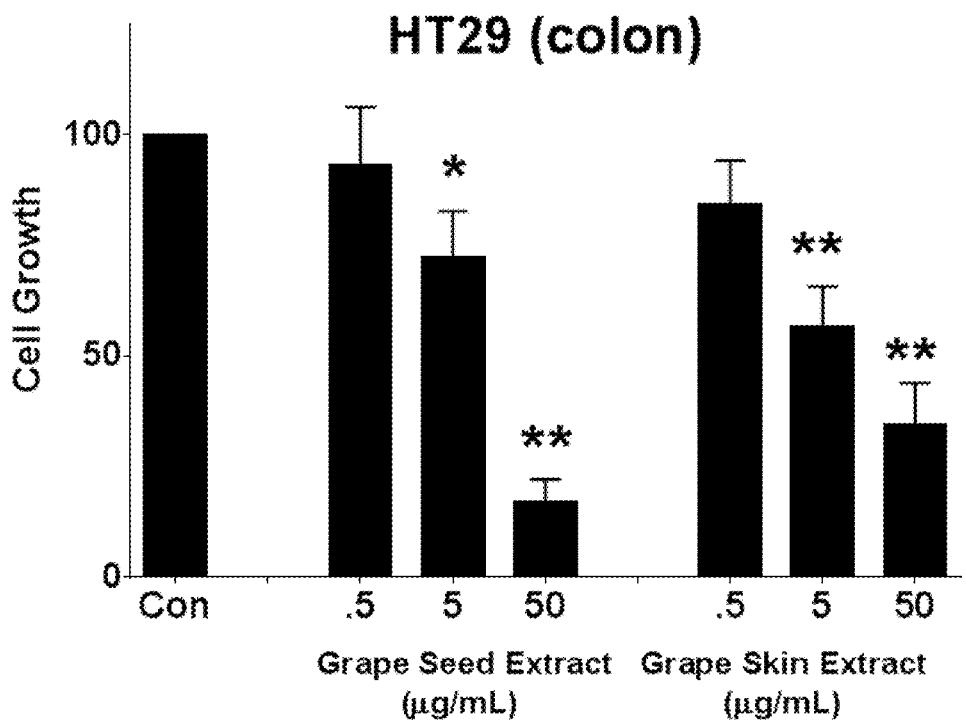
Figure 2L:
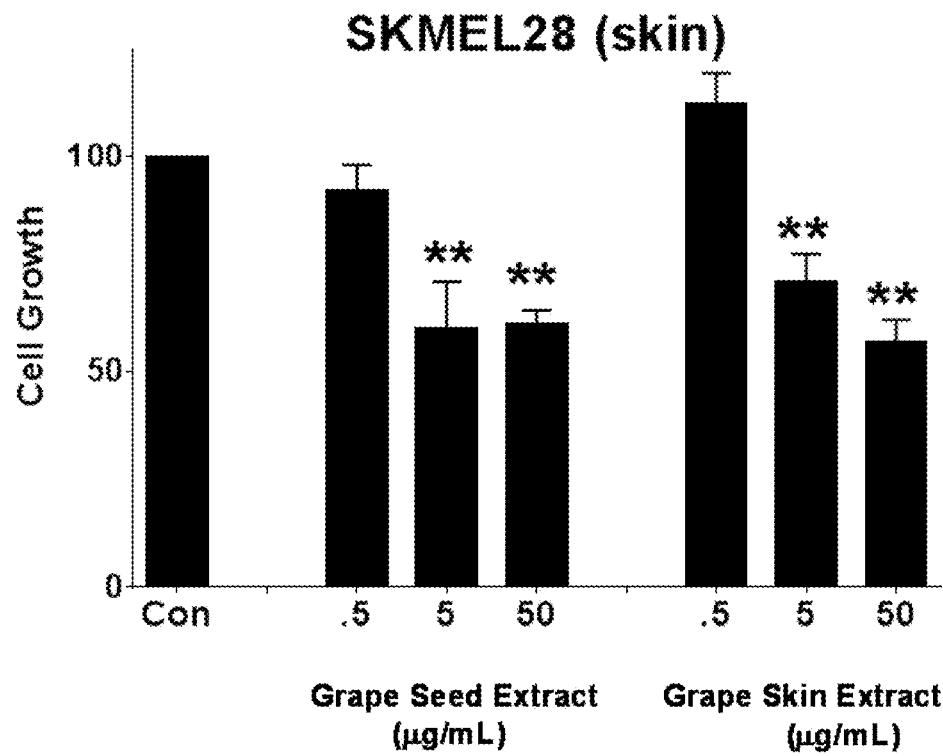
FIGS. 2L-2M show graphs illustrating cell growth analysis for cell lines treated with grape seed extract or grape seed extract made using different methods from those described herein. SKMEL28 and RPMI 7951 human colon cancer cells were incubated with increasing concentrations of either muscadine grape seed or grape skin extracts and cell proliferation was quantified by counting the number of cells per well. The data is presented as the percent of the Control (Con), which was not treated with either extract. $n=6$ for SKMEL28 cells and $n=9$ for RPMI 7951 cells; * denotes $p<0.05$ and ** denotes $p<0.01$. The growth of human skin cancer cells was inhibited by increasing concentrations of either an extract isolated form muscadine grape seeds or grape skins. There was no difference in the proliferation of skin cells treated with either muscadine grape seed or grape skin extracts.
Figure 2M:
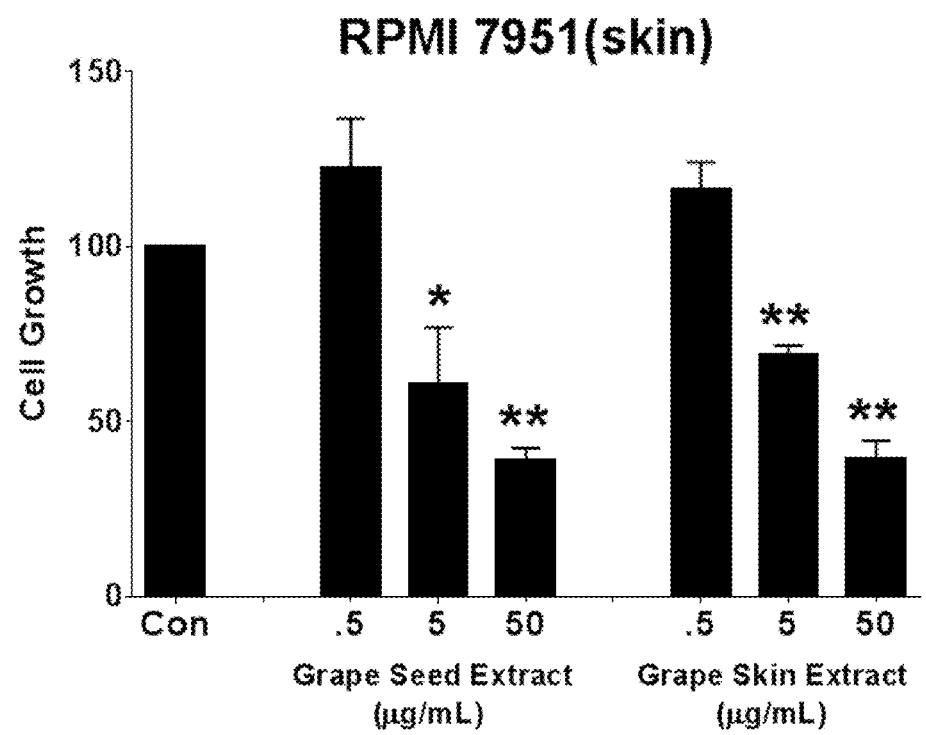
Figure 2N:
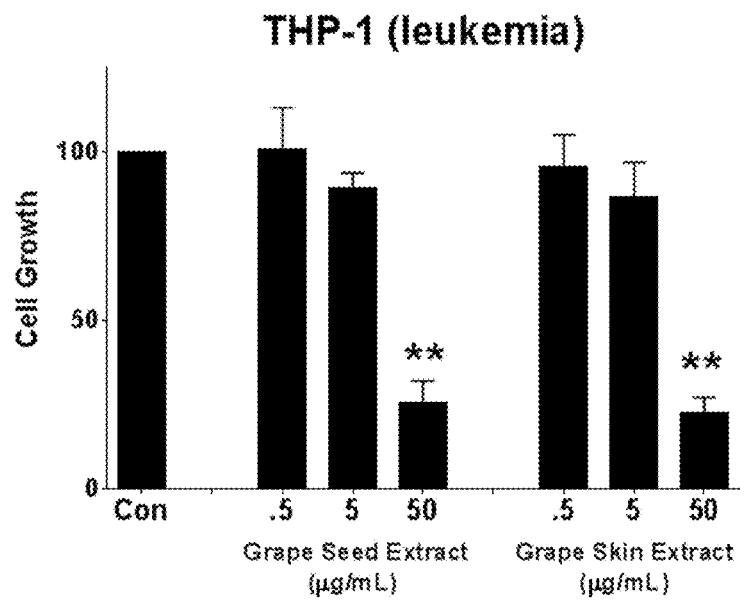
FIGS. 2N-2P show graphs illustrating cell growth analysis for cell lines treated with grape seed extract or grape seed extract made using different methods from those described herein. THP-1—acute human monocytic leukemia cells, HL60—acute human promyelocytic leukemia cells and K562—chronic human myelogenous leukemia cells were incubated with increasing concentrations of either muscadine grape seed or grape skin extracts and cell proliferation was quantified by counting the number of cells per well. The data is presented as the percent of the Control (Con), which was not treated with either extract. n=12 for THP-1 cells, n=12 for HL60 and n=12 for K562 cells; * denotes p<0.05 and ** denotes p<0.01. The growth of human leukemia cells was inhibited by increasing concentrations of either an extract isolated form muscadine grape seeds or grape skins. There was no difference in the proliferation of leukemia cells treated with either muscadine grape seed or grape skin extracts.
Figure 2O:
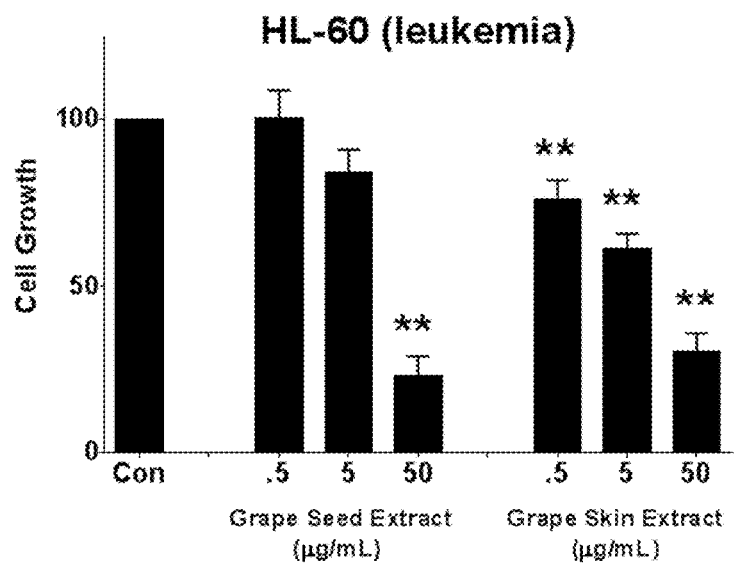
Figure 2P:
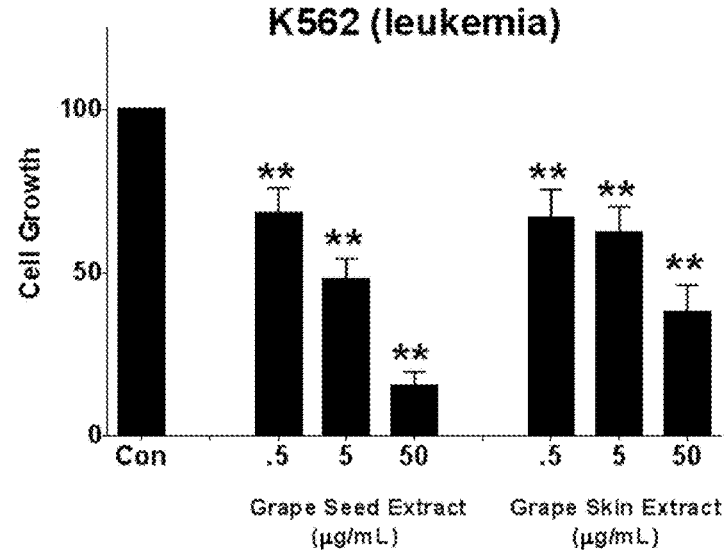

A. Inhibition of Cancer Cell Proliferation by Muscadine Grape Seed and Grape Skin Extracts Actively growing human prostate, breast, lung, glioblastoma, colon, skin and leukemia cells—either 2 or 3 different cell lines—were plated into individual wells of 24 well plates and treated for 7 days with increasing concentrations of extracts from either muscadine grape seeds or skins, to determine whether the extracts reduced prostate cancer cell proliferation. Extracts from both grape seeds and skin reduced the proliferation of all seven types of cancer including human prostate cancer (LnCaP and PC3 cells; FIGS. 2A-2B), breast cancer (ZR-75-1 estrogen receptor positive breast cancer cells, MDA-MB-231 triple negative breast cancer cells and SKBR3 HER2 over-expressing breast cancer cells; FIGS. 2C-2E), lung cancer (A549 and SK-LU-1 cells; FIGS. 2F-2G), glioblastoma (U87 and U373 cells; FIGS. 2H-2I), colon cancer (HCT116 and HT29 cells; FIGS. 2J-2K), skin cancer (SKMEL28 and RPMI 7951 cells; FIGS. 2L-2M) and leukemia (THP-1 acute human monocytic leukemia cells, HL60 acute human promyelocytic leukemia cells, and K562 chronic human myelogenous leukemia cells; FIGS. 2N-2P). The responses were dependent upon the dose of extract that was used and similar responses were obtained with grape seed extract compared to grape skin extract.

Figure 3A:
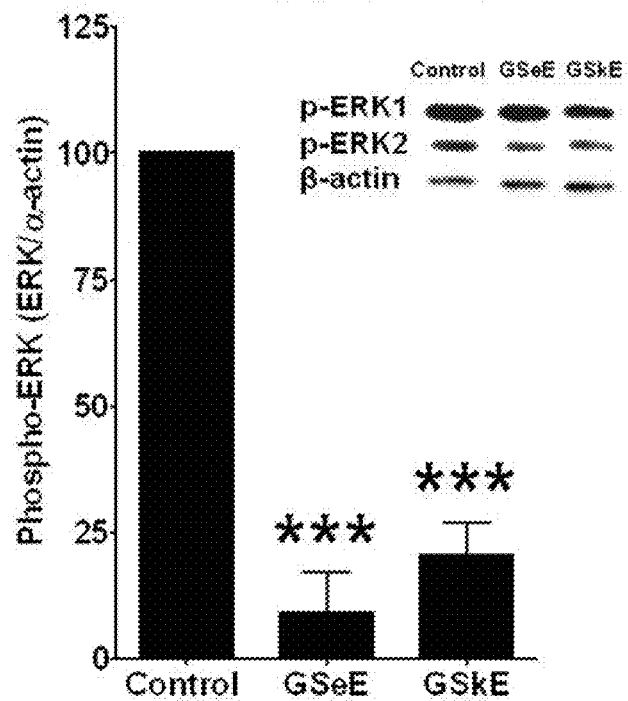
FIGS. 3A-3B show graphs illustrating MAP kinase activity for cell lines treated with grape skin extract or grape seed extract made using different methods from those described. ZR-75-1 human estrogen receptor positive breast cancer and MBA-MD-231 human triple negative breast cancer cells were incubated with 50 μg/mL muscadine grape seed extract (GSeE) or muscadine grape skin extract (GSkE) for 4 h and phospho-ERK (both ERK1 and ERK2) was measured using an antibody from Cell Signaling. The amount of phospho-ERK was quantified by densitometry using β-actin as a loading control. Representative gels are included. n=3-7, *** denotes p<0.001. Both the extract from muscadine grape seeds and muscadine grape skins reduced phospho-ERK1/ERK2 activities in breast cancer cells, suggesting that the extracts inhibit breast cancer cell proliferation. There was no difference in the reduction in proliferation of breast cancer cells by the muscadine grape seed extract or the muscadine grape skin extract.
Figure 3B:
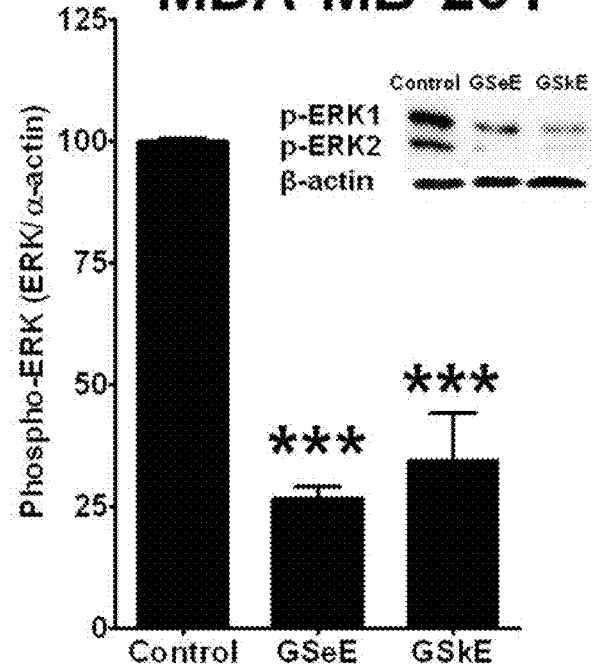

B. Inhibition of MAP Kinase Activity by Muscadine Grape Seed or Grape Skin Extracts Human MDA-MB-231 or ZR-75-1 breast cancer cells were incubated with 50 μg/mL muscadine grape seed or grape skin extract for increasing periods of time. Mitogen-activated protein (MAP) kinase activity was quantified in cell extracts by Western blot hybridization using an antibody against phospho-ERK1/ERK2 from Cell Signaling. The decrease in phospho-ERK activity was calculated by densitometry using β-actin as a loading control. As shown in FIG. 3A and FIG. 3B, respectively, the extracts from both muscadine grape seeds and grape skins caused a significant reduction in phospho-ERK, suggesting that the extracts significantly reduced proliferation. There was no significant difference in the response to grape seed versus grape skin extracts.

Collectively, the in vitro results described in Example 4 demonstrate that these extracts isolated from muscadine grape seeds or muscadine grape skins inhibit the growth of prostate, breast, lung, brain (glioblastoma), colon, and skin cancers as well as leukemia cells. The reduction in breast cancer cell growth was associated with a decrease in the activity of the growth promoting protein kinases, MAP kinases ERK1 and ERK2. These results suggest that extracts from muscadine grapes may reduce tumor growth.

Example 5

Prevention of Breast and Lung Cancer by a Known Liquid Muscadine Grape Extract (l-MGE)

The studies described in this example were performed with muscadine grape seed and grape skin liquid extracts manufactured by the method described in Example 1. This liquid extract is referred to below as "l-MGE".

Part A: Prevention of Breast Tumor Formation by l-MGE in c-neu Mice

Female FVB-Tg(MMTV)NKAMul/J transgenic mouse, in which the activated rat Erbb2 (c-neu) oncogene under the direction of the mouse mammary tumor virus promoter expressed specifically in the mammary gland (c-neu mice), form mammary tumors (the equivalent of human breast cancer) by 6-8 months of age and can be used as a model for the prevention of breast cancer. c-neu mice were treated with a liquid extract from muscadine grape seeds and grape skins (l-MGE) beginning at 3 weeks of age (at the time of weaning) and were sacrificed as soon as the tumors were palpable (at 25 weeks of age) or when the tumors had coalesced (at 31 weeks of age). The dose of l-MGE was approximately 1.0 mg of phenolics for a 25 gram mouse per day (and is equivalent to approximately 10 tablespoons or 148 mL of liquid extract per day for a 70 kg man and an average concentration of 20,000 mg of phenolics/liter of l-MGE). The l-MGE was added to the drinking water and replaced twice per week. There was no difference in water or food intake in mice receiving regular water compared to water with l-MGE. At the time of sacrifice, at either 25 or 31 weeks, the breast tissue was removed and weighed, to determine whether the treatment reduced breast tumor growth. In addition, the gross weight of the mice was determined; the hearts and kidneys were also removed and weighed for subsequent assessment of tissue histology.

Figure 4A:
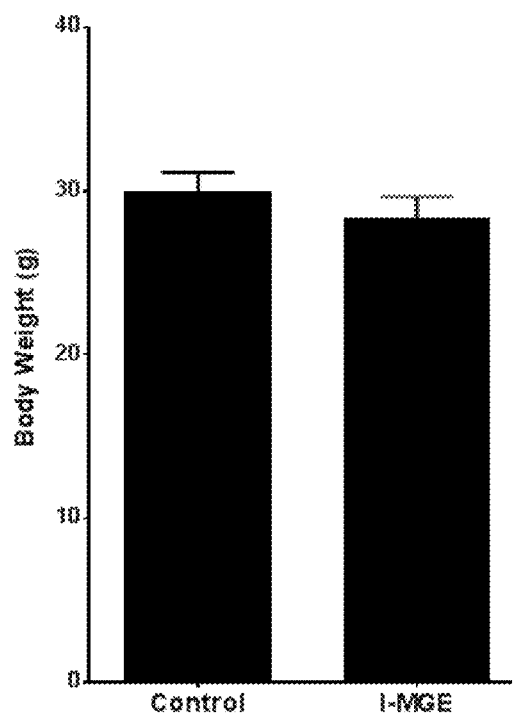
FIGS. 4A-4C show graphs illustrating body weight analysis in a breast cancer mouse model (c-neu mice) treated with muscadine grape seed and muscadine grape skin liquid extract (l-MGE) as described in Example 1. Mice were given l-MGE in their drinking water beginning at 3 weeks of age. Control mice drank regular water. The mice were euthanized after 25 weeks (FIG. 4A) or 31 weeks (FIG. 4B and FIG. 4C) and their mammary tumors were removed and weighed; the mice were weighed, either with tumors (FIG. 4A and FIG. 4B) or without the tumors (FIG. 4C). n=7-12 for tumors from 25 week-old mice and 7-10 for 31 week-old mice; * denotes p<0.05. There was no difference in the body weight of c-neu mice which drank regular water or the l-MGE for 25 weeks. Although there was a difference in the body weight of c-neu mice drinking the l-MGE at 31 weeks of age, the difference was due to the large tumors in these animals; there was no difference in body weight without tumors.
Figure 4B:
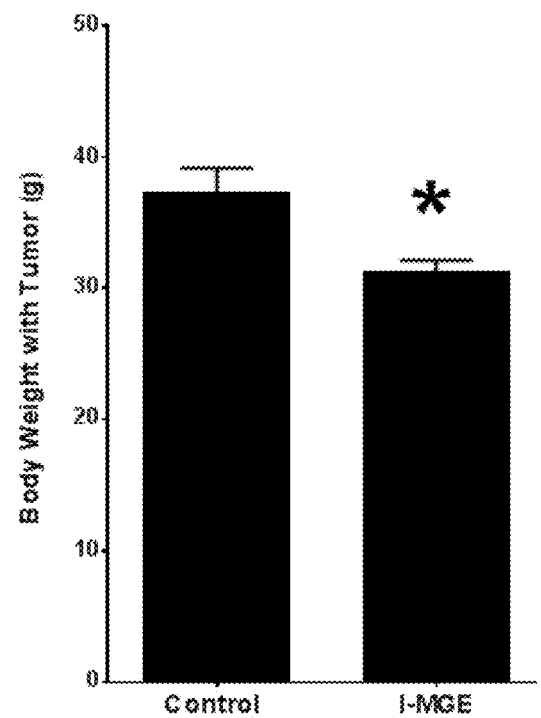
Figure 4C:
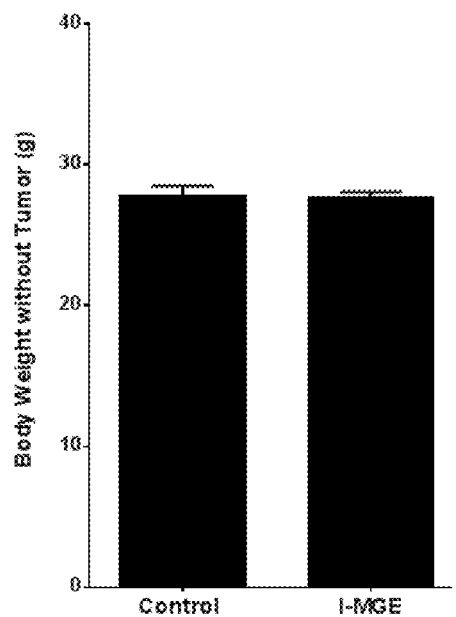

Sixteen (16) mice were treated for an average of 21 week and eighteen (18) mice were treated for an average of 31 weeks (beginning treatment at 3 weeks of age, at the time of weaning). For the 21 week mice, 10 mice drank regular drinking water (Control) and 6 mice drank l-MGE; for the 31 week mice, 10 mice drank regular drinking water (Control) and 8 mice drank water containing the l-MGE. General parameters of body, heart and kidney weights are shown in FIGS. 4A-4C, FIGS. 5A-5B, and FIGS. 6A-6B. There was no difference in body weight in the treated or untreated mice at 25 weeks of age (FIG. 4A). There was a significant difference in the total body weight of the mice drinking water compared to the l-MGE at 31 weeks of age (FIG. 4B). However, this was due to the large size of the tumors in the mice; there was no difference in the weight of the 31 week-old mice without the tumors (FIG. 4C). There was no significant difference in heart weight or kidney weight of mice drinking water (Control) or drinking the l-MGE at either 25 or 31 weeks of age, as shown in FIGS. 5A-5B, and FIGS. 6A-6B, respectively. There were no changes in the eating or drinking habits of the mice during the treatment, in agreement with no gross changes in body, heart or kidney weight. These results suggest that the treatment with l-MGE was well tolerated by the mice.

Figure 7:
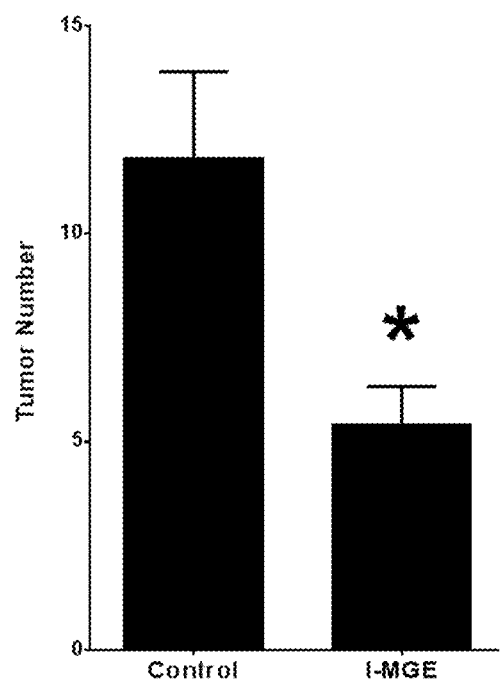
FIG. 7 shows a graph illustrating tumor multiplicity in a breast cancer mouse model (c-neu mice) treated with muscadine grape seed and muscadine grape skin liquid extract (l-MGE) as described in Example 1. Mice were given l-MGE in their drinking water beginning at 3 weeks of age. Control mice drank regular water. The mice were euthanized after 25 weeks and the number of mammary tumors was counted, to determine tumor multiplicity. Individual mammary tumors were removed and weighed, to determine tumor burden (as shown in FIG. 8A-8B). n=7-11; * denotes p<0.05. Treatment of c-neu mice with the l-MGE significantly reduced the number of mammary tumors compared to mice drinking water, indicating that the extract from the muscadine grape reduces tumor multiplicity.
Figure 8A:
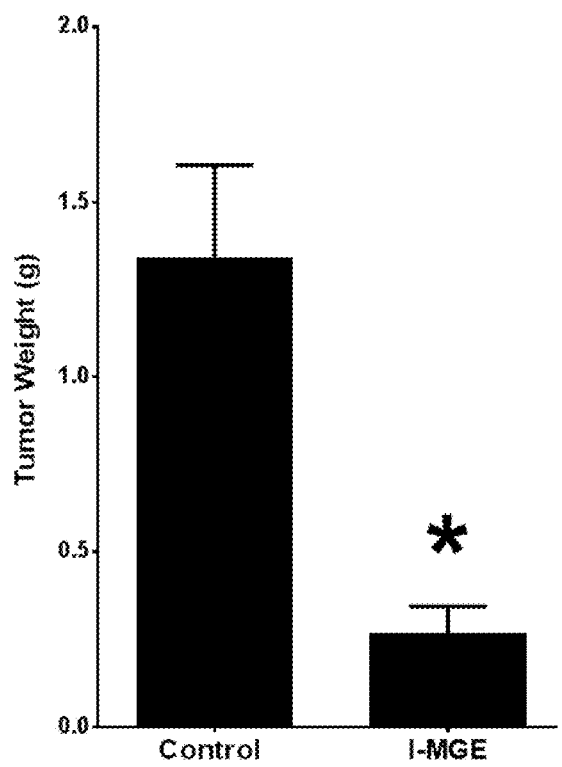
FIGS. 8A-8B show graphs illustrating tumor weight analysis in a breast cancer mouse model (c-neu mice) treated with muscadine grape seed and muscadine grape skin liquid extract (l-MGE) as described in Example 1. Mice were given l-MGE in their drinking water beginning at 3 weeks of age. Control mice drank regular water. The mice were euthanized after 25 weeks (on the left) or 31 weeks (on the right) and their mammary tumors were removed and weighed. n=6-12 for tumors from 25 week old mice and 7-10 for 31 week-old mice; * denotes p<0.05 and ** denotes p<0.01. Treatment of c-neu mice with the l-MGE significantly reduced tumor size compared to mice drinking water, indicating that the extract from the muscadine grape reduces tumor growth.
Figure 8B:
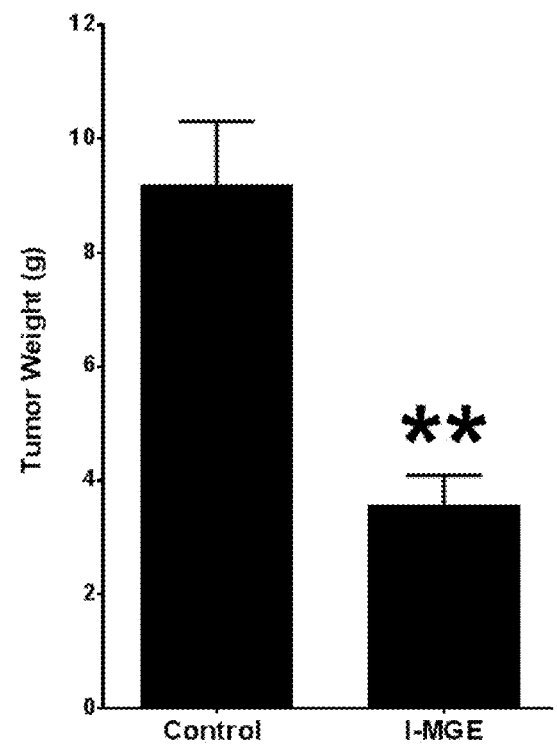

Tumors developed throughout the mammary tissue of female c-neu mice and were palpable by approximately 25 weeks of age. The individual mammary tumors in 25 week-old c-neu mice were counted, removed and weighed, to determine total tumor mass. There was an average of 11.8±2.1 tumors in the mammary tissue of untreated 25 week-old c-neu mice while the number of tumors was reduced to 5.4±0.9 in the mammary tissue of mice treated with the 1-MGE, a reduction of 54% (p=0.0327), as shown in FIG. 7. The collected tumors from 25 week-old untreated mice weighed 1.3±0.3 g while the collected tumors from 25 week-old mice treated with the l-MGE weighed an average of 0.3±0.08 g, a reduction of 77% (p=0.0132), as shown in FIG. 8A. The mammary tumors in 31 week-old c-neu mice had coalesced and the entire tumor mass was removed and weighed. The tumor mass was also reduced in 31 week-old c-neu mice treated with the 1-MGE, from an average of 9.2±1.2 g to an average of 3.6±1.4 g, a reduction of 61% (p=0.0012), as shown In FIG. 8A. This suggests that the l-MGE markedly reduced both breast tumor multiplicity and tumor burden.

Mammary tissue from mice sacrificed at 25 weeks-of-age was fixed in 4% formalin, paraffin embedded and section into 5 micron sections, for immunohistochemical analysis. Sections were incubated with an antibody to Ki67, as a measure of cell proliferation. As shown in FIG. 9, tumors from 25 week-old mice that drank the l-MGE had a significant decrease in the number of proliferating cells compared to untreated mice. The number of cells that were stained for Ki67 was 6.8±1.4 per field in sections from untreated mice compared to 2.9±1.0 cells per field in sections from mice treated with the l-MGE, a reduction of 57% (p=0.384). These results indicate that l-MGE reduces cell proliferation, in agreement with the reduction in cell number observed in cultured breast cancer cells.

Sections of mammary tissue from c-neu mice sacrificed at 25 weeks-of-age were also incubated with an antibody to phospho-ERK1/2, as a measure of active ERK1/2 MAP kinase activities. As shown in FIG. 10, phosphorylated ERK1/2 was significantly reduced in c-neu mice that were treated with the 1-MGE, from 10.5±3.1% in tissues from untreated mice to 2.9±0.9% (n=7-12, p=0.0375), a reduction of 72%. Since ERK1/2 are auto-phosphorylated upon activation, the reduction in phosphorylated ERK1/2 is indicative of a decrease in proliferative MAP kinase activities in the tumor tissues of mice treated with the l-MGE.

Figure 11:
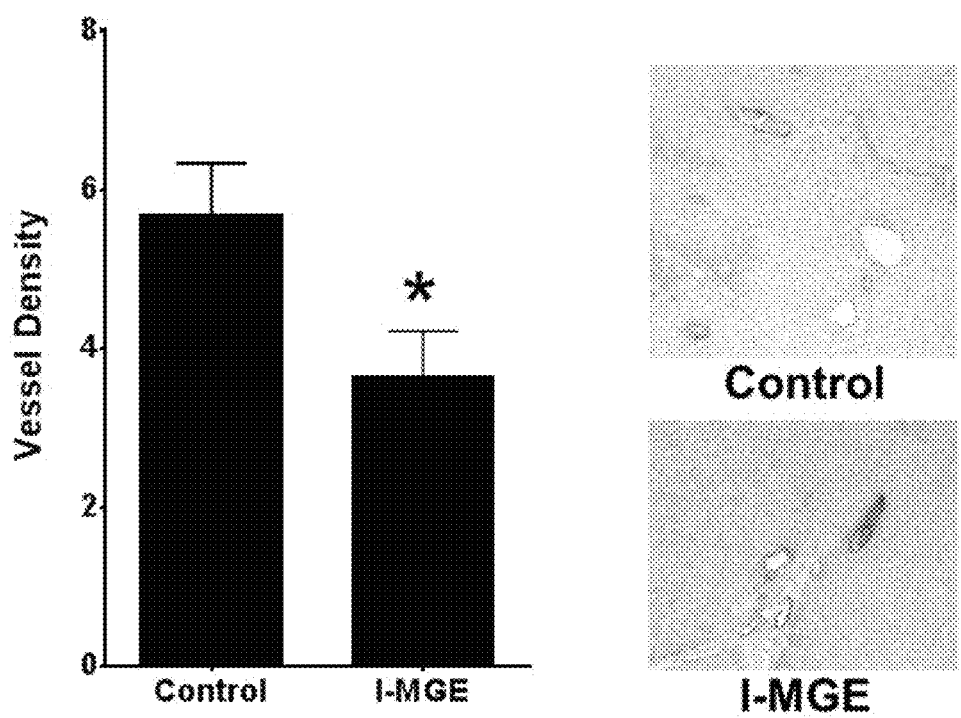
FIG. 11 shows an analysis of angiogenesis in tumors in a breast cancer mouse model (c-neu mice) treated with muscadine grape seed and muscadine grape skin liquid extract (l-MGE) as described in Example 1. Sections of tumors from Control or l-MGE-treated mice c-neu were incubated with an antibody to CD34 and blood vessels were identified by positive immunoreactivity and morphology. A graph showing vessel density is presented next to representative microscopic images. n=6-8, * denotes p<0.05. Treatment of c-neu mice with the l-MGE significantly reduced the number of vessels in the tumors as compared to control mice, suggesting that the grape extract reduces angiogenesis to reduce tumor size.

Tumor sections from c-neu mice drinking regular water (Control) or l-MGE were incubated with an antibody to the endothelial cell marker, CD34, and vessels were identified by a combination of morphology and positive CD34 immunoreactivity. As shown in FIG. 11, tumors from mice drinking l-MGE had fewer blood vessels than mice drinking regular water, from 5.7±0.6 vessels/field in tissues from untreated mice to 3.6±0.6 vessels per field (n=7-12, p=0.0226), a reduction of 37%. This suggests that the grape extract inhibits angiogenesis.

Figure 12:
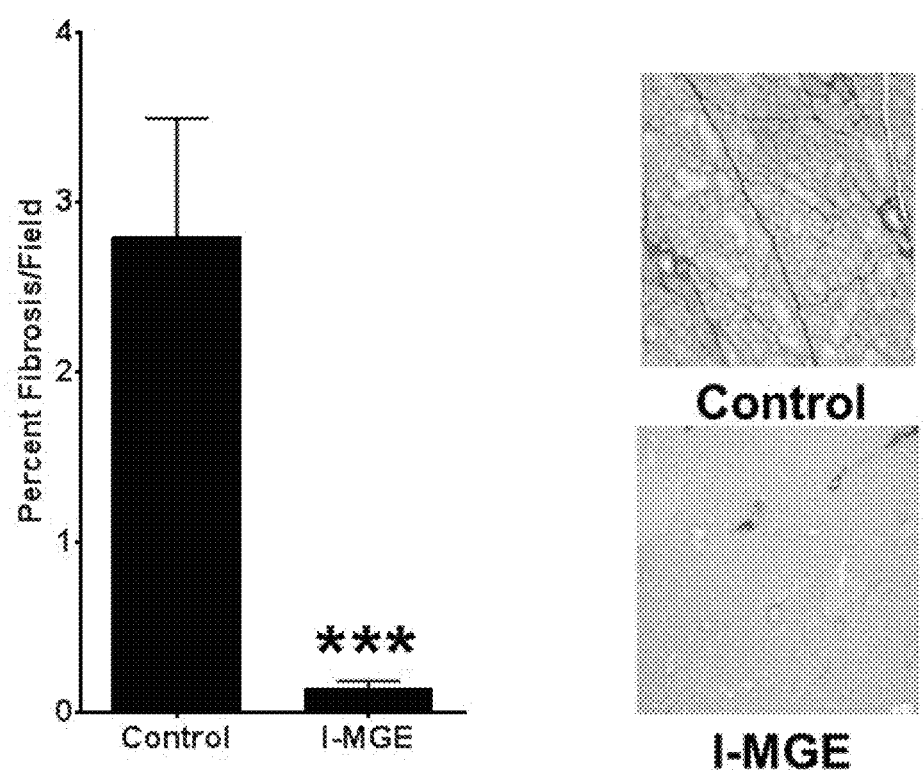
FIG. 12 shows an analysis of fibrosis in tumors in a breast cancer mouse model (c-neu mice) treated with muscadine grape seed and muscadine grape skin liquid extract (l-MGE) as described in Example 1. Sections of tumors from 31 week-old Control or l-MGE-treated c-neu mice were stained with Picrosirius red, to measure tissue fibrosis. A graph showing the percent fibrosis/field is presented next to representative microscopic images. n=6-8, *** denotes p<0.001. Treatment with the l-MGE significantly reduced the amount of staining with Picrosirius red in c-neu breast tumors as compared control mice, indicating that the l-MGE reduces fibrosis within the tumors.

Interstitial tumoral fibrosis was quantified in breast tumor tissue sections from c-neu mice and stained with picrosirius red, a nonspecific collagen stain. Collagen reaction product was markedly reduced by l-MGE administration as compared to controls (FIG. 12). The relative amount of picrosirius red staining was quantified and the amount of collagen within the tumors was expressed as percent fibrosis per field. Treatment with the MGE reduced interstitial fibrosis by more than 90%, from 2.7±0.7 percent fibrosis per field in tumors from the control mice to 0.1±0.05 percent fibrosis per field in the tumors of l-MGE-treated mice (n=7-12, p=0.0005), indicating that the extract reduces cancer-associated fibrosis in breast tumors. Taken together, these studies suggest that l-MGE reduces both breast tumor burden and multiplicity, through decreasing proliferation, angiogenesis and fibrosis, suggesting that extracts from muscadine grapes may represent a novel nutraceutical for the prevention of breast cancer.

Collectively, treatment of c-neu mice with l-MGE reduced tumor burden and multiplicity, in association with a reduction in the proliferative marker Ki67, growth-promoting protein kinase activities, the number of blood vessels and tissue fibrosis. These results suggest that the extract from muscadine grapes may prevent breast cancer.

Part B: Prevention of Lung Tumor Formation by l-MGE in c-neu Mice

The developing fetus is highly sensitive to the carcinogenic effects of dietary and environmental carcinogens in cigarette smoke, charbroiled foods and air pollution following transplacental exposure. Oxidative metabolism of toxicants by both maternal and fetal tissue causes DNA damage which can ultimately result in the initiation of childhood cancers. Due to the latency of cancer formation, in utero exposure to carcinogens may even predispose the individual to cancers developing later in life. BALB/c male mice were mated to C57BL/6 female mice to serve as a model for in utero exposure to environmental toxicants. The pregnant mice were treated on the $17^{th}$ day of gestation by intraperitoneal injection with a 45 mg/kg dose of 3-methylcholanthrene dissolved in olive oil, to induce lung tumors in the fetus. An injection of the olive oil vehicle (0.5 mL/0.35 kg) served as the control. Day 0 was considered as the first day when the vaginal plug was detected. After weaning, cohorts of mice received drinking water alone or water with l-MGE (approximately 1.0 mg phenolics/25 g mouse) and were sacrificed at 12 months of age.

Figure 13A:
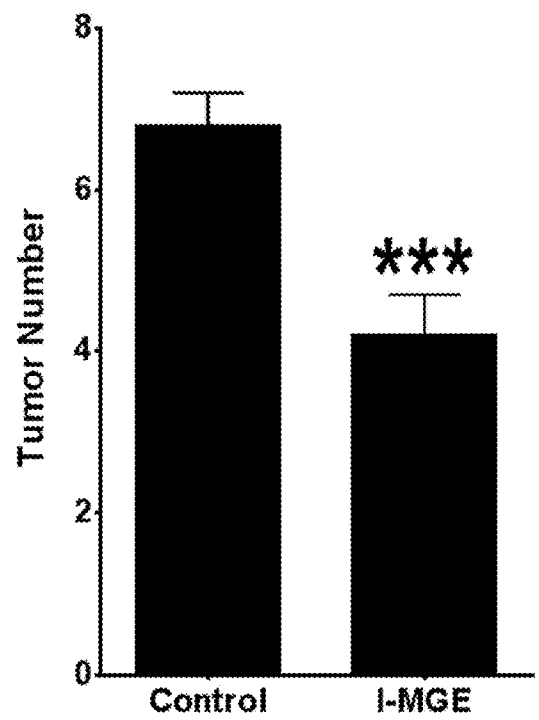
FIGS. 13A-13B shows an analysis of tumor number in a lung cancer mouse model treated with muscadine grape seed and muscadine grape skin liquid extract (l-MGE) as described in Example 1. Female pups from mothers treated with 3-methylcholanthrene received MGE in their drinking water beginning at 3 weeks and were euthanized after 1 year. The total number of tumors (FIG. 13A) or the number of non-coalesced tumors (FIG. 13B) on the lung surface was counted. n=26-32. *** denotes p<0.001. Treatment of mice predisposed to develop lung tumors by in utero exposure to 3-methylcholanthrene with l-MGE significantly reduced the number of lung tumors compared to mice drinking water, indicating that the extract from the muscadine grape reduces tumor multiplicity.
Figure 13B:
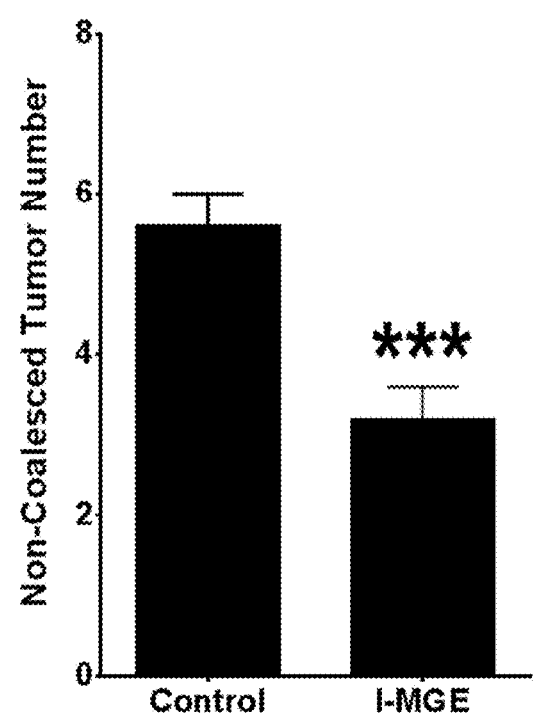
Figure 14A:
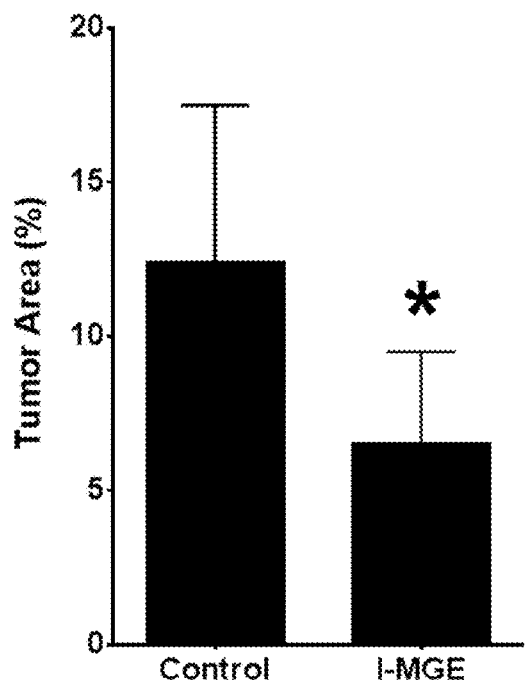
FIGS. 14A-14B shows an analysis of tumor volume in a lung cancer mouse model treated with muscadine grape seed and muscadine grape skin liquid extract (l-MGE) as described in Example 1. Female pups from mothers treated with 3-methylcholanthrene received l-MGE in their drinking water beginning at 3 weeks and were euthanized after 1 year. The total tumor area (in the left panel) or the area of non-coalesced tumors (in the right panel) on the lung surface was counted. n=26-32. *** denotes p<0.001. Treatment of mice predisposed to develop lung tumors by in utero exposure to 3-methylcholanthrene with l-MGE significantly reduced the area of lung tumors compared to mice drinking water, indicating that the extract from the muscadine grape reduces tumor volume.
Figure 14B:
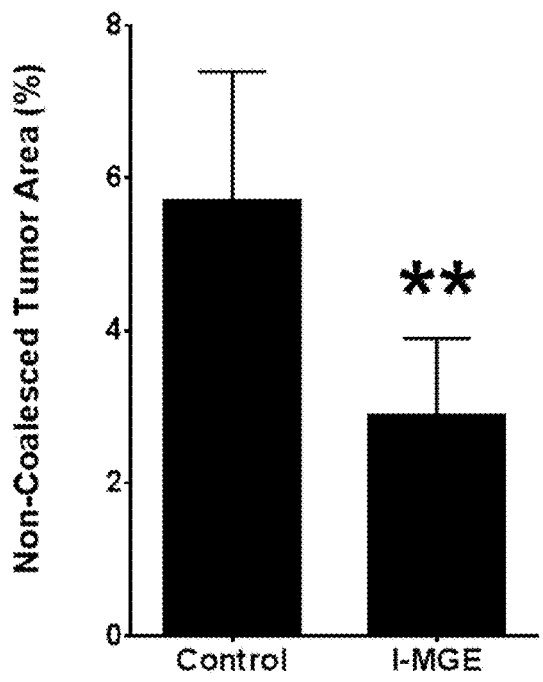

Although all of the mice developed lung tumors, tumor multiplicity was higher in control mice as compared to l-MGE-treated animals (6.8±0.4 total tumors versus 4.2±0.5 total tumors, n=26-32, p=0.0001), as shown in FIGS. 13A-13B. l-MGE also significantly reduced total tumor burden in female mice by approximately 48% as compared to the total tumor tissue found in control mice drinking regular water (12.4±1.9 g versus 6.5±1.2 g, n=26-32, p=0.014), as shown in FIGS. 14A-14B. These results suggest that the l-MGE reduces both the multiplicity and burden of lung tumors in the female off-spring of mice exposed in utero to 3-methylcholanthrene.

Figure 15:
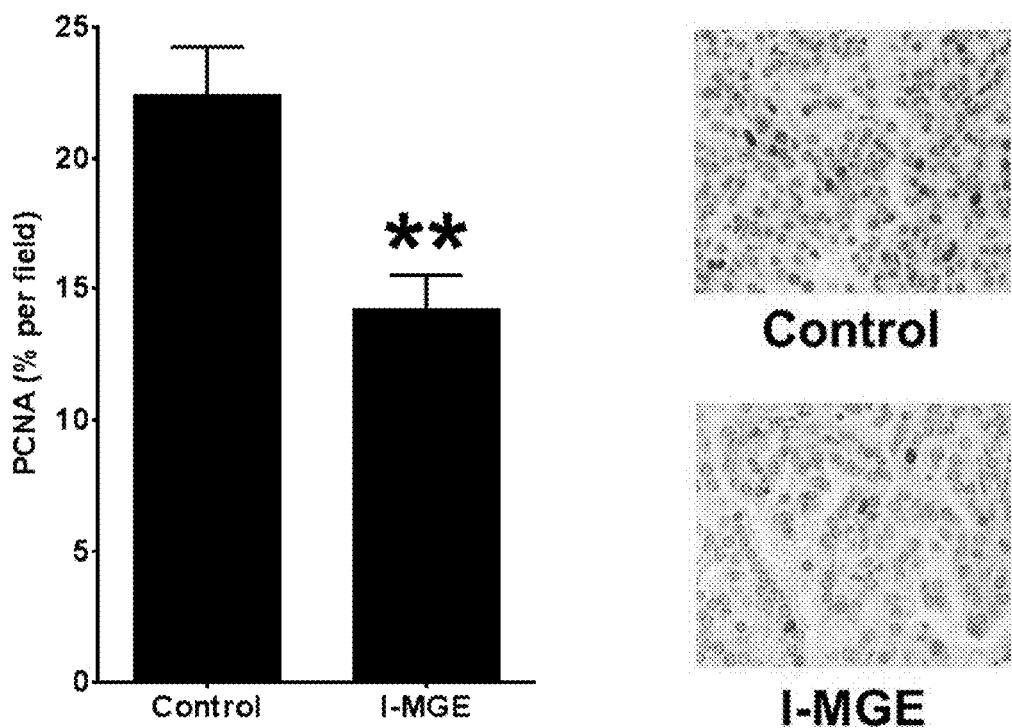
FIG. 15 shows an analysis of proliferation in a lung cancer mouse model treated with muscadine grape seed and muscadine grape skin liquid extract (l-MGE) as described in Example 1. Tumor sections from female offspring of 3-methylcholanthrene-treated mothers were incubated with an antibody to the proliferation marker proliferating cell nuclear antigen (PCNA) and the total number of positively-stained cells per field was counted. A graph showing the percentage PCNA/cell is presented next to representative microscopic images. n=26-32, ** indicates p<0.01. Treatment of mice predisposed to develop lung tumors by in utero exposure to 3-methylcholanthrene with l-MGE significantly decreased the amount of the proliferation marker PCNA, indicating that the l-MGE reduces tumor proliferation in the developing lung tumors of female mice.
Figure 16:
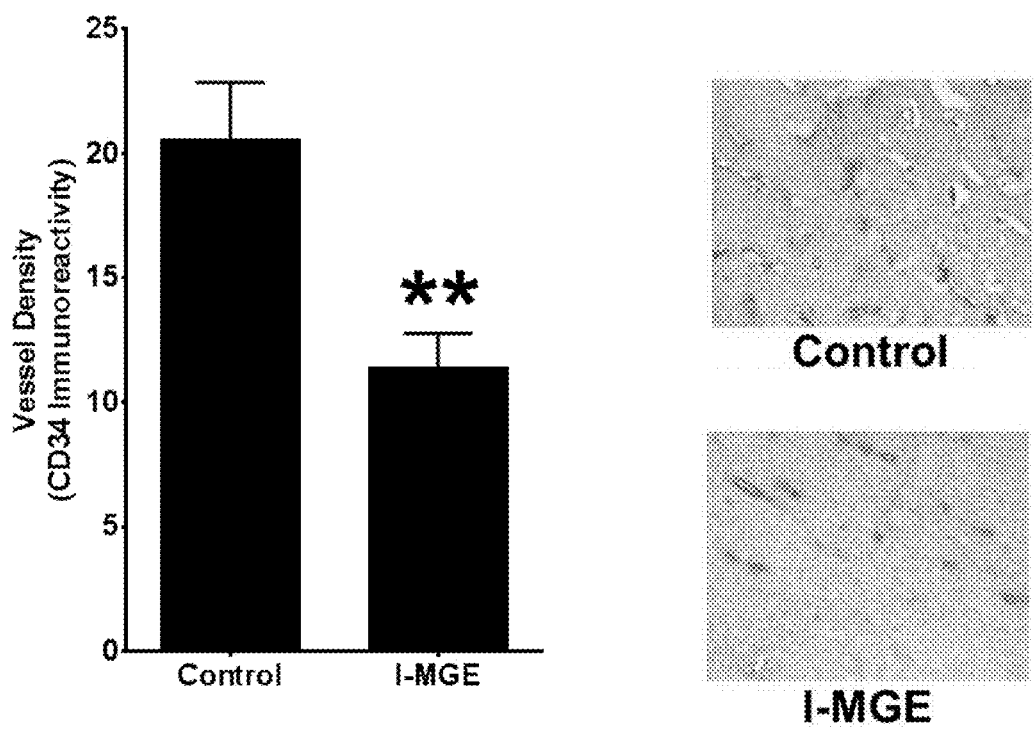
FIG. 16 shows an analysis of angiogenesis in a lung cancer mouse model treated with muscadine grape seed and muscadine grape skin liquid extract (l-MGE) as described in Example 1. Tumor sections from female offspring of 3-methylcholanthrene-treated mothers were incubated with an antibody to CD34 and blood vessels were identified by positive immunoreactivity and morphology and the total number of positively-stained vessels per field was counted. A graph showing vessel density (CD34 immunoreactivity) is presented next to representative microscopic images. n=26-32, ** indicates p<0.01. Treatment of mice predisposed to develop lung tumors by in utero exposure to 3-methylcholanthrene with l-MGE significantly reduced the amount of blood vessels, indicating that the l-MGE reduces angiogenesis in the developing lung tumors of female mice.

Lung tissue from female mice sacrificed after 1 year was fixed in 4% formalin, paraffin-embedded and section into 5 micron sections, for immunohistochemical analysis. Sections were incubated with an antibody to proliferating cell nuclear antigen (PCNA), as a measure of cell proliferation. As shown in FIG. 15, tumor tissue sections from mice administered l-MGE had a significant decrease in PCNA as compared to tumors from control animals (22.4±1.8 versus 14.2±1.3, p=0.0009), suggesting that in part l-MGE reduces tumor burden by decreasing tumor cell proliferation. Lung tumor sections from female mice drinking regular water or l-MGE were incubated with an antibody to the endothelial cell marker, CD34, and vessels were identified by a combination of morphology and positive CD34 immunoreactivity. Treatment with l-MGE significantly reduced blood vessel density in lung tumor tissue as compared to female mice drinking regular water (20.5±2.2 versus 11.3±1.3, p=0.0012), as shown in FIG. 16, suggesting that the grape extract inhibits angiogenesis.

Collectively, these results demonstrate that the l-MGE reduced tumor burden and multiplicity, the proliferative marker PCNA and the number of blood vessels in female mice whose mothers were treated with a chemical carcinogen in utero to predispose the off-spring to develop lung cancer. These results suggest that extracts isolated from muscadine grapes may represent a novel nutraceutical for the prevention of lung tumors induced by in utero exposure to environmental toxicants.

Example 6

Toxicity Assessment of Muscadine Grape Powder Extract (p-MGE) in Rodents

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

The primary goal of the rodent toxicity tests on the p-MGE was to identify the range of doses that caused no adverse effect or was life-threatening. Toxicity tests on the p-MGE were performed in mice, to assess effects of the extract on the general health of the mice as well as their hearts, liver, lungs and kidneys.

Male C57 black mice (8 weeks of age) were randomized into groups to received drinking water alone (Control) or p-MGE in the drinking water at four escalating doses based on the total phenolic content of the p-MGE as determined by the measurement of total phenolics. Daily observations of the mice included evaluations of weight loss (rapid or progressive weight loss), debilitating diarrhea, dehydration or reduced skin turgor, edema, sizable abdominal enlargement or ascites, progressive dermatitis, rough hair coat or unkempt appearance due to lack of grooming, hunched posture indicative of pain, lethargy or persistent decumbency due to loss of appetite, coughing, labored breathing, nasal discharge, jaundice, cyanosis, pallor/anemia, neurological signs indicated by inappropriate head carriage or shaking of the head, bleeding from any orifice, or any condition interfering with daily activities (e.g., eating or drinking, ambulation, or elimination). Prior to sacrifice, the mice were placed in metabolic cages for 24 hours, food intake and fecal production was measured and urine was collected to quantify markers of renal damage. During the $4^{th}$ week of treatment, blood pressure was determined by tail cuff plethysmography in conscious mice and cardiac function was assessed in mice anesthetized with isofluorane, using a non-invasive, small animal VEVO ultrasound imaging system in the M and B modes, to measure or calculate ejection fraction, fractional shortening, stroke volume, heart rate and cardiac output. The mice were sacrificed after one month of treatment; tissues (heart, kidney, lung, liver, spleen and brain) were weighed, fixed in 4% formalin, embedded in paraffin, sectioned at 5 microns and stained with Hematoxylin & Eosin (H&E) for analysis by a veterinary pathologist in the animal resource program at our institution, to assess any gross structural abnormalities.

Four concentrations of the p-MGE were tested. The range of concentrations to be tested was based upon previous studies showing a significant reduction in the number and size of breast tumors in c-neu transgenic mice treated chronically with l-MGE and a similar reduction in size and number of lung tumors in a transplacental model of lung cancer as described above in Example 5. In those studies, a daily concentration of 1 mg of phenolics in the liquid muscadine grape extract/mouse/day was effective at reducing tumor multiplicity and dose. For the toxicity studies in mice, the four doses of the p-MGE tested were 0.25, 0.5, 1.0 and 2.0 mg phenolics/mouse/day, administered to the mice in their drinking water. Since an average mouse of this age weighs approximately 25 g or 0.025 kg, this corresponds to a dose range of 10, 20, 40 and 80 mg phenolics/kg/day.

During the 4 week administration of the p-MGE at the four doses, there were no observations of diarrhea, dehydration, edema, abdominal enlargement, loss of hair coat, reduced grooming, or decreased level of activity, appetite, drinking or breathing. There were no indications of palor, jaundice or cyanosis or any neurological signs of discomfort (inappropriate head carriage or shaking of head). There were no bleeding or discharge from any orifice. These results suggest that the mice were free from any pathology that affected their normal daily activities or health.

Figure 17:
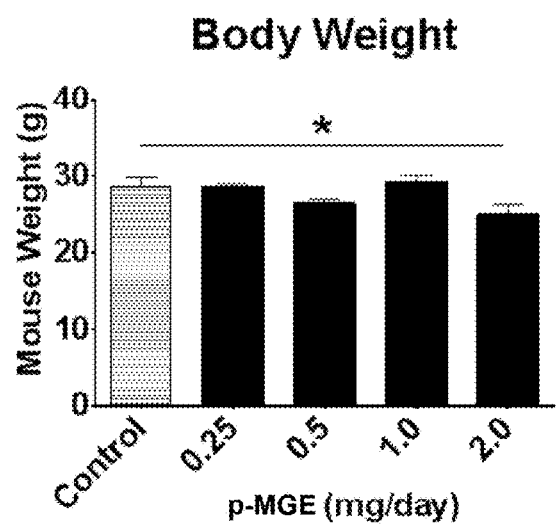
FIG. 17 shows a body weight analysis for mice in a toxicity study assessing the impact of different doses of a muscadine grape seed and muscadine grape skin powder extract (p-MGE) as described in Example 1 according to aspects of this disclosure. Mice in each treatment group were weighed at the end of the treatment period, to determine the effect of p-MGE on mouse weight. There was a small but significant decrease in the weight of the mice using the highest dose of p-MGE compared to the Control. n=5, p<0.05. The weight of the mice at the end of the 4-week treatment period was similar with the three lowest concentrations of the p-MGE compared to the Control group. Mice treated with the highest concentration of p-MGE had a small but significant decrease in total body weight (from 28.6±1.2 grams to 25.0±1.3 grams, which represents less than 15% of their total body weight).
Figure 18A:
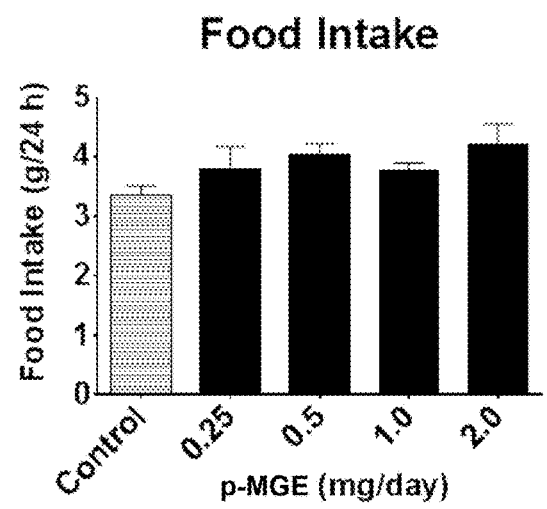
FIGS. 18A-18C show an analysis of mouse food intake, fecal excretion, and urine volume in a toxicity study assessing the impact of different doses of a muscadine grape seed and muscadine grape skin powder extract (p-MGE) as described in Example 1 according to aspects of this disclosure. Mice in each treatment group were placed in metabolic cages for 24 h, during the last week of treatment, in order to measure food intake (FIG. 18A), fecal excretion (FIG. 18B) and urine volume (FIG. 18C). n=5. There was no difference in food intake of mice treated with p-MGE, fecal production, or urine volume.
Figure 18B:
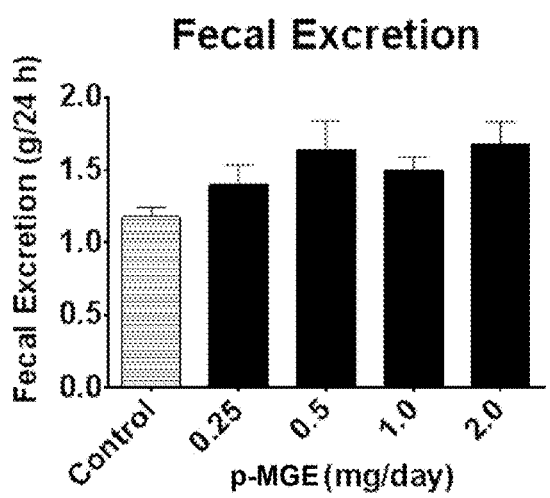

The mice were weighed at the end of the treatment period, to determine the effect of the p-MGE on total body weight. Although there was no effect on body weight in the mice treated with the 3 lower concentrations of p-MGE, the average weight of the mice treated with the highest concentration of p-MGE was slightly reduced compared to the untreated Control group (FIG. 17). However, there was no effect on food intake (FIG. 18A), fecal production (FIG. 18B) or urine volume (FIG. 18C) compared to the untreated mice, measured during the last week of treatment, suggesting little effect of the p-MGE on eating and drinking behaviors.

At the time of sacrifice, various organs (heart, lung, liver, kidney, spleen and brain) were removed and weighed and the organ weights of mice treated with each dose of p-MGE were compared to the untreated Control group. A portion of each organ was fixed in formalin, sectioned and stained with H&E, for assessment by a veterinary pathologist.

At the time of sacrifice, a section of the heart, lung, liver, kidney, spleen and brain (areas in the cortex, cerebellum, hypothalamus and brainstem) were removed and weighed and the organ weights of mice treated with each dose of p-MGE were compared to the untreated Control group. Sections were fixed overnight in 4% paraformaldehyde, placed in 70% ethanol for 2 days, embedded in paraffin, sectioned at 5 microns and stained with H&E. Slides were submitted to the Pathology Section of the Animal Resource Program and examined by a veterinarian pathologist, in a blinded fashion. The results of the examination are tabulated in Table 2 below and summarized below. Representative images are also provided in FIG. 19.

treated with p-MGE compared to untreated Control mice (as shown in FIGS. 22A-22E). These results suggest that the p-MGE had no effect on the structure or function of the heart or the vasculature.

TABLE 2

Pathological Analysis of Tissue Sections

| p-MGE (mg/day) | Heart | Lung | Liver | Kidney | Spleen | Brain |
|---|---|---|---|---|---|---|
| 0 (Control) | 4 wnl 1 pvl | all wnl | 3 wnl 1 with focal emh 1 with glycogenesis | all wnl | all wnl | all wnl |
| 0.25 | all wnl | 4 wnl 1 with mfp (unusual lung lesion) | 3 wnl 1 with focal emh 1 with mild glycogenesis | all wnl | all wnl | 4 wnl 1 with epidermoid cyst arising from surface |
| 0.5 | all wnl | all wnl | 1 wnl 4 with focal emh | all wnl | all wnl | 4 wnl 1 with epidermoid cyst within parenchyma, extending to surface |
| 1.0 | all wnl | all wnl | 3 wnl 2 with mild emh | all wnl | all wnl | all wnl |
| 2.0 | all wnl | all wnl | 4 wnl 1 with few focal emh | all wnl | 3 wnl 1 with emh with poorly differentiated focus, white pulp absent | all wnl | wnl = within normal limits; pvl = perivascular lymphocytes; mfp = multifocal perivbronchial fibrosis; emh = extramedullary hematopoiesis The hearts of the mice in all treatment groups appeared to be within normal limits; one heart of a control mouse had perivascular lymphocytes. The lungs of mice in the control group and all treatment groups were within normal limits except for one mouse in the group treated with the lowest concentration of p-MGE, which had an unusual lung lesion. Although the majority of the livers of mice appeared to be normal, mice in all groups had some degree of extramedullary hematopoiesis, even mice in the control group; this type of hematopoiesis is not unusual in the liver of mice. In addition, some mice had hepatic glycogenosis, which is to some degree physiological and not an indication of injury. The spleens of mice were generally within normal limits with one mouse in the highest p-MGE treatment group having some extramedullary hematopoiesis. Although different areas of the brains of mice were examined and were generally within normal limits, two mice had epiermoid cysts which were thought to be incident benign hamartomas which could interfere with normal neural function from their location and size; however, these are normally clinically silent as the slow increase in size allows for adaptation and compensation by the nervous system to the presence of a space-occupying mass.

Figure 19:
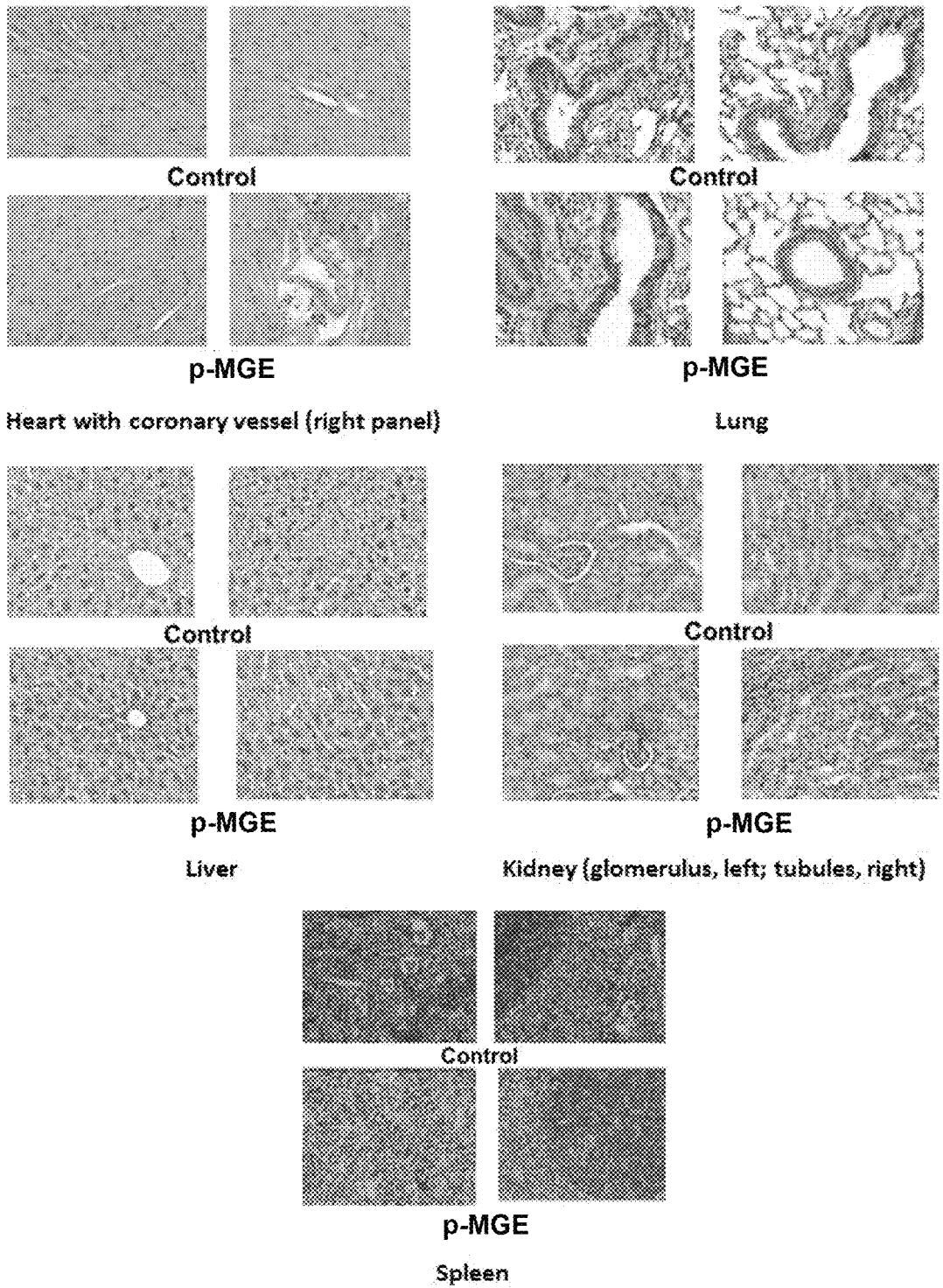
FIG. 19 shows pathological tissue analysis of mice in a toxicity study assessing the impact of different doses of a muscadine grape seed and muscadine grape skin powder extract (p-MGE) as described in Example 1 according to aspects of this disclosure. The hearts, lung, livers, kidneys, spleen and brain of mice in each treatment group were removed. A section of the heart, lung, liver, kidney, and spleen were fixed, embedded in paraffin, sectioned, stained with H&E, and examined by a veterinarian pathologist.
Figure 20:
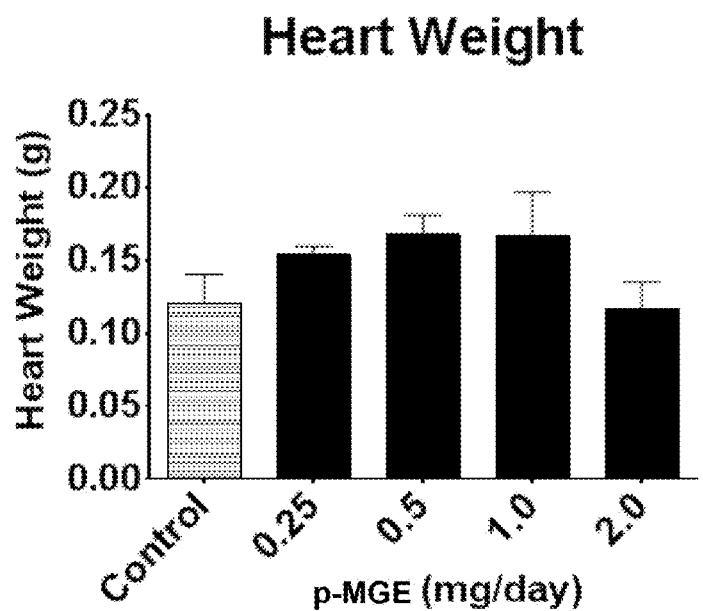
FIG. 20 shows an analysis of mouse heart weight in a toxicity study assessing the impact of different doses of a muscadine grape seed and muscadine grape skin powder extract (p-MGE) as described in Example 1 according to aspects of this disclosure. The hearts of mice in each treatment group were removed and weighed at the end of the treatment period, to determine the effect of p-MGE on heart weight. n=5. There was no difference in heart weight of mice treated with p-MGE.
Figure 21:
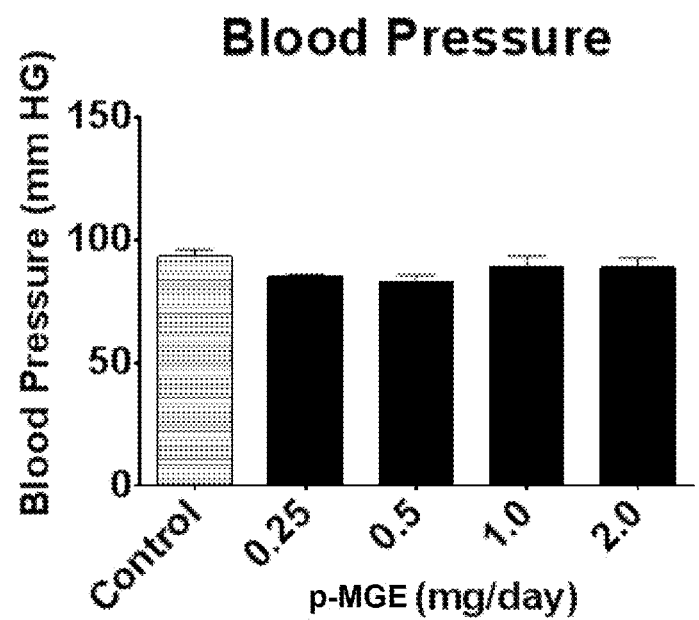
FIG. 21 shows an analysis of mouse blood pressure in a toxicity study assessing the impact of different doses of a muscadine grape seed and muscadine grape skin powder extract (p-MGE) as described in Example 1 according to aspects of this disclosure. Blood pressure was measured by tail cuff plethsmography in unanesthetized mice (who were trained for 1 week for blood pressure measurements). n=5. There was no difference in blood pressure in mice treated for 4 weeks with increasing concentrations of p-MGE as compared to untreated mice (Control).

There was no difference in the weight of the hearts of mice treated with increasing doses of p-MGE, as shown in FIG. 20, nor was there any effect on the structure of the heart, as shown in Table 2 and FIG. 19. Blood pressure was also similar between treated and Control mice (FIG. 21). One of the hearts of an untreated mouse had perivascular lymphocytes but all of the hearts from mice treated with p-MGE were within normal limits. Cardiac parameters—ejection fraction, fractional shortening, cardiac output, stroke volume and heart rate—were all similar in mice There was no difference in the weight of the lungs of mice treated with p-MGE compared to the untreated Control mice (FIG. 23A) and the structure of the lungs were all within normal limits with the exception of one mouse in the lowest p-MGE treatment group which had an unusual lung lesion (see Table 2). Coupled with the lack of any observable effect of the extract on breathing, these results suggest that the p-MGE had no effect on pulmonary structure or function.

The weight of the livers of mice treated with the two lowest p-MGE (0.25 and 0.5 mg phenolics/mouse/day) and the highest p-MGE (2.0 mg phenolics/mouse/day) concentrations were no different than the weight of the livers of the untreated mice. However, the weight of the livers of mice in the 1.0 mg phenolics/mouse/day were slightly increased compared to the Control (FIG. 23B). The majority of the livers of mice appeared to have normal structure although mice in all groups had some degree of extramedullary hematopoiesis, even in the Control group; the pathologist indicated that this type of hematopoiesis is not unusual in the liver of mice (see Table 2). In addition, some mice had hepatic glycogenosis, which the pathologist indicated was physiological and not an indication of injury.

Figure 18C:
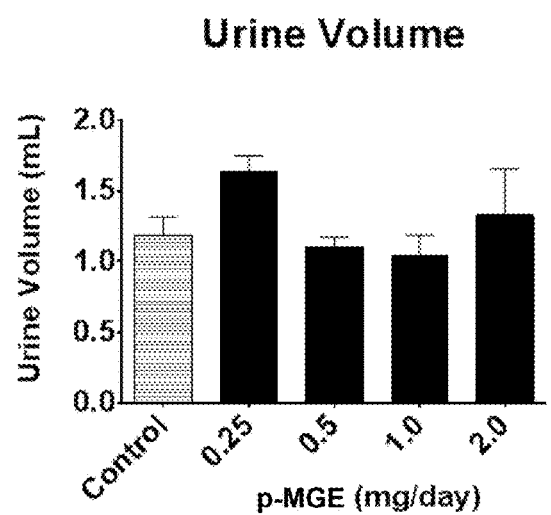
Figure 24A:
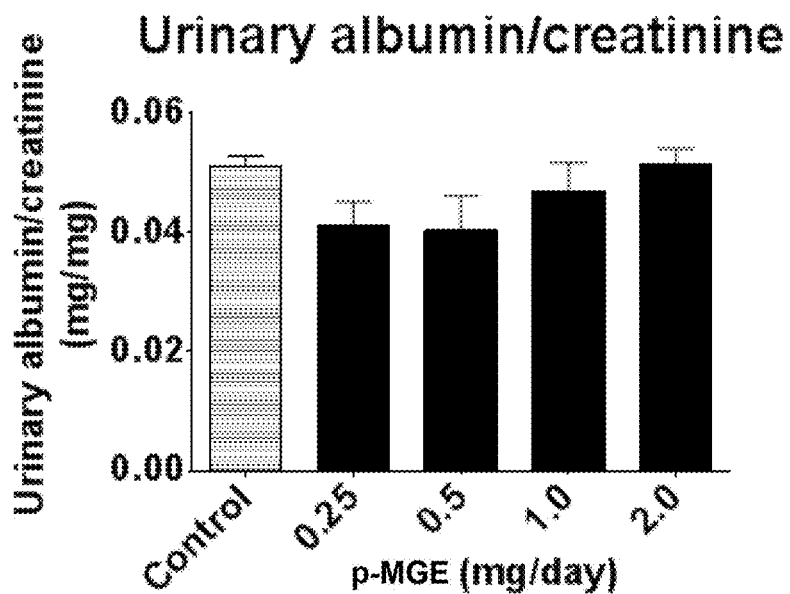
FIGS. 24A-24B show graphs summarizing renal function assessment of mice in a toxicity study assessing the impact of different doses of a muscadine grape seed and muscadine grape skin powder extract (p-MGE) as described in Example 1 according to aspects of this disclosure. The amount of albumin in the urine of untreated and treated mice (collected during week 4 of treatment) was measured by radioimmunoassay and expressed as a measure of urinary creatinine (n=5).
Figure 24B:
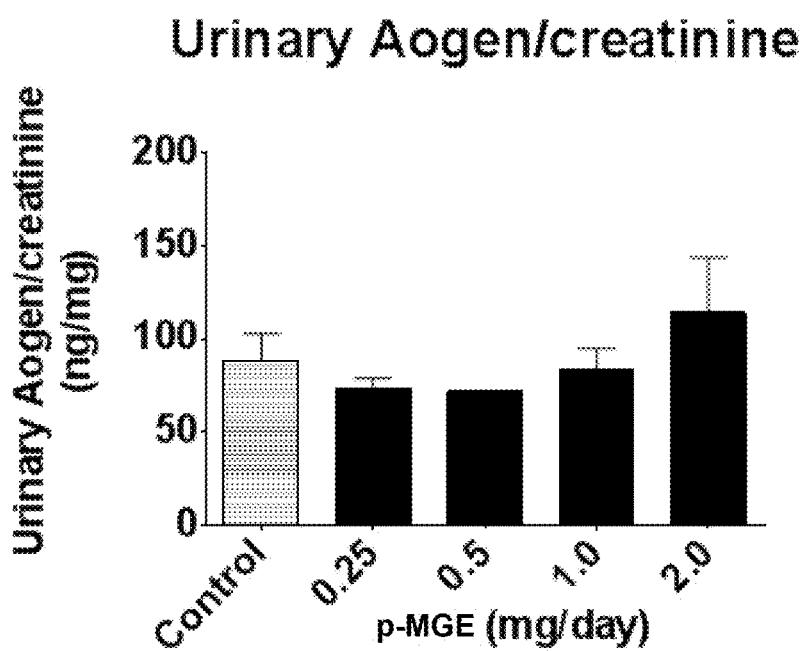

The kidneys of the mice were weighed and there was no difference in the kidney weight of mice treated with p-MGE compared to untreated mice (FIG. 23C). As indicated above, there was no difference in urine volume as shown in FIG. 18C. Urinary albumin and urinary angiotensinogen (Aogen) were measured to assess renal function and their values expressed as a function of urinary creatinine. There was no difference in the amount of urinary albumin in the urine of mice treated with increasing concentrations for 4 weeks compared to untreated mice, as a measure of renal function (FIG. 24A) and in agreement with the lack of any pathology in the glomeruli or tubules of the same animals (see Table 2). In addition, there was no difference in the amount of urinary Aogen between untreated and treated mice (FIG. 24B), suggesting that the p-MGE did not damage the kidney, in agreement with the lack of pathology in the kidney glomeruli and tubules as assessed by pathology (see Table 2).

Spleen weight of mice treated with p-MGE was not significantly different than untreated control mice (FIG. 23D) and the spleens of mice were generally within normal limits with one mouse in the highest p-MGE treatment group having some extramedullary hematopoiesis (see Table 2).

The weight of the brains of mice treated with p-MGE was not significantly different than untreated mice (FIG. 23E). The brains were subdivided into four regions—cortex, cerebellum, hypothalamus and brainstem—and each was examined by the veterinary pathologist. All brain regions examined were within normal limits; however, two mice had epiermoid cysts which were thought to be incident benign hamartomas which the pathologist indicated could interfere with normal neural function from their location and size but are normally clinically silent as the slow increase in size allows for adaptation and compensation by the nervous system to the presence of a space-occupying mass (see Table 2).

Collectively, these results demonstrate that a 4 week treatment of mice with doses of p-MGE of 0.05, 0.1, 0.2 and 0.4 mg phenolics/mL/day had no effect on body weight, organ weight (heart, lung, liver, kidney, brain or spleen) or structure, heart function and blood pressure, or kidney function. These results suggest that the p-MGE was well tolerated by mice at the doses tested.

The doses of p-MGE used for the toxicity studies in mice were 0.05, 0.1, 0.2 and 0.4 mg phenolics/mL/day. As mice drink approximately 5 mL/day, this corresponds to doses of the p-MGE tested were 0.25, 0.5, 1.0 and 2.0 mg total phenolics/mouse/day, administered to the mice in their drinking water. As an average mouse of this age weighs approximately 25 g or 0.025 kg, this corresponds to a dose range of 10, 20, 40 and 80 mg total phenolics/kg/day. Based upon an average mass of 70 kg for a human adult patient, this would correspond to 700, 1400, 2800, and 5600 mg phenolics/day dose range for human adults. This would correspond to taking 5, 10, 21 and 42 capsules/day because the p-MGE capsule contains 162 mg total phenolics/capsule. The amount of phenolics used to treat the mice and the lack of toxicity at these doses suggest that the amount of phenolics in corresponding numbers of capsules would be well tolerated by the patients.

Example 7

Effect of p-MGE on Pregnancy

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

Pregnant rats were treated with p-MGE and the effect of the extract on the health of both the mothers and their off-spring were measured, to determine the safety of administering p-MGE to women of child-bearing age and pregnant mothers. Sprague-Dawley rats were administered p-MGE (0.2 mg/mL in their drinking water), one week prior to mating and throughout the time of their pregnancy. On day 19 of gestation (normal pregnancy in rats is 21 days), the pregnant rats were scanned with the VEVO 2100, to measure uterine and umbilical blood flow and to determine cardiovascular function. The rats were placed into metabolic cages to measure urine excretion, food and water intake, as assessments of maternal health. On day 21 of gestation, the blood pressure of the pregnant rats was measured and the rats/rat pups were sacrificed, to measured pup number, pup weight and the health of the pups.

The cardiac health of the pregnant mothers administered p-MGE in their drinking water was assessed by cardiac ultrasound. There was no effect of the p-MGE on parameters of cardiac contractility and systolic function (stroke volume, ejection fraction, fractional shortening or cardiac output), comparing the pregnant mothers to pregnant rats drinking regular water. There was also no effect on the blood flow to the growing pups, measured as the blood flow through the umbilical vein. These results suggest that the p-MGE does not impair the cardiovascular health of the pregnant mothers. There was also no effect of p-MGE treatment on food or water intake or urine volume, measured by placing the pregnant mothers in metabolic cages for 24 h at day 10-20 of gestation. Blood pressure, measured by tail cuff plethysmography was also not different in pregnant rats drinking regular water or p-MGE. The weight of various organs of the mother (pancreas, liver, spleen, lungs, brain, heart and kidneys) was not different in pregnant mothers drinking regular water or p-MGE. Finally, there was no difference in the number of pups born to mothers drinking p-MGE or in the length of pups from mothers administered p-MGE compared to Controls.

Collectively, these results suggest that the administration of p-MGE to women of child-bearing age or pregnant women will not adversely impact the general health of the mothers or their off-spring, with regard to cardiovascular function, blood pressure, body weight, or organ weight of the mothers or the number or length of the pups. Histological analysis of pups internal organs are ongoing.

Example 8

Effect of p-MGE on Ang II Induced Hypertension

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

The effect of p-MGE on hypertension and hypertension-induced cardiac damage was measured in rats with angiotensin II (Ang II)-induced hypertension. Sprague-Dawley rats (male, 8-12 weeks of age) were treated for 4 weeks with regular drinking water (Control), p-MGE alone (0.2 mg/mL of total phenolics in their drinking water), Ang II alone (24 µg/kg/h via implanted osmotic mini-pump) or p-MGE and Ang II. For a 250 g rat, this amount of p-MGE corresponds to approximately 20 mg phenolics/kg/day. Administration of p-MGE was initiated 1 week prior to treatment with Ang II. Blood pressure was recorded weekly by tail-cuff plethysmography, at the same time of day by the same individual. Echocardiography was performed using the VisualSonics Vevo 2100 High-Resolution Imaging System with a 21 MHz frequency transduction, in rats sedated with isoflurane. Scans to quantify cardiac parameters were taken in M mode parasternal short axis view at mid-papillary level, Tissue Doppler in 4 chamber view at the mitral annulus, and pulse wave Doppler in 4 chamber view to measure transmitral inflow.

Figure 25:
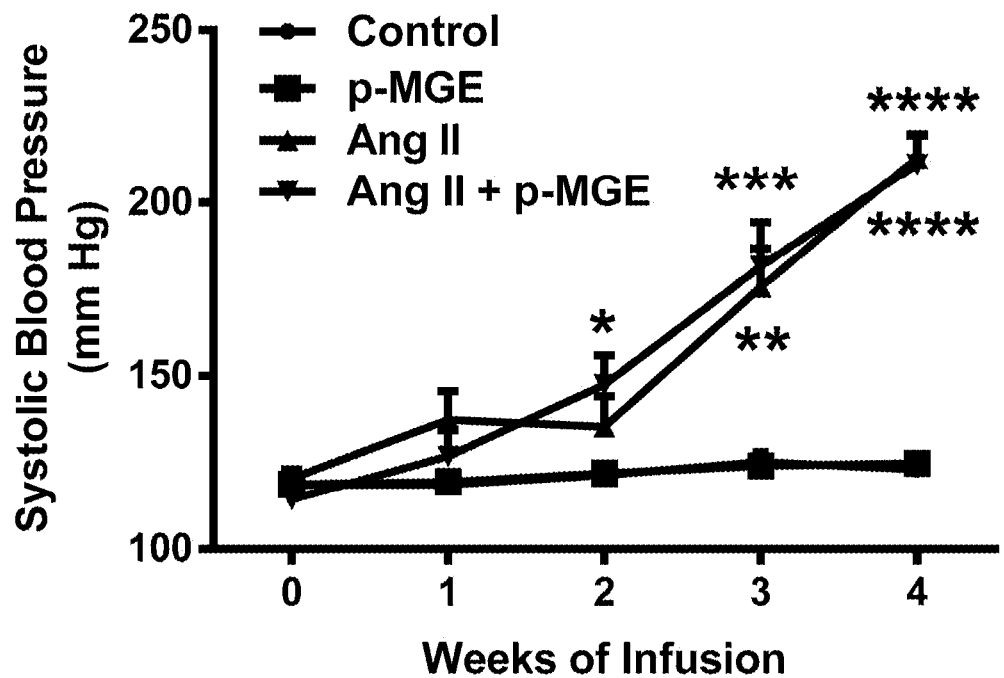
FIG. 25 shows an analysis of the effect of a muscadine grape seed and muscadine grape skin powder extract (p-MGE) as described in Example 1 on blood pressure according to aspects of this disclosure. Systolic blood pressure was measured in male Sprague-Dawley rats treated for 4 weeks with regular drinking water (Control), 0.2 mg/mL p-MGE (p-MGE), Ang II (24 µg/kg/h Ang II administered via an implanted osmotic mini-pump) or Ang II and p-MGE. Blood pressure was measured weekly by tail cuff plethysmography. n=8, * denotes $p<0.05$,  denotes $p<0.005$, * denotes $p<0.001$ and **** denotes $p<0.0001$. In this study, administration of Ang II increased blood pressure in the rats over the 4 week time period. The p-MGE had no effect on the blood pressure of Control rats drinking regular water or rats treated with Ang II, indicated that the p-MGE does not exacerbate hypertension.
Figure 26:
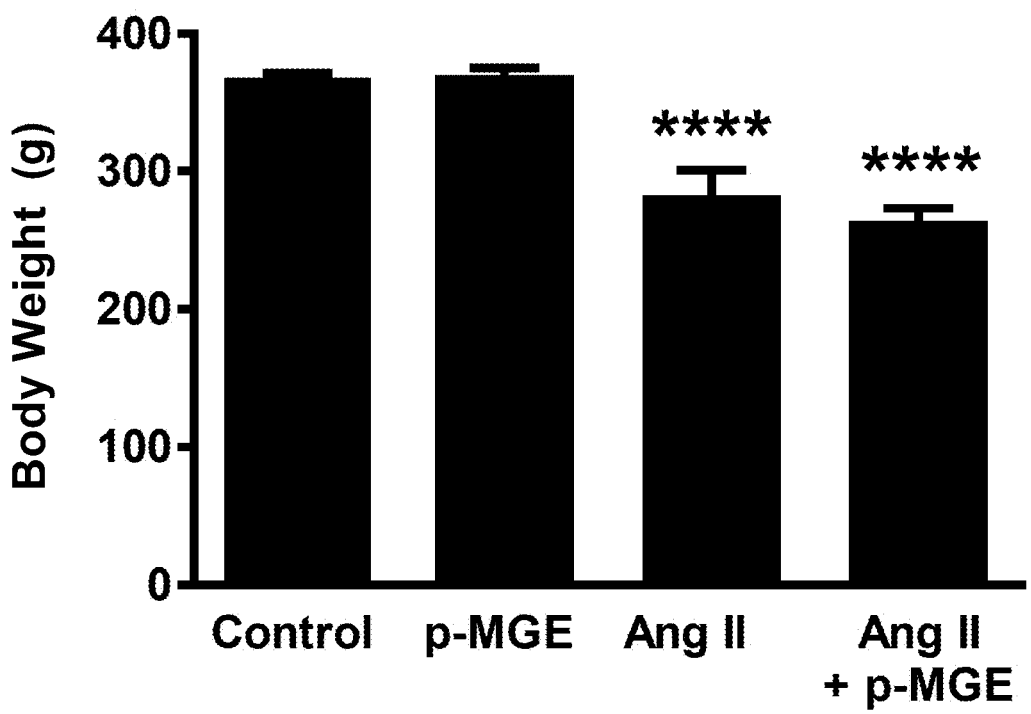
FIG. 26 shows an assessment of body weight for the rats described with respect to FIG. 25 according to aspects of this disclosure. At the end of the 4 week treatment period, the rats were weighed, to determine whether treatment with p-MGE had an effect on the body weight of normotensive or hypertensive rats. n=8, **** denotes $p<0.0001$. Ang II decreased the body weight of rats, in the presence or absence of treatment with p-MGE. Treatment with p-MGE had no effect on body weight, in normotensive, untreated rats or Ang II-treated hypertensive rats, suggesting that p-MGE does not affect body weight.

The systolic blood pressure of rats drinking regular water was not changed over the 4 week treatment period (118.6±2.4 mm Hg at baseline and 123.1±2.3 mm Hg at 4 weeks). Infusion with Ang II significantly increased systolic blood pressure, from 120.4±2.4 mm Hg to 213.1±6.8 mm Hg over the 4 week time period. The addition of the p-MGE to the drinking water did not change systolic blood pressure over the 4 weeks of treatment, in rats with or without treatment with Ang II, as shown in FIG. 25. At the end of 4 weeks of treatment, the rats were weighed, to determine if the p-MGE had an effect on body weight. Although Ang II reduced body weight over the 4 week treatment period, p-MGE had no effect on body weight, in the absence or presence of Ang II, as shown in FIG. 26. At the time of sacrifice, the hearts were removed and weighed and the tibia were dissected and measured, to determine heart weight/tibia length, as a gross measure of cardiac hypertrophy. There was no difference in heart weight/tibia length in any of the treatment groups (data not shown). These results indicate that treatment with p-MGE does not exacerbate Ang II-induced hypertension or the Ang II-induced reduction in body weight.

The ejection fraction of the heart and fractional shortening were measured in M mode parasternal short axis view at the mid-papillary level, using the VisualSonics Vevo 2100 High-Resolution Imaging System, as a measure of systolic function. As shown in FIG. 27A-27B, neither the ejection fraction nor the fractional shortening of the heart was different in rats with hypertension compared to normotensive rats. In addition, there was no effect of p-MGE on the ejection fraction or fractional shortening of the heart of either normotensive or hypertensive rats. This suggests that neither Ang II nor p-MGE have an effect on cardiac contractility.

To measure the effect of p-MGE on remodeling of the left ventricle, the thickness of the posterior wall of the left ventricle, the diameter of the left ventricle at the end of diastole, and the thickness of the wall of the left ventricle were measured in normotensive and Ang II-dependent hypertensive rats following 4 weeks of treatment with p-MGE, using the M mode parasternal short axis view at the level of the mid-papillary muscle. As shown in FIG. 28A-28C, Ang II increased the thickness of the posterior wall of the left ventricle as well as the relative wall thickness (Panels A and C) while decreasing the diameter of the left ventricle (Panel B), suggesting that Ang II or the Ang II-dependent increase in blood pressure caused hypertrophy of the left ventricle, increasing the wall thickness and reducing the cavity of the ventricle. Co-administration of p-MGE had no effect on wall thickness or the inner diameter of the left ventricle, in either normotensive or hypertensive rats. These results suggest that Ang II causes left ventricular remodeling while co-administration of the p-MGE neither exacerbates nor reduces left ventricular remodeling.

Figure 29A:
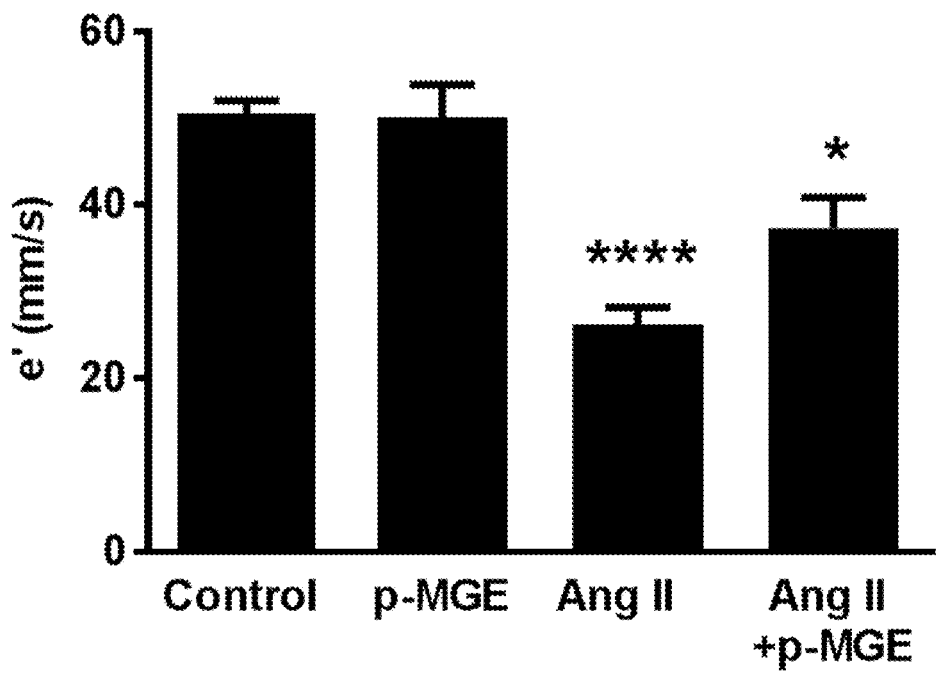
FIG. 29A-29B show assessment of diastolic function in the rats described with respect to FIG. 28A-28B that were treated with Ang II, p-MGE, or both, for 4 weeks according to aspects of this disclosure.
Figure 29B:
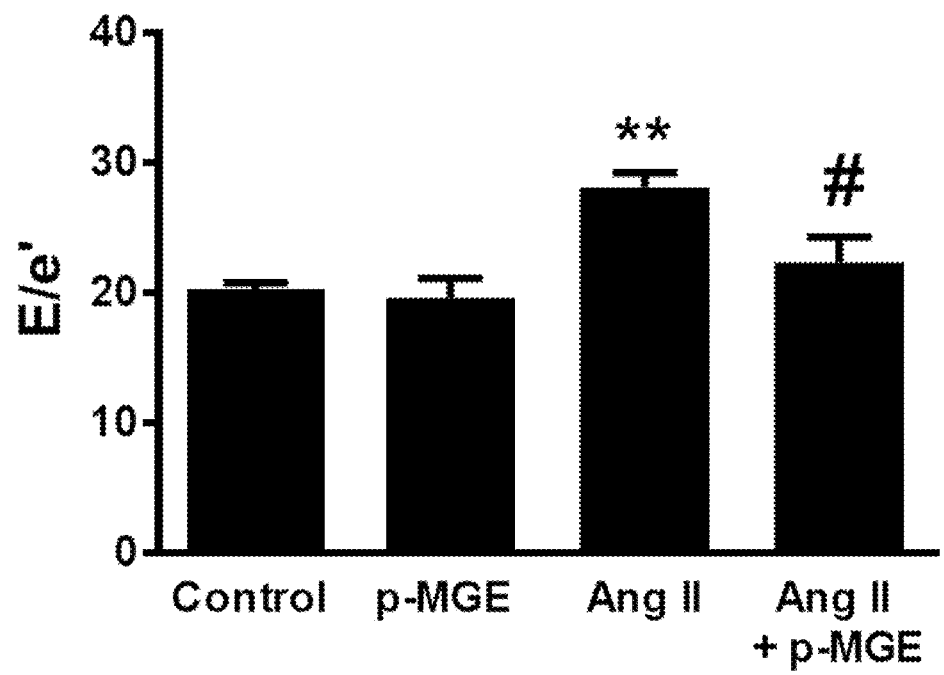
Figure 30A:
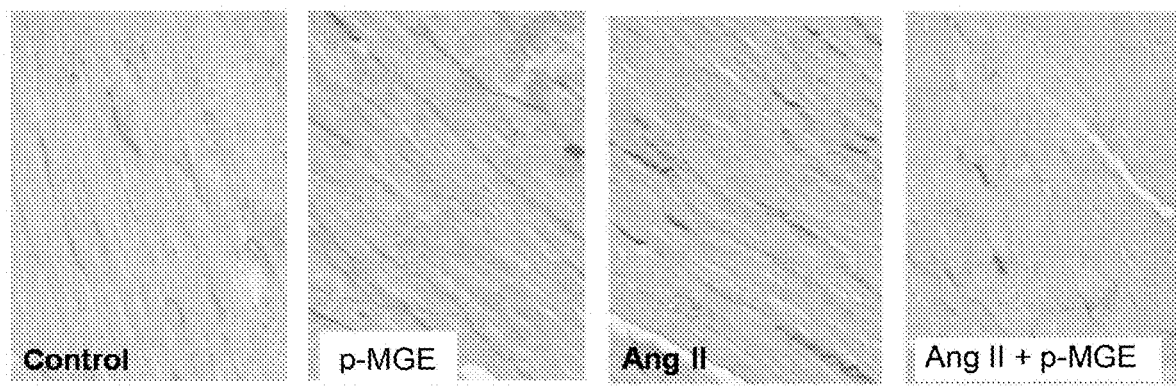
FIG. 30A-30B show assessment of hypertension-induced cardiac damage in the rats described with respect to FIG. 28A-28B that were treated with Ang II, p-MGE, or both, for 4 weeks according to aspects of this disclosure. Left ventricular sections of the hearts were stained with Picrosirius red to identify total collagen, which was quantified in 4 images from the left ventricle of each rat. n=8; **** p<0.0001 compared to control; # p<0.05 compared to Ang II. p-MGE co-administration ameliorated the Ang II-mediated increase in interstitial fibrosis in the left ventricle, suggesting that the extract may attenuate hypertension-induced cardiac damage.
Figure 30B:
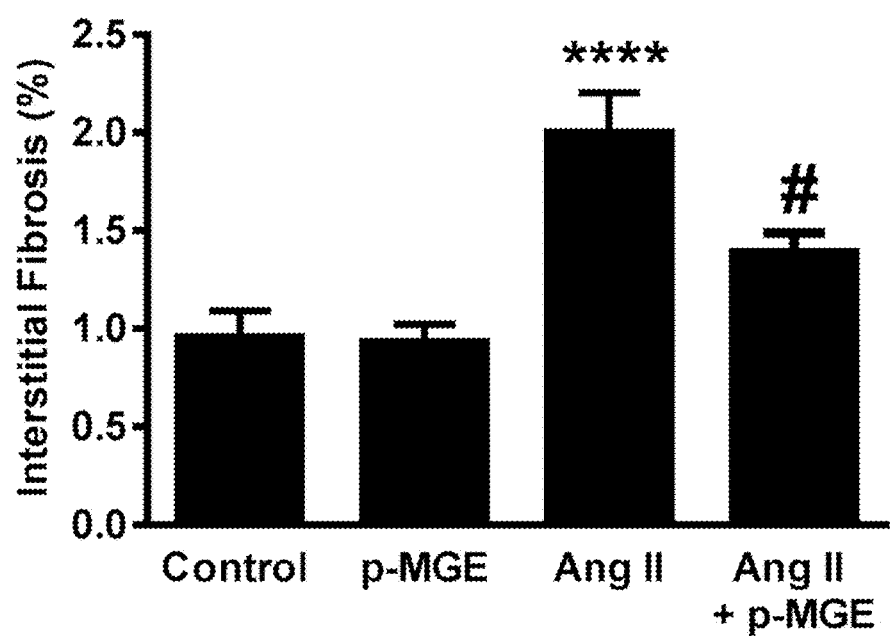

Diastolic function was measured as e', to assess the relaxation of the left ventricle, and E/e', to assess the filling pressure of the left ventricle. As shown in FIG. 29A-29B, a 4-week treatment with Ang II reduced e', suggesting that Ang II or the Ang II-mediated increase in blood pressure reduced the ability of the left ventricle to relax during diastole. Although treatment with p-MGE tended to prevent the reduction in e', the results did not reach statistical significance. However, E/e' was significantly increased by treatment with Ang II and the increase in E/e' was prevented by co-administration of p-MGE. These results indicate that Ang II causes diastolic dysfunction and that co-administration of p-MGE improves the Ang II-induced diastolic dysfunction.

Sections of the hearts of treated rats were fixed in formalin, embedded in paraffin and cut into 5 micron sections. Sections from each heart were stained with Picrosirius red, to identify total collagen deposition. As show in FIG. 30A-30B, Ang II increased the amount of interstitial fibrosis, shown as the increase in red staining in the representative images and quantified in the graph. Co-administration with p-MGE attenuated the Ang II-mediated increase in collagen, to reduce the total collagen staining which will decrease the stiffness of the left ventricle. This may account for the ability of the extract to decrease the stiffness of the ventricle and reduce diastolic dysfunction.

Figure 31A:
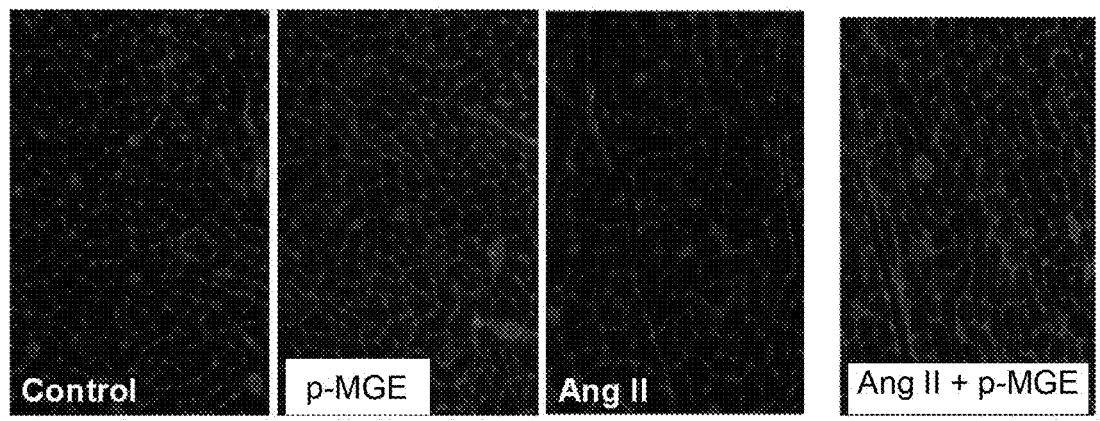
FIG. 31A-31B show assessment of hypertension-induced cardiac damage in the rats described with respect to FIG. 28A-28B that were treated with Ang II, p-MGE, or both, for 4 weeks according to aspects of this disclosure. Sections of the left ventricle of the hearts were stained with wheat germ agglutinin to outline cardiomyocytes. Mean cross-sectional area (MCSA) was averaged from at least four separate images from each animal. * p<0.05 compared to control; # p<0.05 compared to Ang II alone. The Ang II-increased cardiomyocyte MCSA was attenuated by co-administration of p-MGE, suggesting that cardiomyocyte hypertrophy may be ameliorated by administration of p-MGE.
Figure 31B:
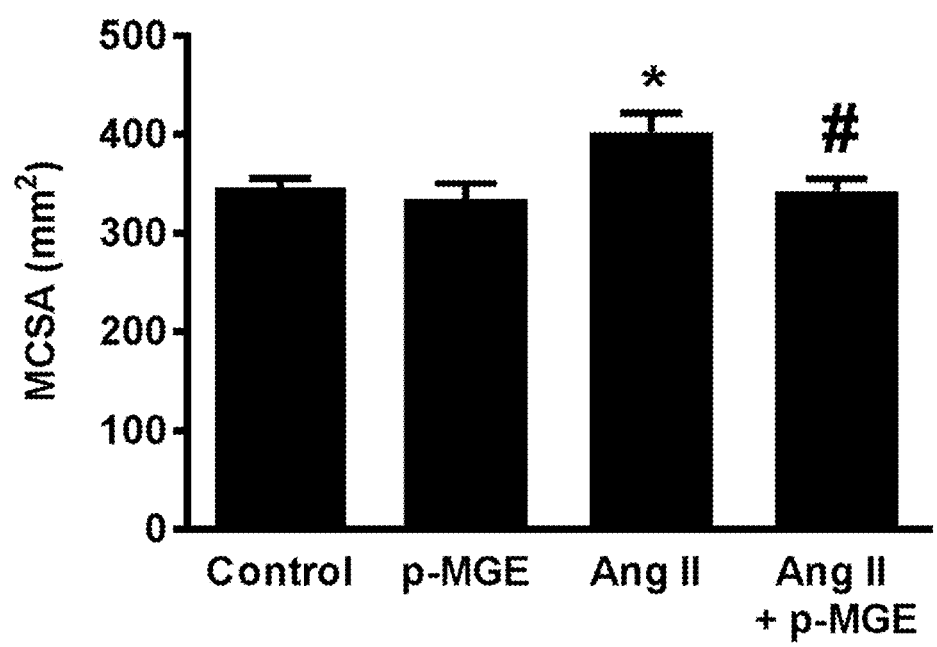

Sections of the hearts of treated rats were also stained with an antibody to wheat germ agglutinin, to outline the cell membrane of individual cardiomyocytes. The mean cross-sectional area (MCSA) was then determined, as shown in FIG. 31A-31B. Ang II or the Ang II-mediated hypertension increased the MCSA of the myocytes in the left ventricle, to cause cardiac hypertrophy. Co-administration of p-MGE significantly attenuated the Ang II-mediated increase in myocyte area, indicating the p-MGE reduced cardiomyocyte hypertrophy. This decrease in cardiac hypertrophy may also contribute to the ability of the p-MGE to reduce diastolic dysfunction.

Collectively, these results demonstrate the p-MGE does not exacerbate Ang II-induced hypertension and cardiac damage. Furthermore, the extract significantly attenuated diastolic dysfunction, in association with a reduction in cardiac interstitial fibrosis and cardiomyocyte size. These results suggest that p-MGE can be safely used in patients with hypertension and may protect the heart from hypertension-induced fibrosis and diastolic dysfunction.

Example 9

Efficacy of Muscadine Grape Seed and Skin Powder Extract (p-MGE) in Breast Tumors The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

The efficacy of p-MGE on breast tumor growth was determined by measuring tumor growth in female mice treated with p-MGE at increasing doses. The $4^{th}$ inguinal mammary pads of athymic mice (female, 15-20 g, 5-6 weeks of age) were injected with $3\times10^6$ actively growing MDA-MB-231 human triple negative breast cancer cells (suspended 50:50 in Matrigel). The mice were group housed in cages with HEPA-filtered air on 12-h light/dark cycles and were fed regular rat chow ad libitum. Tumor size was measured twice a week in conscious animals, using a caliper, and tumor volume was calculated using the formula for a semi-ellipsoid $(4/3\pi r^3)/2)$]. When the tumors reached a size of 100 mm$^3$, the mice were randomized for treatment with 0.05, 0.1, 0.2, or 0.4 mg phenolics/mL of p-MGE in the drinking water (corresponding to doses of 0.25, 0.5, 1 and 2 mg phenolics/mouse/day for a 25 g mouse); Control mice drank regular water. After 4 weeks of treatment, the mice were sacrificed and the tumors were weighed.

The volume of human triple negative breast tumors growing in athymic mice increased over a 4 week period. Treatment with p-MGE caused a dose-dependent reduction in tumor volume which was significantly different than the control mice at all four doses tested after the 4 weeks of treatment, as shown in FIG. 32A. The weight of the tumors was also dose-dependently reduced compared to mice drinking regular water (Control), as shown in FIG. 32B.

Figure 32F:
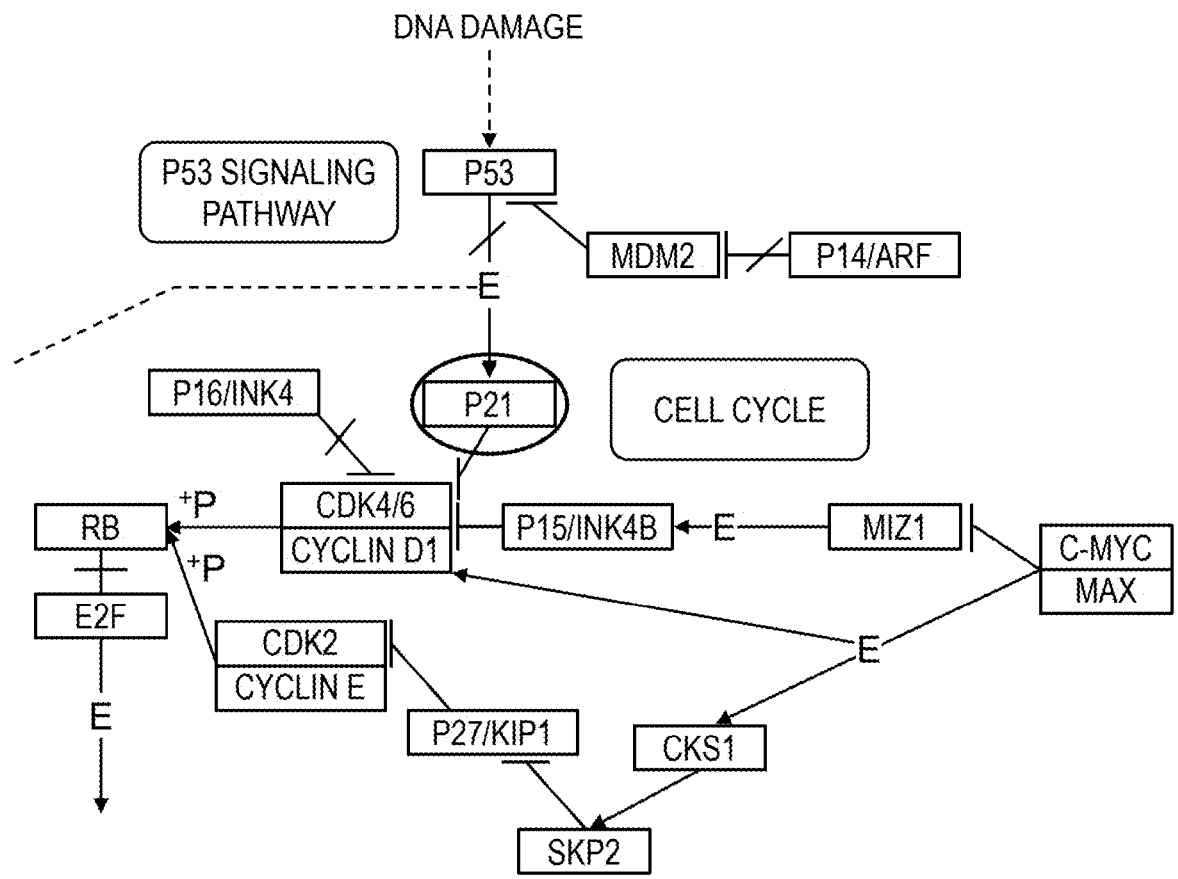

To identify the mechanism(s) for the reduction in tumor growth by p-MGE, RNA was isolated from tumors that were not treated (Control) and tumors treated with 0.1 mg phenolics/mL and genes encoding key proteins and enzymes that participate in cell growth were quantified by RT-PCR. As shown in FIG. 32C, the mitogen-activated protein (MAP) kinase phosphatase (MAKP1), also known as dual-specificity phosphatase 1 (DUSP), was significantly increased by treatment with p-MGE. As DUSP1 reduces the activity of MAP kinases, an increase in DUSP1 could account for the reduction in MAP kinase activities observed in breast cancer cells. In contrast, platelet-derived growth factor (PDGF) was significantly reduced in the tumors from mice treated with p-MGE compared to control mice, as shown in FIG. 32D. Since PDGF is a major growth factor that is involved in MAP kinase signaling, the p-MGE-induced reduction in PDGF could also participate in the reduction in tumor growth by treatment with p-MGE. Regulation of the cell cycle is also important in tumor growth and is complex, involving numerous regulatory proteins, protein kinases and cyclins. p-MGE significantly increased p21 in the tumors of mice treated with p-MGE compared to the tumors of control mice, as shown in FIG. 32E. Since p21 is an inhibitor that regulates the activity of cyclin-dependent protein kinases/cyclins, as shown in the pathway in FIG. 32F, its reduction by treatment with p-MGE could also participate in the p-MGE-induced reduction in tumor size.

Collectively, these results demonstrate that concentrations from 0.05 to 0.4 mg/mL p-MGE reduced the volume and weight of human triple negative breast tumors in athymic mice. The associated increase in the MAP kinase phosphatase DUSP1, the reduction in the growth factor PDGF and the increase in the cyclin-dependent protein kinase inhibitor p21 could participate in the reduction in breast tumor growth in mice treated with p-MGE, suggesting that treatment with p-MGE may be a novel treatment for women with breast cancer.

Example 10

Effect of p-MGE on Brain-Specific Metastatic Cells

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

Triple negative breast cancer cells lines which specifically metastasize to the brain were developed, to study the effect of p-MGE on brain-specific triple negative breast cancer in vitro and in vivo. Two syngeneic mouse models of triple negative breast cancer metastasis to the brain were developed at Wake Forest School of Medicine via serial selection of cells (5×) through the brain of syngeneic hosts following intra-arterial injection ('triple negative' 4T1.luc2-Br5 in Balb/c mice and ER+ Eo771.luc-Br5 in C57Bl/6 mice). The resulting cells are highly specific for the brain. Three additional human brain metastatic cell lines were obtained (HER2+ MDA-MB-361 and MCF7-HER2-Br3 was kindly provided by Dr. Pat Steeg and 'triple negative' MDA-MB-231Br was kindly provided by Dr. Janet Price). These cell lines were used to test the effect of p-MGE on metastatic growth, by measuring clonogenic growth, proliferation, DNA damage and apoptosis.

Cells of the 4T1.luc2-Br5 and ER+ Eo771.luc-Br5 were seeded at clonogenic density in 6 well tissue culture plates and allowed to adhere overnight, after which they were treated with p-MGE and the cells allowed to grow for 10-14 days. The clonogenic efficiency was calculated as the number of colonies formed as a percentage of cells seeded, then normalized to control. As shown in FIG. 33, at a dose of 7.5 μg/mL, p-MGE decreased clonogenic survival of 4T1.luc2-Br5 cells by 50%. The Eo771.luc.Br5 cells were slightly more sensitive to p-MGE, showing 33% inhibition at 5 μg/mL and 91% inhibition at 7.5 μg/mL.

Figure 34A:
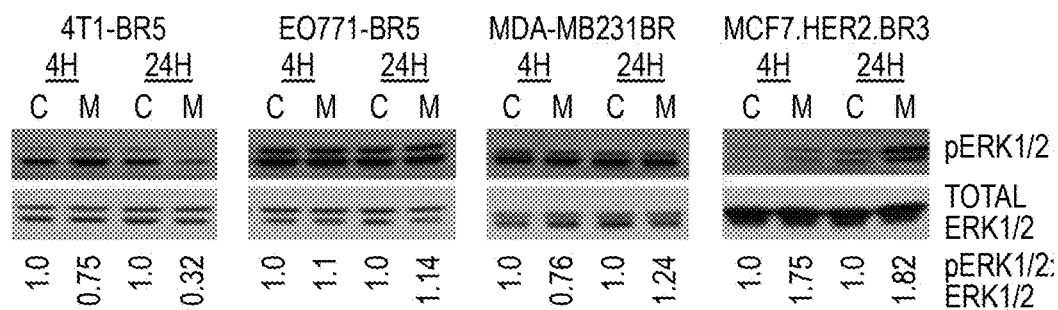
FIG. 34A shows the effect of a muscadine grape seed and muscadine grape skin powder extract (p-MGE) as described in Example 1 on growth of brain-specific breast cancer cell lines according to aspects of this disclosure. Brain-specific breast cancer cells (4T1-Br5, Eo771-Br5, MDA-MB231Br, and MCF7.HER2.Br3) were incubated with 10 µg/mL p-MGE (M) or without p-MGE (C for control) as indicated and analyzed by Western blot for phosphorylated ERK1/2 (pERK1/2) compared to total ERK1/2. Blots shown are representative of 3 independent experiments; quantification below represents the mean values from 3 independent experiments. After a 24 h treatment with p-MGE, the 4T1-Br5 showed a significant decrease in ERK1/2 phosphorylation (68% decrease, p<0.05), suggesting that a reduction in the phosphorylation and activation of MAP kinases may participate in the p-MGE-induced reduction in cell growth. In contrast, phospho-ERK1/2 were not changed in Eo771, MDA-MB-231 or MCF-HER1 brain-specific breast cancer cells, suggesting that different pathways may participate in the inhibition in cell growth in different types of breast cancer cells.

To begin to identify the molecular mechanisms for the inhibition of the growth of metastatic brain cells, cells were incubated with p-MGE (10 μg/mL for 4 or 24 h) and cell lysates were probed by Western blot analysis. As shown in FIG. 34A, cell lysates were probed with an antibody to the activated mitogen activation protein (MAP) kinase, phosphorylated ERK1/2. The relative phosphorylation of ERK1/2 with respect to total ERK1/2 protein was obtained by densitometry using ImageJ. p-MGE treatment for 24 h caused a 68±3% decrease in phosphorylated ERK in the 4T1.luc2.Br5 cell line compared its corresponding control ($p<0.05$), while no consistent significant change in ERK1/2 phosphorylation was observed with the Eo771.luc.Br5, MDA-MB-231Br, or MCF7.HER2.Br3 cell lines, suggesting that the proliferative protein kinases may participate in the p-MGE-induced inhibition of cell growth in 4T1 triple negative brain-specific cells but not all brain-specific metastatic breast cancer cells.

Figure 34B:
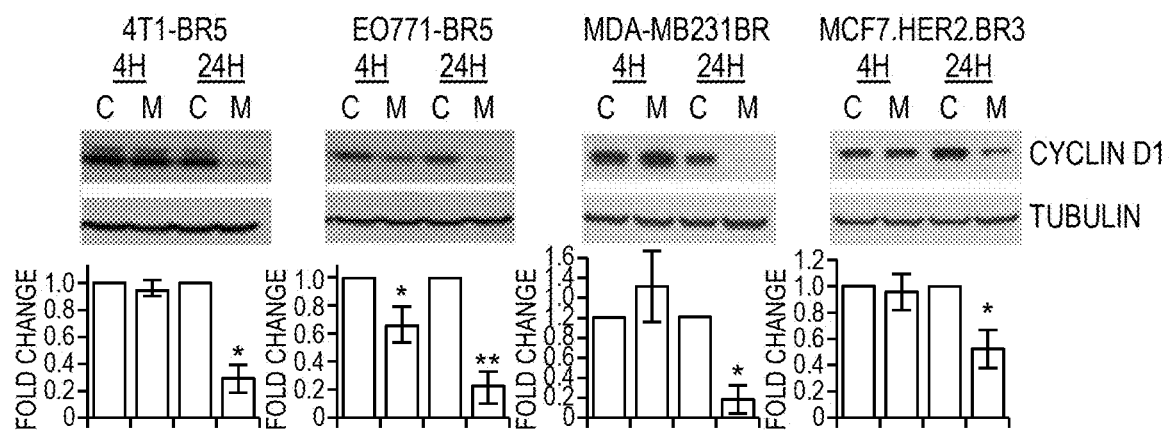
FIG. 34B shows the effect of a muscadine grape seed and muscadine grape skin powder extract (p-MGE) as described in Example 1 on growth of brain-specific breast cancer cell lines according to aspects of this disclosure. Brain specific breast cancer cells (4T1-Br5, Eo771-Br5, MDA-MB231Br, and MCF7.HER2.Br3) were incubated with 10 µg/mL p-MGE (M) or without p-MGE (C for Control) for either 4 h or 24 h and then probed with an antibody to cyclin D1 by Western blot analysis; tubulin was used as a loading control. * denotes p<0.05 and ** denotes P<0.01. p-MGE caused a decrease in cyclin D1 following a 24 h treatment in 4T1 triple negative, E0771 ER+, MDA-MB-231 triple negative, and MCF7.HER2 ER+/HER2-overexpressing cell lines, suggesting that the extract reduced progression through the cell cycle to reduce growth.

Brain-specific lysates were also probed with an antibody to cyclin D1, to determine whether p-MGE decreases cell growth by a reduction in the cell cycle. Cyclin D1 is a major regulator of cell cycle progression and proliferation. As shown in FIG. 34B, data suggest that p-MGE treatment for 24 h decreased cyclin D1 protein levels in 4T1.luc2.Br5, Eo771.luc.Br5, and MDA-MB-231Br cells, suggesting that the extract may regulate the cell cycle to reduce proliferation.

Finally, brain specific breast cancer cell lysates were probed with antibodies to PARP and caspase 3, to determine whether p-MGE increases apoptosis as a mechanism to reduce the growth of breast cancer cells. As shown in FIG. 35, p-MGE treatment (10 μg/mL for 24 h) induced apoptosis in the 4T1.luc2.Br5 cells, demonstrated by the detection of cleaved PARP as well as the active cleaved form of caspase 3 by Western blot. In contrast, no PARP or caspase 3 cleavage was observed in Eo771.luc.Br5, MDA-MB-231Br, or MCF7.HER2.Br3 under these conditions (FIG. 35 and not shown). These results suggest that p-MGE stimulates apoptosis in some but not all brain-specific breast cancer cells, as part of the mechanism for the reduction in cell growth.

Example 11

Effect of p-MGE on Breast Cancer Proliferation and Migration [NEW]

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

A. Triple Negative Breast Cancer (TNBC)

To determine the effect of p-MGE on metastatic breast cancer growth, we assessed the ability of triple negative breast cancer (TNBC) cells to proliferate and migrate, in in vitro studies using the IncuCyte Zoom real-time imaging system. As shown in FIG. 36A and FIG. 36B, the proliferation of MDA-MB-231 human TNBC cells was decreased in a dose-dependent manner by increasing concentrations of p-MGE. After 48 h of treatment, 25 µg/mL p-MGE reduced growth from 2.7±0.2 to 1.4±0.1 nuclei/mm$^2$, an inhibition of 48% compared to untreated or Control cells. As shown in FIG. 37A-37C, similar dose-dependent attenuation of proliferation was observed in 3 additional TNBC cell lines: (1) BT549 human TNBC cells, after 48 h of treatment, 25 µg/mL p-MGE reduced growth from 1.6±0.1 to 0.9±0.1 nuclei/mm$^2$, an inhibition of 44% compared to untreated or Control cells; (2) BT-20 human TNBC cells, after 48 h of treatment, 25 µg/mL p-MGE reduced growth from 1.5±0.1 to 1.1±0.1 nuclei/mm$^2$, an inhibition of 27% compared to untreated or Control cells; and (3) 4T1 mouse TNBC cells, after 48 h of treatment, 25 µg/mL p-MGE reduced growth from 3.0±0.3 to 1.2±0.2 percent confluence, an inhibition of 60% compared to untreated or Control cells. Increasing concentrations of p-MGE reduced the phosphorylation and activation of ERK1 and ERK2 by 40% at 10 µg/mL p-MGE and by 80% at 20 µg/mL p-MGE, as shown in FIG. 38A-38D, suggesting that p-MGE decreases MAP kinase activities to reduce the proliferation of triple negative breast cancer cells.

To identify pathways involved in the inhibition of triple negative breast cancer cell growth by p-MGE, 4T1 mouse triple negative breast cancer cells were pre-incubated in reduced serum media for 24 h followed by incubation with 20 µg/mL p-MGE for increasing periods of time, from 1 to 12 h. RNA was isolated in TRIzol, according to the manufacturer's instruction, and submitted to the Wake Forest University Comprehensive Cancer Center Genomics Core for analysis of gene expression profiling using RNAseq. A number of genes were altered by treatment with p-MGE over the 12 h time course; further analysis by RT-PCR and Western blot hybridization will be required to verify these changes in gene expression. EPIG (a method for Extracting microarray gene expression Patterns and Identifying co-expressed Genes) Global Gene Pattern analysis of these gene arrays identified 2009 genes across 9 distinct patterns which were either up-regulated, down-regulated or not significantly changed by treatment with p-MGE, as shown in FIG. 39. Families of genes that were up-regulated by p-MGE included 29 genes involved in the inflammatory or lipopolysaccharide (LPS) response, 272 genes involved in the viral defense or interferon beta (IFNβ) response and 741 genes involved in autophagy or the endoplasmic reticulum (ER) stress response. In contrast, 96 genes were down-regulated that are involved in nucleosome assembly or the innate immune response and 748 genes which were involved in the cell cycle or cell division (in agreement with changes in MAP kinase signaling and proteins involved in regulation of the cell cycle). Four additional patterns of genes showed no significant enrichment.

TNBC is an aggressive form of breast cancer that metastasizes to various organs in the body, including the lung, liver, bone and brain and metastatic breast cancer is often the cause of death in women with TNBC. As a first step in the cascade leading to metastatic growth, TNBC cells migrate away from the primary tumor, intravasate into the blood stream to travel to distant sites, extravasate into the tissues and proliferate to form metastatic tumors. The migration of TNBC cells was analyzed using the IncuCyte™ Zoom system to measure movement into a "wound" made by denuding an 800 µm zone in the center of a confluent monolayer of cells. The cell lines tested were 4T1 cells, MB-MDA-231 cells, and BT-549 cells. A representative set of images for an experiment performed with MB-MDA-231 is shown in FIG. 40A. The denuded area is seen as the central light grey horizontal strip across each image, with the medium grey areas at the top and bottom of the images being the areas of confluent cells on each side of the denuded area. The distance traveled into the wound by the cells from above and below the denuded strip was then recorded and measured every 2 h over a 24 to 48 h treatment period with increasing concentrations of p-MGE. The migration of the cells is visualized in the images for t=12 h and t=24 h as the darkest grey zones encroaching into the light grey denuded area. As shown in FIG. 40B, movement of the MDA-MB-231 human TNBC cells into the denuded zone increased with time; the reduction in distance travel was dependent on the amount of p-MGE. Similarly, as shown in FIG. 40C and FIG. 40D, 4T1 cells traveled into the wound during the treatment period, with a dose-dependent reduction in cell migration. Similar results were obtained in experiments assessing BT-549 TNBC cells (data not shown).

Collectively, these results suggest that p-MGE reduces the proliferation and migration of TNBC cells, which would decrease the migration/invasion of TNBC to distant metastatic sites. p-MGE reduces the phosphorylation and activation of the MAP kinases ERK1/2. Recent gene expressing profiling has identified a large number of genes which are up-regulated, down-regulated or not altered in 4T1 triple negative breast cancer cells incubated with p-MGE, suggesting that numerous pathways participate in the regulation of cell growth by the extract. These results suggest that p-MGE may reduce both primary and invasive growth in TNBC, which is the primary cause of death in this aggressive form of breast cancer.

B. HER2 Over-Expressing Breast Cancer

Human epidermal growth factor receptor 2 (HER2) over-expressing breast cancer is characterized by increased expression of HER2. HER2-positive breast cancer is an aggressive form of breast cancer and often metastasizes to various organs in the body, including the lung, liver, bone and brain. The estrogen receptor (ER) or the progesterone receptor (PR) may or may not be present in HER2 breast cancer. Although targeted therapy for HER2 over-expressing breast cancer includes monoclonal antibody therapeutic trastuzumab, commercially available as Herceptin®, 20% of patients who have primary disease and 70% of patients with metastatic disease do not respond to this drug and 70% of those who initially respond progress to metastatic disease. Thus, there is a clear need for additional drugs for patients with primary or metastatic HER2 positive breast cancer. This study assessed the impact of p-MGE on the ability of HER2 positive human SKBr3 breast cells to proliferate in vitro using the IncuCyte Zoom real-time imaging system. The cells were seeded into 96-well plates and treated with increasing concentrations of p-MGE, calculated as µg phenolics/mL of culture media. Cell proliferation was measured at 48 h and quantified as the percent of proliferation in control mice treated with water alone. As shown in FIG. 41A, the proliferation of SKBr3 cells was decreased in a dose-dependent manner by increasing concentrations of p-MGE; treatment with 40 µg/mL p-MGE reduced proliferation by 60% compared to Control.

To identify the molecular mechanisms that participate in the inhibition of HER2 over-expressing breast cancer cells, SKBr3 cells were incubated with 20 μg/mL p-MGE for increasing periods of time and cell lysates were analyzed by Western blots using (1) an antibody for AKT phosphorylated on serine 473, (2) an antibody for AKT phosphorylated on threonine 308, and (3) an antibody for phosphorylated mTOR (p-mTOR). Gels were analyzed using the GelDoc and immunoreactive bands were normalized for loading by analysis of the total amount of protein loaded/lane. One of the primary pathways activated in breast cancer cells and tumors is the AKT/protein kinase B pathway, leading to increased proliferation and survival. As shown in FIG. 41B and FIG. 41C, treatment of SKBr3 cells with 20 μg/mL p-MGE caused a time dependent reduction in AKT phosphorylated on either serine 473 or threonine 308, respectively. After 16 h of treatment, phosphorylation of AKT on either serine 473 or threonine 308 was reduced 60% by p-MGE. The primary target that is activated in response to phosphorylated Akt is the mammalian target of rapamycin, mTOR. Treatment of SKBr3 cells with increasing concentrations of p-MGE also caused a dose dependent increase in phosphorylated and activated mTOR, as shown in FIG. 41D. After 16 h of treatment, phosphorylation of mTOR was reduced 50% by p-MGE.

These results demonstrate that treatment of HER2 over-expressing breast cancer cells with p-MGE reduces AKT/mTOR signaling which may participate in the reduction in proliferation, suggesting that the extract may be a useful treatment for patients with HER2 breast cancer.

Example 12

Efficacy of p-MGE in Combination With Radiation

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

Over two thirds of cancer patients receive treatment with radiation during the course of their disease. Radiation therapy, whether delivered as partial/whole brain radiation therapy or as targeted Gamma Knife therapy, sometimes with surgery, remains the standard of care for the treatment of brain metastatic lesions in breast cancer patients. We treated brain specific breast cancer cells with p-MGE, in the presence and absence of radiation, to determine the effect of the combined treatment. Mouse brain specific metastatic breast cancer cells of the 4T1.luc2.BR5 or Eo771.luc.Br5 cell lines were seeded at clonogenic density in 6 well culture plates for 24 h and then treated with p-MGE for 24 h. After the 24 h drug treatment, cells were either sham-irradiated or irradiated with 1-6 Gy of $^{137}$Cs γ rays at a dose rate of ~4 Gy/min and the cells incubated for another 10-14 days. At that time, the colonies were stained with crystal violet and colonies containing ≥50 cells scored as clonogenic survivors. The fractional survival (f) was calculated as the number of colonies formed divided by the number of cells seeded multiplied by the plating efficiency of the sham-irradiated cells. Combined modality survival curves were corrected for the drug-alone kill to assess the radiosensitization potential of the p-MGE. As shown in FIG. 42A and FIG. 42B, treatment with p-MGE did not significantly increase radiation sensitivity. However, as seen in FIG. 42C and FIG. 42D, administration of p-MGE and 2 Gy radiation (a relevant fraction dose for treatment of patients with brain metastases) resulted in greater loss then either treatment alone, suggesting an additive effect.

These results suggest the p-MGE can be safely used in combination with radiation therapy and that the combination therapy may be more effective than either individual therapy alone.

Example 13

Efficacy of p-MGE in Combination With Tamoxifen

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

The majority of breast tumors are of the ER+ subtype, based on the presence of the estrogen receptor (ER) on the surface of the tumor cells. The growth of ER+ breast tumors can be significantly reduced by blockade of the estrogen receptor with receptor antagonists such as tamoxifen or by drugs which block the production of estrogen (aromatase inhibitors), which are routinely used as standard-of-care for the treatment of ER+ breast cancer. The efficacy of p-MGE in reducing the growth of ER+ breast tumor growth breast tumor growth was determined by measuring ER+ tumor growth in female mice treated with p-MGE, alone or in the presence of the ER+ receptor antagonist tamoxifen, administered in the mouse chow. The $4^{th}$ inguinal mammary pads of athymic mice (female, 15-20 g, 5-6 weeks of age) were injected with 1×10$^6$ actively growing ZR-75-1 or MCF7 human ER+ breast cancer cells. The mice were group housed in cages with HEPA-filtered air on 12-h light/dark cycles and were fed regular rat chow ad libitum. Tumor size was measured twice a week in conscious animals, using a caliper, and tumor volume was calculated using the formula for a semi-ellipsoid $(4/3\pi r^3)/2)$]. When the tumors reached a size of 30 mm$^3$, the mice were randomized for treatment with either 0.1 mg phenolics/mL drinking water (corresponding to doses of 0.5 mg phenolics/mouse/day for a 25 g mouse), an approximate dose of 32 mg/kg/d tamoxifen (TAM, administered by replacement of regular mouse chow with chow containing tamoxifen) or with the combination of p-MGE and tamoxifen; Control mice drank regular water. After 7 weeks of treatment for the mice containing ZR-75-1 human ER+ breast tumors or 5 weeks of treatment for the mice containing MCF7 ER+ breast tumors, the mice were sacrificed and the tumors were removed and weighed.

The size and weight of ZR-75-1 ER+ breast tumors or of MC7 ER+ tumors was increased over the period of treatment, as shown in FIG. 43 and FIG. 46, respectively. Treatment with p-MGE significantly reduced the growth of ZR-75-1 or MCF tumors, suggesting the extract is effective in ER+ breast tumors. As expected, tamoxifen reduced the growth of both ER+ tumors, by blocking the estrogen receptor to reduce proliferation. In both ZR-75-1 and MCF tumors, the combination of p-MGE and tamoxifen further reduced tumor growth, compared to the effect of either p-MGE or tamoxifen alone. Similar reductions in tumor weight were observed in both ZR-75-1 and MCF7 tumors, as shown in FIGS. 44 and 47. The reduction in tumor volume and weight of the ZR-75-1 tumors by treatment with p-MGE, tamoxifen or the combination was associated with a reduction in the number of cells which were positive for the proliferation marker Ki67, as shown in FIG. 45.

Collectively, these results demonstrate that p-MGE reduced the growth of ER+ human breast tumors. The combination of treatment with p-MGE with the estrogen receptor antagonist tamoxifen further reduced tumor growth compared to either treatment alone, suggesting that the p-MGE and tamoxifen can be used in combination. These results suggest that treatment with p-MGE may be a novel treatment for women with ER+ breast cancer, either alone or in combination with the estrogen receptor antagonist tamoxifen, which is standard-of-care for women with ER+ breast cancer.

Example 14

Effect of p-MGE on LNCaP Prostate Tumors

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

The efficacy of p-MGE was determined by measuring LNCaP prostate tumor growth in mice treated with p-MGE at increasing doses. Athymic mice (male, 15-20 g, 5-6 weeks of age) were injected subcutaneously on the lower flank with $1.6 \times 10^6$ LNCaP human prostate cancer cells (suspended 50:50 in Matrigel). The mice were group housed in cages with HEPA-filtered air on 12-h light/dark cycles and were fed regular rat chow ad libitum. Tumor size was measured twice a week in conscious animals, using a caliper, and tumor volume was calculated using the formula for a semi-ellipsoid $(4/3\pi r^3)/2)$]. When the tumors reached a size of 100 mm$^3$, the mice were randomized for treatment with increasing doses of p-MGE from 0.05, 0.1, 0.2 and 0.4 mg phenolics/mL drinking water (corresponding to 0.25, 0.5, 1 and 2 mg phenolics/mouse/day for a 25 g mouse); Control mice drank regular water. After 5 weeks of treatment, the mice were sacrificed and the tumors were weighed.

The volume of prostate tumors growing in the flank of nude mice increased to 765.2±101.8 mm$^3$ in untreated mice over the 5 week treatment period while the tumors of mice treated with 0.1 mg phenolics/mL increased in volume to 364.2±108.9 mm$^3$ and, with 0.4 mg phenolics/mL, to 190.2±26.4 mm$^3$, as shown in FIG. 48. The weight of prostate tumors from mice drinking either regular water (Control) or increasing concentrations of p-MGE was also reduced, as shown in FIG. 49. Tumors were fixed in paraformaldehyde, embedded in paraffin, sectioned and stained with an antibody to Ki67, as a marker of proliferation. As shown in FIG. 50, treatment with 0.1 mg phenolics/mL caused a 36% reduction in the number of Ki67 positive cells per field, suggesting that p-MGE reduces the proliferation of prostate tumor cells.

Sections of tumors were also stained with an antibody to CD34, which labels endothelial cells, to identify blood vessels in the tumor and determine the effect of p-MGE on the number of blood vessels. As shown in FIG. 51, treatment with 0.1 mg phenolics/mL significantly reduced the number of blood vessels. RNA was isolated from both Control and p-MGE-treated tumors and the relative expression of the angiogenic factors vascular endothelial growth factor (VEGF) and placental growth factor (PLGF) were measured by RT-PCR, as shown in FIG. 52. Treatment with p-MGE reduced both VEGF and PLGF in prostate tumors compared to Control, suggesting that a reduction in pro-angiogeneic factors is associated with the p-MGE-induced reduction in blood vessels.

Collectively, these results show that p-MGE reduces human prostate tumor growth in a mouse model, in association with a reduction in proliferation and angiogenesis, suggesting that p-MGE may be an effective treatment for prostate cancer.

Example 15

Effect of p-MGE on Radiation-Induced Fibrosis

The studies described in this example were performed with muscadine grape seed and grape skin powder extracts manufactured by the method described in Example 1. Specifically, the powder extract was made from the liquid extract described above in Example 5. Below, the powder extract is referred to as "p-MGE."

A. p-MGE and Radiation-Induced Muscle Fibrosis

Many patients with cancer receive radiation treatment as part of their standard of care. For example, patients with soft tissue sarcoma are routinely treated with radiation, leading to skeletal muscle fibrosis and joint contracture. Treatment with radiation can cause a progressive deposition of collagen within the muscle tissues and the adjacent dermis. Increased collagen deposition within tissues reduces tissue elasticity and leads to functional stiffening, which is a substantial and severe source of pain and morbidity in individuals who receive radiation treatment.

B. p-MGE Prevents Skeletal Muscle Fibrosis Skeletal Muscle after Irradiation

Radiation treatment for soft tissue sarcoma involves irradiation of muscle leading to deposition of collagen within the muscle and stiffening of the limb. To determine the effect of p-MGE on radiation-induced skeletal muscle fibrosis, the right hind limb of 16 week old, female Swiss Albino mice received a simulated course of radiation therapy modeling the treatment of humans who have an extremity sarcoma (4 total fractions of 7.3 Gray (Gy)/fraction provided twice weekly for two weeks. The p-MGE (0.1 mg/mL) was delivered continuously in the drinking water for 6 days prior to radiation therapy and for 6 weeks after radiation therapy was completed. Tibialis anterior (TA) muscles were processed for histology and examined for changes in morphology [hematoxylin and eosin (H&E) stain] and fibrosis (Masson' s Trichrome stain). Irradiated muscle showed distinct areas of active inflammation, which were primarily contained to the endomysial space, as shown in FIG. 53. Qualitatively, this inflammation appeared to be lessened in irradiated muscles from mice treated with p-MGE. Masson's Trichrome stain was used to identify areas of tissue fibrosis and was quantified using ImageJ software. Treatment with p-MGE reduced radiation treatment-induced fibrosis to the levels of non-irradiated, as shown in FIG. 54.

To determine the mechanism(s) of the p-MGE-induced reduction in fibrosis, the right hind limb of 8 week old female athymic mice received a course of radiation therapy that again simulated the treatment of soft tissue sarcoma by applying the biologic equivalent dose for what is used for the treatment of extremity sarcoma in humans: Four total fractions of 7.3 Gray (Gy)/fraction were provided twice weekly for two weeks and p-MGE was delivered in the drinking water (0.1 mg/mL) for 6 days prior to initiating radiation therapy and throughout the study. Biomarkers of fibrosis and collagen deposition were characterized at the completion of the six weeks of the radiation therapy. Transforming growth factor beta (TGFβ) is a known stimulator of collagen production and increases within the skeletal muscle of pigs after irradiation. Increased intramuscular TFGβ was observed in mice at the end of the 8 weeks of radiation and p-MGE treatment significantly reduced the radiation-induced production of TGFβ, as shown in FIG. 55A. TFGβ signaling promotes the production of connective tissue growth factor (CTGF), another hallmark of tissue fibrosis. As shown in FIG. 55B, radiation treatment also increased the production of CTGF, which was significantly reduced by co-administration of p-MGE. TFGβ also initiates SMAD signaling, which increases collagen production; SMAD proteins are a family of proteins that, upon phosphorylation, enter the nucleus and act as transcription factors to increase the production of pro-fibrotic proteins. Radiation treatment increased the expression of SMAD2, which was significantly reduced by administration of p-MGE, shown in FIG. 55C. These results suggest that radiation treatment activates the TGBβ/CTGF/SMAD pathway to increased tissue fibrosis and that p-MGE reduces fibrosis by attenuating this pathway.

C. p-MGE Reduces Radiation-Induced Bone Damage

Approximately half of the 1.7 million new cancer diagnoses annually will be treated with therapeutic ionizing radiation. As improvements in cancer screening and treatment have decreased patient mortality for most types of cancer, radiation therapy-induced bone fractures are also a major concern. Particularly debilitating are femoral and pelvic insufficiency fractures that occur at high rates in patients that receive pelvic radiation therapy for cervical, rectal and anal cancer; necrosis of the jaw resulting from radiation treatment also occurs in head and neck cancer survivors. Radiation therapy is therefore a major risk factor for bone damage and fractures in cancer patients, which serves as a major source of functional impairment, pain, and mortality. The cause of radiation therapy-induced bone damage that occurs clinically is unclear, but is historically attributed to a persistent damage to osteoblasts which leads to lowered bone formation and bone mineral density. However, radiation treatment also rapidly increases the number and activity of bone-resorbing osteoclasts which leads to loss of bone.

To determine the effect of p-MGE on the formation of osteoclasts, preosteoclasts (RAW264.7 cells) were treated with 2 Gy of irradiation after a 24 h pretreatment with either 0.0001, 0.0002, or 0.0004 µg/mL of p-MGE. A single 2 Gy dose of radiation is the equivalent of one fractional radiation therapy treatment which is known to increase osteoclast numbers within the first week of exposure, leading to acute bone loss; this dose of radiation also induces significant early bone loss at irradiated sites in rodents and an increase in the formation of osteoclasts in cell culture models. As shown in FIG. 56, treating preosteoclast RAW264.7 cells with 0.0001, 0.0002, and 0.0004 µg/mL of p-MGE for 24 hours prior to 2 Gy irradiation prevented the early, radiation-induced increase in osteoclast numbers observed on Day 7. This suggests that treatment with the grape extract will reduce the radiation-induced increase in active osteoclasts which may reduce bone resorption and prevent bone loss.

These studies demonstrate that p-MGE protects muscle from radiation-induced fibrosis, through a reduction in the TGBβ/CTGF/SMAD pathway that results in increased expression of pro-fibrotic proteins. In addition, the radiation-induced increased in osteoblast formation is reduced by p-MGE. These results suggest that administration of p-MGE to patients treated with radiation therapy may reduce the radiation-induced increase in fibrosis and osteoblast formation, resulting in a decrease in the associated muscle stiffness and bone loss.

Example 16

Characterization of p-MGE in Comparison to Other Muscadine Grape Products

The studies described in this example were performed with muscadine grape seed and grape skin powder extracts manufactured by the method described in Example 1. Specifically, the powder extract was made from the liquid extract described above in Example 5. Below, the liquid extract is referred to as "l-MGE" and the powder extract is referred to as "p-MGE."

The contents of capsules from 9 different commercially available products made from muscadine grapes were analyzed for total phenolic content/capsule, using a modification of the colorimetric Folin-Ciocalteau method and gallic acid as a standard. The capsules were stored at ambient temperature (room temperature of approximately 65° F. to 72° F.) and, when tested, the contents of capsules were resuspended in water and homogenized using a Tissue-Lyzer™ (Qiagen) prior to the measurement of total phenolics. The amount of phenolics was quantified per capsule, as shown in FIG. 57. The commercial products that were analyzed are described in Table 3 below. The total phenolic content of the capsules varied from a high of 178.9 mg±6 for the p-MGE to 11.8 mg±0.9 for the Muscadine Grape Seed product from Biopower Nutrition (BP). Compared to the Muscadine Berries product from Earth Natural Supplements, the p-MGE formulation had 12.4 times greater total phenolic content per capsule and 14.9 times greater total phenolic content based on the mg phenolics/gram powder.

Individual polyphenolics that are present in four of the products—catechin, gallic acid, epicatechin, ellagic acid, procyanadin, and catechin-gallate (cat-gall)—were measured on a Shimadzu ultra-high performance liquid chromatography (UPLC) coupled to mass spectroscopy detection (UPLC-MS) and identified by comparison to standards. As shown in FIG. 58, UPLC-MS analysis of individual phenolic components showed that p-MGE primarily contained epitcatechin, gallic acid, procyanidin, catechin and catechin-gallate. Nature's Pearl (NP) made from seeds contained primarily epitcatechin and gallic acid, while the Muscadine Plus Dietary Supplement from Muscadine Naturals, produced from skins, and the Muscadinex, a skin/seed product, contained primarily ellagic and gallic acid. p-MGE contained significantly higher levels of epitcatechin [22.0±0.7 mg/g], gallic acid [13.5±0.6 mg/g], procyanidin B [7.1±0.3 mg/g], ellagic acid [4.7±0.4 mg/g], catechin [2.7±0.1 mg/g] and catechin gallate [1.8±0.1 mg/g] as compared to the other supplements. Other phenolics including resveratrol, quercetin and myricetin were below the assay detection limit in all four of the products analyzed. Among the muscadine products tested, p-MGE contained the highest total phenolic content that reflects higher levels of epitcatechin, gallic acid, ellagic acid, catechin and procyanidin.

TABLE 3

Comparison of commercially available products made from muscadine grapes

| Name | Abbr. | Source | Lot # | DOM or ED[1] | Content | mg powder/ capsule[2] | mg phenolics/ gram powder[3] | mg phenolics/ capsule[4] |
|---|---|---|---|---|---|---|---|---|
| p-MGE | p-MGE | Piedmont Research & Development Corp., Advance, NC | 013-1 | DOM: Jan. 13, 2015 | Powder; seed and skin | 446 | 363.9 | 162.3 |
| Premium Muscadine Grape Seed Dietary Supplement | NP | Nature's Pearl, Advance, NC | 218B | DOM: August 2013 | Seeds | 544 | 72.1 | 39.2 |
| Muscadine Plus Dietary Supplement | MN | Muscadine Naturals, Inc., Warsaw, NC | 1503483 | ED: April 2018 | Powder; skins | 480 | 55.2 | 26.5 |
| Premium Muscadine | NF | Nature's Force Dietary Supplement, Sun Prairie, WI | Not provided | Not provided | Skins, seeds, pulp | 607 | 74.3 | 45.1 |
| Muscadine Berries | EN | Earth Natural Supplements, Florida | 106-670-053 | ED: December 2016 | Berries | 537 | 24.4 | 13.1 |
| Muscadine Grape Seed | BP | Biopower Nutrition, FL | 12082013 | ED: December 2016 | Seeds | 521 | 42.2 | 22 |
| Muscadine Grape Seed Herbal Supplement | VIT | Vitacost, Lexington, NC | NSI 3007301 | ED: May 2016 | Seeds, skins | 556 | 63.1 | 35.1 |
| Muscadinex Dietary Supplement | NCMH | NC Muscadine Health, Pine Level, NC | 1026505 | ED: December 2017 | Seeds, skins | 654 | 49.4 | 32.3 |
| Pure Muscadine Grape Seed | BN | Biotech Nutritions, Novi, MI | 7980 | ED: January 2018 | Seeds | 745 | 69.8 | 52 |
| Muscadine Grape Seed | FHN | Fresh Health Nutrition, Novi, MI | 7980 | ED: January 2018 | Seeds | | | |

[1]DOM: date of manufacture; ED: expiration date
[2]Capsules of each product were emptied and the contents weighed. These values listed are an average of the amount of product in 3 capsules tested.
[3]An aqueous extract of the capsule contents was made at the concentration of 10 mg/mL (using Tissuelyzer followed by removal of insoluble material. Total amount of phenolics in extract was measured using the Folin-Ciocalteau method gallic acid as a standard. The concentration of total phenolics (mg phenolics/gram) of the original powder for each product was then calculated. These values listed are an average from 3 capsules tested.
[4]The concentration of total phenolics in each capsule was then calculated using the values determined from ft nt 2 and 3 (mg phenolics/capsule), which is plotted in the graph shown in FIG. 57.

During the preparation of the p-MGE, a liquid preparation (l-MGE) is commercially processed by the technique of spray film, to produce the powdered form of MGE which is then encapsulated. The p-MGE was compared to the l-MGE by UHPLC-MS analysis. As shown in the tracings in FIG. 59, which amplifies the species present with a molecular size of approximately 500 to 2000, there were dear differences between the two preparations. as visualized in the red boxes. The p-MGE, contained components with peaks at molecular sizes of 706 and 1033 that were clearly absent in the l-MGE, while the l-MGE contains components with peaks at molecular sizes of 730 and 1288 that were clearly absence in the p-MGE. Ongoing studies are assessing the identity of these peaks.

The total phenolics in 3 different preparations of p-MGE were measured using the Folin-Ciocalteau method over a two year period, to determine the stability of the product. Lots tested were: Lot #013-1 ("p-MGE2"; DOM: Jan. 13, 2015) (in use in Phase 1 trial described in Example 18); Lot # 086-1 ("p-MGE3"; DOM: Mar. 27, 2015); and Lot #219-1 ("p-MGE4"; DOM: Aug. 7, 2015). As shown in Table 4 below, the phenolic content of the 3 preparations of p-MGE was fairly stable over the two year period of testing.

TABLE 4

Testing of Muscadine Grape Extract Powder For Total Phenolics (mg gallic acid/g powder MGE)

| | Spring, 2015* | Oct. 30, 2015** | May 16, 2016** | Feb. 1, 2017** |
|---|---|---|---|---|
| p-MGE2 | 266.7 | 341.5 | 259.8 | 267.0 |
| p-MGE3 | 327.5 | 277.9 | 240.7 | 214.2 |
| p-MGE4 | 309.8 | 270.5 | 296.7 | 224.4 |

*Measured at Brunswick Laboratories, Southborough, MA, on Apr. 17, 2015 (p-MGE2), May 5, 2015 (p-MGE3), and Jul. 10, 2015 (p-MGE4).
**Measured in the Cell and Molecular Biology Core Laboratory, WFSM, Winston-Salem, NC, on dates indicated.

The p-MGE was tested for microbial content as well as pesticides and heavy metals. The aerobic count, yeast and mold count, *E. coli, Staphylococcus aureus,* salmonella, enterobacteriaceae and pseudomonas aeruginosa counts were either low or absent, over a 16 month period, as shown in Table 5 below. In addition, pesticides, mercury, lead, cadmium and arsenic were all low and with regulatory limitations.

TABLE 5

Testing of Muscadine Grape Extract
Powder For Microbes, Pesticides,
and Heavy Metals

| Test | Oct. 30, 2015* | Feb. 14, 2017** |
|---|---|---|
| Aerobic Count | <10 cpu/g | <10 cpu/g |
| Yeast and Mold Count | <10 cpu/g | <10 pcu/g |
| E. coli | Absence | Absence |
| Staphylococcus aureus | Absence | Absence |
| Salmonella | Absence | Absence |
| Enterobacteriaceae | <10 cpu/g | ND |
| Pseudomonas aeruginosa | ND | Absence |
| Pesticides | ND | Conforms to USP |
| Mercury | ND | 0.16 ppm |
| Lead | ND | 0.05 ppm |
| Cadmium | ND | <0.01 ppm |
| Arsenic | ND | 0.19 ppm |

ND—not determined
*Measured at Nature's Pearl, Advance, NC; p-MGE2 (Lot # 013-1; DOM1/13/15; in use for Phase 1)
**Measured at LABOFINE, Quebec, Canada; p-MGE2

Example 18

Clinical Studies Assessing Treatment With p-MGE in Subjects With Advanced Malignancies A. Phase 1 Study of Muscadine Grape Seed and Skin Powder Extract (p-MGE) in Advanced Malignancy A Phase 1 clinical trial (IND 128937) entitled "Phase 1 Study of Muscadine Grape Extract (MGE) in Advanced Malignancy" is ongoing, having started on Jan. 9, 2016 (ClinicalTrials.gov Identifier: NCT02583269). The therapeutic used in the trial is a muscadine grape seed and grape skin powder extract (p-MGE) manufactured according to the method described in Example 1 and formulated as 162 mg total phenolics (440 mg total powder extract) in a hypromellose capsule. The study design is a standard 3+3 dose escalation statistical design, beginning with a dose of 2 pills per day (morning and evening) and progressing stepwise to 4, 6, 8 and 10 pills per day (half in the morning and the remainder in the evening). The patient population is adult patients with metastatic or unresectable malignancy who have failed or declined standard therapies. The purpose of the study is to determine the safety and maximum tolerated dose of p-MGE administration to adult patients in this patient population. Secondary objectives will be to evaluate change in phenolic levels, cytokines, and growth factors in patients taking the p-MGE to observe overall response rate, progression-free survival, and overall survival, to assess global quality of life and fatigue, and to assess adherence to the p-MGE treatment. The study status is open and enrolling.

The criteria for inclusion in the study include any adult 18+ years with solid tumor malignancies which are metastatic or unresectable. All patients must have either failed or refused standard therapies. The patients need to have an ECOG status of ≤2, adequate organ/marrow function, an absolute neutrophil count>1000/mcL, a platelet count of ≥50,000/mcL, total bilirubin within normal institutional limits, Aspartate aminotransferase (AST) (serum glutamic oxaloacetic transaminase [SGOT]/alanine aminotransferase (ALT) (serum glutamate pyruvate transaminase [SGPT]) ≤2.5×institutional upper limit or normal, creatinine clearance≥40 mL/min, stable supplement usage for >2 weeks prior to starting study and willingness not to change while on study, a life expectancy of >3 months and willingness and ability to consent to be in the study. Exclusion criteria include any chemotherapy or radiotherapy within 2 weeks of enrollment, receiving any investigational cancer-directed agent, a history of allergic reactions to p-MGE or similar compounds, an inability to take oral medications or a history of malabsorption due to bowel resection or gastrointestinal disease, the presence of uncontrolled diarrhea or persistent nausea/vomiting requiring daily antiemetic therapy for 21 days prior to enrollment and uncontrolled intercurrent illnesses including infection, congestive heart failure, unstable angina pectoris, cardiac arrhythmia, psychiatric illness/social situation that may limit adherence or pregnant or breast feeding. Patients with primary brain tumors were also excluded.

Patients will receive full supportive care during the course of the study (transfusions of blood products, antibiotics, antiemetics, anti-inflammatory or narcotic analgesics, medications for chronic concomitant conditions, treatment for life-threatening medical problems).

Primary outcome measure will be dose limiting toxicity (DLT) assessed at 4 weeks. Adverse events/toxicity will be assessed at weeks 4, 8, and every 4 weeks thereafter if the patient remains on the treatment.

The study is structured as a 3+3 dose-escalation study, as described, and is ongoing. Level 1: Three (3) patients will be treated with 2 capsules per day (324 mg total phenolics) for 30 days. If the treatment is well-tolerated and the tumors of the patients have not progressed, these 3 patients will continue treatment (for another 30 days and then monitored). Level 2: A second group of 3 patients will be treated with 4 capsules per day (648 mg total phenolics) and assessed after 30 days. If this treatment is well-tolerated, and the tumors of the patients have not progressed, these 3 patients will again continue treatment (for another 30 days and then monitored). Level 3: The same format will be followed for administering 6 capsules per day (972 mg total phenolics). The same format will be followed for Level 4, administering 8 capsules per day (972 mg total phenolics) (currently enrolling) and, subsequently, Level 5, administering 10 capsules per day (1620 mg total phenolics). If any of these groups have a dose-limiting toxicity, an additional 3 patients will be treated at that dose. If the 3 additional patients have no toxicity, then the next dose was/will be used in the study.

In Year 1 of this single-site study, 10 individuals were enrolled, 3 females and 7 males. Of those, 90% were 70 years or older, 90% were non-Hispanic white, while 10% were non-Hispanic black. At the time of the first annual report (reporting on the first year of study, from Jan. 9, 2016 through Jan. 8, 2017, as summarized in the table below), 9 subjects had completed treatment. Of those 9, 2 terminated the study early—1 in level 2 (4 pills per day) due to an adverse experience—and 3 additional patients were added at level 2. During the first 2 months of year 2 of the clinical trial, the $10^{th}$ patient from the Year 1 enrollment went off study and 4 additional patients were enrolled. Level 1 (n=3) was completed in 10 weeks; Level 2 (n=7) was completed in 20 weeks, and Level 3 (n=3) was completed in 5 weeks. With the exception of 1 participant, all patients appeared to be compliant with their dosing, appointments, and completion of pill diaries at home.

| | |
|---|---|
| Total Enrollment in Year 1 | 10 |
| Total Treated for Minimum of 4 Weeks (primary endpoint) | 8 |
| Terminated Study Early (prior to primary endpoint @ 4 weeks) | 2 |

| | |
|---|---|
| Off treatment (progression) | 1 |
| Off treatment (adverse event) | 1 |
| Off Treatment | 9 |
| Total Remaining on Study at the End of Year 1 | 1 |

The expected adverse events (AEs) with p-MGE administration are flatulence, diarrhea, nausea, dyspepsia, and abdominal cramping. In the first annual report, only two AEs were reported which were Grade 2 or higher and which might be attributable to p-MGE; one subject had grade 3 constipation and another had grade 2 diarrhea, both possibly attributable to p-MGE. The patient with grade 3 constipation was hospitalized with suspected bowel obstruction. Further workup revealed disease progression as the likely cause of his symptoms. It was ultimately determined that the patient had progressive metastatic disease and it was not certain if p-MGE played a role in his symptoms. No IND safety reports were submitted during year 1 and no participants died while enrolled in the study. Those with disease progression were removed from the study per the protocol, prior to hospice care or death.

The average time on-study for the first 9 participants was 7.4 weeks, with a range of 1 to 20 weeks. The reasons for leaving the study were disease progression (1 patient), a dose-limiting toxicity (1 patient), withdrawal to hospice (1 patient) or non-compliance (1 patient). The cancer diagnosis of the first 14 participates, by group, includes: pancreatic (3), apendiceal (1), rectal (1), intrahepatic bile ducts (1), genitourinary/prostate (4), peritoneal sarcoma (1), lung (2) and thyoma (1).

The clinical assessment of the patients includes one patient with colorectal cancer who experienced clinical improvement on p-MGE with stabilization of tumor marker assessed by blood work and mixed response to therapy in imaging at 8 weeks. This patient received the lowest dose and remained on study for 5 months before tumor progression. A second patient with gastrointestinal primary tumor completed 6 and ½ months of therapy at the second dose prior to disease progression. The results at this stage of the Phase 1 clinical trial suggest that the p-MGE is well tolerated at doses up to 6 capsules per day (3 in the AM and 3 in the PM) for a total daily dose of 972 mg total phenolics.

Overall response rate (CR, PR, and SD) will be assessed at 8 weeks. Progression free survival and overall survival will be assessed using the Kaplan-Meier method, with follow-up every 6±2 weeks until progression, monitoring survival study endpoints (median survival rates and associated 95% confidence intervals; censor at date of last contact). Quality of life (Functional Assessment of Cancer Therapy-General (FACT-G) measure and fatigue using the PROMIS Fatigue-Short Form will also be assessed, as will adherence to the treatment regimen.

B. Phase 2 Studies of Muscadine Grape Seed and Skin Powder Extract (p-MGE) in Advanced Prostate and Breast Cancer Two Phase 2 clinical studies on the effect of p-MGE in advanced prostate and breast cancer are expected to be initiated in 2017, with preparation of IND submissions to the FDA ongoing. The same formulation of p-MGE will be used as described in Part A for the Phase I clinical trial.

A Phase 2 clinical trial in prostate cancer patients will be a randomized, double-blinded, placebo-controlled study of p-MGE versus placebo in men with biochemically-recurrent prostate cancer. The patient population will be men with prostate adenocardinoma whose definitive therapy is complete, who have no metastasis but have rising prostate specific antigen (PSA). It is anticipated that two hundred (200) patients will be randomized into a placebo and treatment group who will receive 8 capsules per day and who will be followed every three months. The primary endpoint assessment will be at 9 months with up to 12 months of follow-up to measure recurrent and survival. The primary outcome will be a reduction in the rate of PSA increase and disease-free survival. A significant reduction in the rate of the increase in PSA in the patients receiving the p-MGE as compared to patients receiving the placebo or an increase in the length of disease-free survival will be interpreted as a positive impact of the extract on metastatic prostate cancer.

A Phase 2 clinical trial in breast cancer patients will be a randomized, double blind, placebo-controlled study in women with triple negative breast cancer who have completed adjuvant chemotherapy within the prior 6 months. The patient population will be women with stage 1-3 triple negative breast cancer (160 patients) who will be randomized to a placebo or p-MGE treatment group (at the level of 8 capsules/day). The primary endpoint will be fatigue assessed at 6 months. Patients will be followed every 6 months for up to 24 months for recurrence and survival outcomes. A significant reduction in fatigue measured as (PROMIS-fatigue, improved mood as assessed by CES-D, less sleep disturbance as assess by the Pittsburgh sleep quality index, fewer cognitive complaints as assessed by Functional Assessment of Cancer Therapy [FACT]-Cog, improved global health-related quality of life (FACT-B), improved physical performance on the Short Physical Performance Battery, physical fitness in a 6 minute walk, Peak VO2 and decreased adiposity by dual energy x-ray absorptiometry (DXA) in women with triple negative breast cancer who are taking the p-MGE as compared to the placebo will be interpreted as a positive impact of the extract on metastatic triple negative breast cancer.

All printed patents and publications referred to in this disclosure are hereby incorporated by reference herein in their entirety.

What is claimed is:

1. A method of manufacturing a liquid extract from muscadine grape seeds and skins, the method comprising combining a liquid extract from muscadine grape seeds and a liquid extract from muscadine grape skins, wherein
   (A) the liquid extract from muscadine grape seeds is produced by:
      (i) contacting muscadine grape seeds with water to form a grape seed extraction mixture;
      (ii) heating the grape seed extraction mixture at a temperature in a range of 120° F. to 200° F., during the heating additional water is added to the grape seed extraction mixture;
      (iii) cooling the grape seed extraction mixture;
      (iv) filtering the grape seed extraction mixture to remove solids thereby forming a grape seed filtrate;
      (v) adding a food preservative to the grape seed filtrate;
      (vi) cooling the grape seed filtrate to form a cooled grape seed filtrate; and
      (vii) filtering the cooled grape seed filtrate to produce a liquid extract from muscadine grape seeds, and
   (B) the liquid extract from muscadine grape skins is produced by:
      (i) contacting muscadine grape skins with water to form a grape skin extraction mixture;

(ii) heating the grape skin extraction mixture at a temperature in a range of 120° F. to 200° F., during the heating additional water is added to the grape skin extraction mixture;
(iii) cooling the grape skin extraction mixture;
(iv) filtering the grape skin extraction mixture to remove solids thereby forming a grape skin filtrate;
(v) adding a food preservative to the grape skin filtrate;
(vi) cooling the grape seed filtrate to form a cooled grape skin filtrate; and
(vii) filtering the cooled grape skin filtrate to produce a liquid extract from muscadine grape skins.

2. The method of claim 1, wherein the muscadine grape seeds and the muscadine grape skins are separated from a muscadine grape pomace and from each other prior to (A) or (B).

3. The method of claim 1, wherein the liquid extract from muscadine grape seeds and skins comprises ellagic acid catechin, gallic acid, epicatechin, procyanadin, and/or catechin-gallate.

4. The method of claim 1, wherein the water is distilled water, optionally wherein the distilled water is fractional vapor compression distilled water.

5. The method of claim 1, wherein the liquid extract from muscadine grape seeds and the liquid extract from muscadine grape skins are combined at a ratio in a range of about 50:50 to about 85:15 (volume/volume (v/v)).

6. The method of claim 1, wherein the liquid extract from muscadine grape seeds and the liquid extract from muscadine grape skins are combined at a ratio in a range of about 85% to about 65% liquid extract from muscadine grape seeds to about 15% to about 35% liquid extract from muscadine grape skins.

7. The method of claim 1, wherein grape seed extraction mixture comprises muscadine grape seeds in a ratio in a range of about 4.5 lbs of muscadine grape seeds to about 0.5 gallons water to about 4.5 lbs of grape seeds to about 2.5 gallons of water.

8. The method of claim 1, wherein the additional water is added to the grape seed extraction mixture to achieve a ratio in a range of about 1 lb muscadine grape seeds to about 0.92 gallons of water to about 1 lb of muscadine grape seeds to about 4.6 gallons of water.

9. The method of claim 1, wherein the grape skin extraction mixture comprises muscadine grape skins in a ratio in a range of about 2 lbs of muscadine grape skins to about 0.5 gallons of water to about 2 lbs of muscadine grape skins to about 1.25 gallons of water, optionally about 2 lbs to about 1 gallon of water.

10. The method of claim 1, wherein the heating is performed for about 1 to about 6 hours, optionally about 1 to about 2 hours.

11. The method of claim 1, wherein the additional water is added to the grape seed extraction mixture and/or the grape skin extraction mixture in a plurality of portions during the heating.

12. The method of claim 11, wherein the portion of additional water is added during the heating at about every 5 min to about every 60 min or about every 5 min to about every 60 min.

13. The method of claim 1, wherein the food preservative is added to the grape seed filtrate and/or to the grape skin filtrate at an amount of about 0.1% to about 1% (w/v).

14. The method of claim 1, wherein the grape seed extraction mixture and/or the grape skin extraction mixture is cooled to a temperature of about 40° F. to about 170° F.

15. The method of claim 1, wherein the grape seed extraction mixture and/or the grape skin extraction mixture is/are filtered through a filter having a sieve size from about 20 microns to about 50 microns.

16. The method of claim 1, wherein the grape seed filtrate and/or grape skin filtrate is/are cooled at a temperature from about 35° F. to about 45° F., optionally for about 24 hours to about 120 hours.

17. The method of claim 1, wherein filtering the cooled grape seed filtrate and/or cooled grape skin filtrate comprises filtering the cooled grape seed filtrate and/or cooled grape skin filtrate through a filter having a sieve size from about 1 micron to about 10 microns.

18. The method of claim 1, wherein food grade ethanol is added to the filtered cooled filtrate of (A)(vii) and/or (B)(vii).

19. A method of manufacturing a muscadine grape-derived powder extract comprising spray-drying the liquid extract produced by the method of claim 1.

* * * * *